US010202588B2

(12) United States Patent
Ledbetter et al.

(10) Patent No.: US 10,202,588 B2
(45) Date of Patent: Feb. 12, 2019

(54) THERAPEUTIC NUCLEASE COMPOSITIONS AND METHODS

(75) Inventors: Jeffrey A. Ledbetter, Seattle, WA (US); Martha Hayden-Ledbetter, Seattle, WA (US); Keith Elkon, Seattle, WA (US); Xizhang Sun, Seattle, WA (US)

(73) Assignee: The University of Washington, Seattle, WA (US)

( * ) Notice: Subject to any disclaimer, the term of this patent is extended or adjusted under 35 U.S.C. 154(b) by 1362 days.

(21) Appl. No.: 13/822,215

(22) PCT Filed: Apr. 27, 2012

(86) PCT No.: PCT/US2012/035614
§ 371 (c)(1),
(2), (4) Date: Mar. 11, 2013

(87) PCT Pub. No.: WO2012/149440
PCT Pub. Date: Nov. 1, 2012

(65) Prior Publication Data
US 2014/0044711 A1  Feb. 13, 2014

Related U.S. Application Data

(60) Provisional application No. 61/480,961, filed on Apr. 29, 2011, provisional application No. 61/617,241, filed on Mar. 29, 2012.

(51) Int. Cl.
| | | |
|---|---|---|
| A61K 39/00 | (2006.01) |
| C12N 9/22 | (2006.01) |
| C07K 16/44 | (2006.01) |
| A61K 47/68 | (2017.01) |
| C07K 1/00 | (2006.01) |
| A61K 38/46 | (2006.01) |

(52) U.S. Cl.
CPC .............. *C12N 9/22* (2013.01); *A61K 47/68* (2017.08); *A61K 47/6815* (2017.08); *C07K 16/44* (2013.01); *A61K 38/465* (2013.01); *C07K 2319/30* (2013.01); *C12Y 301/27005* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,941,763 A | 3/1976 | Sarantakis |
| 4,683,202 A | 6/1987 | Mullis |
| 4,683,195 A | 7/1987 | Mullis et al. |
| 4,800,159 A | 1/1989 | Mullis et al. |
| 4,965,188 A | 10/1990 | Mullis et al. |
| 5,428,130 A | 6/1995 | Capon et al. |
| 5,453,269 A | 9/1995 | Haber et al. |
| 5,559,212 A | 9/1996 | Ardelt |
| 5,637,481 A | 6/1997 | Ledbetter et al. |
| 5,648,260 A | 6/1997 | Winter et al. |
| 5,658,570 A | 8/1997 | Newman et al. |
| 5,739,277 A | 4/1998 | Presta et al. |
| 5,834,250 A | 11/1998 | Wells et al. |
| 5,840,296 A | 11/1998 | Raines et al. |
| 5,840,840 A | 11/1998 | Rybak et al. |
| 5,869,046 A | 2/1999 | Presta et al. |
| 5,955,073 A | 9/1999 | Rybak et al. |
| 5,973,116 A | 10/1999 | Epenetos et al. |
| 5,989,830 A | 11/1999 | Davis et al. |
| 6,096,871 A | 8/2000 | Presta et al. |
| 6,121,022 A | 9/2000 | Presta et al. |
| 6,175,003 B1 | 1/2001 | Saxena |
| 6,194,551 B1 | 2/2001 | Idusogie et al. |
| 6,239,257 B1 | 5/2001 | Ardelt |
| 6,242,195 B1 | 6/2001 | Idusogie et al. |
| 6,277,375 B1 | 8/2001 | Ward |
| 6,280,991 B1 | 8/2001 | Raines |
| 6,348,343 B2 | 2/2002 | Lazarus et al. |
| 6,391,607 B1 | 5/2002 | Lazarus et al. |
| 6,482,626 B2 | 11/2002 | Baker et al. |
| 6,528,624 B1 | 3/2003 | Idusogie et al. |
| 6,538,124 B1 | 3/2003 | Idusogie et al. |
| 6,653,104 B2 | 11/2003 | Goldenberg |
| 6,660,843 B1 | 12/2003 | Feige et al. |
| 6,716,974 B1 | 4/2004 | MacIag et al. |
| 6,737,056 B1 | 5/2004 | Presta |
| 6,821,505 B2 | 11/2004 | Ward |
| 6,998,253 B1 | 2/2006 | Presta et al. |
| 7,033,572 B2 | 4/2006 | Goldenberg |
| 7,067,298 B2 | 6/2006 | Latham et al. |
| 7,074,592 B2 | 7/2006 | Ashkenazi et al. |
| 7,083,784 B2 | 8/2006 | Dall'Acqua et al. |

(Continued)

FOREIGN PATENT DOCUMENTS

| | | |
|---|---|---|
| CL | 2438-2013 | 8/2013 |
| CL | 2013-02428 | 8/2014 |

(Continued)

OTHER PUBLICATIONS

Eisenman et al. Lupus 2017, 26:825-834 (Year: 2017).*
A study of RSLV-132 in Subjects with Primary Sjogren's Syndrome. US National Library of Medicine. Feb. 23, 2018 (Year: 2018).*
National Institutes of Health/US National Library of Medicine, Feb. 23, 2018 (Year: 2018).*
Australian First Office Action, Australian Application No. 2012249360, dated Mar. 7, 2014, 19 pages.

(Continued)

*Primary Examiner* — Chun W Dahle

(74) *Attorney, Agent, or Firm* — Fenwick & West LLP

(57) ABSTRACT

Hybrid nuclease molecules and methods for treating an immune-related disease or disorder in a mammal, and a pharmaceutical composition for treating an immune-related disease in a mammal.

84 Claims, 25 Drawing Sheets

Specification includes a Sequence Listing.

(56) References Cited

U.S. PATENT DOCUMENTS

| | | |
|---|---|---|
| 7,098,016 B2 | 8/2006 | Raines et al. |
| 7,118,751 B1 | 10/2006 | Ledbetter et al. |
| 7,247,302 B1 | 7/2007 | Rosok et al. |
| 7,317,091 B2 | 1/2008 | Lazar et al. |
| 7,364,731 B2 | 4/2008 | Idusogie et al. |
| 7,407,785 B2 | 8/2008 | Lazarus et al. |
| 7,416,875 B2 | 8/2008 | Raines et al. |
| 7,544,487 B2 | 6/2009 | Goldenberg et al. |
| 7,655,757 B2 | 2/2010 | Raines et al. |
| 7,662,925 B2 | 2/2010 | Lazar et al. |
| 7,754,208 B2 | 7/2010 | Ledbetter et al. |
| 7,754,209 B2 | 7/2010 | Ledbetter et al. |
| 7,807,409 B2 | 10/2010 | Kopetzki |
| 7,829,084 B2 | 11/2010 | Ledbetter et al. |
| 8,029,782 B2 | 10/2011 | Klink et al. |
| 8,067,548 B2 | 11/2011 | Wang et al. |
| 8,642,752 B2 | 2/2014 | Swayze et al. |
| 8,697,065 B2 | 4/2014 | Strong et al. |
| 8,841,416 B2 | 9/2014 | Ledbetter et al. |
| 8,937,157 B2 | 1/2015 | Ledbetter et al. |
| 2002/0103125 A1 | 8/2002 | Ashkenazi et al. |
| 2005/0054832 A1 | 3/2005 | Lazar et al. |
| 2005/0136049 A1 | 6/2005 | Ledbetter et al. |
| 2005/0158307 A1 | 7/2005 | Spies et al. |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2006/0040262 A1 | 2/2006 | Morris et al. |
| 2006/0235208 A1 | 10/2006 | Lazar et al. |
| 2006/0263774 A1 | 11/2006 | Clark et al. |
| 2007/0025982 A1 | 2/2007 | Ledbetter et al. |
| 2007/0059306 A1 | 3/2007 | Grosmaire et al. |
| 2007/0111281 A1 | 5/2007 | Sondermann et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0237779 A1 | 10/2007 | Ledbetter et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0057056 A1 | 3/2008 | Lazar et al. |
| 2008/0181892 A1 | 7/2008 | Ledbetter et al. |
| 2008/0227958 A1 | 9/2008 | Thompson et al. |
| 2008/0242845 A1 | 10/2008 | Lazar et al. |
| 2008/0279850 A1 | 11/2008 | Brady et al. |
| 2008/0293121 A1 | 11/2008 | Lazarus et al. |
| 2009/0148447 A1 | 6/2009 | Ledbetter et al. |
| 2009/0175867 A1 | 7/2009 | Thompson et al. |
| 2009/0196870 A1 | 8/2009 | Ledbetter et al. |
| 2009/0214539 A1 | 8/2009 | Grosmaire et al. |
| 2009/0258005 A1 | 10/2009 | Gill et al. |
| 2009/0274692 A1 | 11/2009 | Tan et al. |
| 2010/0015661 A1 | 1/2010 | Dubel et al. |
| 2010/0034820 A1 | 2/2010 | Ledbetter et al. |
| 2010/0099101 A1 | 4/2010 | Behrens et al. |
| 2010/0203052 A1 | 8/2010 | Ledbetter et al. |
| 2010/0279932 A1 | 11/2010 | Ledbetter et al. |
| 2010/0330089 A1 | 12/2010 | Damle et al. |
| 2011/0033483 A1 | 2/2011 | Thompson et al. |
| 2011/0081345 A1 | 4/2011 | Moore et al. |
| 2011/0091461 A1 | 4/2011 | Ledbetter et al. |
| 2011/0105729 A1 | 5/2011 | Ledbetter et al. |
| 2011/0123440 A1 | 5/2011 | Hansen et al. |
| 2011/0151515 A1 | 6/2011 | Heifetz et al. |
| 2011/0171208 A1 | 7/2011 | Tan et al. |
| 2012/0225066 A1 | 9/2012 | Ledbetter et al. |
| 2013/0089546 A1 | 4/2013 | Ledbetter et al. |
| 2013/0177561 A1 | 7/2013 | Ledbetter et al. |
| 2013/0183308 A1 | 7/2013 | Ledbetter et al. |
| 2013/0184334 A1 | 7/2013 | Ledbetter et al. |
| 2014/0178479 A1 | 6/2014 | Bakhru et al. |
| 2014/0227269 A1 | 8/2014 | Ledbetter et al. |
| 2015/0152399 A1 | 6/2015 | Ledbetter et al. |

FOREIGN PATENT DOCUMENTS

| | | |
|---|---|---|
| CN | 1852976 A | 10/2006 |
| CN | 101990439 A | 3/2011 |
| CN | 102770533 A | 11/2012 |
| EP | 0036676 A1 | 9/1981 |
| EP | 0058481 A1 | 8/1982 |
| EP | 0088046 A2 | 9/1983 |
| EP | 0133988 A2 | 3/1985 |
| EP | 0143949 A1 | 6/1985 |
| JP | 2004-525630 A | 8/2004 |
| JP | 2006-512407 A | 4/2006 |
| JP | 2007-525443 A | 9/2007 |
| JP | 2012-537194 | 3/2013 |
| JP | 2014-508143 | 8/2014 |
| WO | WO 88/07089 A1 | 9/1988 |
| WO | PCT/US93/00829 | 8/1993 |
| WO | WO 96/14339 A1 | 5/1996 |
| WO | WO 98/05787 A1 | 2/1998 |
| WO | WO 98/23289 A1 | 6/1998 |
| WO | WO 99/25044 A1 | 5/1999 |
| WO | WO 99/51642 A1 | 10/1999 |
| WO | WO 99/58572 A1 | 11/1999 |
| WO | WO 00/009560 A2 | 2/2000 |
| WO | WO 00/032767 A1 | 6/2000 |
| WO | WO 00/042072 A2 | 7/2000 |
| WO | WO 01/02440 A1 | 1/2001 |
| WO | WO 02/044215 A2 | 6/2002 |
| WO | WO 02/060919 A2 | 8/2002 |
| WO | WO 02/060955 A2 | 8/2002 |
| WO | WO 02/072605 A2 | 9/2002 |
| WO | WO 02/096948 A2 | 12/2002 |
| WO | WO 03/074569 A2 | 9/2003 |
| WO | WO 04/016750 A2 | 2/2004 |
| WO | WO 04/029207 A2 | 4/2004 |
| WO | WO 04/035752 A2 | 4/2004 |
| WO | WO 2004/029207 A2 | 4/2004 |
| WO | WO 04/063351 A2 | 7/2004 |
| WO | WO 04/074455 A2 | 9/2004 |
| WO | WO 04/099249 A2 | 11/2004 |
| WO | WO 2004/099249 A2 | 11/2004 |
| WO | WO 05/018572 A2 | 3/2005 |
| WO | WO 05/040217 A2 | 5/2005 |
| WO | WO 05/047327 A2 | 5/2005 |
| WO | WO 05/063815 A2 | 7/2005 |
| WO | WO 2005/063808 A1 | 7/2005 |
| WO | WO 05/070963 A1 | 8/2005 |
| WO | WO 05/077981 A2 | 8/2005 |
| WO | WO 2005/080586 A1 | 9/2005 |
| WO | WO 05/092925 A2 | 10/2005 |
| WO | WO 05/123780 A2 | 12/2005 |
| WO | WO 06/019447 A1 | 2/2006 |
| WO | WO 06/047350 A2 | 5/2006 |
| WO | WO 06/085967 A2 | 8/2006 |
| WO | WO 07/122511 A2 | 11/2007 |
| WO | WO 2007/122511 A2 | 11/2007 |
| WO | WO 2007/141580 A2 | 12/2007 |
| WO | WO 2008/037311 A1 | 4/2008 |
| WO | WO 2009/015345 A1 | 1/2009 |
| WO | WO 2009/064777 A2 | 5/2009 |
| WO | WO 2011/053982 A2 | 5/2011 |
| WO | WO 2012/149440 A2 | 11/2012 |

OTHER PUBLICATIONS

Australian First Office Action, Australian Application No. 2010313103, dated Mar. 14, 2014, 4 pages.
Australian First Office Action, Australian Application No. 2013203097, dated Mar. 14, 2014, 4 pages.
Chinese Second Office Action, Chinese Application No. 201080060471.1, dated Feb. 27, 2014, 15 pages.
Egyptian Office Action, Egyptian Application No. PCT1666/2013, dated May 24, 2014, 2 pages.

(56) References Cited

OTHER PUBLICATIONS

Georgian Office Action, Georgian Application No. AP 2012 013299, dated May 13, 2014, 2 pages, (with English summary).
Ledbetter, J.A., "Discovery of Biological Drugs: Seattle at the Leading Edge," Grand Rounds, Department of Medicine, University of Washington, Feb. 4, 2010, 36 pages.
United States Office Action, U.S. Appl. No. 14/174,167, dated May 8, 2014, 18 pages.
Australian Second Office Action, Australian Application No. 2012249360, dated Nov. 27, 2015, 3 pages.
Canadian First Office Action, Canadian Application No. 2,834,626, dated Feb. 5, 2015, 6 pages.
Canadian Second Office Action, Canadian Application No. 2,834,626, dated Jan. 12, 2016, 3 pages.
Canadian Second Office Action, Canadian Application No. 2,779,612, dated Dec. 8, 2015, 7 pages.
Chilean First Office Action, Chilean Application No. 03123-2013, dated Feb. 25, 2015, 13 pages (with concise explanation of relevance).
Chilean Second Office Action, Chilean Application No. 03123-2013, dated Nov. 13, 2015, 25 pages.
Chinese Third Office Action, Chinese Application No. 201080060471.1, dated Aug. 26, 2014, 12 pages.
Chinese Fourth Office Action, Chinese Application No. 201080060471.1, dated May 14, 2015, 9 pages.
Chinese Fifth Office Action, Chinese Application No. 201080060471.1, dated Dec. 16, 2015, 4 pages.
Chinese First Office Action, Chinese Application No. 201280032451.2, dated Dec. 11, 2014, 21 pages.
Chinese Second Office Action, Chinese Application No. 201280032451.2, dated Nov. 10, 2015, 17 pages.
Colombian First Office Action, Colombian Application No. 13 279038, dated May 29, 2015, 13 pages (with concise explanation of relevance).
Eurasian Office Action, Eurasian Application No. 201391585/28, dated Jun. 25, 2015, 4 pages.
European Extended Search Report, European Application No. 12777116.0, dated Jun. 3, 2015, 7 pages.
Georgian Office Action, Georgian Application No. AP 2012 013299, dated Oct. 27, 2015, 3 pages (with concise explanation of relevance).
Gillies, S.D. et al., "Improving the Efficacy of Antibody-Interleukin 2 Fusion Proteins by Reducing Their Interaction with Fc Receptors," Cancer Research, May 1, 1999, pp. 2159-2166, vol. 59.
Israel First Office Action, Israel Application No. 219475, dated Jun. 19, 2014, 4 pages (with concise explanation of relevance).
Israel Second Office Action, Israel Application No. 219475, dated May 14, 2015, 6 pages (with concise explanation of relevance).
Israel First Office Action, Israel Application No. 229074, dated Nov. 11, 2015, 5 pages (with concise explanation of relevance).
Japanese First Office Action, Japanese Application No. 2012-537194, dated Nov. 27, 2014, 28 pages.
Japanese Second Office Action, Japanese Application No. 2012-537194, dated Nov. 9, 2015, 15 pages (with concise explanation of relevance).
Jefferis, R. et al., "Interaction Sites on Human IgG-Fc for FcγR: Current Models," Immunology Letters, Jun. 3, 2002, pp. 57-65, vol. 82, No. 1-2.
Johnson, R.J. et al., "Inhibition of Human Pancreatic Ribonuclease by the Human Ribonuclease Inhibitor Protein," J. Mol. Biol., 2007, pp. 434-449, vol. 368.
Karasinska, J.M., "Searching for the Aircardi-Goutieres Syndrome Genes: TREX1 and Ribonuclease H2 Make the Cut," Clin. Genet., 2006, pp. 457-461, vol. 70.
Kenyan Office Action, Kenyan Application No. KE/P/2013/1931, dated Sep. 14, 2015, 5 pages.
Lovgren, T. et al., "Induction of Interferon-α by Immune Complexes or Liposomes Containing Systemic Lupus Erythematosus Autoantigen- and Sjogren's Syndrome Autoantigen-Associated RNA," Arthritis & Rheumatism, Jun. 2006, pp. 1917-1927, vol. 54, No. 6.

Menzel, C. et al., "Human Antibody RNase Fusion Protein Targeting CD30+ Lymphomas," Blood, Apr. 1, 2008, pp. 3830-3837, vol. 111, No. 7.
Mexican First Office Action, Mexican Application No. 12/005062, dated Jun. 9, 2014, 6 pages.
Mexican Second Office Action, Mexican Application No. 12/005062, dated Feb. 9, 2015, 13 pages.
Mexican Third Office Action, Mexican Application No. 12/005062, dated Oct. 2, 2015, 9 pages.
Mexican First Office Action, Mexican Application No. 13/012612, dated Jun. 26, 2015, 7 pages.
New Zealand Application No. 599842, Filed Nov. 2, 2010, Not yet published [Copy Not Enclosed].
New Zealand Application No. 628189, Filed Nov. 2, 2010, Not yet published [Copy Not Enclosed].
New Zealand First Office Action, New Zealand Application No. 628189, dated Aug. 21, 2014, 3 pages.
New Zealand First Office Action, New Zealand Application No. 616989, dated Aug. 25, 2014, 2 pages.
New Zealand Second Office Action, New Zealand Application No. 599842, dated Aug. 21, 2014, 3 pages.
New Zealand Third Office Action, New Zealand Application No. 599842, dated Dec. 12, 2014, 3 pages.
Shak, S. et al., "Recombinant Human DNase I Reduces the Viscosity of Cystic Fibrosis Sputum," Proc. Natl. Acad. Sci. USA, Dec. 1990, pp. 9188-9192, vol. 87.
Sondermann, P. et al., "The 3.2 ANG Crystal Structure of the Human IgG1 Fc Frahment-FcγRIII Complex," Nature, Jul. 20, 2000, pp. 267-273, vol. 406, No. 6793.
Stavenhagen, J.B. et al., "Fc Optimization of Therapeutic Antibodies Enhances Their Ability to Kill Tumor Cells in Vitro and Controls Tumor Expansion in Vivo Via Lof-Affinity Activating Fcγ Receptors," Cancer Research, 2007, pp. 8882-8890, vol. 67.
Strohl, W.R., "Optimization of Fc-Mediated Effector Functions of Monoclonal Antibodies," Curr. Opin. Biotechnol., (Nov. 11, 2009) vol. 20, p. 685-691.
Sun, X. et al., "Increased RNase Expression Reduces Inflammation and Prolongs Survival in TLR7 Transgenic Mice," The Journal of Immunology, Feb. 4, 2013, 9 pages.
Thai Office Action, Thai Application No. 1301006180, dated Apr. 23, 2015, 2 pages (with concise explanation of relevance).
United States Office Action, U.S. Appl. No. 13/505,421, dated Jun. 12, 2014, 13 pages.
United States Restriction Requirement, U.S. Appl. No. 14/174,167, dated Apr. 15, 2014, 6 pages.
United States Office Action, U.S. Appl. No. 14/174,167, dated Aug. 25, 2014, 12 pages.
United States Advisory Action, U.S. Appl. No. 14/174,167, dated Oct. 17, 2014, 4 pages.
Canadian Office Action, Canadian Application No. 2,779,615, dated Sep. 25, 2013, 5 pages.
GenBank Accession No. CAA55817.1 (May 20, 1994), Filipenko, M.L.et al., NCBI Sequence Viewer v2.0, 3 pages, [online] [Retrieved on Dec. 12, 2013] Retrieved from the Internet at <URL: http://www.ncbi.nlm.nih.gov/protein/CAA55817.1>.
United States Restriction Requirement, U.S. Appl. No. 13/197,731, dated Nov. 16, 2012, 7 pages.
United States Office Action, U.S. Appl. No. 13/505,421, dated Oct. 22, 2013, 13 pages.
Carsana, A. et al. "Structure of the Bovine Pancreatic Ribonuclease Gene: The Unique Intervening Sequence in the 5' Untranslated Region Contains a Promoter-Like Element," Nucleic Acids Research, Jun. 24, 1988, pp. 5491-550, vol. 16, No. 12.
Colombian Office Action, Colombian Application No. 15 234237, dated May 12, 2016, 12 pages (with concise explanation of relevance).
Mexican Office Action, Mexican Application No. 13/012612, dated Feb. 9, 2016, 8 pages.
Ukrainian Office Action, Ukrainian Application No. A201312889, dated Jul. 13, 2016, 8 pages (with concise explanation of relevance).
Canadian Office Action, Canadian Application No. 2,834,626, dated Dec. 22, 2017, 3 pages.

(56) References Cited

OTHER PUBLICATIONS

Israel Office Action, Israel Application No. 229074, dated Sep. 6, 2017, 8 pages (with concise explanation of relevance).
Japanese Office Action, Japanese Application No. 2016-243950, dated Sep. 28, 2017, 4 pages.
Japanese Office Action, Japanese Application No. 2016-045546, dated Oct. 16, 2017, 2 pages.
New Zealand Second Examination Report, New Zealand Application No. 717398, dated Nov. 14, 2017, 2 pages.
New Zealand First Examination Report, New Zealand Application No. 735554, dated Nov. 14, 2017, 2 pages.
New Zealand Second Examination Report, New Zealand Application No. 717205, dated Nov. 20, 2017, 3 pages.
New Zealand First Examination Report, New Zealand Application No. 735379, dated Nov. 20, 2017, 5 pages.
Peruvian Office Action, Peruvian Application No. 2425, dated Sep. 25, 2017, 18 pages.
Philippines Office Action, Philippines Application No. 1/2013/502441, dated Aug. 8, 2017, 3 pages.
Beintema J.J. et al., "Differences in Glycosylation Pattern of Human Secretory Ribonucleases," Biochem. J., 1988, pp. 501-505, vol. 255.
Berland, R., et al., "Toll-like Receptor 7-Dependent Loss of B Cell Tolerance in Pathogenic Autoantibody Knockin Mice," Immunity, Sep. 2006, pp. 429-440, vol. 25.
Bitonti, A.J. et al., "Pulmonary Delivery of an Erythropoietin Fc Fusion Protein in Non-Human Primates Through an Immunolobulin Transport Pathway," PNAS, Jun. 29, 2004, pp. 9763-9768, vol. 101, No. 26.
Boix, E. et al., "Mammalian Antimicrobial Proteins and Peptides: Overview on the RNase A Superfamily Members Involved in Innate Host Defence," Molecular BioSystems, 2007, pp. 317-335, vol. 3.
Brekke, O.H. et al., "Human IgG Isotype-Specific Amino Acid Residues Affecting Complement-Mediated Cell Lysis and Phagocytosis," European Journal of Immunology, 1994, pp. 2542-2547, vol. 24.
Brekke, O.H. et al., "Therapeutic Antibodies for Human Diseases at the Dawn of the Twenty-First Century," Nature Reviews, Jan. 2003, pp. 52-62, vol. 2.
Canfield, Stephen M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).
Chinese Office Action, Chinese Application No. 201080060471.1, dated Apr. 12, 2013, 20 pages.
Davis, Jr., J.C. et al., "Recombinant Human Dnase I (rhDNase) in Patients with Lupus Nephritis," Lupus, 1999, pp. 68-76, vol. 8.
Dübel, S., "Novel Recombinant Antibody Constructs and Fusion Proteins for Therapy and Research," Department of Biotechnology, Technical University of Braunschweig, Germany, Jun. 17, 2008, 15 pages.
Dwyer, M.A. et al., "Expression and Characterization of a DNase I-Fc Fusion Enzyme," The Journal of Biological Chemistry, Apr. 2, 1999, pp. 9738-9743, vol. 274, No. 14.
Extended European Search Report, European Patent Application No. 10827655.1, dated Jun. 24, 2013, 12 pages.
Fenton et al., "Anti-dsDNA Antibodies Promote Initiation, and Acquired Loss of Renal Dnase1 Promotes Progression of Lupus Nephritis in Autoimmune (NZBxNZW)F1 Mice," PloS One, 2009 (published online Dec. 2009), p. e8474, vol. 4, No. 12.
Fujihara, J. et al., "Comparative Biochemical Properties of Vertebrate Deoxyribonuclease I," Comparative Biochemistry and Physiology, Part B, 2012, pp. 263-273, vol. 163.
Gavalchin, J. et al., "The NZB X SWR Model of Lupus Nephritis. I. Cross-Reactive Idiotypes of Monoclonal Anti-DNA Antibodies in Relation to Antigenic Specificity, Charge, and Allotype. Identification of Interconnected Idiotype Families Inherited from the Normal SWR and the Autoimmune NZB Parents," The Journal of Immunology, Jan. 1, 1987, pp. 128-137, vol. 138.

GenBank Accession No. CAA11830, Nov. 20, 1998, 2 pages, [Online] Retrieved from the Internet<URL:http://www.ncbi.nlm.nih.gov/protein/CAA11830>.
Invitation to Pay Additional Fees, and, Where Applicable, Protest Fee, PCT Application No. PCT/US10/55131, Feb. 9, 2011, 2 pages.
Linsley, P.S. et al., "CTLA-4 Is a Second Receptor for the B Cell Activation Antigen B7," J. Exp. Med., Sep. 1991, pp. 561-569, vol. 174.
Macanovic, M. et al., "The treatment of systemic lupus erythematosus (SLE) in NZB/W $F_1$ hybrid mice; studies with recombinant murine DNase and with dexamethasone," Clin Exp Immunol, 1996, pp. 243-252, vol. 106.
Martinez-Valle, F. et al., "DNase 1 Activity in Patients with Systemic Lupus Erythematosus: Relationship with Epimediological, Clinical Immunological and Therapeutical Features," Lupus, 2009, pp. 418-423, vol. 18, No. 5.
Menzel, et al., "Human Antibody RNase Fusion Protein Targeting CD30+ Lymphomas," Blood, Apr. 2008, pp. 3830-3837, vol. 111, No. 7.
New Zealand Examination Report, New Zealand Application No. 599842, dated Feb. 11, 2013, 3 pages.
"Nuclease (biology)," Brittanica Online Encyclopedia, 1 page, [Online] [Retrieved on Feb. 20, 2013], Retrieved from the Internet<URL:http://www.britannica.com/EBchecked/topic/421887/nuclease?sections=421887main&vie . . . >.
Pan, C.Q. et al., "$Ca^{2+}$-Dependent Activity of Human DNase I and Its Hyperactive Variants," Protein Science, 1999, pp. 1780-1788, vol. 8.
Pan, C.Q. et al., "Improved Potency of Hyperactive and Actin-Resistant Human DNase I Variants for Treatment of Cystic Fibrosis and Systemic Lupus Erythematosus," The Journal of Biological Chemistry, Jul. 17, 1998, pp. 18374-18381, vol. 273, No. 29.
PCT International Search Report and Written Opinion, PCT Application No. PCT/US10/55131, dated Apr. 29, 2011, 18 pages.
PCT International Search Report and Written Opinion, PCT Application No. PCT/US12/35614, dated Sep. 4, 2012, 17 pages.
Rodriguez, A.M. et al., "Identification, Localization and Expression of Two Novel Human Genes Similar to Deoxyribonuclease I," Genomics, 1997, pp. 507-513, vol. 42.
Shak, S. et al., "Recombinant Human DNase I Reduces the Viscosity of Cystic Fibrosis Sputum," Proc. Natl. Acad. Sci., Dec. 1990, pp. 9188-9192, vol. 87.
Skolnick, J. et al., "From Genes to Protein Structure and Function: Novel Applications of Computational Approaches in the Genomic Era," TIBTECH, Jan. 2000, pp. 34-39, vol. 18.
United States Office Action, U.S. Appl. No. 13/197,731, dated Feb. 27, 2013, 17 pages.
United States Restriction Requirement, U.S. Appl. No. 13/505,421, dated Apr. 16, 2013, 8 pages.
Whisstock, J.C. et al., "Prediction of Protein Function from Protein Sequence and Structure," Quarterly Reviews of Biophysics, Cambridge University Press, 2003, pp. 307-340, vol. 36, No. 3.
Yasuda, T. et al., "A Biochemical and Genetic Study on All Non-Synonymous Single Nucleotide Polymorphisms of the Gene Encoding Human Deoxyribonuclease I Potentially Relevant to Autoimmunity," The International Journal of Biochemistry & Cell Biology, 2010, pp. 1216-1225, vol. 42.
Zeng, Z. et al., "Cloning and Characterization of a Novel Human DNase," Biochemical and Biophysical Research Communication, 1997, pp. 499-504, vol. 231.
Chan, A.G. et al., "Therapeutic Antibodies for Autoimmunity and Inflammation," Nature Reviews Immunology, May 2010, pp. 301-316, vol. 10.
European Examination Report, European Application No. 10827655.1, dated Feb. 12, 2016, 4 pages.
Japanese Office Action, Japanese Application No. 2014-508143, dated Mar. 23, 2016, 10 pages.
New Zealand First Examination Report, New Zealand Application No. 717205, dated Mar. 9, 2016, 3 pages.
New Zealand First Examination Report, New Zealand Application No. 717398, dated Mar. 15, 2016, 2 pages.

(56) References Cited

OTHER PUBLICATIONS

Chinese Fourth Office Action, Chinese Application No. 201280032451.2, dated Feb. 28, 2017, 4 pages (with concise explanation of relevance).
Indian First Examination Report, Indian Application No. 4709/CHENP/2012, dated Feb. 21, 2017, 9 pages.
Japanese Office Action, Japanese Application No. 2016-045546, dated Jan. 18, 2016, 6 pages (with concise explanation of relevance).
Korean Office Action, Korean Application No. 10-2012-7014363, dated Nov. 21, 2016, 4 pages (with concise explanation of relevance).
Mexican Third Office Action, Mexican Application No. 13/012612, dated Feb. 14, 2016, 12 pages.
Canadian Third Office Action, Canadian Application No. 2,779,615, dated Mar. 6, 2017, 8 pages.
Clark, E.A. et al., "CD16-Mediated Antibody Dependent Cellular Cytotoxicity is Required for B Cell Depletion by a Small Modular ImmunoPharmaceutical Specific for CD20," Blood, 2003, Abstract#2388, p. 646a, vol. 102, No. 11.
United States Restriction Requirement, U.S. Appl. No. 14/516,161, dated Jan. 26, 2017, 6 pages.
United States Restriction Requirement, U.S. Appl. No. 14/599,567, dated Apr. 6, 2017, 5 pages.
Korean Office Action, Korean Application No. 10-2012-7014363, dated Jul. 27, 2017, 8 pages (with concise explanation of relevance).
United States Office Action, U.S. Appl. No. 14/599,567, dated Jul. 21, 2017, 9 pages.
United States Restriction Requirement, U.S. Appl. No. 13/197,731, dated Aug. 3, 2012, 11 pages.
United States Restriction Requirement, U.S. Appl. No. 13/197,731, dated Aug. 17, 2012, 11 pages.
United States Restriction Requirement, U.S. Appl. No. 13/505,421, dated Aug. 6, 2013, 8 pages.
Video of Medicine Grand Rounds on Feb 4, 2010 by Jeffrey Ledbetter, Research.
Professor of Medicine, Division of Rheumatology; Affiliate Associate Professor of Microbiology University of Washington School of Medicine, [Copy Not Enclosed], Can be Viewed at <http://depts.washington.edu/medweb/conferences/GRarchive.html#ledbetter>.
European Extended Search Report, European Application No. 16198956.1, dated May 4, 2017, 8 pages.
Australian Second Examination Report, Australian Application No. 2016201790, dated Nov. 11, 2016, 3 pages.
Australian First Examination Report, Australian Application No. 2016202135, dated Nov. 11, 2016, 4 pages.
Chinese Third Office Action, Chinese Application No. 201280032451.2, dated Aug. 5, 2016, 11 pages.
European Examination Report, European Application No. 12777116.0, dated Oct. 25, 2016, 4 pages.
Guo, J. et al., "Clinical Applications of DNaseq," International Journal of Pathology and Clinical Medicine, Apr. 2009, pp. 125-129, vol. 29, No. 2 (with English abstract).
Indonesian Office Action, Indonesian Application No. WO0201305523, dated Sep. 20, 2016, 4 pages.
Israel Office Action, Israel Application No. 219475, dated Aug. 22, 2016, 7 pages (with concise explanation of relevance).
Ni, Y. et al., "Research Progress of DNaseq," International Journal of Pathology and Clinical Medicine, Dec. 2006, pp. 531-535, vol. 26, No. 6.
Prince, W.S. et al., "Pharmacodynamics of Recombinant Human DNase I in Serum," Clin. Exp. Immunol., 1998, pp. 289-296, vol. 113.
Zhao, W-P. et al., "Relationship Between RNA Released from Mouse Apoptotic Murine Splenocytes and Autoimmune Disease," Chinese Journal of Biochemistry and Molecular Biology, 2003, pp. 662-666, vol. 19, No. 5 (with English abstract).
Israel Office Action, Israel Application No. 219475, dated Jan. 22, 2018, 3 pages (with concise explanation of relevance).
Mexican First Office Action, Mexican Application No. 14/013439, dated Nov. 21, 2017, 6 pages.
Canadian Office Action, Canadian Application No. 2,779,615, dated Feb. 13, 2018, 4 pages.
Indian Examination Report, Indian Application No. 8851/CHENP/2013, dated Mar. 26, 2018, 9 pages.

* cited by examiner

RSLV-124 Retains Full Enzyme Activity In Vivo

Figure 3

RSLV-124 Protein Concentration

- Following administration to mice, RSLV-124 in serum was captured via plate-bound anti-human Fc.
- The associated RNase activity was assessed.
- Based on comparison to RNase, the quantity of RSLV-124 was estimated (µg/ml).

Derived protein concentrations agreed well with those determined by a direct ELISA. As such, RSLV-124 appears to maintain full activity in vivo.

*y-axis: RSLV-124 Captured in Serum, µg/mL*
*x-axis: Hours Post Dosage*

Legend: Mouse #221, Mouse #220

Figure 4

RNase Enzymatic Activity of Protein-A Purified Nuclease Fc Fusion Proteins Using SRED Assay

Enzyme Kinetic Analysis of RNase Activity of RNase Fc Fusion Proteins

L-B Fitting Results

| Curve Name | Well ID | Curve Formula | A | B | R2 | Vmax | Km |
|---|---|---|---|---|---|---|---|
| L-B_SPL1 | rRNaseA | Y=A*X+B | 1.17E-08 | 8.41E-09 | 0.988 | 1.2E+08 | 1.3912 |
| L-B_SPL2 | hRNaseWT-SCCH-WTIgG | Y=A*X+B | 1.26E-08 | 7.34E-09 | 0.966 | 1.4E+08 | 1.71662 |
| L-B_SPL3 | RSLV125 | Y=A*X+B | 3.22E-08 | 2.45E-09 | 0.994 | 4.1E+08 | 13.1429 |
| L-B_SPL4 | RSLV126 | Y=A*X+B | 2.31E-08 | 5.08E-09 | 0.996 | 2E+08 | 4.54724 |
| L-B_SPL5 | hRNaseG88D-SCCH-TMIgG | Y=A*X+B | 1.66E-08 | 7.66E-09 | 0.975 | 1.3E+08 | 2.1671 |

Figure 13

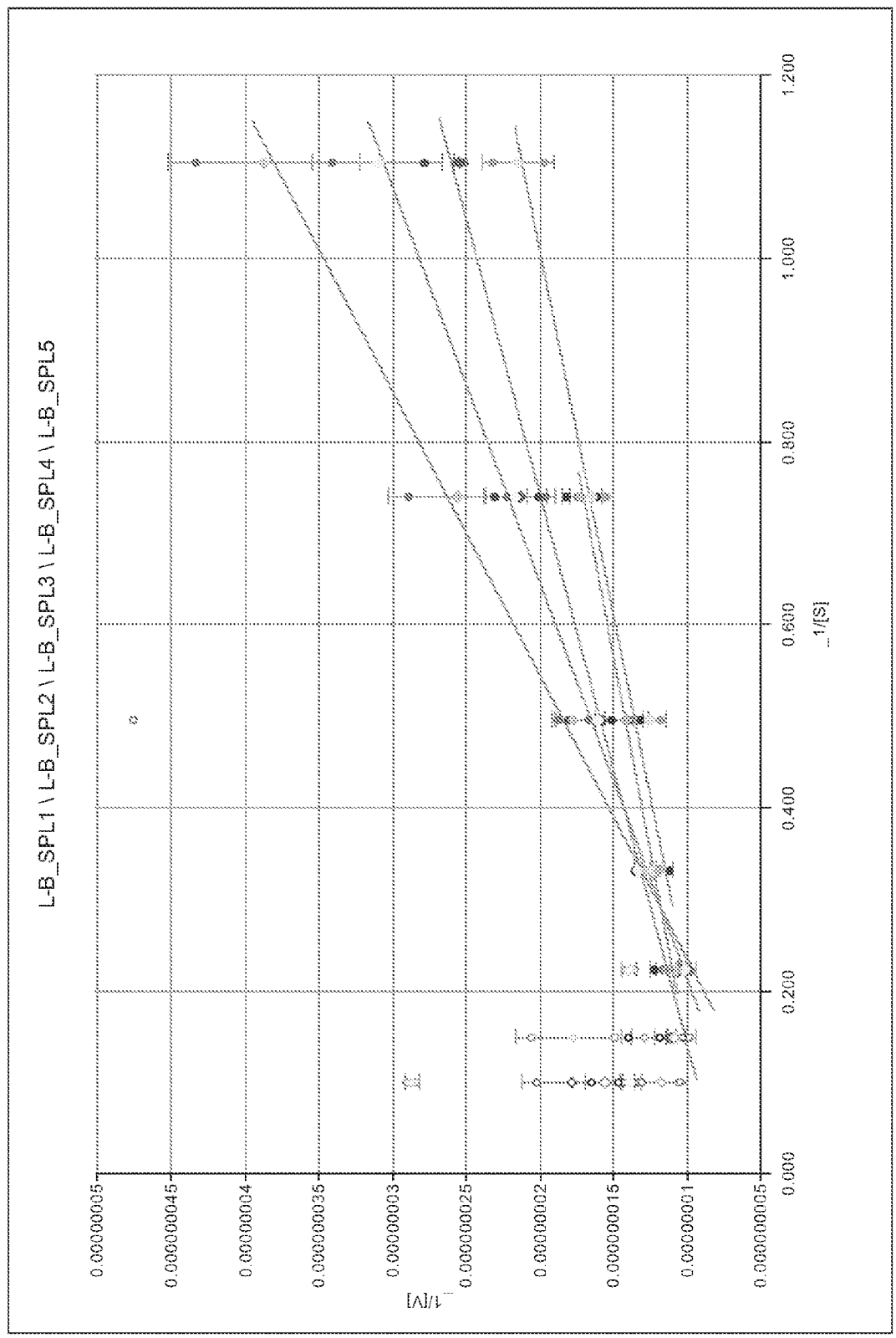
Fig. 13 (Con't)

Analysis of Cytotoxicity in THP1 Cells Treated with RNase Fc Fusion Proteins with Wild Type and Mutant Fc Domains
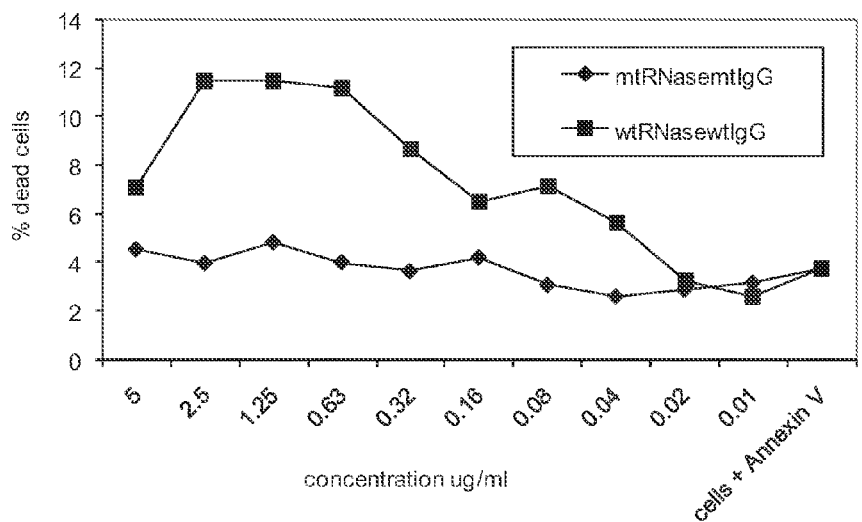
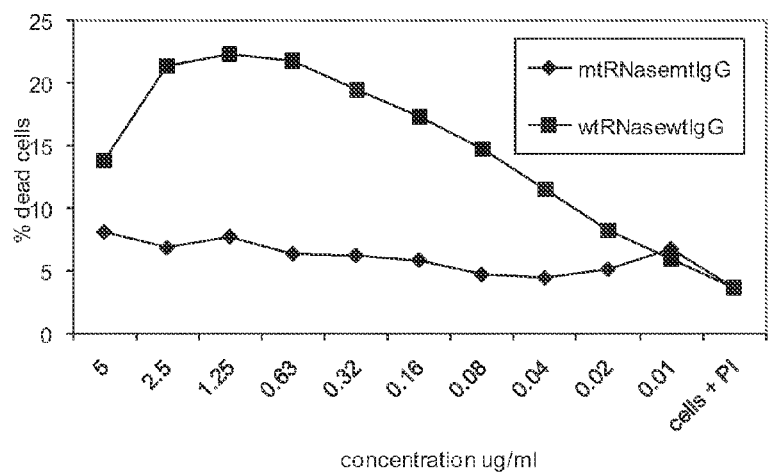
Figure 14

Figure 17

THERAPEUTIC NUCLEASE COMPOSITIONS AND METHODS

CROSS REFERENCE TO RELATED APPLICATIONS

This application claims priority to U.S. Provisional Application No. 61/480,961, filed Apr. 29, 2011 and U.S. Provisional Application No. 61/617,241, filed Mar. 29, 2012, and is the National Stage of International Application No. PCT/US2012/035614, filed Apr. 27, 2012. This application is also related to: International Patent Application No. PCT/US2010/055131, filed Nov. 2, 2010; U.S. Provisional Application No. 61/257,458, filed Nov. 2, 2009; and U.S. Provisional Application No. 61/370,752, filed Aug. 4, 2010. The entire disclosures of the foregoing applications are hereby incorporated by reference in their entirety for all purposes.

STATEMENT REGARDING FEDERALLY SPONSORED RESEARCH OR DEVELOPMENT

This invention was made with government support under grants NS065933 and AR048796 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 27, 2013, is named 20832US_CRF_sequencelisting.txt and is 186,782 bytes in size.

BACKGROUND

Excessive release of (ribo)nucleoprotein particles from dead and dying cells can cause lupus pathology by two mechanisms: (i) Deposition or in situ formation of chromatin/anti-chromatin complexes causes nephritis and leads to loss of renal function; and (ii) nucleoproteins activate innate immunity through toll-like receptor (TLR) 7, 8, and 9 as well as TLR-independent pathway(s). Release of nucleoproteins can serve as a potent antigen for autoantibodies in SLE, providing amplification of B cell and DC activation through co-engagement of antigen receptors and TLRs. Thus, there exists a need for a means to remove inciting antigens and/or attenuate immune stimulation, immune amplification, and immune complex mediated disease in subjects in need thereof.

SUMMARY

Disclosed herein is a hybrid nuclease molecule comprising a first nuclease domain and a modified Fc domain, wherein the first nuclease domain is operatively coupled to the Fc domain. The Fc domain is modified such that the molecule has reduced cytotoxicity relative to a hybrid nuclease molecule having an unmodified Fc domain. In some embodiments, the hybrid nuclease molecule has an Fc domain which has been modified to decrease binding to Fcγ receptors, complement proteins, or both. In some emboidments, the hybrid nuclease molecule has reduced cytotoxicity at least 1, 2, 3, 4, or 5-fold compared to a control molecule e.g., a hybrid nuclease molecule without a modified Fc domain.

In some embodiments, the hybrid nuclease molecule further includes a first linker domain, and the first nuclease domain is operatively coupled to the modified Fc domain by the first linker domain.

In some aspects, a hybrid nuclease molecule includes a modified Fc domain which is a mutant, IgG1 Fc domain. In some aspects, a mutant Fc domain comprises one or more mutations in the hinge, CH2, and/or CH3 domains. In some aspects, the Fc domain comprises an amino acid sequence having one or more of the mutations P238S, P331S, SCC, SSS (residues 220, 226, and 229), G236R, L328R, L234A, and L235A. In some aspects, a mutant Fc domain includes a P238S mutation. In some aspects, a mutant Fc domain includes a P331S mutation. In some aspects, a mutant Fc domain includes a P238S mutation and a P331S mutation. In some aspects, a mutant Fc domain comprises P238S and/or P331S, and may include mutations in one or more of the three hinge cysteines. In some aspects, a mutant Fc domain comprises P238S and/or P331S, and/or one or more mutations in the three hinge cysteines. In some aspects, a mutant Fc domain comprises P238S and/or P331S, and/or mutations in one of the three hinge cysteines (located at residue 220 by EU numbering) to SCC (wherein CCC refers to the three cysteines present in the wild type hinge domain). In some aspects, a mutant Fc domain comprises P238S and/or P331S, and/or mutations in the three hinge cysteines (located at residues 220, 226 and 229 by EU numbering) to SSS. In some aspects, a mutant Fc domain comprises P238S and P331S and mutations in the three hinge cysteines. In some aspects, a mutant Fc domain comprises P238S and P331S and SCC. In some aspects, a mutant Fc domain comprises P238S and P331S and SSS. In some aspects, a mutant Fc domain includes P238S and SCC. In some aspects, a mutant Fc domain includes P238S and SSS. In some aspects, a mutant Fc domain includes P331S and SCC. In some aspects, a mutant Fc domain includes P331S and SSS. In some aspects, a mutant Fc domain includes mutations in one or more of the three hinge cysteines. In some aspects, a mutant Fc domain includes mutations in the three hinge cysteines. In some aspects, a mutant Fc domain includes a mutation in the three hinge cysteines to SCC. In some aspects, a mutant Fc domain includes mutations in the three hinge cysteines to SSS. In some aspects, a mutant Fc domain includes SCC. In some aspects, a mutant Fc domain includes SSS.

In some aspects, a nucleic acid encoding a mutant Fc domain is as shown in SEQ ID NO:59. In some aspects, a mutant Fc domain is as shown in SEQ ID NO:60. In some aspects, a nucleic acid encoding a mutant Fc domain is as shown in SEQ ID NO:71. In some aspects, a mutant Fc domain is as shown in SEQ ID NO:72. In some aspects, a nucleic acid encoding a mutant Fc domain is as shown in SEQ ID NO:73. In some aspects, a mutant Fc domain is as shown in SEQ ID NO:74. In some aspects, a nucleic acid encoding a mutant Fc domain is shown in SEQ ID NO:75. In some aspects, a mutant Fc domain is as shown in SEQ ID NO:76. In some aspects, a nucleic acid encoding a mutant Fc domain is as shown in SEQ ID NO:87. In some aspects, a mutant Fc domain is as shown in SEQ ID NO:88. In some aspects, a nucleic acid encoding a mutant Fc domain is as shown in SEQ ID NO:89. In some aspects, a mutant Fc domain is as shown in SEQ ID NO:90.

In some aspects, a hybrid nuclease molecule comprises a wild-type, human RNase1 domain linked to a mutant, human IgG1 Fc domain comprising SCC, P238S, and P331S, or to a mutant, human IgG1 Fc domain comprising SSS, P238S, and P331S. In some aspects, a nucleic acid encoding a hybrid nuclease molecule is as shown in SEQ ID NO: 61, 77, or 91. In some aspects, a hybrid nuclease molecule is as shown in SEQ ID NO:209, 62, 78, 92, or 94.

In some aspects, a hybrid nuclease molecule comprises a wild-type, human RNase1 domain linked via a (Gly$_4$Ser)$_4$ linker (SEQ ID NO: 108) domain to a mutant, human IgG1 Fc domain comprising SCC, P238S, and P331S, or to a mutant, human IgG1 Fc domain comprising SSS, P238S, and P331S. In some aspects, a nucleic acid encoding a hybrid nuclease molecule is as shown in SEQ ID NO: 63, or 79. In some aspects, a hybrid nuclease molecule is as shown in SEQ ID NO: 64, or 79.

In some aspects, a hybrid nuclease molecule comprises a human DNase1 G105R A114F domain linked via a (Gly$_4$Ser)$_4$ linker (SEQ ID NO: 108) domain to a mutant, human IgG1 Fc domain comprising SCC, P238S, and P331S linked via a NLG linker domain to a wild-type, human RNase1 domain. In some aspects, a hybrid nuclease molecule comprises a human DNase1 G105R A114F domain linked via a (Gly$_4$Ser)$_4$ linker (SEQ ID NO: 108) domain to a mutant, human IgG1 Fc domain comprising SSS, P238S, and P331S, linked via a NLG linker domain to a wild-type, human RNase1 domain. In some aspects, a nucleic acid encoding a hybrid nuclease molecule is as shown in SEQ ID NO: 65, or 81. In some aspects, a hybrid nuclease molecule is as shown in SEQ ID NO: 66, or 82.

In other embodiments, a hybrid nuclease molecule comprises an amino acid sequence set forth in SEQ ID NO: 62, 64, 78, 80, 92, or 96, or a hybrid nuclease molecule comprising an amino acid sequence at least 90% identical to the amino acid sequence set forth in SEQ ID NO: 62, 64, 78, 80, 92, or 96. In some aspects, a hybrid nuclease molecule comprises an amino acid sequence set forth in SEQ ID NO: 96. In other aspects, a hybrid nuclease molecule comprises an amino acid sequence set forth in SEQ ID NO: 66, 68, 70, 82, 84, 86, 94, or 98, or a hybrid nuclease molecule comprising an amino acid sequence at least 90% identical to the amino acid sequence set forth in SEQ ID NO: 66, 68, 70, 82, 84, 86, 94, or 98. In other aspects, a hybrid nuclease molecule comprises an amino acid sequence set forth in SEQ ID NO: 98.

In some aspects, a hybrid nuclease molecule comprises a wild-type, human RNase1 domain linked via a (Gly$_4$Ser)$_4$ linker (SEQ ID NO: 108) domain to a mutant, human IgG1 Fc domain comprising SCC, P238S, and P331S linked via a NLG linker domain to a human DNase1 G105R A114F domain. In some aspects, a hybrid nuclease molecule comprises a wild-type, human RNase1 domain linked via a (Gly$_4$Ser)$_4$ linker (SEQ ID NO: 108) domain to a mutant, human IgG1 Fc domain comprising SSS, P238S, and P331S, linked via a NLG linker domain to a human DNase1 G105R A114F domain. In some aspects, a nucleic acid encoding a hybrid nuclease molecule is as shown in SEQ ID NO: 67, or 83. In some aspects, a hybrid nuclease molecule is shown in SEQ ID NO: 68, or 84.

In some aspects, a hybrid nuclease molecule comprises a wild-type, human RNase1 domain linked to a mutant, human IgG1 Fc domain comprising SCC, P238S, and P331S linked via a NLG linker domain to a human DNase1 G105R A114F domain. In some aspects, a hybrid nuclease molecule comprises a wild-type, human RNase1 domain linked to a mutant, human IgG1 Fc domain comprising SSS, P238S, and P331S linked via a NLG linker domain to a human DNase1 G105R A114F domain. In some aspects, a nucleic acid encoding a hybrid nuclease molecule is shown in SEQ ID NO: 69, 85, or 93. In some aspects, a hybrid nuclease molecule is shown in SEQ ID NO: 70, 86, 94, or 98.

In some aspects, cytotoxicity induced by a hybrid nuclease molecule is reduced when compared to a control molecule. In some aspects, cytotoxicity induced by a hybrid nuclease molecule is reduced about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% when compared to a control molecule. In some aspects, the hybrid nuclease molecule has about 3-5 fold, or at least about 3 fold reduced cytotoxicity as compared to a hybrid nuclease molecule having having an unmodified Fc domain (e.g., a wild type Fc domain).

In some aspects, the activity of a hybrid nuclease molecule having a DNase is not less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or >30-fold less than the activity of a control DNase molecule. In some aspects, the activity of a hybrid nuclease molecule having a DNase is about equal to the activity of a control DNase molecule. In some aspects, the activity of a hybrid nuclease molecule having an RNase is not less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or >30-fold less than the activity of a control RNase molecule. In some aspects, the activity of a hybrid nuclease molecule having an RNase is about equal to the activity of a control RNase molecule.

In some embodiments, a hybrid nuclease molecule is a polypeptide, wherein the amino acid sequence of the first nuclease domain comprises a human, wild-type RNase amino acid sequence, wherein the first linker domain is (Gly4Ser)n, where n is 0, 1, 2, 3, 4 or 5 (SEQ ID NO: 109), wherein the amino acid sequence of the Fc domain comprises a human, mutant IgG1 Fc domain amino acid sequence, and wherein the first linker domain is coupled to the C-terminus of the first nuclease domain and the N-terminus of the Fc domain. In some embodiments, a hybrid nuclease molecule is a polypeptide comprising or consisting of a sequence shown in Table 1.

In some embodiments, a hybrid nuclease molecule comprises wild-type, human DNase1 linked to a mutant, human IgG1 Fc domain. In some embodiments, a hybrid nuclease molecule comprises human DNase1 G105R A114F linked to a mutant, human IgG1 Fc domain by a (Gly$_4$Ser)$_n$ linker domain where n=0, 1, 2, 3, 4, or 5 (SEQ ID NO: 109). In some embodiments, a hybrid nuclease molecule comprises wild-type, human RNase1 linked to a mutant, human IgG1 Fc domain linked to wild-type, human DNase1. In some embodiments, a hybrid nuclease molecule comprises wild-type, human RNase1 linked to a mutant, human IgG1 Fc domain linked to human DNase1 G105R A114F. In some embodiments, a hybrid nuclease molecule is a polypeptide, wherein the amino acid sequence of the first nuclease domain comprises a RNase amino acid sequence, wherein the first linker domain is between 5 and 32 amino acids in length, wherein the amino acid sequence of the Fc domain comprises a human, Fc domain amino acid sequence, and wherein the first linker domain is coupled to the C-terminus of the first nuclease domain and the N-terminus of the Fc domain. In some embodiments, the linker domain includes (Gly$_4$Ser)$_5$ (SEQ ID NO: 110) and restriction sites BglII, AgeI, and XhoI. In some embodiments, a hybrid nuclease molecule is a polypeptide, wherein the amino acid sequence of the first nuclease domain comprises a human RNase amino acid sequence, wherein the first linker domain is a NLG peptide between 5 and 32 amino acids in length, wherein the amino acid sequence of the Fc domain comprises a human, mutant Fc domain amino acid sequence, and wherein the first linker domain is coupled to the C-terminus of the first nuclease domain and the N-terminus of the Fc domain.

In some embodiments, the Fc domain does not substantially bind to an Fc receptor on a human cell. In some embodiments, the Fc domain is modified to decrease binding to Fcγ receptors, complement proteins, or both. In some aspects Fc receptor binding is reduced about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% when compared to a control molecule. In some aspects, the hybrid nuclease molecule has decrease Fc receptor binding by 3-5 fold, or at least about 3 fold as compared to a hybrid nuclease molecule having having an unmodified Fc domain (e.g., a wild type Fc domain).

In some embodiments, the serum half-life of the molecule is significantly longer than the serum half-life of the first nuclease domain alone. In some embodiments, the nuclease activity of the first nuclease domain of the molecule is the same or greater than the nuclease domain alone. In some embodiments, administration of the molecule to a mouse increases the survival rate of the mouse as measured by a mouse Lupus model assay. In some aspects, the hybrid nuclease molecule degrades circulating RNA, DNA or both. In other aspects, the hybrid nuclease molecule degrades RNA, DNA or both in immune complexes. In some embodiments, hybrid nuclease molecule inhibits interferon-α production. In some aspects interferon-α production is reduced about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% when compared to a control molecule.

In some embodiments, a hybrid nuclease molecule includes a leader sequence. In some embodiments, the leader sequence is human VK3LP peptide from the human kappa light chain family, and the leader sequence is coupled to the N-terminus of the first nuclease domain. In embodiments, the VK3LP has the sequence set forth in SEQ ID NO: 100.

In some embodiments, the molecule is a polypeptide. In some embodiments, the molecule is a polynucleotide.

In some embodiments, the first nuclease domain comprises an RNase. In some embodiments, the RNase is a human RNase. In some embodiments, the RNase is a polypeptide comprising an amino acid sequence at least 90% identical to an RNase amino acid sequence set forth in Table 1. In some embodiments, the RNase is a human RNase A family member. In some embodiments, the RNase is a human pancreatic RNase1.

In some embodiments, the first nuclease domain comprises a DNase. In some embodiments, the DNase is a human DNase. In some embodiments, the DNase is a polypeptide comprising an amino acid sequence at least 90% identical to a DNase amino acid sequence set forth in Table 1. In some embodiments, the DNase is selected from the group consisting of human DNase I, TREX1, and human DNase 1L3.

In some embodiments, the Fc domain is a human Fc domain. In some embodiments, the Fc domain is a mutant Fc domain. In some embodiments, the Fc domain is a mutant Fc domain comprising SSS, P238S, and/or P331S. In some embodiments, the Fc domain is a human IgG1 Fc domain. In some embodiments, the Fc domain is a polypeptide comprising an amino acid sequence at least 90% identical to an Fc domain amino acid sequence set forth in Table 1.

In some embodiments, the first linker domain has a length of about 1 to about 50 amino acids. In some embodiments, the first linker domain has a length of about 5 to about 31 amino acids. In some embodiments, the first linker domain has a length of about 15 to about 25 amino acids. In some embodiments, the first linker domain has a length of about 20 to about 32 amino acids. In some embodiments, the first linker domain has a length of about 20 amino acids. In some embodiments, the first linker domain has a length of about 25 amino acids. In some embodiments, the first linker domain has a length of about 18 amino acids. In some embodiments, the first linker domain comprises a gly/ser peptide. In some embodiments, the gly/ser peptide is of the formula $(Gly_4Ser)_n$, wherein n is a positive integer selected from the group consisting of 1, 2, 3, 4, 5, 6, 7, 8, 9, and 10 (SEQ ID NO: 111). In some embodiments, the gly/ser peptide includes $(Gly_4Ser)_3$ (SEQ ID NO: 112). In some embodiments, the gly/ser peptide includes $(Gly_4Ser)_4$ (SEQ ID NO: 108). In some embodiments, the gly/ser peptide includes $(Gly_4Ser)_5$ (SEQ ID NO: 110). In some embodiments, the first linker domain includes at least one restriction site. In some embodiments, the first linker domain includes about 12 or greater nucleotides including at least one restriction site. In some embodiments, the first linker domain includes two or more restriction sites. In some embodiments, the first linker domain includes a plurality of restriction sites. In some embodiments, the first linker domain comprises an NLG peptide. NLG peptides contain an N-linked glycosylation consensus sequence. In embodiments, the NLG peptide has a sequence as set forth in SEQ ID NO: 99. In some embodiments, the first linker domain comprises an N-linked glycosylation site.

In some embodiments, the first nuclease domain is linked to the N-terminus of the Fc domain. In some embodiments, the first nuclease domain is linked to the C-terminus of the Fc domain.

In some embodiments, the hybrid nuclease molecule further includes a second nuclease domain. In some embodiments, the first and second nuclease domains are distinct nuclease domains. In some embodiments, the first and second nuclease domains are the same nuclease domains. In some embodiments, the second nuclease domain is linked to the C-terminus of the Fc domain. In some embodiments, the second nuclease domain is linked to the N-terminus of the Fc domain. In some embodiments, the second nuclease domain is linked to the C-terminus of the first nuclease domain. In some embodiments, the second nuclease domain is linked to the N-terminus of the first nuclease domain.

Also disclosed herein is a dimeric polypeptide comprising a first polypeptide and a second polypeptide, wherein the first polypeptide comprises a first nuclease domain, and an Fc domain, wherein the first nuclease domain is operatively coupled to the Fc domain. In some embodiments, the second polypeptide is a second hybrid nuclease molecule comprising a second nuclease domain, and a second Fc domain, wherein the second nuclease domain is operatively coupled to the second Fc domain.

Also disclosed herein is a pharmaceutical composition comprising at least one hybrid nuclease molecule and/or at least one dimeric polypeptide as described herein, and a pharmaceutically acceptable excipient.

Also disclosed herein is a nucleic acid molecule encoding a hybrid nuclease molecule disclosed herein. Also disclosed herein is a recombinant expression vector comprising a nucleic acid molecule disclosed herein. Also disclosed herein is a host cell transformed with a recombinant expression vector disclosed herein.

Also disclosed herein is a method of making a hybrid nuclease disclosed herein, comprising: providing a host cell comprising a nucleic acid sequence that encodes the hybrid nuclease molecule; and maintaining the host cell under conditions in which the hybrid nuclease molecule is expressed.

Also disclosed herein is a method for treating or preventing a condition associated with an abnormal immune response, comprising administering to a patient in need thereof an effective amount of an isolated hybrid nuclease molecule disclosed herein. In some embodiments, the condition is an autoimmune disease. In some embodiments, the autoimmune disease is selected from the group consisting of insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus (SLE), and connective tissue disease. In some embodiments, the autoimmune disease is SLE.

Also disclosed herein is a method of treating SLE comprising administering to a subject a nuclease-containing composition in an amount effective to degrade immune complexes containing RNA, DNA or both RNA and DNA. In some aspects, the composition includes a pharmaceutically acceptable carrier and a hybrid nuclease molecule as described herein. In other aspects, the composition includes a hybrid nuclease molecule comprising an amino acid sequence set forth in SEQ ID NO: 62, 64, 66, 68, 70, 78, 80, 82, 84, 86, 92, 94, 96, or 98.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 discloses "(gly4ser)3" as SEQ ID NO: 112, "(gly4ser)4" as SEQ ID NO: 108, "(gly4ser)5" as SEQ ID NO: 110, and "(gly4ser)n" as SEQ ID NO: 125.

Figure 3:
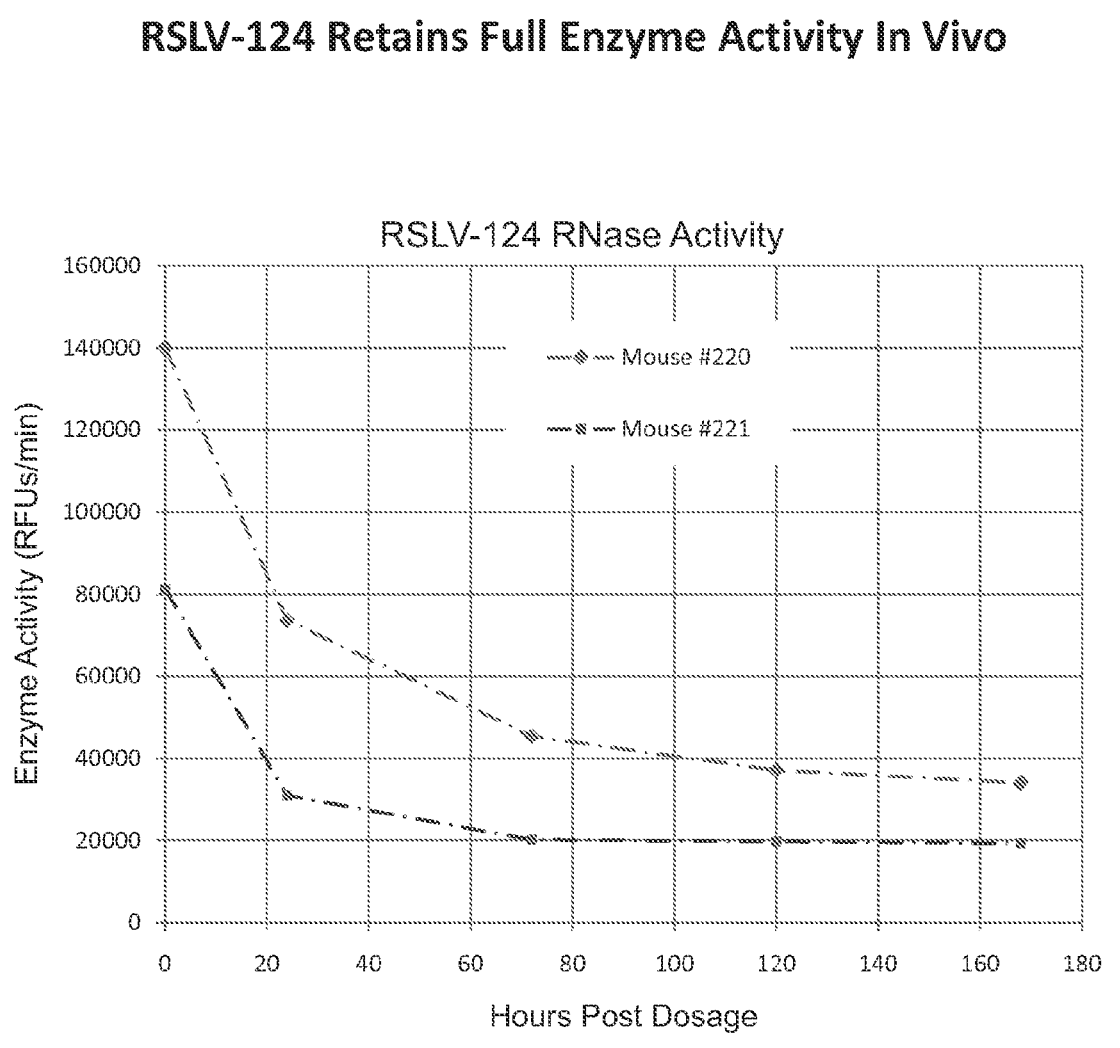

FIG. 3 shows results of an RNase enzymatic activity assay on RLSV-124 recovered from mouse serum as measured in relative fluorescence units (RFU's) over time.

FIG. 4 shows the concentration of RSLV-124 in mouse serum as extrapolated from the RNase enzymatic activity of the molecule.

FIGS. 11a and 11bdisclose "(G4S)4" as SEQ ID NO: 108.

FIG. 13 shows a Lineweaver Burk plot of the different molecules tested.

FIG. 14 shows cytotoxicity data graphing the percentage of dead cells as a function of concentration of fusion protein for RNaseIg molecules with a wild type or mutant Fc domain.

FIG. 17 shows the in vivo ability of RSLV-132 to inhibit RNA-induced interferon-α production.

DETAILED DESCRIPTION

Figure 1:
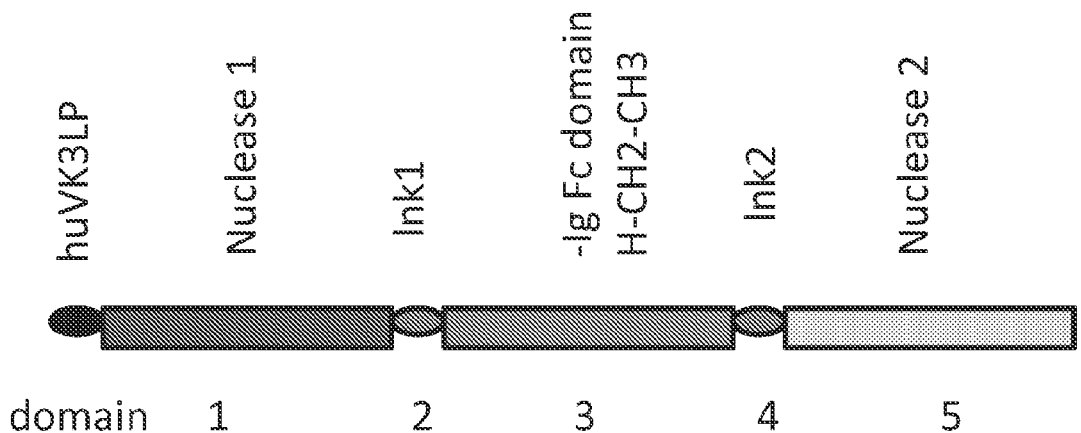
FIG. 1 shows a prototype structure for creating different embodiments of hybrid nuclease molecules.
Figure 2:
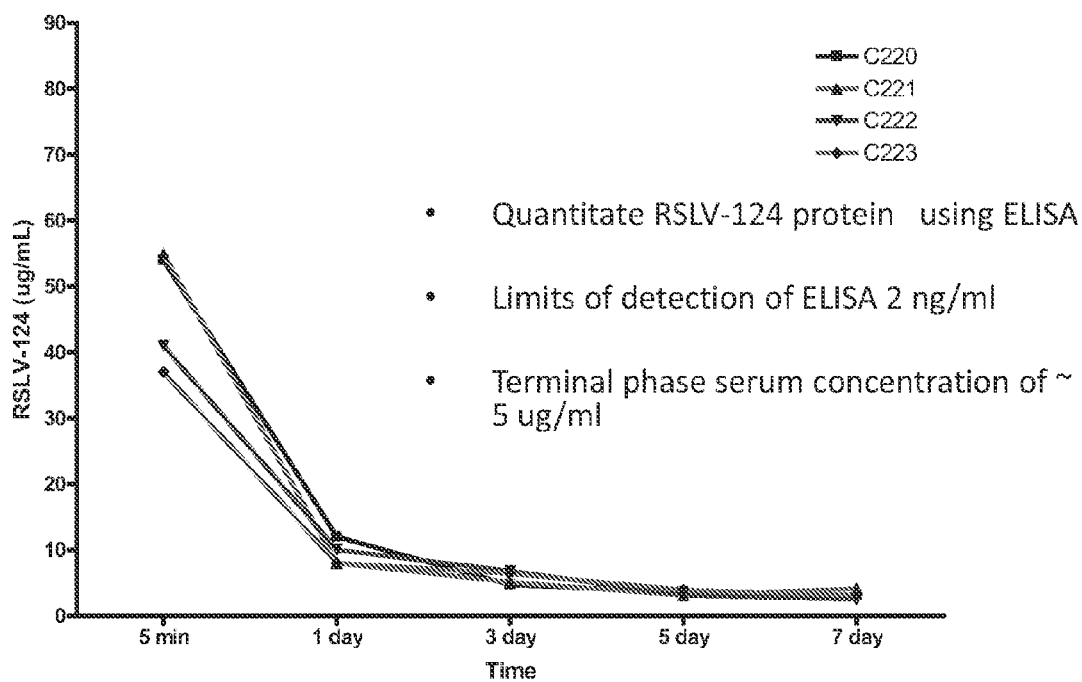
FIG. 2 shows the concentration of RSLV-124 recovered from mouse serum following a single intravenous injection.
Figure 5:
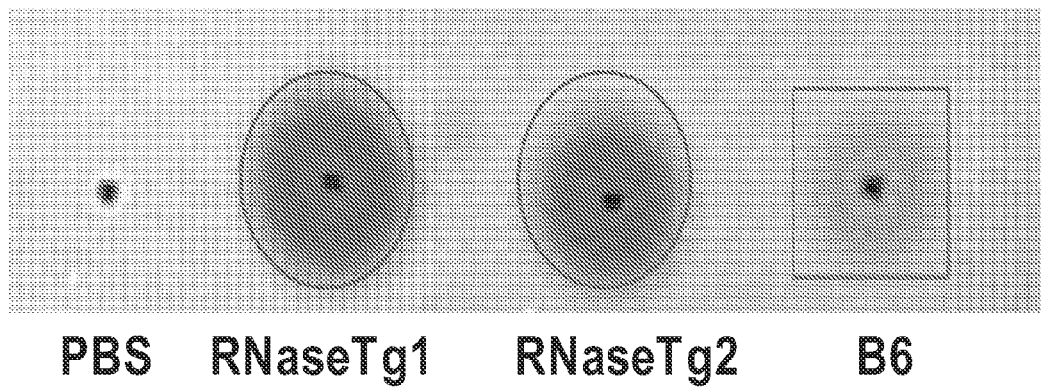
FIG. 5 shows single radial enzyme diffusion (SRED) analysis of serum from two RNase transgenic (Tg) mice compared to a normal B6 mouse.
Figure 6:
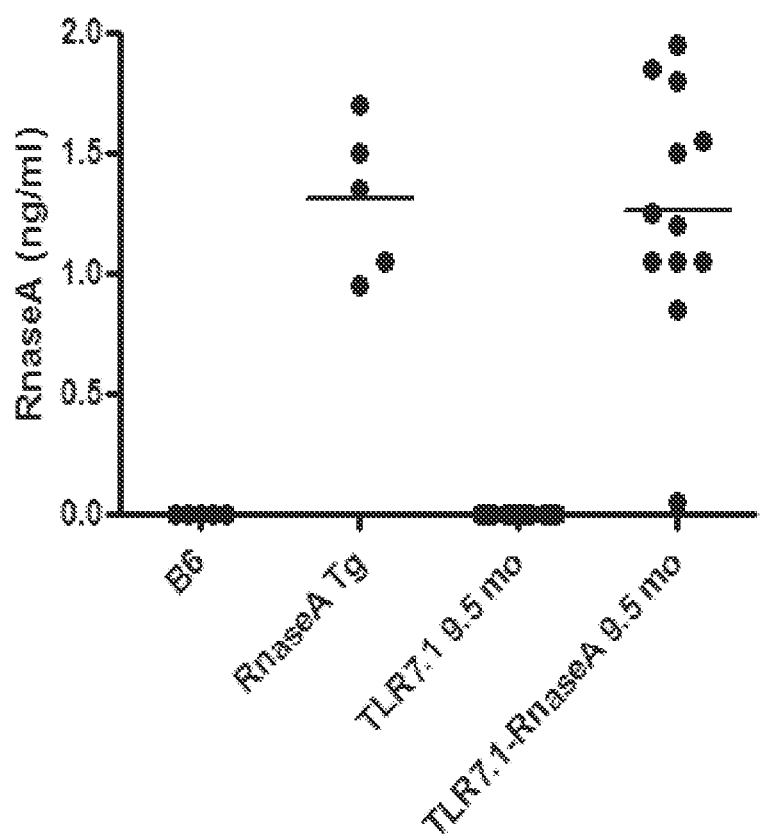
FIG. 6 shows the concentration of RNaseA in Tg and double Tg (DTg) mice measured by ELISA. Each dot represents the concentration measured in an individual mouse.

Systemic lupus erythematosus (SLE) is a multisystem autoimmune disease characterized by the presence of high titer autoantibodies directed against self nucleoproteins. There is strong evidence that defective clearance or processing of dead and dying cells in SLE leads to disease, predominantly through accumulation of ribo- and deoxyribonucleoproteins (abbreviated nucleoproteins). The nucleoproteins cause damage through three mechanisms: i) activation of the innate immune system to produce inflammatory cytokines; ii) serve as antigens to generate circulating immune complexes; and iii) serve as antigens to generate in situ complex formation at local sites such as the kidney. The present invention is based, at least in part, on the discovery that digestion of the extracellular nucleic acids has a therapeutic effect in vivo.

Accordingly, the present invention provides methods for treating diseases characterized by defective clearance or processing of apoptotic cells and cell debris, such as SLE, by administering an effective amount of a nuclease activity to degrade extracellular RNA and DNA containing complexes. Such treatment can inhibit production of Type I interferons (IFNs) which are prominent cytokines in SLE and are strongly correlated with disease activity and nephritis.

In one embodiment, a subject is treated by administering a nuclease activity which is a DNase or an RNase activity, preferably in the form of a hybrid nuclease molecule. In one aspect, the nuclease activity is a first nuclease domain. In another aspect, the nuclease domain is coupled to a modified Fc domain such that the molecule has reduced cytotoxicity. In one aspect a hybrid nuclease molecule includes a second nuclease domain.

In another aspect, a method of treating SLE is provided in which an effective amount of a nuclease-containing composition is administered to a subject. In one aspect, treatment results in degradation of immune complexes containing RNA, DNA or both RNA and DNA. In another aspect, treatment results in inhibition of Type I interferons, such as interferon-α in a subject. In one aspect, a method of treating a subject comprises administering an effective amount of a composition of a hybrid nuclease molecule comprising an amino acid sequence set forth in SEQ ID NO: 62, 64, 66, 68, 70, 78, 80, 82, 84, 86, 92, 94, 96, or 98. In another aspect, the composition is a hybrid nuclease molecule comprising an amino acid sequence set forth in SEQ ID NO: 96 or 98.

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "hybrid nuclease molecule" refers to polynucleotides or polypeptides that comprise at least one nuclease domain and at least one Fc domain. Hybrid nuclease molecules are also referred to as fusion protein(s) and fusion gene(s). For example, in one embodiment, a hybrid nuclease molecule can be a polypeptide comprising at least one Fc domain linked to a nuclease domain such as DNase and/or RNase. As another example, a hybrid nuclease molecule can include an RNase nuclease domain, a linker domain, and an Fc domain. Examples of hybrid nuclease molecules include SE ID NO:62, 64, 66, 68, 70, 78, 80, 82, 84, 86, 92, 94, 96, and 98. Other examples are described in more detail below. In one embodiment a hybrid nuclease molecule of the invention can include additional modifications. In another embodiment, a hybrid nuclease molecule may be modified to add a functional moiety (e.g., PEG, a drug, or a label).

As used herein, a "hybrid bispecific nuclease molecule," or a "binuclease molecule" refer to a hybrid nuclease molecule with 2 or more nuclease domains, e.g., a DNase domain and an RNase domain.

In certain aspects, the hybrid nuclease molecules of the invention can employ one or more "linker domains," such as polypeptide linkers. As used herein, the term "linker domain" refers to a sequence which connects two or more domains in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect a nuclease domain to an Fc domain. Preferably, such polypeptide linkers can provide flexibility to the polypeptide molecule. In certain embodiments the polypeptide linker is used to connect (e.g., genetically fuse) one or more Fc domains and/or one or more nuclease domains. A hybrid nuclease molecule of the invention may comprise more than one linker domain or peptide linker.

As used herein, the term "gly-ser polypeptide linker" refers to a peptide that consists of glycine and serine residues. An exemplary gly/ser polypeptide linker comprises the amino acid sequence Ser(Gly$_4$Ser)n. In one embodiment, n=1 (SEQ ID NO: 113). In one embodiment, n=2 (SEQ ID NO: 114). In another embodiment, n=3, i.e., Ser(Gly$_4$Ser)3 (SEQ ID NO: 115). In another embodiment, n=4, i.e., Ser(Gly$_4$Ser)4 (SEQ ID NO: 116). In another embodiment, n=5 (SEQ ID NO: 117). In yet another embodiment, n=6 (SEQ ID NO: 118). In another embodiment, n=7 (SEQ ID NO: 119). In yet another embodiment, n=8 (SEQ ID NO: 120). In another embodiment, n=9 (SEQ ID NO: 121). In yet another embodiment, n=10 (SEQ ID NO: 122). Another exemplary gly/ser polypeptide linker comprises the amino acid sequence Ser(Gly$_4$Ser)n. In one embodiment, n=1 (SEQ ID NO: 113). In one embodiment, n=2 (SEQ ID NO: 114). In a preferred embodiment, n=3 (SEQ ID NO: 115). In another embodiment, n=4 (SEQ ID NO: 116). In another embodiment, n=5 (SEQ ID NO: 117). In yet another embodiment, n=6 (SEQ ID NO: 118).

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, the term "Fc region" shall be defined as the portion of a native immunoglobulin formed by the respective Fc domains (or Fc moieties) of its two heavy chains.

As used herein, the term "Fc domain" refers to a portion of a single immunoglobulin (Ig) heavy chain wherein the Fc domain does not comprise an Fv domain. As such, Fc domain can also be referred to as "Ig" or "IgG." In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). In one embodiment, an Fc domain of the invention comprises at least the portion of an Fc molecule known in the art to be required for FcRn binding. In another embodiment, an Fc domain of the invention comprises at least the portion of an Fc molecule known in the art to be required for FcγR binding. In one embodiment, an Fc domain of the invention comprises at least the portion of an Fc molecule known in the art to be required for Protein A binding. In one embodiment, an Fc domain of the invention comprises at least the portion of an Fc molecule known in the art to be required for protein G binding. An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc domain includes molecules in monomeric or multimeric form, whether digested from whole antibody or produced by other means. The assignment of amino acids residue numbers to an Fc domain is in accordance with the definitions of Kabat. See, e.g., *Sequences of Proteins of Immunological Interest* (Table of Contents, Introduction and Constant Region Sequences sections), 5th edition, Bethesda, Md.:NIH vol. 1:647-723 (1991); Kabat et al., "Introduction" *Sequences of Proteins of Immunological Interest*, US Dept of Health and Human Services, NIH, 5th edition, Bethesda, Md. vol. 1:xiii-xcvi (1991); Chothia & Lesk, *J. Mol. Biol.* 196:901-917 (1987); Chothia et al., *Nature* 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain retains an effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting hybrid nuclease molecules. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide of the invention consists of, consists essentially of, or comprises an amino acid sequence selected from Table 1 and functionally active variants thereof. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in Table 1. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence set forth in Table 1. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence set forth in Table 1.

In an embodiment, the peptides of the invention are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, siRNA design and generation (see, e.g., the Dharmacon siDesign website), and the like. In an embodiment, the nucleotide sequence of the invention comprises, consists of, or consists essentially of, a nucleotide sequence selected from Table 1. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in Table 1. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in Table 1. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in Table 1.

Preferred hybrid nuclease molecules of the invention comprise a sequence (e.g., at least one Fc domain) derived from a human immunoglobulin sequence. However, sequences may comprise one or more sequences from another mammalian species. For example, a primate Fc domain or nuclease domain may be included in the subject sequence. Alternatively, one or more murine amino acids may be present in a polypeptide. In some embodiments, polypeptide sequences of the invention are not immunogenic and/or have reduced immunogenicity.

It will also be understood by one of ordinary skill in the art that the hybrid nuclease molecules of the invention may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. An isolated nucleic acid molecule encoding a non-natural variant of a hybrid nuclease molecule derived from an immunoglobulin (e.g., an Fc domain) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The peptide hybrid nuclease molecules of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The term "ameliorating" refers to any therapeutically beneficial result in the treatment of a disease state, e.g., an autoimmune disease state (e.g., SLE), including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Compositions
Hybrid Nuclease Molecules

In some embodiments, a composition of the invention includes a hybrid nuclease molecule. In some embodiments, a hybrid nuclease molecule includes a nuclease domain operatively linked to an Fc domain. In some embodiments, a hybrid nuclease molecule includes a nuclease domain linked to an Fc domain. In some embodiments the hybrid nuclease molecule is a nuclease protein. In some embodiments, the hybrid nuclease molecule is a nuclease polynucleotide.

In some embodiments, the nuclease domain is linked to the Fc domain via a linker domain. In some embodiments, the linker domain is a linker peptide. In some embodiments, the linker domain is a linker nucleotide. In some embodiments, the hybrid nuclease molecule includes a leader molecule, e.g., a leader peptide. In some embodiments, the leader molecule is a leader peptide positioned at the N-terminus of the nuclease domain. In embodiments, a hybrid nuclease molecule of the invention comprises a leader peptide at the N-terminus of the molecule, wherein the leader peptide is later cleaved from the hybrid nuclease molecule. Methods for generating nucleic acid sequences encoding a leader peptide fused to a recombinant protein are well known in the art. In embodiments, any of the hybrid nuclease molecules of the present invention can be expressed either with or without a leader fused to their N-terminus. The protein sequence of a hybrid nuclease molecule of the present invention following cleavage of a fused leader peptide can be predicted and/or deduced by one of skill in the art. Examples of hybrid nuclease molecules of the present invention additionally including a VK3 leader peptide (VK3LP), wherein the leader peptide is fused to the N-terminus of the hybrid nuclease molecule, are set forth in SEQ ID NOS: 92 (RSLV-132) and 94 (RSLV-133). The corresponding nucleotide sequences are set forth in SEQ ID NOS: 91 and 93, respectively. In embodiments, following cleavage of the VK3 leader, these hybrid nuclease molecules have the sequences as set forth in SEQ ID NOS: 96 (RSLV-132) and 98 (RSLV-133), respectively. The corresponding nucleotide sequences are set forth in SEQ ID NOS: 95 and 97, respectively. In some embodiments, a hybrid nuclease molecule of the present invention is expressed without a leader peptide fused to its N-terminus, and the resulting hybrid nuclease molecule has an N-terminal methionine.

In some embodiments, the hybrid nuclease molecule will include a stop codon. In some embodiments, the stop codon will be at the C-terminus of the Fc domain.

In some embodiments, the hybrid nuclease molecule further includes a second nuclease domain. In some embodiments, the second nuclease domain is linked to the Fc domain via a second linker domain. In some embodiments, the second linker domain will be at the C-terminus of the Fc domain. FIG. 1 shows at least one embodiment of a hybrid nuclease molecule. In some embodiments, a hybrid nuclease molecule includes a sequence shown in Table 1.

In some embodiments, a hybrid nuclease molecule is an RNase molecule or DNase molecule or a multi-enzyme molecule (e.g., both RNase and DNase or two RNA or DNA nucleases with different specificity for substrate) attached to an Fc domain that specifically binds to extracellular immune complexes. In some embodiments, the Fc domain does not effectively bind Fcγ receptors. In one aspect, the hybrid nuclease molecule does not effectively bind C1q. In other aspects, the hybrid nuclease molecule comprises an in frame Fc domain from IgG1. In other aspects, the hybrid nuclease molecule further comprises mutations in the hinge, CH2, and/or CH3 domains. In other aspects, the mutations are P238S, P331S or N297S, and may include mutations in one or more of the three hinge cysteines. In some such aspects, the mutations in one or more of three hinge cysteines can be SCC or SSS. In other aspects, the molecules contain the SCC hinge, but are otherwise wild type for human IgG1 Fc CH2 and CH3 domains, and bind efficiently to Fc receptors, facilitating uptake of the hybrid nuclease molecule into the endocytic compartment of cells to which they are bound. In other aspects, the molecule has activity against single and/or double-stranded RNA substrates.

In some aspects, a hybrid nuclease molecule includes a mutant Fc domain. In some aspects, a hybrid nuclease molecule includes a mutant, IgG1 Fc domain. In some aspects, a mutant Fc domain comprises one or more mutations in the hinge, CH2, and/or CH3 domains. In some aspects, a mutant Fc domain includes a P238S mutation. In some aspects, a mutant Fc domain includes a P331S mutation. In some aspects, a mutant Fc domain includes a P238S mutation and a P331S mutation. In some aspects, a mutant Fc domain comprises P238S and/or P331S, and may include mutations in one or more of the three hinge cysteines. In some aspects, a mutant Fc domain comprises P238S and/or P331S, and/or one or more mutations in the three hinge cysteines. In some aspects, a mutant Fc domain comprises P238S and/or P331S, and/or mutations in the three hinge cysteines to SSS or in one hinge cysteine to SCC. In some aspects, a mutant Fc domain comprises P238S and P331S and mutations in the three hinge cysteines. In some aspects, a mutant Fc domain comprises P238S and P331S and either SCC or SSS. In some aspects, a mutant Fc domain comprises P238S and P331S and SCC. In some aspects, a mutant Fc domain includes P238S SSS. In some aspects, a mutant Fc domain includes P331S and either SCC or SSS. In some aspects, a mutant Fc domain includes mutations in one or more of the three hinge cysteines. In some aspects, a mutant Fc domain includes mutations in the three hinge cysteines. In some aspects, a mutant Fc domain includes mutations in the three hinge cysteines to SSS. In some aspects, a mutant Fc domain includes mutations in one of the three hinge cysteines to SCC. In some aspects, a mutant Fc domain includes SCC or SSS. In some aspects, a mutant Fc domain is as shown in any of SEQ ID NOs 59, 60, 71-76, or 87-90. In some aspects, a hybrid nuclease molecule is as shown in any of SEQ ID NOs 62, 64, 66, 68, 70, 78, 80, 82, 84, 86, 92, 94, 96, or 98. In some aspects, a hybrid nuclease molecule comprises a wild-type, human RNase1 domain linked to a mutant, human IgG1 Fc domain comprising SCC, P238S, and P331S, or a mutant, human IgG1 Fc domain comprising SSS, P238S, and P331S. In some aspects, a nucleic acid sequence encoding a hybrid nuclease molecule is as shown in SEQ ID NO: 61, 77, or 91. In some aspects, a hybrid nuclease molecule is shown in SEQ ID NO: 62, 78, 92, or 96.

In some aspects, a hybrid nuclease molecule comprises a wild-type, human RNase1 domain linked via a (Gly$_4$Ser)4 linker (SEQ ID NO: 108) domain to a mutant, human IgG1 Fc domain comprising SCC, P238S, and P331S or a mutant, human IgG1 Fc domain comprising SSS, P238S, and P331S. In some aspects, a nucleic acid sequence encoding a hybrid nuclease molecule is shown in SEQ ID NO: 63, or 79. In some aspects, a hybrid nuclease molecule is shown in SEQ ID NO: 64, or 80.

In some aspects, a hybrid nuclease molecule comprises a human DNase1 G105R A114F domain linked via a (Gly$_4$Ser)4 linker (SEQ ID NO: 108) domain to a mutant, human IgG1 Fc domain comprising SCC, P238S, and P331S linked via a NLG linker domain to a wild-type, human RNase1 domain. In some aspects, a hybrid nuclease molecule comprises a human DNase1 G105R A114F domain linked via a (Gly$_4$Ser)4 linker (SEQ ID NO: 108) domain to a mutant, human IgG1 Fc domain comprising SSS, P238S, and P331S linked via a NLG linker domain to a wild-type, human RNase1 domain. In some aspects, a nucleic acid sequence encoding a hybrid nuclease molecule is shown in SEQ ID NO: 65, or 81. In some aspects, a hybrid nuclease molecule is shown in SEQ ID NO: 66, or 82.

In some aspects, a hybrid nuclease molecule comprises a wild-type, human RNase1 domain linked via a (Gly$_4$Ser)4 linker (SEQ ID NO: 108) domain to a mutant, human IgG1 Fc domain comprising SCC, P238S, and P331S linked via a NLG linker domain to a human DNase1 G105R A114F domain. In some aspects, a hybrid nuclease molecule comprises a wild-type, human RNase1 domain linked via a (Gly$_4$Ser)4 linker (SEQ ID NO: 108) domain to a mutant, human IgG1 Fc domain comprising SSS, P238S, and P331S linked via a NLG linker domain to a human DNase1 G105R A114F domain. In some aspects, a nucleic acid sequence encoding a hybrid nuclease molecule is shown in SEQ ID NO: 67, or 83. In some aspects, a hybrid nuclease molecule is shown in SEQ ID NO: 68, or 84.

In some aspects, a hybrid nuclease molecule comprises a wild-type, human RNase1 domain linked to a mutant, human IgG1 Fc domain comprising SCC, P238S, and P331S linked via a NLG linker domain to a human DNase1 G105R A114F domain. In some aspects, a hybrid nuclease molecule comprises a wild-type, human RNase1 domain linked to a mutant, human IgG1 Fc domain comprising SSS, P238S, and P331S linked via a NLG linker domain to a human DNase1 G105R A114F domain. In some aspects, a nucleic acid sequence encoding a hybrid nuclease molecule is shown in SEQ ID NO: 69, 85, or 93. In some aspects, a hybrid nuclease molecule is shown in SEQ ID NO: 70, 86, 94, or 98.

In some aspects, the activity of the hybrid nuclease molecule is detectable in vitro and/or in vivo. In some aspects, the hybrid nuclease molecule binds to a cell, a malignant cell, or a cancer cell and interferes with its biologic activity.

In another aspect, a multifunctional RNase molecule is provided that is attached to another enzyme or antibody having binding specificity, such as an scFv targeted to RNA or a second nuclease domain with the same or different specificities as the first domain.

In another aspect, a multifunctional DNase molecule is provided that is attached to another enzyme or antibody having binding specificity, such as an scFv targeted to DNA or a second nuclease domain with the same or different specificities as the first domain.

In another aspect, a hybrid nuclease molecule is adapted for preventing or treating a disease or disorder in a mammal by administering an hybrid nuclease molecule attached to an Fc region, in a therapeutically effective amount to the mammal in need thereof, wherein the disease is prevented or treated. In other aspects, the disease or disorder is an autoimmune disease or cancer. In some such aspects, the autoimmune disease is insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

In some embodiments, the targets of the RNase enzyme activity of RNase hybrid nuclease molecules are primarily extracellular, consisting of, e.g., RNA contained in immune complexes with anti-RNP autoantibody and RNA expressed on the surface of cells undergoing apoptosis. In some embodiments, the RNase hybrid nuclease molecule is active in the acidic environment of the endocytic vesicles. In some embodiments, an RNase hybrid nuclease molecule includes a wild-type (wt) Fc domain in order to, e.g, allow the molecule to bind FcR and enter the endocytic compartment through the entry pathway used by immune complexes. In some embodiments, an RNase hybrid nuclease molecule including a wt Fc domain is adapted to be active both extracellularly and in the endocytic environment (where TLR7 can be expressed). In some aspects, this allows an RNase hybrid nuclease molecule including a wt Fc domain to stop TLR7 signaling through previously engulfed immune complexes or by RNAs that activate TLR7 after viral infection. In some embodiments, the wt RNase of an RNase hybrid nuclease molecule is not resistant to inhibition by an RNase cytoplasmic inhibitor. In some embodiments, the wt RNase of an RNase hybrid nuclease molecule is not active in the cytoplasm of a cell.

In some embodiments, a hybrid nuclease molecule including a wt Fc domain is used for therapy of an autoimmune disease, e.g., SLE.

In some embodiments, Fc domain binding to an Fc receptor (FcR) is increased, e.g., via alterations of glycosylation and/or changes in amino acid sequence. In some embodiments, a hybrid nuclease molecule has one or more Fc alterations that increase FcR binding.

Alternative ways to construct a hybrid nuclease molecule attached to an Fc domain are envisioned. In some embodiments, the domain orientation can be altered to construct an Ig-RNase molecule or an Ig-DNase molecule or an RNase-Ig molecule or an RNase-Ig molecule that retains FcR binding and has active nuclease domains.

In some embodiments, DNase hybrid nuclease molecules include a wt Fc domain that can allow, e.g., the molecules to undergo endocytosis after binding FcR. In some embodiments, the DNase hybrid nuclease molecules can be active towards extracellular immune complexes containing DNA, e.g., either in soluble form or deposited as insoluble complexes.

In some embodiments, hybrid nuclease molecules include both DNase and RNase. In some embodiments, these hybrid nuclease molecules can improve the therapy of SLE because they can, e.g., digest immune complexes containing RNA, DNA, or a combination of both RNA and DNA; and when they further include a wt Fc domain, they are active both extracellularly and in the endocytic compartment where TLR7 and TLR9 can be located.

In some embodiments, linker domains include (gly4ser) 3, 4 or 5 variants (SEQ ID NO: 123) that alter the length of the linker by 5 amino acid progressions. In another embodiment, a linker domain is approximately 18 amino acids in length and includes an N-linked glycosylation site, which can be sensitive to protease cleavage in vivo. In some embodiments, an N-linked glycosylation site can protect the hybrid nuclease molecules from cleavage in the linker domain. In some embodiments, an N-linked glycosylation site can assist in separating the folding of independent functional domains separated by the linker domain.

In some embodiments, hybrid nuclease molecules can include both mutant and/or wild type human IgG1 Fc domains. In some embodiments, the hybrid nuclease molecules can be expressed from both COS transient and CHO stable transfections. In some embodiments, both the CD80/86 binding and the RNase activity are preserved in a hybrid nuclease molecule. In some embodiments, hybrid nuclease molecules include DNase1L3-Ig-linker-RNase constructs. In some embodiments, a hybrid nuclease molecule includes a DNase1-Ig-linker-RNase construct or an RNase-Ig-linker-DNase construct. In some embodiments, fusion junctions between enzyme domains and the other domains of the hybrid nuclease molecule is optimized.

In some embodiments, hybrid nuclease molecules include DNase-Ig hybrid nuclease molecules and/or hybrid DNase-RNase hybrid nuclease molecules.

In some embodiments, a hybrid nuclease molecule includes TREX1. In some embodiments, a TREX1 hybrid nuclease molecule can digest chromatin. In some embodiments, a TREX1 hybrid nuclease molecule is expressed by a cell. In some embodiments, the expressed hybrid nuclease molecule includes murine TREX-1 and a murine (wt or mutant) Fc domain. In some embodiments, a 20-25 amino acid (aa) linker domain between TREX1 and the IgG hinge can be required to allow DNase activity. In some embodiments, a hybrid nuclease molecule with a 15 aa linker domain is not active. In some embodiments, use of the 20 and 25 amino acid linker domains (plus 2 or more amino acids to incorporate restriction sites) results in functional activity as measured by chromatin digestion. In some embodiments, a hydrophobic region of approximately 72 aa can be removed from the COOH end of TREX-1 prior to fusion to the Fc domain via the linker domain. In some embodiments, a 20 amino acid linker domain version of the hybrid nuclease molecule exhibits high expression levels compared to controls and/or other hybrid nuclease molecules. In some embodiments, kinetic enzyme assays are used to compare the enzyme activity of hybrid nuclease molecules and controls in a quantitative manner.

In some embodiments, further optimization of the fusion junction chosen for truncation of a TREX1 enzyme can be used to improve expression of the hybrid nuclease molecules.

In some embodiments, the hybrid nuclease molecule includes a human TREX1-linker-Ig Fc domain hybrid nuclease molecule with 20 and/or 25 aa linker domains. In some embodiments, the linker domain(s) are variants of a (gly4ser)4 (SEQ ID NO: 108) or (gly4ser)5 (SEQ ID NO: 110) cassette with one or more restriction sites attached for incorporation into the hybrid nuclease molecules construct. In some embodiments, because of the head-to-tail dimerization useful for TREX1 enzyme activity; a flexible, longer linker domain can be used to facilitate proper folding.

In some embodiments, the hybrid nuclease molecule is a TREX1-tandem hybrid nuclease molecule. In some embodiments, an alternative method for facilitating head-to-tail folding of TREX1 is to generate a TREX1-TREX1-Ig hybrid hybrid nuclease molecule that incorporates two TREX1 domains in tandem, followed by a linker domain and an Ig Fc domain. In some embodiments, positioning of TREX1 cassettes in a head-to-tail manner can be corrected for head-to tail folding on either arm of the immunoenzyme and introduce a single TREX1 functional domain into each arm of the molecule. In some embodiments, each immunoenzyme of a hybrid nuclease molecule has two functional TREX1 enzymes attached to a single IgG Fc domain.

In some embodiments, the hybrid nuclease molecule includes TREX1-linker1-Ig-linker2-RNase.

In some embodiments, the hybrid nuclease molecule includes RNase-Ig-linker-TREX1. In some embodiments, cassettes are derived for both amino and carboxyl fusion of each enzyme for incorporation into hybrid nuclease molecules where the enzyme configuration is reversed. In some embodiments, the RNase enzyme exhibits comparable functional activity regardless of its position in the hybrid nuclease molecules. In some embodiments, alternative hybrid nuclease molecules can be designed to test whether a particular configuration demonstrates improved expression and/or function of the hybrid nuclease molecule components.

In some embodiments, the hybrid nuclease molecule includes 1L3-Ig. In some embodiments, the 1L3 DNase is constructed from a murine sequence and expressed. In some embodiments, the enzyme is active. In some embodiments, a murine 1L3 DNase-Ig-RNase hybrid nuclease is constructed and expressed. In some embodiments, the molecule includes human 1L3-Ig, human 1L3-Ig-RNase, and/or human RNase-Ig-1L3.

In some embodiments, the hybrid nuclease molecule includes DNase1-Ig. In some embodiments, a naturally occurring variant allele, A114F, which shows reduced sensitivity to actin is included in a DNase1-Ig hybrid nuclease molecule. In some embodiments, this mutation is introduced into a hybrid nuclease molecule to generate a more stable derivative of human DNase1. In some embodiments, a DNase1-linker-Ig containing a 20 or 25 aa linker domain is made. In some embodiments, hybrid nuclease molecules include RNase-Ig-linker-DNase1 where the DNase1 domain is located at the COOH side of the Ig Fc domain. In some embodiments, hybrid nuclease molecules are made that incorporate DNase1 and include: DNase1-linker-Ig-linker2-RNase, and/or RNase-Ig-linker-DNase1.

Another aspect of the present invention is to use gene therapy methods for treating or preventing disorders, diseases, and conditions with one or more hybrid nuclease molecules. The gene therapy methods relate to the introduction of hybrid nuclease molecule nucleic acid (DNA, RNA and antisense DNA or RNA) sequences into an animal to achieve expression of the polypeptide or polypeptides of the present invention. This method can include introduction of one or more polynucleotides encoding a hybrid nuclease molecule polypeptide of the present invention operatively linked to a promoter and any other genetic elements necessary for the expression of the polypeptide by the target tissue.

In gene therapy applications, hybrid nuclease molecule genes are introduced into cells in order to achieve in vivo synthesis of a therapeutically effective genetic product. "Gene therapy" includes both conventional gene therapies where a lasting effect is achieved by a single treatment, and the administration of gene therapeutic agents, which involves the one time or repeated administration of a therapeutically effective DNA or mRNA. The oligonucleotides can be modified to enhance their uptake, e.g., by substituting their negatively charged phosphodiester groups by uncharged groups.

Fc Domains

In some embodiments, a hybrid nuclease molecule includes an Fc domain. The Fc domain does not contain a variable region that binds to antigen. In embodiments, the Fc domain does not contain a variable region. Fc domains useful for producing the hybrid nuclease molecules of the present invention may be obtained from a number of different sources. In preferred embodiments, an Fc domain of the hybrid nuclease molecule is derived from a human immunoglobulin. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the hybrid nuclease molecule Fc domain or portion thereof may be derived from any immunoglobulin class, including IgM, IgG, IgD, IgA, and IgE, and any immunoglobulin isotype, including IgG1, IgG2, IgG3, and IgG4. In a preferred embodiment, the human isotype IgG1 is used.

In some aspects, a hybrid nuclease molecule includes a mutant Fc domain. In some aspects, a hybrid nuclease molecule includes a mutant, IgG1 Fc domain. In some aspects, a mutant Fc domain comprises one or more mutations in the hinge, CH2, and/or CH3 domains. In some aspects, a mutant Fc domain includes a P238S mutation. In some aspects, a mutant Fc domain includes a P331S mutation. In some aspects, a mutant Fc domain includes a P238S mutation and a P331S mutation. In some aspects, a mutant Fc domain comprises P238S and/or P331S, and may include mutations in one or more of the three hinge cysteines. In some aspects, a mutant Fc domain comprises P238S and/or P331S, and/or one or more mutations in the three hinge cysteines. In some aspects, a mutant Fc domain comprises P238S and/or P331S, and/or mutations in a hinge cysteine to SCC or in the three hinge cysteines to SSS. In some aspects, a mutant Fc domain comprises P238S and P331S and mutations in at least one of the three hinge cysteines. In some aspects, a mutant Fc domain comprises P238S and P331S and SCC. In some aspects, a mutant Fc domain comprises P238S and P331S and SSS. In some aspects, a mutant Fc domain includes P238S and SCC or SSS. In some aspects, a mutant Fc domain includes P331S and SCC or SSS. In some aspects, a mutant Fc domain includes mutations in one or more of the three hinge cysteines. In some aspects, a mutant Fc domain includes mutations in the three hinge cysteines. In some aspects, a mutant Fc domain includes mutations in one of the three hinge cysteines to SCC. In some aspects, a mutant Fc domain includes SCC. In some aspects, a mutant Fc domain includes mutations in the three hinge cysteines to SSS. In some aspects, a mutant Fc domain includes SSS. In some aspects, a nucleic acid sequence encoding a mutant Fc domain is shown in SEQ ID NOs 59, 71, 73, 75, 87, or 89. In some aspects, a mutant Fc domain is as shown as in SEQ ID NOs 60, 72, 74, 76, 88, or 90. In some aspects, a nucleic acid sequence encoding a hybrid nuclease molecule is as shown in SEQ ID NOs 61, 63, 65, 67, 69, 77, 79, 81, 83, 85, 91, 93, 95 or 97. In some aspects, a hybrid nuclease molecule is as shown in SEQ ID NOs 62, 64, 66, 68, 70, 78, 80, 82, 84, 86, 92, 94, 96, or 98.

A variety of Fc domain gene sequences (e.g., human constant region gene sequences) are available in the form of publicly accessible deposits. Constant region domains comprising an Fc domain sequence can be selected having a particular effector function (or lacking a particular effector function) or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The hybrid nuclease molecules of the invention may comprise one or more Fc domains (e.g., 2, 3, 4, 5, 6, 7, 8, 9, 10, or more Fc domains). In one embodiment, the Fc domains may be of different types. In one embodiment, at least one Fc domain present in the hybrid nuclease molecule comprises a hinge domain or portion thereof. In another embodiment, the hybrid nuclease molecule of the invention comprises at least one Fc domain which comprises at least one CH2 domain or portion thereof. In another embodiment, the hybrid nuclease molecule of the invention comprises at least one Fc domain which comprises at least one CH3 domain or portion thereof. In another embodiment, the hybrid nuclease molecule of the invention comprises at least one Fc domain which comprises at least one CH4 domain or portion thereof. In another embodiment, the hybrid nuclease molecule of the invention comprises at least one Fc domain which comprises at least one hinge domain or portion thereof and at least one CH2 domain or portion thereof (e.g, in the hinge-CH2 orientation). In another embodiment, the hybrid nuclease molecule of the invention comprises at least one Fc domain which comprises at least one CH2 domain or portion thereof and at least one CH3 domain or portion thereof (e.g, in the CH2-CH3 orientation). In another embodiment, the hybrid nuclease molecule of the invention comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the hybrid nuclease molecule comprises at least one complete Fc region derived from one or more immunoglobulin heavy chains (e.g., an Fc domain including hinge, CH2, and CH3 domains, although these need not be derived from the same antibody). In other embodiments, the hybrid nuclease molecule comprises at least two complete Fc domains derived from one or more immunoglobulin heavy chains. In preferred embodiments, the complete Fc domain is derived from a human IgG immunoglobulin heavy chain (e.g., human IgG1).

In another embodiment, a hybrid nuclease molecule of the invention comprises at least one Fc domain comprising a complete CH3 domain. In another embodiment, a hybrid nuclease molecule of the invention comprises at least one Fc domain comprising a complete CH2 domain. In another embodiment, a hybrid nuclease molecule of the invention comprises at least one Fc domain comprising at least a CH3 domain, and at least one of a hinge region, and a CH2 domain. In one embodiment, a hybrid nuclease molecule of the invention comprises at least one Fc domain comprising a hinge and a CH3 domain. In another embodiment, a hybrid nuclease molecule of the invention comprises at least one Fc domain comprising a hinge, a CH2, and a CH3 domain. In preferred embodiments, the Fc domain is derived from a human IgG immunoglobulin heavy chain (e.g., human IgG1).

The constant region domains or portions thereof making up an Fc domain of a hybrid nuclease molecule of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, a hybrid nuclease molecule can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In another embodiment, a hybrid nuclease molecule of the invention comprises one or more truncated Fc domains that are nonetheless sufficient to confer Fc receptor (FcR) binding properties to the Fc region. Thus, an Fc domain of a hybrid nuclease molecule of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In one embodiment, a hybrid nuclease molecule of the invention lacks one or more constant region domains of a complete Fc region, i.e., they are partially or entirely deleted. In a certain embodiments hybrid nuclease molecules of the invention will lack an entire CH2 domain (ΔCH2 constructs). Those skilled in the art will appreciate that such constructs may be preferred due to the regulatory properties of the CH2 domain on the catabolic rate of the antibody. In certain embodiments, hybrid nuclease molecules of the invention comprise CH2 domain-deleted Fc regions derived from a vector (e.g., from IDEC Pharmaceuticals, San Diego) encoding an IgG1 human constant region domain (see, e.g., WO 02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

Changes to Fc Amino Acids

In certain embodiments, an Fc domain employed in a hybrid nuclease molecule of the invention is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

The amino acid substitution(s) of an Fc variant may be located at a position within the Fc domain referred to as corresponding to the portion number that that residue would be given in an Fc region in an antibody.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the hybrid nuclease molecules of the invention comprise an Fc variant comprising more than one amino acid substitution. The hybrid nuclease molecules of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers an improvement in at least one effector function imparted by an Fc domain comprising said wild-type Fc domain (e.g., an improvement in the ability of the Fc domain to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

In some aspects, an Fc domain includes changes in the region between amino acids 234-238, including the sequence LLGGP at the beginning of the CH2 domain. In some aspects, an Fc variant alters Fc mediated effector function, particularly ADCC, and/or decrease binding avidity for Fc receptors. In some aspects, sequence changes closer to the CH2-CH3 junction, at positions such as K322 or P331 can eliminate complement mediated cytotoxicity and/or alter avidity for FcR binding. In some aspects, an Fc domain incorporates changes at residues P238 and P331, e.g., changing the wild type prolines at these positions to serine. In some aspects, alterations in the hinge region at one or more of the three hinge cysteines, to encode CCC, SCC, SSC, SCS, or SSS at these residues can also affect FcR binding and molecular homogeneity, e.g., by elimination of unpaired cysteines that may destabilize the folded protein.

The hybrid nuclease molecules of the invention may employ art-recognized Fc variants which are known to impart an improvement in effector function and/or FcR binding. Specifically, a hybrid nuclease molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

Other amino acid mutations in the Fc domain are contemplated to reduce binding to the Fc gamma receptor and Fc gamma receptor subtypes. For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety.

Further mutations contemplated for use include, e.g., those described in U.S. Pat. App. Pub. No. 2006/0235208, published Oct. 19, 2006 and incorporated herein by reference in its entirety. This publications describe Fc variants that exhibit reduced binding to Fc gamma receptors, reduced antibody dependent cell-mediated cytotoxicity, or reduced complement dependent cytotoxicity, that comprise at least one amino acid modification in the Fc region, including 232G, 234G, 234H, 235D, 235G, 235H, 236I, 236N, 236P, 236R, 237K, 237L, 237N, 237P, 238K, 239R, 265G, 267R, 269R, 270H, 297S, 299A, 299I, 299V, 325A, 325L, 327R, 328R, 329K, 330I, 330L, 330N, 330P, 330R, and 331L (numbering is according to the EU index), as well as double mutants 236R/237K, 236R/325L, 236R/328R, 237K/325L, 237K/328R, 325L/328R, 235G/236R, 267R/269R, 234G/235G, 236R/237K/325L, 236R/325L/328R, 235G/236R/237K, and 237K/325L/328R. Other mutations contemplated for use as described in this publication include 227G, 234D, 234E, 234G, 234I, 234Y, 235D, 235I, 235S, 236S, 239D, 246H, 255Y, 258H, 260H, 264I, 267D, 267E, 268D, 268E, 272H, 272I, 272R, 281D, 282G, 283H, 284E, 293R, 295E, 304T, 324G, 324I, 327D, 327A, 328A, 328D, 328E, 328F, 328I, 328M, 328N, 328Q, 328T, 328V, 328Y, 330I, 330L, 330Y, 332D, 332E, 335D, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 297 and 298, an insertion of A between positions 297 and 298, an insertion of S between positions 297 and 298, an insertion of D between positions 297 and 298, an insertion of G between positions 326 and 327, an insertion of A between positions 326 and 327, an insertion of T between positions 326 and 327, an insertion of D between positions 326 and 327, and an insertion of E between positions 326 and 327 (numbering is according to the EU index). Additionally, mutations described in U.S. Pat. App. Pub. No. 2006/0235208 include 227G/332E, 234D/332E, 234E/332E, 234Y/332E, 234I/332E, 234G/332E, 235I/332E, 235S/332E, 235D/332E, 235E/332E, 236S/332E, 236A/332E, 236S/332D, 236A/332D, 239D/268E, 246H/332E, 255Y/332E, 258H/332E, 260H/332E, 264I/332E, 267E/332E, 267D/332E, 268D/332E, 268E/332E, 268E/332E, 268D/332E, 268E/330Y, 268D/330Y, 272R/332E, 272H/332E, 283H/332E, 284E/332E, 293R/332E, 295E/332E, 304T/332E, 324I/332E, 324G/332E, 324I/332D, 324G/332D, 327D/332E, 328A/332E, 328T/332E, 328V/332E, 328I/332E, 328F/332E, 328Y/332E, 328M/332E, 328D/332E, 328E/332E, 328N/332E, 328Q/332E, 328A/332D, 328T/332D, 328V/332D, 328I/332D, 328F/332D, 328Y/332D, 328M/332D, 328D/332D, 328E/332D, 328N/332D, 328Q/332D, 330L/332E, 330Y/332E, 330I/332E, 332D/330Y, 335D/332E, 239D/332E, 239D/332E/330Y, 239D/332E/330L, 239D/332E/330I, 239D/332E/268E, 239D/332E/268D, 239D/332E/327D, 239D/332E/284E, 239D/268E/330Y, 239D/332E/268E/330Y, 239D/332E/327A, 239D/332E/268E/327A, 239D/332E/330Y/327A, 332E/330Y/268 E/327A, 239D/332E/268E/330Y/327A, Insert G>297-298/332E, Insert A>297-298/332E, Insert S>297-298/332E, Insert D>297-298/332E, Insert G>326-327/332E, Insert A>326-327/332E, Insert T>326-327/332E, Insert D>326-327/332E, Insert E>326-327/332E, Insert G>235-236/332E, Insert A>235-236/332E, Insert S>235-236/332E, Insert T>235-236/332E, Insert N>235-236/332E, Insert D>235-236/332E, Insert V>235-236/332E, Insert L>235-236/332E, Insert G>235-236/332D, Insert A>235-236/332D, Insert S>235-236/332D, Insert T>235-236/332D, Insert N>235-236/332D, Insert D>235-236/332D, Insert V>235-236/332D, and Insert L>235-236/332D (numbering according to the EU index) are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination.

In certain embodiments, a hybrid nuclease molecule of the invention comprises an amino acid substitution to an Fc domain which alters the antigen-independent effector functions of the antibody, in particular the circulating half-life of the antibody. Such hybrid nuclease molecules exhibit either increased or decreased binding to FcRn when compared to hybrid nuclease molecules lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the hybrid nuclease molecules of the invention exhibit reduced transport across the epithelium of kidney glomeruli from the vasculature. In another embodiment, the hybrid nuclease molecules of the invention exhibit reduced transport across the blood brain barrier (BBB) from the brain, into the vascular space. In one embodiment, a hybrid nuclease molecule with altered FcRn binding comprises at least one Fc domain (e.g., one or two Fc domains) having one or more amino acid substitutions within the "FcRn binding loop" of an Fc domain. Exemplary amino acid substitutions which altered FcRn binding activity are disclosed in International PCT Publication No. WO05/047327 which is incorporated by reference herein.

In other embodiments, a hybrid nuclease molecule of the invention comprises an Fc variant comprising an amino acid substitution which alters the antigen-dependent effector functions of the polypeptide, in particular ADCC or complement activation, e.g., as compared to a wild type Fc region. In exemplary embodiment, said hybrid nuclease molecules exhibit altered binding to an Fc gamma receptor (e.g., CD16). Such hybrid nuclease molecules exhibit either increased or decreased binding to FcR gamma when compared to wild-type polypeptides and, therefore, mediate enhanced or reduced effector function, respectively. Fc variants with improved affinity for FcγR5 are anticipated to enhance effector function, and such molecules have useful applications in methods of treating mammals where target molecule destruction is desired. In contrast, Fc variants with decreased FcγR binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation. In one embodiment, the polypeptide comprising an Fc exhibits at least one altered antigen-dependent effector function selected from the group consisting of opsonization, phagocytosis, complement dependent cytotoxicity, antigen-dependent cellular cytotoxicity (ADCC), or effector cell modulation as compared to a polypeptide comprising a wild type Fc region.

In one embodiment the hybrid nuclease molecule exhibits altered binding to an activating FcγR (e.g. FcγI, FcγIIa, or FcγRIIIa). In another embodiment, the hybrid nuclease molecule exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

A hybrid nuclease molecule of the invention may also comprise an amino acid substitution which alters the glycosylation of the hybrid nuclease molecule. For example, the Fc domain of the hybrid nuclease molecule may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the hybrid nuclease molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO05/018572 and US Patent Publication No. 2007/0111281, which are incorporated by reference herein.

In other embodiments, a hybrid nuclease molecule of the invention comprises at least one Fc domain having engineered cysteine residue or analog thereof which is located at the solvent-exposed surface. Preferably the engineered cysteine residue or analog thereof does not interfere with an effector function conferred by the Fc. More preferably, the alteration does not interfere with the ability of the Fc to bind to Fc receptors (e.g. FcγRI, FcγRII, or FcγRIII) or complement proteins (e.g. C1q), or to trigger immune effector function (e.g., antibody-dependent cytotoxicity (ADCC), phagocytosis, or complement-dependent cytotoxicity (CDCC)). In preferred embodiments, the hybrid nuclease molecules of the invention comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the hybrid nuclease molecule of the invention may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the hybrid nuclease molecules of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the hybrid nuclease molecules of the invention may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Linker Domains

In some embodiments, a hybrid nuclease molecule includes a linker domain. In some embodiments, a hybrid nuclease molecule includes a plurality of linker domains. In some embodiments, the linker domain is a polypeptide linker. In certain aspects, it is desirable to employ a polypeptide linker to fuse one or more Fc domains to one or more nuclease domains to form a hybrid nuclease molecule.

In one embodiment, the polypeptide linker is synthetic. As used herein the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., an Fc domain sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc domains are juxtaposed to ensure proper folding and formation of a functional Fc domain. Preferably, a polypeptide linker compatible with the instant invention will be relatively non-immunogenic and not inhibit any non-covalent association among monomer subunits of a binding protein.

In certain embodiments, the hybrid nuclease molecules of the invention employ a polypeptide linker to join any two or more domains in frame in a single polypeptide chain. In one embodiment, the two or more domains may be independently selected from any of the Fc domains or nuclease domains discussed herein. For example, in certain embodiments, a polypeptide linker can be used to fuse identical Fc domains, thereby forming a homomeric Fc region. In other embodiments, a polypeptide linker can be used to fuse different Fc domains (e.g. a wild-type Fc domain and a Fc domain variant), thereby forming a heteromeric Fc region. In other embodiments, a polypeptide linker of the invention can be used to genetically fuse the C-terminus of a first Fc domain (e.g. a hinge domain or portion thereof, a CH2 domain or portion thereof, a complete CH3 domain or portion thereof, a FcRn binding portion, an FcγR binding portion, a complement binding portion, or portion thereof) to the N-terminus of a second Fc domain (e.g., a complete Fc domain).

In one embodiment, a polypeptide linker comprises a portion of an Fc domain. For example, in one embodiment, a polypeptide linker can comprise an immunoglobulin hinge domain of an IgG1, IgG2, IgG3, and/or IgG4 antibody. In another embodiment, a polypeptide linker can comprise a CH2 domain of an IgG1, IgG2, IgG3, and/or IgG4 antibody. In other embodiments, a polypeptide linker can comprise a CH3 domain of an IgG1, IgG2, IgG3, and/or IgG4 antibody. Other portions of an immunoglobulin (e.g. a human immunoglobulin) can be used as well. For example, a polypeptide linker can comprise a CH1 domain or portion thereof, a CL domain or portion thereof, a VH domain or portion thereof, or a VL domain or portion thereof. Said portions can be derived from any immunoglobulin, including, for example, an IgG1, IgG2, IgG3, and/or IgG4 antibody.

In exemplary embodiments, a polypeptide linker can comprise at least a portion of an immunoglobulin hinge region. In one embodiment, a polypeptide linker comprises an upper hinge domain (e.g., an IgG1, an IgG2, an IgG3, or IgG4 upper hinge domain). In another embodiment, a polypeptide linker comprises a middle hinge domain (e.g., an IgG1, an IgG2, an IgG3, or an IgG4 middle hinge domain). In another embodiment, a polypeptide linker comprises a lower hinge domain (e.g., an IgG1, an IgG2, an IgG3, or an IgG4 lower hinge domain).

In other embodiments, polypeptide linkers can be constructed which combine hinge elements derived from the same or different antibody isotypes. In one embodiment, the polypeptide linker comprises a chimeric hinge comprising at least a portion of an IgG1 hinge region and at least a portion of an IgG2 hinge region. In one embodiment, the polypeptide linker comprises a chimeric hinge comprising at least a portion of an IgG1 hinge region and at least a portion of an IgG3 hinge region. In another embodiment, a polypeptide linker comprises a chimeric hinge comprising at least a portion of an IgG1 hinge region and at least a portion of an IgG4 hinge region. In one embodiment, the polypeptide linker comprises a chimeric hinge comprising at least a portion of an IgG2 hinge region and at least a portion of an IgG3 hinge region. In one embodiment, the polypeptide linker comprises a chimeric hinge comprising at least a portion of an IgG2 hinge region and at least a portion of an IgG4 hinge region. In one embodiment, the polypeptide linker comprises a chimeric hinge comprising at least a portion of an IgG1 hinge region, at least a portion of an IgG2 hinge region, and at least a portion of an IgG4 hinge region. In another embodiment, a polypeptide linker can comprise an IgG1 upper and middle hinge and a single IgG3 middle hinge repeat motif. In another embodiment, a polypeptide linker can comprise an IgG4 upper hinge, an IgG1 middle hinge and a IgG2 lower hinge.

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula (Gly$_4$Ser)n, wherein n is a positive integer (e.g., 1, 2, 3, 4, or 5) (SEQ ID NO: 124). A preferred gly/ser linker is (Gly$_4$Ser)4 (SEQ ID NO: 108). Another preferred gly/ser linker is (Gly$_4$Ser)3 (SEQ ID NO: 112). Another preferred gly/ser linker is (Gly$_4$Ser)5 (SEQ ID NO: 110). In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as (Gly$_4$Ser)n (SEQ ID NO: 125)).

In one embodiment, a polypeptide linker of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a polypeptide linker of the invention. In one embodiment, a polypeptide linker of the invention comprises a hinge domain which does not comprise a naturally occurring number of cysteines, i.e., the polypeptide linker comprises either fewer cysteines or a greater number of cysteines than a naturally occurring hinge molecule.

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a one preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. For example, mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term "about" indicates +/− two amino acid residues. Since linker length must be a positive integer, the length of from about 1 to about 50 amino acids in length, means a length of from 1 to 48-52 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Nuclease Domains

In certain aspects, a hybrid nuclease molecule includes a nuclease domain. Accordingly, the hybrid nuclease molecules of the invention typically comprise at least one nuclease domain and at least one linked Fc domain. In certain aspects, a hybrid nuclease molecule includes a plurality of nuclease domains.

In some embodiments, a nuclease domain is substantially all or at least an enzymatically active fragment of a DNase. In some embodiments, the DNase is a Type I secreted DNase, preferably a human DNase such as DNase 1. Exemplary DNase 1 domains are set forth in SEQ ID NOs 48-53 and 102. An exemplary human DNase 1 is described at UniProtKB entry P24855 (SEQ ID NO:49 and 102). In some embodiments, the DNase is DNase 1 and/or a DNase 1-like (DNaseL) enzyme, 1-3. An exemplary human Dnase 1-like enzyme, 1-3 is described at UniProtKB entry Q13609 (SEQ ID NO:57 and 103). In some embodiments, the DNase is TREX1 (Three prime repair exonuclease 1). An exemplary human TREX1 is described at UniProtKB entry Q9NSU2 (SEQ ID NO:104). Preferably the human TREX1 is a C-terminal truncated human TREX1 lacking intracellular nuclear targeting sequences, e.g., a human TREX1 lacking 72 C-terminal amino acids as set forth in SEQ ID NO:105.

In some embodiments, a nuclease domain is substantially all or at least an enzymatically active fragment of an RNase. In some embodiments, the RNase is an extracellular or secretory RNase of the RNase A superfamily, e.g., RNase A, preferably a human pancreatic RNase. An exemplary human Rnase is described at UniProtKB entry P07998 (SEQ ID NO:58 and 101).

In one embodiment, the nuclease domain is operably linked (e.g., chemically conjugated or genetically fused (e.g., either directly or via a polypeptide linker)) to the N-terminus of an Fc domain. In another embodiment, the nuclease domain is operably linked (e.g., chemically conjugated or genetically fused (e.g., either directly or via a polypeptide linker)) to the C-terminus of an Fc domain. In other embodiments, a nuclease domain is operably linked (e.g., chemically conjugated or genetically fused (e.g., either directly or via a polypeptide linker)) via an amino acid side chain of an Fc domain. In certain exemplary embodiments, the nuclease domain is fused to an Fc domain via a human immunoglobulin hinge domain or portion thereof.

In certain embodiments, the hybrid nuclease molecules of the invention comprise two or more nuclease domains and at least one Fc domain. For example, nuclease domains may be operably linked to both the N-terminus and C-terminus of an Fc domain. In other exemplary embodiments, nuclease domains may be operably linked to both the N- and C-terminal ends of multiple Fc domains (e.g., two, three, four, five, or more Fc domains) which are linked together in series to form a tandem array of Fc domains.

In other embodiments, two or more nuclease domains are linked to each other (e.g., via a polypeptide linker) in series, and the tandem array of nuclease domains is operably linked (e.g., chemically conjugated or genetically fused (e.g., either directly or via a polypeptide linker)) to either the C-terminus or the N-terminus of a Fc domain or a tandem array of Fc domains. In other embodiments, the tandem array of nuclease domains is operably linked to both the C-terminus and the N-terminus of a Fc domain or a tandem array of Fc domains.

In other embodiments, one or more nuclease domains may be inserted between two Fc domains. For example, one or more nuclease domains may form all or part of a polypeptide linker of a hybrid nuclease molecule of the invention.

Preferred hybrid nuclease molecules of the invention comprise at least one nuclease domain (e.g., RNase or DNase), at least one linker domain, and at least one Fc domain.

In certain embodiments, the hybrid nuclease molecules of the invention have at least one nuclease domain specific for a target molecule which mediates a biological effect.

In another embodiment, binding of the hybrid nuclease molecules of the invention to a target molecule (e.g. DNA or RNA) results in the reduction or elimination of the target molecule, e.g., from a cell, a tissue, or from circulation.

In certain embodiments, the hybrid nuclease molecules of the invention may comprise two or more nuclease domains. In one embodiment, the nuclease domains are identical, e.g., RNase and RNase, or TREX1 and TREX1. In another embodiment, the nuclease domains are different, e.g., DNase and RNase.

In other embodiments, the hybrid nuclease molecules of the invention may be assembled together or with other polypeptides to form binding proteins having two or more polypeptides ("multimers"), wherein at least one polypeptide of the multimer is a hybrid nuclease molecule of the invention. Exemplary multimeric forms include dimeric, trimeric, tetrameric, and hexameric altered binding proteins and the like. In one embodiment, the polypeptides of the multimer are the same (ie. homomeric altered binding proteins, e.g. homodimers, homotetramers). In another embodiment, the polypeptides of the multimer are different (e.g. heteromeric).

Methods of Making Hybrid Nuclease Molecules

The hybrid nuclease molecules of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Pharmaceutical Compositions and Therapeutic Methods of Use

In certain embodiments, a hybrid nuclease molecule is administered alone. In certain embodiments, a hybrid nuclease molecule is administered prior to the administration of at least one other therapeutic agent. In certain embodiments, a hybrid nuclease molecule is administered concurrent with the administration of at least one other therapeutic agent. In certain embodiments, a hybrid nuclease molecule is administered subsequent to the administration of at least one other therapeutic agent. In other embodiments, a hybrid nuclease molecule is administered prior to the administration of at least one other therapeutic agent. As will be appreciated by one of skill in the art, in some embodiments, the hybrid nuclease molecule is combined with the other agent/compound. In some embodiments, the hybrid nuclease molecule and other agent are administered concurrently. In some embodiments, the hybrid nuclease molecule and other agent are not administered simultaneously, with the hybrid nuclease molecule being administered before or after the agent is administered. In some embodiments, the subject receives both the hybrid nuclease molecule and the other agent during a same period of prevention, occurrence of a disorder, and/or period of treatment.

Pharmaceutical compositions of the invention can be administered in combination therapy, i.e., combined with other agents. In certain embodiments, the combination therapy comprises nuclease molecule, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for pharmaceutical compositions comprising a hybrid nuclease molecule together with a pharmaceutically acceptable diluent, carrier, solubilizer, emulsifier, preservative and/or adjuvant.

In certain embodiments, the invention provides for pharmaceutical compositions comprising a hybrid nuclease molecule and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, a hybrid nuclease molecule and/or a therapeutic molecule is linked to a half-life extending vehicle known in the art. Such vehicles include, but are not limited to, polyethylene glycol, glycogen (e.g., glycosylation of the hybrid nuclease molecule), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising a hybrid nuclease molecule, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a hybrid nuclease molecule, with or without at least one additional therapeutic agent, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired hybrid nuclease molecule, with or without additional therapeutic agents, in a pharmaceutically acceptable vehicle. In certain embodiments, a vehicle for parenteral injection is sterile distilled water in which a hybrid nuclease molecule, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a hybrid nuclease molecule, with or without at least one additional therapeutic agent, can be formulated as a dry powder for inhalation. In certain embodiments, an inhalation solution comprising a hybrid nuclease molecule, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, a hybrid nuclease molecule, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a hybrid nuclease molecule and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a hybrid nuclease molecule, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a hybrid nuclease molecule, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a hybrid nuclease molecule, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a hybrid nuclease molecule, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of a hybrid nuclease molecule and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising a hybrid nuclease molecule, with or without at least one additional therapeutic agent, in an ex vivo manner. In such instances, cells, tissues and/or organs that have been removed from the patient are exposed to a pharmaceutical composition comprising a hybrid nuclease molecule, with or without at least one additional therapeutic agent, after which the cells, tissues and/or organs are subsequently implanted back into the patient.

In certain embodiments, a hybrid nuclease molecule and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The hybrid nuclease molecules of the instant invention are particularly effective in the treatment of autoimmune disorders or abnormal immune responses. In this regard, it will be appreciated that the hybrid nuclease molecules of the present invention may be used to control, suppress, modulate, treat, or eliminate unwanted immune responses to both external and autoantigens. In yet other embodiments the polypeptides of the present invention may be used to treat immune disorders that include, but are not limited to, insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

Kits

A kit can include a hybrid nuclease molecule disclosed herein and instructions for use. The kits may comprise, in a suitable container, a hybrid nuclease molecule disclosed herein, one or more controls, and various buffers, reagents, enzymes and other standard ingredients well known in the art.

The container can include at least one vial, well, test tube, flask, bottle, syringe, or other container means, into which a hybrid nuclease molecule may be placed, and in some instances, suitably aliquoted. Where an additional component is provided, the kit can contain additional containers into which this component may be placed. The kits can also include a means for containing the hybrid nuclease molecule and any other reagent containers in close confinement for commercial sale. Such containers may include injection or blow-molded plastic containers into which the desired vials are retained. Containers and/or kits can include labeling with instructions for use and/or warnings.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B(1992).

Example 1. General Approach for Generating Hybrid Nuclease Molecules

Hybrid nuclease molecules were designed to incorporate desired structures and functional activity of single enzyme or multi-enzyme structures as modular cassettes with compatible restriction enzyme sites for shuttling and domain exchange. The schematic structure of different embodiments of hybrid nuclease molecules is illustrated in FIG. 1. The nucleotide and amino acid sequences of representative hybrid nuclease molecules are shown in Table 1.

Human cDNAs were isolated from human pancreas RNA (Ambion) or human PBMC RNA from normal human peripheral blood lymphocytes (approximately 5×10e6) using QIAgen RNAeasy kits (Valencia, Calif.) and QIAshredder kits to homogenize cell lysates (Qiagen, Valencia, Calif.). Human PBMCs were isolated from heparinized human blood diluted 1:1 in D-PBS and layered over LSM Lymphocyte Separation Medium (MP Biomedicals, Irvine, Calif.) Ficoll gradients.

Mouse spleen RNA was isolated using QIAgen RNAeasy kits (Valencia, Calif.) from approximately 5×10e6 splenocytes. Cells were pelleted by centrifugation from the culture medium, and 5×10e6 cells were used to prepare RNA. RNA was isolated from the cells using the QIAGEN RNAeasy kit (Valencia, Calif.) total RNA isolation kit and QIAGEN QIAshredder according to the manufacturer's instructions accompanying the kit. One to two microgram (1-2 µg) of total RNA was used as template to prepare cDNA by reverse transcription. The RNA, 300 ng random primers, and 500 ng Oligo dT (12-18) (SEQ ID NO: 126), and 1 µl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 µl in the presence of 5 times second strand buffer and 0.1 M DTT provided with the enzyme. The reverse transcription reaction was allowed to proceed at 50° C. for one hour.

Between 10-100 ng cDNA was used in PCR amplification reactions using primers specific for the nuclease gene of interest (RNaseA, RNase1, DNase1, Trex1, DNase1L3, etc.) or initial cloning reactions, primers were designed to isolate the full length cDNA or truncation products encoding the gene of interest. Full length or shortened PCR fragments were isolated by agarose gel electrophoresis, and purified using Qiagen QIAquick columns to remove nucleotides, primers, and unwanted amplified products. Purified fragments were cloned into pCR2.1 TOPO cloning vectors (Invitrogen, Carlsbad, Calif.) and transformed into TOP 10 competent bacteria. Isolated colonies were picked into Luria Broth media containing 50 ug/ml carbenicillin, and grown overnight to isolate plasmids. TOPO clones were screened for inserts of the correct size by digestion with EcoRI (NEB, Ipswich, Mass.) restriction enzyme and agarose gel electrophoresis of digested fragments. DNA sequence analysis of positive clones was performed with ABI Ready Reaction Mix v 3.1 and analyzed using an ABI 3730 XL DNA sequencer. Once correct clones were obtained, further sequence modifications were designed and PCR reactions performed to generate the desired alleles or expression cassettes. Truncation products and alleles were generated by PCR mutagenesis using overlapping primers for introduction of mutations at specific positions in the genes. Linkers were synthesized by overlapping PCR using internal overlapping primers and successive rounds of PCR to attach additional sequence to each terminus. Hybrid nuclease molecules were assembled as a string of several interchangeable cassettes. Molecules of the preferred embodiment contain a fixed leader peptide, a nuclease cassette, an optional cassette encoding a choice of several different polypeptide linkers, an –Ig Fc domain cassette with either a STOP codon or a linker at the carboxyl end of the CH3 domain, and for resolvICase type molecules, a second linker cassette, followed by a second nuclease cassette. FIG. 1 illustrate the cassette type structure of these hybrid nuclease molecules and examples of potential sequences inserted at each position. Once hybrid nuclease molecules were assembled, they were transferred to a mammalian expression plasmid pDG appropriate for transient expression in COS7 or other cells and stable expression in CHO DG44 cells using selection for DHFR with methotrexate.

Transient Expression of Hybrid Nuclease Molecules

COS-7 cells were transiently transfected with expression vector pDG containing hybrid nuclease molecule gene inserts. The day before transfection, cells were seeded at 4×10e5 cells per 60 mm dish in 4 ml DMEM (Thermo-Fisher/Mediatech cell gro)+10% FBS tissue culture media. DMEM basal media was supplemented with 4.5 g/L glucose, sodium pyruvate, L-glutamine 4 mM, and non-essential amino acids. Fetal bovine serum (Hyclone, Logan, Utah ThermoFisher Scientific) was added to media at 10% final volume. Cells were incubated at 37° C., 5% CO2 overnight and were approximately 40-80% confluent on the day of transfection. Plasmid DNA was prepared using Qiagen (Valencia, Calif.) QIAprep miniprep kits according to manufacturer's instructions, and eluted in 50 ul EB buffer. DNA concentrations were measured using a Nanodrop 1000 (Thermo Fisher Scientific, Wilmington Del.) spectrophotometer. Plasmid DNA was transfected using Polyfect (Qiagen, Valencia, Calif.) transfection reagent according to manufacturer's instructions, using 2.5 ug plasmid DNA per 60 mm dish and 15 ul polyfect reagent in 150 ul serum free DMEM transfection cocktails. After complex formation, reactions were diluted into 1 ml cell growth media containing serum and all supplements, and added drop-wise to the plates containing 3 ml fresh DMEM complete culture media. Transient transfections were incubated for 48-72 hours prior to harvesting culture supernatants for further analysis.

Generation of Stable CHO DG44 Transfectants Expressing the Hybrid Nuclease Molecules of Interest Stable production of the hybrid nuclease molecules was achieved by electroporation of a selectable, amplifiable plasmid, pDG, containing the nuclease-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 µg each of plasmid and carrier DNA was used to transfect $10^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2×DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Invitrogen/Life Technologies). Media for transfections under selection contained varying levels of methotrexate (Sigma-Aldrich) as selective agent, ranging from 50 nM to 1 µM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 50 nM methotrexate. Once clonal outgrowth was sufficient, serial dilutions of culture supernatants from master wells were screened for expression of hybrid nuclease molecules by use of an –IgG sandwich ELISA. Briefly, NUNC immulon II plates were coated overnight at 4° C. with 7.5 microgram/ml F(ab'2) goat anti-mouse IgG (KPL Labs, Gaithersburg, Md.) or 2 ug/ml goat anti-human or anti-mouse IgG (Jackson Immunoresearch, West Grove Pa.) in PBS. Plates were blocked in PBS/2-3% BSA, and serial dilutions of culture supernatants incubated at room temperature for 2-3 hours. Plates were washed three times in PBS/0.05% Tween 20, and incubated with horseradish peroxidase conjugated F(ab')2 goat anti-mouse IgG2a (Southern Biotechnologies) and goat anti-mouse IgG (KPL) mixed together, each at 1:3500 in PBS/1.0% BSA, or in horseradish peroxidase conjugated F(ab')2 goat anti-human IgG1 (Jackson Immunoresearch, West Grove, Pa.) at 1:2500 for 1-2 hours at room temperature. Plates were washed four times in PBS/0.05% Tween 20, and binding detected with SureBlue Reserve, TMB substrate (KPL Labs, Gaithersburg, Md.). Reactions were stopped by addition of equal volume of 1N HCl, and plates read at 450 nM on a Spectramax Pro plate reader (Microdevices, Sunnyvale Calif.). The clones with the highest production of the hybrid nuclease molecule were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the Excell 302 complete media contained an increased concentration of methotrexate, such that only the cells that amplified the DHFR plasmid could survive.

Supernatants were collected from CHO cells expressing the hybrid nuclease molecule, filtered through 0.2 µm PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7), and bound protein was eluted using 0.1 M citrate buffer, pH 3.0. Fractions were collected and protein concentration was determined at 280 nM using a Nanodrop (Wilmington Del.) microsample spectrophotometer, and blank determination using 0.1 M citrate buffer, pH 3.0. Fractions containing hybrid nuclease molecules were pooled, and buffer exchange performed by serial spins in PBS using centricon concentrators followed by filtration through 0.2 µm filter devices, to reduce the possibility of endotoxin contamination.

Example 2: Construction of RNase-Ig Fusion Genes

Murine RNase 1 was amplified as a full-length cDNA from an EST library (from Dr. C. Raine, Albert Einstein School of Medicine, Bronx, N.Y.) who sent the clone to our laboratory without an MTA. Sequence specific 5' and 3' primers used were from the published sequences. The sequence of the clone was verified by sequencing analysis. The Genebank accession number is NCBI geneID 19752. Full length human RNase 1 was isolated from random primed and oligo dT primed cDNA derived from human pancreas total RNA (Ambion/Applied Biosystems, Austin, Tex.).

Once a full-length clone was isolated, primers were designed to create a fusion gene with the mouse IgG2a or human IgG1 (SEQ ID NO:40) Fc domains. Two different primers were designed for the 5' sequence fused at the amino terminus of the Fc tail; the first incorporated the native leader peptide from mouse (or human) RNase, while the second attached an AgeI site to the amino terminus of RNase at the predicted signal peptide cleavage site in order to fuse the RNase to a human VKIII leader peptide that we already had cloned and used for other expression studies. For the murine RNase, the sequence of the first primer is:

```
mribNL5'
30mer (RNase 5' with native leader and
HindIII + Kozak)
                                  (SEQ ID NO: 1)
gTT AAg CTT gCC ACC ATg ggT CTg gAg AAg TCC CTC ATT CTg-3'
```

The second primer creates a gene fusion junction between an existing leader sequence and the mature sequence at the 5' end of the RNase, at or near the predicted leader peptide cleavage site.

```
27mer (RNase 5' mature sequence
(no leader, with AgeI site)
                                  (SEQ ID NO: 2)
5'-gAT ACC ACC ggT Agg gAA TCT gCA gCA CAg AAg TTT CAg-3'
```

The sequence of the 3' primer for fusion to murine IgG2a at the carboxy end of RNase and the amino terminus of the Fc tail is as follows:

```
mrib3NH2
28mer (RNase 3' end with XhoI site
for fusion to mIgG2a).
                                       (SEQ ID NO: 3)
5'-ggC TCg AgC ACA gTA gCA TCA AAg tGG ACT ggT ACg TAg g-3'
```

Two more oligos were designed to create an −Ig-RNase fusion gene, where the −Ig tail is amino terminal to the RNase enzyme domain.

```
mrib5X
36mer RNase 5' end with linker aa and XbaI site for
fusion to carboxy end of Fc domain.
                                                    (SEQ ID NO: 4)
5'-AAA TCT AgA CCT CAA CCA ggT Agg gAA TCT gCA gCA CAg AAg TTT CAg-3' mrib3X
31mer RNase 3' end with two stop codons and XbaI site
for fusion to carboxy end of Fc domain.
                                                    (SEQ ID NO: 5)
5'-TCT AgA CTA TCA CAC AgT AgC ATC AAA gTg gAC Tgg TAC gTA g-3'
```

Example 3: Isolation of Human and Mouse-Fc Domains and Introduction of Mutations into the Coding Sequence For isolation of mouse and human Fc domains (SEQ ID NO:40), RNA was derived from mouse or human tissue as follows. A single cell suspension was generated from mouse spleen in RPMI culture media. Alternatively, human PBMCs were isolated from fresh, whole blood using Lymphocyte Separation Media (LSM) Organon Teknika (Durham, N.C.), buffy coats harvested according to manufacturer's directions, and cells washed three times in PBS prior to use. Cells were pelleted by centrifugation from the culture medium, and $2 \times 10^7$ cells were used to prepare RNA. RNA was isolated from the cells using the QIAGEN RNAeasy kit (Valencia, Calif.) total RNA isolation kit and QIAGEN QIAshredder columns according to the manufacturer's instructions accompanying the kits. One microgram (4 μg) of total RNA was used as template to prepare cDNA by reverse transcription. The RNA, 300 ng random primers, and 500 ng Oligo dT (12-18) (SEQ ID NO: 126), and 1 μl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of second strand buffer and 0.1 M DTT provided with the enzyme. The reverse transcription reaction was allowed to proceed at 50° C. for one hour. cDNA was purified using QIAquick (QIAGEN) PCR purification columns according to manufacturer's directions, and eluted in 40 microliters EB buffer prior to use in PCR reactions.

Wild type mouse and human-Fc domains were isolated by PCR amplification using the cDNA described above as template. The following primers were used for initial amplification of wild type sequences, but incorporated the desired mutational changes in the hinge domain:

```
mahIgG1CH2M: 47 mer
                                                    (SEQ ID NO: 6)
5'-tgtccaccgtgtccagcacctgaactcctgggtggatcgtcagtcttcc-3' hIgG1-5scc: 49 mer
                                                    (SEQ ID NO: 7)
5'-agatctcgagcccaaatcttctgacaaaactcacacatgtccaccgtgt-3' mahIgG1S: 51 mer
                                                    (SEQ ID NO: 8)
5'-tctagattatcatttacccggagacagagagaggctcttctgcgtgtagtg-3' muIgG2aCH2: 58mer
                                                    (SEQ ID NO: 9)
5'-cctccatgcaaatgcccagcacctaacctcttgggtggatcatccgtcttcatcttcc-3' mIgG2a-5scc: 47mer
                                                    (SEQ ID NO: 10)
5'-gaagatctcgagcccagaggtcccacaatcaagccctctcctcca-3' mIgG2a3S: 48mer
                                                    (SEQ ID NO: 11)
5'-gtttctagattatcatttacccggagtccgagagaagctcttagtcgt-3'
```

PCR reactions were performed using a C1000 thermal cycler (BioRad, Hercules Calif.) or an Eppendorf thermal cycler (ThermoFisher Scientific, Houston Tex.). Reactions included an initial denaturation step at 95° C. for 2 minutes, followed by 34 cycles with a 94° C., 30 sec denaturation, 50°

C., 30 sec annealing, and 72° C., 1 minute extension step, followed by a final 4 minute extension at 72° C. Once wild type tails were isolated, the fragments were TOPO cloned into pCR2.1 vectors, DNA prepared using the QIAGEN spin plasmid miniprep kits according to manufacturer's instructions and clones sequenced using ABI Dye Terminator v3.1 sequencing reactions according to manufacturer's instructions.

DNA from the correct clones were used as templates in overlap extension PCRs to introduce mutations at the desired positions in the coding sequence for mouse IgG2a or human-IgG1. PCR reactions were set up using the full length wild type clones as template (1 microliter), 50 pmol 5' and 3' primers to PCR each portion of the –Fc domain up to and including the desired mutation site from each direction, and PCR hi fidelity Supermix (Invitrogen, Carlsbad Calif.), in 50 microliter reaction volumes using a short amplification cycle. As an example of the overlapping PCR mutagenesis, the primer combination used to introduce the P331S mutation into human-IgG1, was as follows:

A 5' subfragment was amplified using the full-length wild type clone as template, and the 5' primer was hIgG1-5scc: 5'-agatctcgagcccaaatcttctgacaaaactcacacatgtccaccgtgt-3' (SEQ ID NO:12), while the 3' primer was P331AS: 5'-gttttctcgatggaggctgggagggctttgttggagacc-3' (SEQ ID NO:13). A 3' subfragments was amplified using the full-length wild type clone as template and the 5' primer was P331S: 5' aaggtctccaacaaagccctcccagcctccatcgagaaaacaatctcc-3' (SEQ ID NO:14), while the 3' primer was mahIgG1S: 5'-tctagattatcatttacccggagacagagagaggctcttctgcgtgtagtg-3' (SEQ ID NO:15).

Once subfragments were amplified and isolated by agarose gel electrophoresis, they were purified by QIAquick gel purification columns and eluted in 30 microliters EB buffer according to manufacturer's instructions. Two rounds of PCR were then performed with the two subfragments as overlapping templates in new reactions. The cycler was paused and the 5' (hIgG1-5scc, see above) and 3' (mahIgG1S, see above) flanking primers were added to the reactions (50 pmol each). PCR amplifications were then carried out for 34 cycles at the conditions described for the wild type molecules above. Full length fragments were isolated by gel electrophoresis, and TOPO cloned into pCR2.1 vectors for sequence analysis. Fragments from clones with the correct sequence were then subcloned into expression vectors for creation of the different hybrid nuclease molecules described herein.

Figure 7:
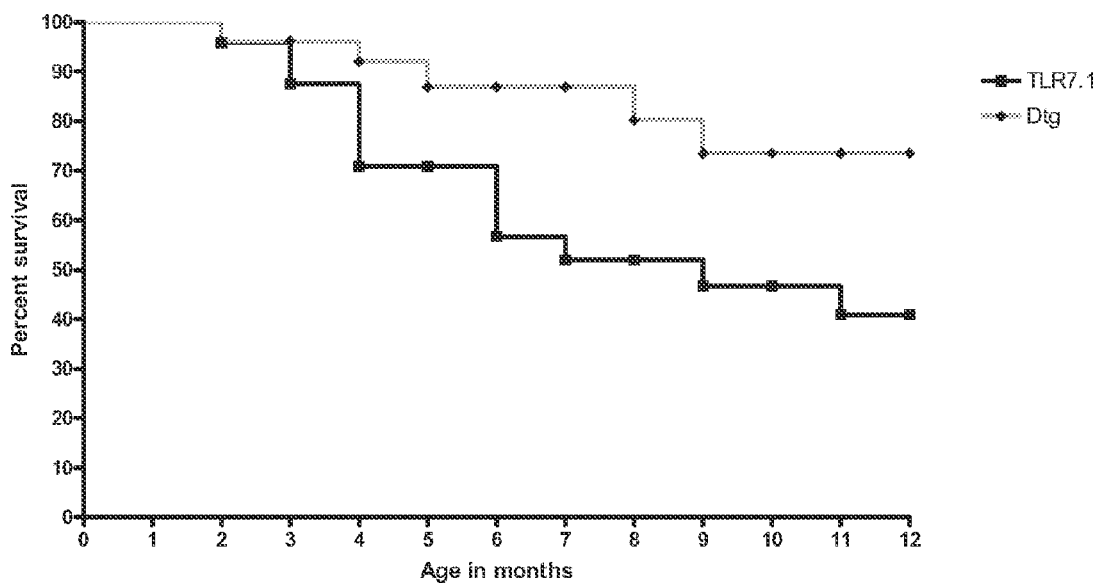
FIG. 7 shows survival of TLR7.1 Tg versus TLR7.1× RNaseA DTg mice

Example 4: Quantitation of RSLV-124 Protein and RNase Enzyme Activity in Mouse Sera In Vivo Mouse Stability Analysis of RSLV-124 Construct (SEQ ID NO:106).

Four mice (C220, C221, C222, C223) were injected intravenously with a single injection of RSLV-124 at time zero. At various times following the injection blood samples were collected and analyzed for the presence of RSLV-124 protein (a human wild type RNase linked to a wild-type human IgG1 Fc domain (SEQ ID NO:106)) and RNase enzymatic activity. To detect the RSLV-124 compound in mouse serum, an ELISA was developed which captures the human Fc from the mouse serum followed by detection of the human RNase. When the ELISA was run on the blood samples of the four mice the presence of RSLV-124 protein was detected at five minutes following a single intravenous injection of 150 ug, at between 38 μg/ml to 55 μg/ml (FIG. 2). At one day post injection the concentration of RSLV-124 dropped rapidly to between 8 μg/ml to 12 μg/ml. The blood concentration of the drug remained relatively stable for the duration of the analysis out to seven days where blood levels of the drug were approximately 5 μg/ml. The same blood samples used to measure the RSLV-124 protein by ELISA were used to quantitate the RNase enzymatic activity of the drug. The RNaseAlert QC system from Ambion (Cat # AM1966) was used to measure the enzyme kinetics of the RSLV-124 protein in mouse blood samples with some modifications. The drug compound was captured from mouse serum onto the RNaseAlert assay plate using a human anti-Fc monoclonal antibody and quantitated by measurement of fluorescence per the Ambion kit instructions. Analysis of the relative fluorescent units (RFU's) of the RSLV-124 molecule showed between 80,000-140,000 RFU's at five minutes after injection (FIG. 3). The RFU's declined rapidly in parallel with the protein concentration, remaining relatively stable at between 18,000-40,000 RFU's out to day seven. The RNaseAlert QC system was used to develop a standard curve using known quantities of protein, from this standard curve the RFU's of the RSLV-124 in the blood samples were used to extrapolate the protein concentration of RSLV-124. From this analysis it was determined that the protein concentration present in the mouse blood over the seven day experiment as calculated using the RNase enzymatic activity assay were very similar to the values that were measured using the ELISA (FIG. 4). From these experiments it was concluded that the RSLV-124 compound is stable in vivo in mouse circulation over seven days and retains its enzymatic activity, suggesting that the compound is not susceptible to degradation in vivo in the mouse since nearly 100% of the enzymatic activity is retained over seven days in the mouse circulation. Since Fc fusion proteins are often susceptible to degradation in the circulation this finding further confirms the use of the RNase-Fc fusion proteins as valuable drugs.

Example 5: Phenotype of TLR7.1×RNaseA Double Transgenic Mice

Mice were created that overexpress RNaseA (RNase Tg). This nuclease is expressed at high levels in RNase Tg mice. We have developed both a single radial diffusion (SRED) method (FIG. 5 and a much more quantitative ELISA to quantify RNase in the serum (FIG. 6). Both assays show a significant increase in RNase activity in the RNase Tg. Quantitation of the level of RNase in FIG. 6 compared with wild type B6 mice showed there was an approximately 10-fold increase in RNase in the RNase Tg. We crossed RNaseA Tg with TLR7.1 Tg mice to create the double Tg (DTg). TLR7.1 mice have 8-16 copies of TLR7 and develop a very aggressive, rapidly progressive lupus-like disease and start to die at 3 mo of age with a median survival of 6 mo. In a preliminary analysis, we bled DTg and littermate controls at 3 mo of age to see whether the DTg mice exhibited signs of improvement. As shown in FIG. 5, DTg mice had very high levels of RNase in their serum (equivalent to >13 U/ml RNase based on our standard with specific activity of 993 U/mg). RNaseA concentration in Tg and DTg mice was also measured by ELISA assay as shown in FIG. 6. The RNase A Tg and TLR7.1×RNaseA Dtg mice have RNase A serum concentrations between 1-2 ng/ml.

Detailed method for Rnase A ELISA

1. Coat plate with anti-RnaseA Abcam Ab(ab6610): 2.5-10 ug/ml O/N in 4 C.
2. Wash plate 3 times with 0.05% Tween/1×PBS
3. Block with 1% BSA in PBS for at least 1 hour 4. Wash plate 3 times with 0.05% Tween/1×PBS
5. Load samples. Sample dilutions at 1:50
6. Incubate Rm Temp for 2 hours
7. Wash plate 3 times with 0.05% Tween/1×PBS
8. Prepare dilution of biotin labeled Anti Rnase Ab at dilution of 1:4500 (2.2 ug/ml). Leave RT for 1 hour (Rockland 200-4688: 10 mg/ml).
9. Wash plate 3 times
10. Dilute StrepAV HRP (Biolegend 405210) 1:2500. Cover with foil and leave at RT for 25-30 min.
11. Wash 6 times, let the liquid sit in wells for at least 30 seconds in between washes.
12. Add BD OptEIA substrate A+B 1:1. Wait until color changes 5-10 min max. Don't let the top well standard go over 1.0. Add 80 ul. (CatNos: 51-2606KC; ReagentA, 51-2607KC; ReagentB)
13. Add 40 ul of 1M sulfuric acid to stop reaction Product/Reagent Information:
RNaseA Ab: ab6610 (90 mg/ml)
ELISA buffer: 1% BSA in PBS
ELISA wash buffer: 0.05% Tween/1×PBS
Anti RNaseA biotin conjugated Ab: Rockland: 200-4688 (10 mg/ml)
Strep AV HRP: Biolegend 405210
BD OptEIA reagent A and B: 51-2606KC and 51-2607KC Example 6. Survival Curves for TLR7.1 Transgenic Mouse Strains There was a highly significant difference between the DTg and the TLR7.1 littermate controls in survival. As shown in FIG. 7, at 10 months, 61% of TLR7.1 mice had died, whereas 31% of DTg mice had died. This data shows that overexpression of RNaseA exerted a strong therapeutic effect. The reasons why TLR7.1 mice die prematurely is not entirely clear, although severe anemia, thrombocytopenia, and glomerulonephritis could play a part. To determine whether red cell and platelet counts were positively impacted by RNaseA expression in the DTg mice, we performed blood counts but found no differences between the TLR7.1 and DTg mice. In contrast, there was a significant improvement in kidney histopathology in the DTg mice. We observed decreased deposition of IgG and C3 in DTg mice. PAS staining, which reflects inflammation in the mesangium was also reduced in DTg mice compared to TLR7.1 littermate controls. When we have now compared macrophage infiltration of the kidneys using anti-MAC-2 (galectin3) antibody (Lyoda et al. Nephrol Dial Transplat 22: 3451, 2007), there were many fewer mac-2 positive cells in the glomeruli of the DTg mice. The results of counting 20 glomeruli per mouse in 5 mice in each group revelaed mean+/−SE of 3.8+/−1.1 and 1.4+/−0.2 for single versus DTg respectively, p=0.05. In addition, we quantified glomerular tuft size and observed a significant reduction in glomerular tuft size in the DTg mice (179+/−41 versus 128+/−16.8 um2 in single versus DTg respectively, p=0.037). In summary, TLR7.1×RNaseA DTg mice survive longer than their single Tg TLR7.1 littermates and have less inflammation and injury in their kidneys. This finding indicates that removing RNA immune complexes in this mouse model significantly improved overall mortality and decreased kidney damage and overall imflammation associated with this lupus-like pathology.

Example 7. Analysis of IRGs in Spleens of TLR Tg Mice

Figure 8:
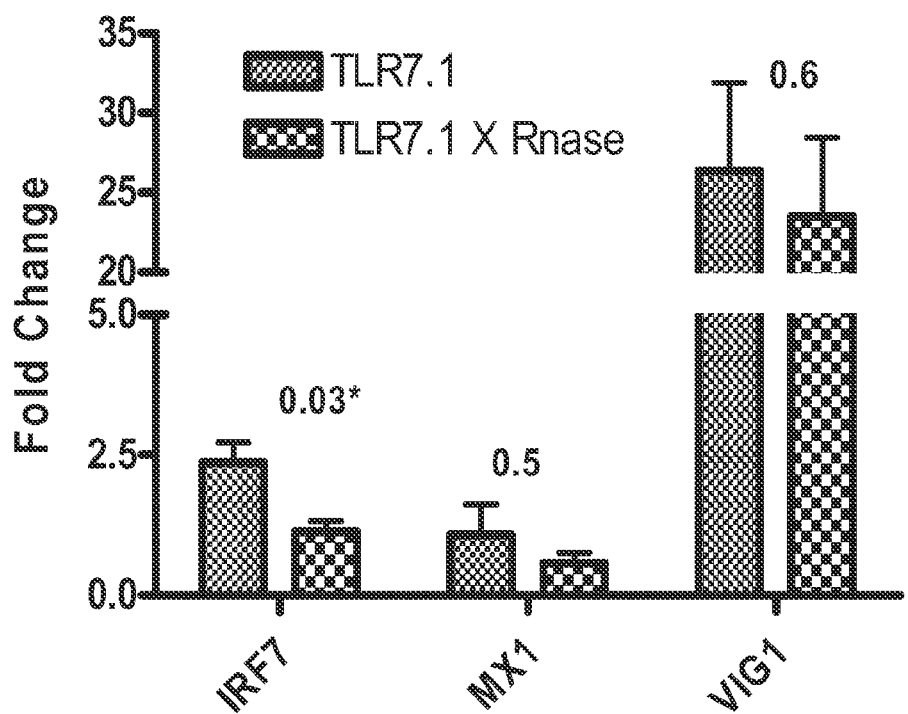
FIG. 8 shows quantitative PCR of IRGs in spleens of Tg versus DTg mice.

Analysis of interferon response genes (IRGs) in the spleens of TLR7.1 Tg and TLR7.1×RNaseA DTg mice mice showed that expression of the IRF7 gene (Interferon regulatory factor 7 (UniProtKB P70434)) was significantly lower in the DTg mice (p=0.03). Some other IRGs including MX1 (Interferon-induced GTP-binding protein Mx1 (UniProtKB P09922)) and VIG1 (Radical S-adenosyl methionine domain containing protein 2 (UniProtKB Q8CBB9)) were lower in DTg mice compared to Tg mice, but the differences were not significant. (FIG. 8). Quantitative PCR was performed as follows: total RNA was isolated from mouse spleens using the RNeasy mini kit (Qiagen, Valencia, Calif., USA), DNase treated using Turbo DNA-free (Applied Biosystems, Foster City, Calif., USA) and first-strand cDNA was produced with the RNA-to-cDNA kit (Applied Biosystems) using random primers. The 260/280 was between 1.7 and 2.0 for isolated RNA measured with a NanoDrop (Thermo Scientific, Waltham, Mass., USA). cDNA was diluted to an equivalent of 1 ng/ul total RNA and 8u1 were used per reaction. Primers for the reference gene (18s) and genes of interest (GOI) were synthesized (IDT, Coralville, Iowa, USA) and diluted to the appropriate concentrations for qPCR using molecular grade water. BLAST results of the primers show specific sequence homology only to the reference gene or GOI. Reactions in duplicate (20 ul) were run on an ABI Fast 7500 system using a 1:1 mix of template and primer to SensiMix SYBR low-ROX master mix (Bioline, London, UK). Relative quantification was calculated using the $2^{-ddCT}$ method with age matched wild type B6 mice as baseline to determine fold changes for each GOI. The dissociation curves for the reactions show a single melt peak for each gene. The standard curve showed similar amplification efficiencies for each gene and that template concentrations were within the linear dynamic range for each of primer set.

Example 8: Construction and Expression of DNase1-Ig Single and Dual Enzyme Hybrid Nuclease Molecules Naturally occurring alleles of human DNase1 or DNase1 like molecules have been reported. The A114F mutation has been previously reported to occur in natural variants of human DNAse1 like enzymes, and to result in actin resistance of the enzymes containing this sequence change. See Pan, C Q, Dodge T H, Baker D L, Prince W E, Sinicropi D V, and Lazarus R A. J Biol Chem 273: 18374-18381, (1998); Zhen A, Parmelee D, Hyaw H, Coleman T A, Su K, Zhang J, Gentz R, Ruben S, Rosen C, and Li Y. Biochem and Biophys Res Comm 231: 499-504 (1997); and Rodriguez A M, Rodin D, Nomura H, Morton C C, Weremowicz S, and Schneider M C. Genomics 42: 507-513 (1997), all of which are herein incorporated by reference.

Similarly, the G105R mutation has been reported recently as a single nucleotide polymorphism in the gene encoding human DNAse 1 that is polymorphic in some or all populations, and that is relevant to autoimmunity. (See Yasuda T, Ueki M, Takeshita H, Fujihara J, Kimura-Kataoka K, Lida R, Tsubota E, Soejima M, Koda Y, Dato H, Panduro A. Int J Biochem Cell Biol 42(7): 1216-1225 (2010), herein incorporated by reference). Allelic variants at this position resulted in high activity harboring DNase 1 isoforms relative to wild type. Another naturally occurring, polymorphic mutation (R21S) has also been reported to confer higher activity. (See Yasuda, supra)

SLE patients have been reported to have significantly decreased levels of DNase1 activity (See Martinez-Valle F, Balada E, Ordi-Ros J, Bujan-Rivas S, Sellas-Fernandez A, Vilardell-Tarres M. Lupus 18(5): 418-423 (2009), herein incorporated by reference).

Naturally occurring enzyme variants may thus be less immunogenic when administered to patients, since these isoforms occur in the human population. We reasoned that the combination of the actin resistant properties of alleles similar to A114F with the increased enzymatic activity of alleles like G105R would generate novel allelic variants of human DNase1 that might show improved clinical activity in vitro and in vivo. To our knowledge, ours is the first report of this new mutant form of DNase1 generated from a combination of two naturally occurring variants G105R and A114F.

Human DNase 1 was isolated as described previously from human pancreas RNA (Ambion), by random primed cDNA and PCR using the following primer sets:

```
5'hDNase1-age:
                                  (SEQ ID NO: 16)
GTT ACC GGT CTG AAG ATC GCA GCC TTC AAC ATC

CAG

5'hDNase1-bx:
                                  (SEQ ID NO: 17)
GTT CTC GAG ATC TTT CAG CAT CAC CTC CAC TGG

ATA GTG
```

Alternatively, the 3' DNase cassettes were amplified by PCR using the following primer pair.

```
3'hDNase1-RV:
                                  (SEQ ID NO: 18)
GTT GAT ATC CTG AAG ATC GCA GCC TTC AAC ATC

CAG

3'hDNase1-stop:
                                  (SEQ ID NO: 19)
GTT TCT AGA TTA TCA CTT CAG CAT CAC CTC CAC

TGG ATA GTG
```

PCR reactions were performed using 50 pmol each primer, 2 ul cDNA, in a total volume of 50 ul using Platinum PCR Supermix as previously described. The amplification profile was 94 C 30 sec; 55 C 30 sec; 68 C 90 sec for 35 cycles.

Once the wild type gene was amplified by PCR, the fragments were subjected to gel electrophoresis and 850 by fragments purified by QIAquick column purification. Fragments were cloned into pCR2.1, transformed by TOPO cloning according to manufacturer's instructions as described for the other constructs. Once sequence was verified, PCR primers were used to generate subfragments containing naturally occurring alleles for DNase1 that have been reported to improve specific activity and improve resistance to the inhibitory activity of actin. These subfragments contained overlapping sequence, permitting amplification of complete DNase1 subclones containing the desired allelic variations. COS 7 cells were transiently transfected in 60 mm dishes using Polyfect (Qiagen, Valencia, Calif.) transfection reagent. Plasmid DNA was prepared using the Qiagen QIAprep miniprep kits according to manufacturer's instructions. Plasmids were eluted in 50 ul EB buffer. DNA concentration was measured using the Nanodrop and an aliquot equivalent to 2.5 ug plasmid DNA used for each transfection reaction. Each DNaseIg) or RNase-Ig-DNase) expression cassette was inserted into the mammalian expression vector pDG, a derivative of pcDNA3.1. Transfected cells were incubated for 72 hours at 37° C., 5% CO2 prior to harvest of culture supernatants for further analysis. Culture supernatants were harvested, residual cells centrifuged from the solution, and the liquid transferred to new tubes.

COS-7 cells were transiently transfected with plasmids containing human DNase1 wild type or naturally occurring DNase 1 mutant alleles (G105R and/or A114F)) fused to the wild type human IgG1 Fc domain. This hinge-CH2-CH3 cassette contains a single C→S mutation in the hinge region to eliminate the first cysteine in this domain since it is unpaired due to absence of its pairing partner present in the light chain of the antibody. In addition, more complex multi-nuclease fusion proteins were also expressed from COS cell transient transfections.

Example 9: Isolation of Human-Ig Tails, Introduction of Mutations into the Coding Sequence, and Construction of Mutant Nuclease Molecules For isolation of mutant human Ig Fc domains, RNA was derived from human PBMCs isolated from fresh, whole blood using Lymphocyte Separation Media (LSM) Organon Teknika (Durham, N.C.), buffy coats harvested according to manufacturer's directions, and cells washed three times in PBS prior to use. Cells were pelleted by centrifugation from the culture medium, and 2×107 cells were used to prepare RNA. RNA was isolated from the cells using the QIAGEN RNAeasy kit (Valencia, Calif.) total RNA isolation kit and QIAGEN QIAshredder columns according to the manufacturer's instructions accompanying the kits. One microgram (4 μg) of total RNA was used as template to prepare cDNA by reverse transcription. The RNA, 300 ng random primers, and 500 ng Oligo dT (12-18) (SEQ ID NO: 126), and 1 μl, 125 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of second strand buffer and 0.1 M DTT provided with the enzyme. The reverse transcription reaction was allowed to proceed at 50° C. for one hour. cDNA was purified using QIAquick (QIAGEN) PCR purification columns according to manufacturer's directions, and eluted in 40 microliters EB buffer prior to use in PCR reactions.

Wild type human-Ig Fc domains were isolated by PCR amplification using the cDNA described above as template. The mutant-Ig fragments were isolated by PCR directed mutagenesis, using appropriate PCR primers containing the desired mutations and the wild type cassettes as template. PCR reactions were performed using a C1000 thermal cycler (BioRad, Hercules Calif.). Reactions included an initial denaturation step at 95° C. for 2 minutes, followed by 34 cycles with a 94° C., 30 second denaturation, 55° C., 30 second annealing, and 72° C., 1 minute extension step, followed by a final 4 minute extension at 72° C. Once full length mutant tails were isolated, the fragments were TOPO cloned into pCR2.1 vectors, DNA prepared using the QIAGEN spin plasmid miniprep kits according to manufacturer's instructions and clones sequenced using ABI Dye Terminator v3.1 sequencing reactions according to manufacturer's instructions.

Recombinant molecules were generated by PCR mutagenesis using overlap extension PCR with mutated oligonucleotides.

The following oligonucleotides were used to derive these molecules.

CS-P238S 5-1:
(SEQ ID NO: 20)
TCT CCA CCG AGC CCA GCA CCT GAA CTC CTG GGA

GGA TCG TCA GTC TTC CTC TTC CCC C (58mer)

SSSH-5-2:
(SEQ ID NO: 21)
AGA TCT CGA GCC CAA ATC TTC TGA CAA AAC TCA

CAC ATC TCC ACC GAG CCC AGC ACC T (58 mer)

P331S-S:
(SEQ ID NO: 22)
GTC TCC AAC AAA GCC CTC CCA GCC TCC ATC GAG

AAA ACC ATC TCC A (46mer)

P331S-AS:
(SEQ ID NO: 23)
TGG AGA TGG TTT TCT CGA TGG GGG CTG GGA GGG

CTT TGT TGG AGA CC (47mer)

hIgG1-3'WTnogt:
(SEQ ID NO: 24)
TCT AGA TTA TCA TTT TCC CGG AGA GAG AGA GAG

GCT CTT CTG CGT GTA GTG (51mer)

The P238S mutation and SSS substitutions for SCC were introduced by PCR mutagenesis using two overlapping 5' oligos in sequential PCR reactions. The first PCR reaction included the following 5' primer that incorporates the P238S mutation within its sequence: CS-P238S 5-1: TCT CCA CCG AGC CCA GCA CCT GAA CTC CTG GGA GGA TCG TCA GTC TTC CTC TTC CCC C (58mer). (SEQ ID NO: 25)

The second PCR reaction included the following 5' primer that overlapped the first primer and added on the mutated hinge residues to the P238S mutant: SSSH-5-2: AGA TCT CGA GCC CAA ATC TTC TGA CAA AAC TCA CAC ATC TCC ACC GAG CCC AGC ACC T (58 mer). (SEQ ID NO: 26)

DNA from the correct clones was used as template in overlap extension PCRs to introduce mutations at the desired internal positions in the coding sequence for human-IgG1. PCR reactions were set up using the full length clones as template (1 microliter), 50 pmol 5' and 3' primers to PCR each portion of the -Ig tail up to and including the desired mutation site from each direction, and PCR hi fidelity Supermix (Invitrogen, Carlsbad Calif.), in 50 microliter reaction volumes using a short amplification cycle. As an example of the overlapping PCR mutagenesis, the primer combination used to introduce the P331S mutation into the human-IgG1 with the already introduced P238S mutation was as follows:

A 5' subfragment was amplified using the full-length wild type clone as template, and the 5' primer was SSSH-5-2: AGA TCT CGA GCC CAA ATC TTC TGA CAA AAC TCA CAC ATC TCC ACC GAG CCC AGC ACC T (58 mer) (SEQ ID NO: 21), while the 3' primer was P331S-AS: TGG AGA TGG TTT TCT CGA TGG GGG CTG GGA GGG CTT TGT TGG AGA CC (47mer). (SEQ ID NO: 27)

A 3' subfragments was amplified using the full length wild type clone as template and the 5' primer: P331S-S: GTC TCC AAC AAA GCC CTC CCA GCC TCC ATC GAG AAA ACC ATC TCC A (46mer) (SEQ ID NO: 22), while the 3' primer was hIgG1-3'WTnogt: TCT AGA TTA TCA TTT TCC CGG AGA GAG AGA GAG GCT CTT CTG CGT GTA GTG (51mer). (SEQ ID NO: 28)

Once subfragments were amplified and isolated by agarose gel electrophoresis, they were purified by QIAquick gel purification columns and eluted in 30 microliters EB buffer according to manufacturer's instructions. Two rounds of PCR were then performed with the two subfragments as overlapping templates in new reactions. The cycler was paused and the 5' and 3' flanking primers were added to the reactions (50 pmol each). PCR amplifications were then carried out for 34 cycles at the conditions described for the wild type molecules above. Full length fragments were isolated by gel electrophoresis, and TOPO cloned into pCR2.1 vectors for sequence analysis. Fragments from clones with the correct sequence were then subcloned into expression vectors for creation of the different nuclease molecules described herein.

For multispecific nuclease molecules, PCR reactions were performed using an alternative primer for the 3' end of the Fc domain, removing the STOP codon and adding on the NLG linker and the EcoRV restriction site to the molecules to facilitate fusion to the rest of the cassettes. The primer sequence is listed below: 5' GAT ATC CTG CAC GCT AGG GCT GCT CAC ATT 3'. (SEQ ID NO: 29)

RSLV mutant nucleases were constructed by fusing the mutated human -Ig tails to the wild type RNase domain with or without a linker separating the two domains. RSLV 125 and RSLV126 fuse human RNase to the mutant hinge and IgG1 Fc domain. RSLV125 contains no linker, while RSLV 126 contains the (gly4ser)4 linker (SEQ ID NO: 108) as a (BglII-XhoI) fragment inserted between the nuclease domain and hinge regions. RSLV-125 incorporates a wild type RNase cassette fused directly to an SSS (rather than CCC or wild type) version of the human IgG1 hinge, and a P238S, P331S mutant human IgG1 Fc domain (SEQ ID NO:61-62).

RSLV 126 incorporates a wild type RNase cassette fused to a (gly4ser)4 linker (SEQ ID NO: 108) domain, followed by the SSS mutant hinge, and a P238S-P331S double mutant Fc domain (SEQ ID NO:63-64).

RSLV-127 is a multinuclease fusion construct that incorporates an amino terminal human DNase (G105R/A114F) fused to a (gly4ser)4 linker (SEQ ID NO: 108) domain, followed by an SSS mutant hinge and P238S-P331S double mutant Fc domain fused to an NLG linker domain and followed by a C terminal wild type RNase domain (SEQ ID NO:65-66).

RSLV-128 is a multinuclease fusion construct that incorporates an amino terminal wild type human RNase domain, fused to a (gly4ser)4 linker (SEQ ID NO: 108) domain, followed by an SSS mutant hinge and P238S-P331S double mutant Fc domain fused to an NLG linker domain and followed by a C terminal mutant DNase (G105R/A114F) domain (SEQ ID NO:67-68).

RSLV-129 is a multispecific fusion construct that incorporates an amino terminal wild type human RNase domain, fused to an SSS mutant hinge and P238S-P331S double mutant Fc domain fused to an NLG linker domain and followed by a C terminal mutant DNase (G105R/A114F) domain (SEQ ID NO:69-70).

RSLV-132 incorporates a wild type RNase cassette fused directly to an SCC version of the human IgG1 hinge, and a P238S, P331S mutant human IgG1 Fc domain (SEQ ID NOS: 91-92 and 95-96).

RSLV-133 is a multispecific fusion construct that incorporates an amino terminal wild type human RNase domain, fused to an SCC mutant hinge and P238S-P331S double mutant Fc domain fused to an NLG linker domain and followed by a C terminal mutant DNase (G105R/A114F) domain (SEQ ID NOS: 93-94 and 97-98).

Additional versions of RSLV-125-RSLV-129 with an SCC hinge are shown in Table 1 as RSLV-125-2 (SEQ ID NO:77-78), RSLV-126-2 (SEQ ID NO:79-80), RSLV-127-2 (SEQ ID NO:81-82), RSLV-128-2 (SEQ ID NO:83-84), and RSLV-129-2 (SEQ ID NO:85-86).

Figure 9:
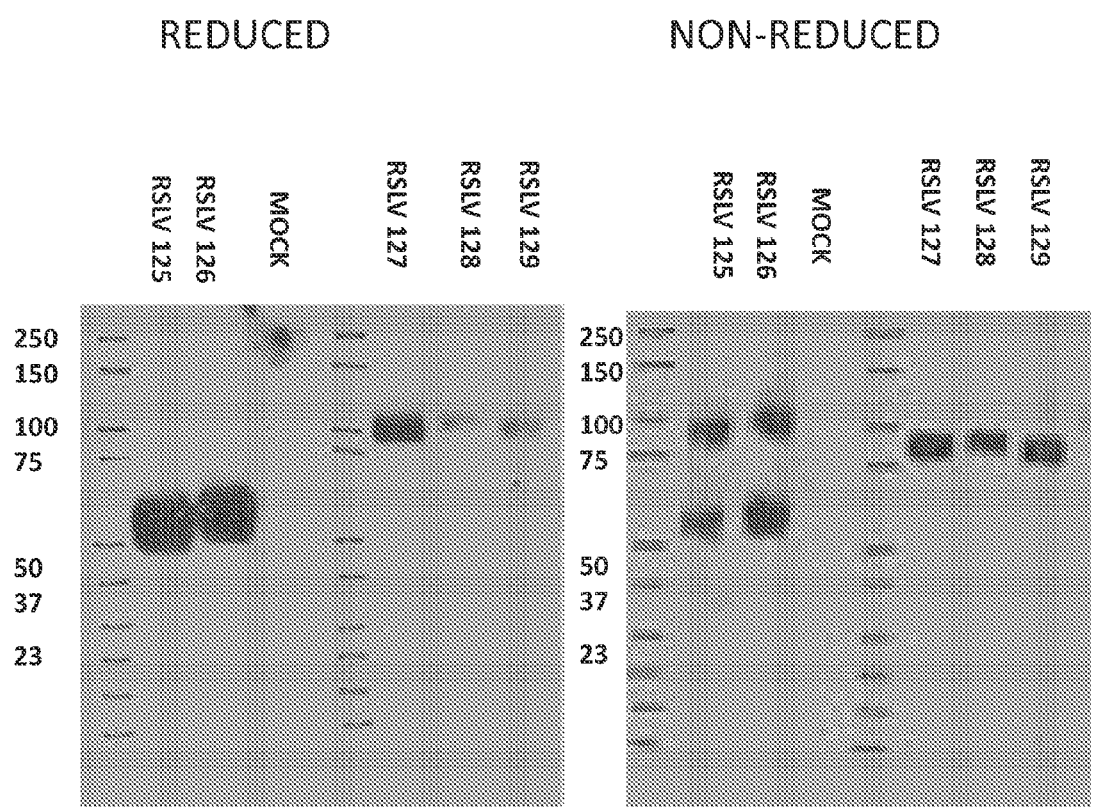
FIG. 9 shows a Western Blot on COS transfection supernatants from RSLV 125-129 constructs (SEQ ID NOs 208-217).

Example 10: Western Blot on RSLV 125-129 Fusion Proteins Expressed from COS7 Transfections FIG. 9 shows a Western Blot on COS transfection supernatants from RSLV 125-129 constructs. Expression plasmids containing RSLV 125, 126, 127, 128, or 129 were transfected into COS7 cells using Polyfect transfection reagent and supernatants harvested after 48 hours. In addition to the single nuclease molecules contained in RSLV 125 and 126, more complex multi-nuclease fusion proteins were also expressed from COS cell transient transfections, encoded by RSLV 127, 128, and 129. Western blot analysis was performed on supernatants from transient transfectants. The molecules shown in FIG. 9 contain human RNase1 fused to the human SSS IgG1 hinge, and Ig G1 P238S-P331S Fc domain or include human RNase1 (wild type) fused to the SSS hinge-(P238S-331S)CH2-CH3 Fc domain of human IgG1, followed by a novel linker containing an N-linked glycosylation site to protect the linker domain from protease cleavage, and the mutant allele G105R-A114F form of human DNase1 at the carboxy terminus of the molecule. In addition, RSLV 127 encodes the human DNase1 mutant above at the amino terminus and the RNase 1 WT at the carboxy terminus of the mutant-Ig tail. COS supernatants were harvested after 72 hours and 0.5 ml samples were immunoprecipitated overnight at 4° C. with 100 ul protein A-agarose beads. Protein A beads were centrifuged and washed twice in PBS prior to resuspending in SDS-PAGE loading buffer, for NuPAGE gels—reducing or nonreducing LDS sample buffer (Invitrogen, Carlsbad, Calif.). Samples were heated according to manufacturer's instructions, protein A beads centrifuged to pellet, and sample buffer loaded onto 5-12% NuPAGE gradient gels. Samples were electrophoresed at 150 volts for 1.5-2 hours, and gels blotted to nitrocellulose membranes at 30 mAmp for 1 hour. Western blots were blocked in TBS/5% non-fat milk overnight. Blots were incubated with 1:2500 HRP (horseradish peroxidase) conjugated goat anti-human IgG (Fc specific, Jackson Immunoresearch) for 1.5 hours at room temperature, washed in PBS/0.5% Tween20 five or more times, and blots developed using ECL reagent. The results demonstrate that the construction of the nuclease Fc fusion proteins was successful and the proteins are readily expressed from COS cells. Furthermore analyzing the reducing and non-reducing profiles for these nuclease Fc fusion proteins confirms that the DNA constructs encode proteins of the appropriate molecular weight. The pattern on non-reducing SDS-PAGE confirms the di-sulfide bonding properties of the proteins are consistent with the expected behavior of the constructs.

Figure 10:
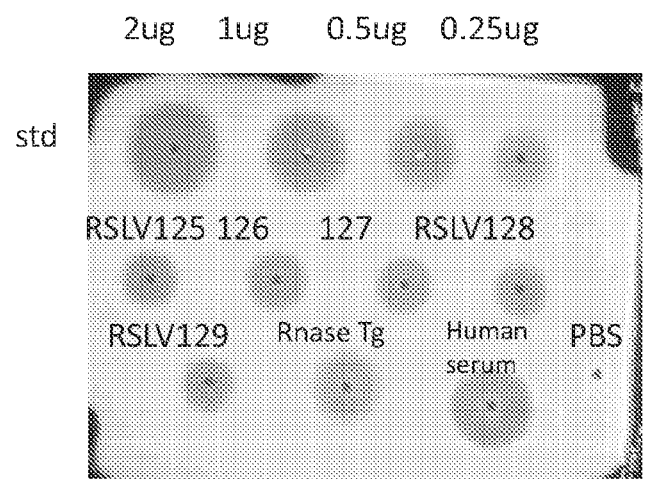
FIG. 10 shows SRED analysis comparing aliquots of protein A purified proteins from RSLV transfected COS supernatants.

Example 11: SRED Analysis of Affinity Purified Proteins from COS7 Transfectants FIG. 10 shows SRED analysis comparing aliquots of protein A purified proteins from RSLV transfected COS supernatants from Example 10. A 2% agarose gel was prepared with distilled water. Poly-IC (Sigma) was dissolved in distilled water at 3 mg/ml. The gel plate was prepared as follows: 1.5 ml reaction buffer (0.2M Tris-HCl pH 7.0, 40 mM EDTA and 0.1 mg/ml ethidium bromide), 1 ml Poly-IC and 0.5 ml water were place in the tube and maintained at 50° C. for 5 min. 3 ml of the agarose (kept at 50° C.) was added to the tube. The mixture was immediately poured onto a glass plate. Sampling wells were punched in the gel. 2 μl of each control, serum sample, or affinity purified RSLV proteins, was loaded into wells and the gel was incubated at 37° C. for 4 hours in the moist chamber. Then the gel was incubated in a buffer (20 mM sodium acetate pH5.2, 20 mg/ml ethidium bromide) on ice for 30 min. and read under UV. Gels were photographed on a UV transilluminator using a Kodak digital camera DC290 system equipped with ethidium bromide filters and analyzed using Kodak Molecular Imaging software. The results from the RNase enzymatic activity assay indicate that the constructs all contain catalytically active RNase moieties

Example 12: In Gel DNase Activity of RSLV Nuclease Molecules

Figure 11A:
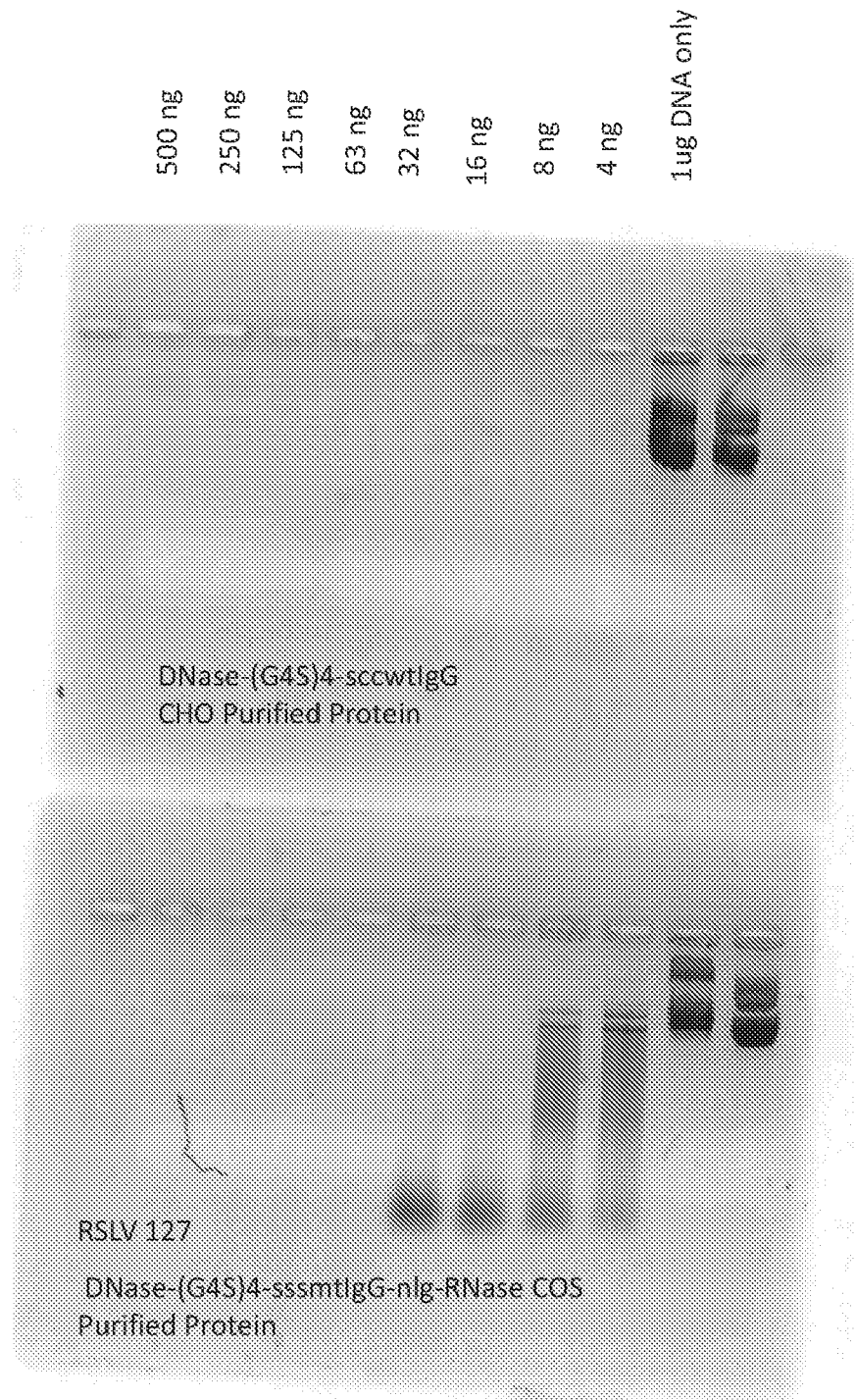
FIG. 11a-c shows results from a DNase nuclease activity assay performed on protein A purified protein from COST supernatants transfected with RSLV fusion plasmids.
Figure 11B:
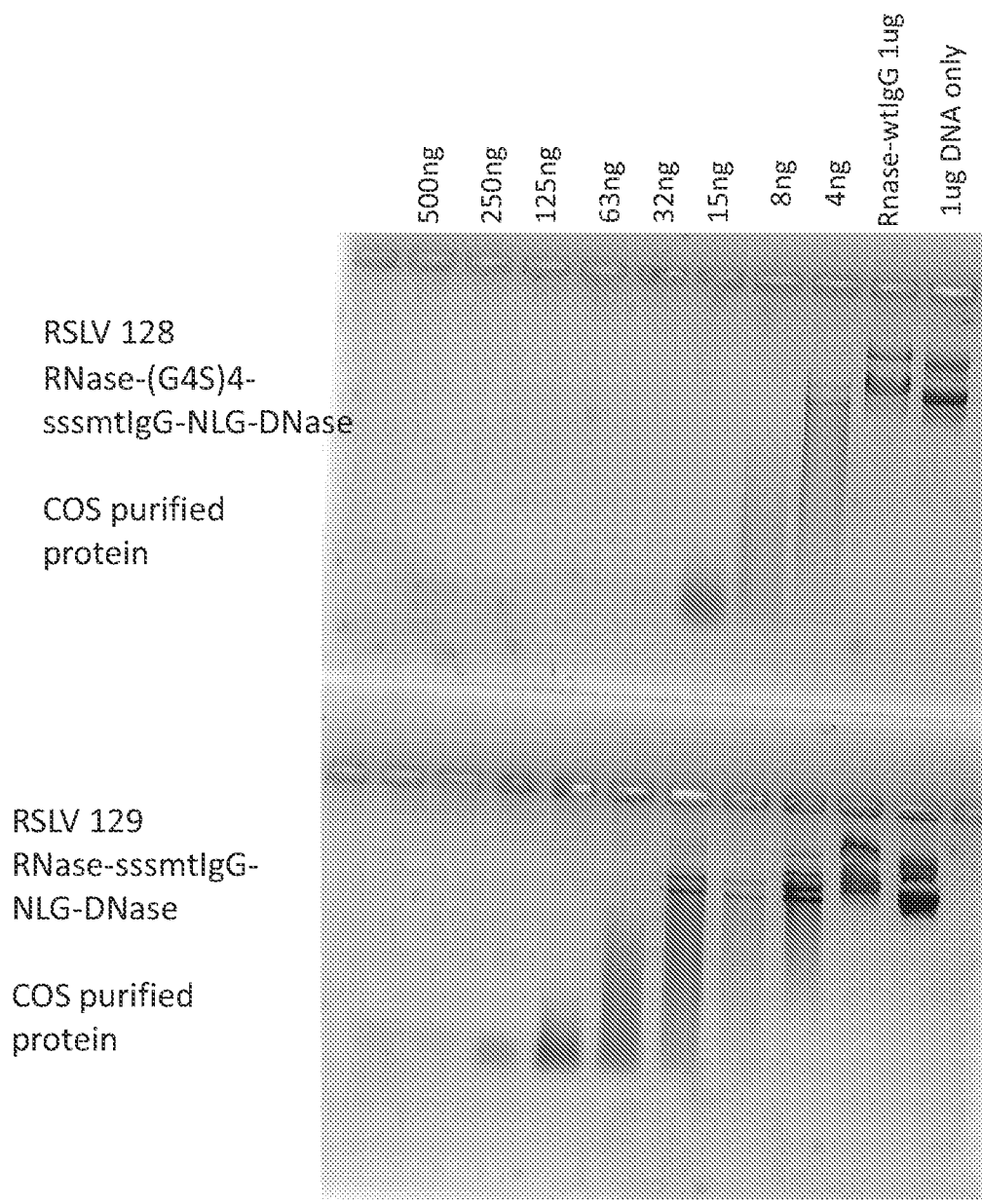
Figure 11C:
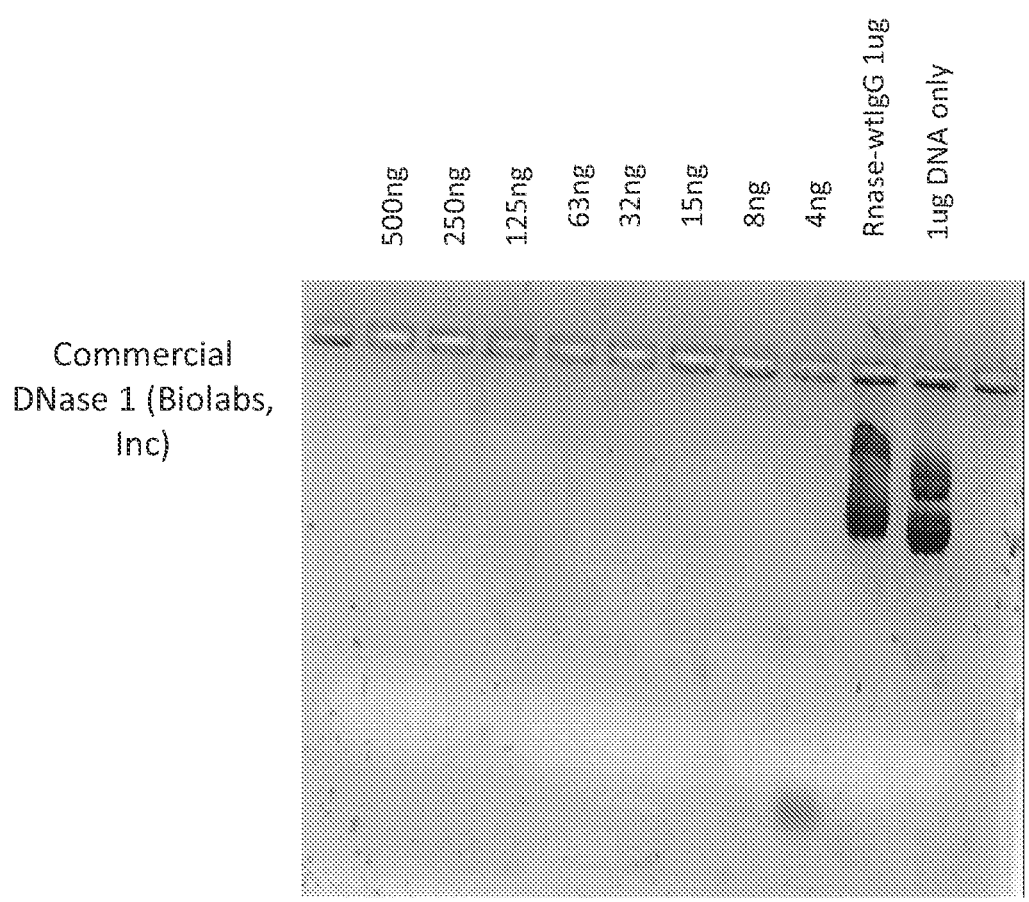

FIG. 11 shows results from a DNase nuclease activity assay performed on protein A purified protein from COST supernatants transfected with the RSLV fusion plasmids in Example 10. FIG. 11 shows five panels (11a, 11b, 11c), with each gel panel showing the digestion pattern with decreasing amounts of the indicated fusion protein and 1 microgram of plasmid DNA. Each protein was serially diluted in two-fold increments in nuclease free water from 500 ng to 4 ng of enzyme. To each sample, was added 1 ug PDG plasmid DNA, incubated for 30 minutes at 37 degrees. One-half of each sample was subjected to agarose gel electrophoresis for 30 minutes at 100 volts using 1.2% TAE agarose gels. FIG. 11c shows the results of an in gel DNase enzyme activity assay using commercially available DNase 1 (Biolabs, Inc.). The far right lane is a negative control with the DNA alone and no enzyme, the lane to the left of that is another negative control, this is an RNase-Ig molecule which has RNase activity but no DNase activity, as expected the plasmid DNA remains intact and is not digested in both cases. The results demonstrate that commercially available DNase1 enzyme is highly active and digests all the DNA at most of the concentrations tested. The results in FIGS. 11a and 11b show the DNase activity of four different nuclease Fc fusion constructs. The top panel in FIG. 11a shows the ability of a DNase-Ig fusion protein to digest the plasmid DNA, as is apparent from the gel, this enzyme digests all the DNA at all concentrations tested is as active, or more active than commercially available DNase 1. In the lower panel of FIG. 11a is a bi-specific nuclease Fc fusion protein with the DNase on the amino terminus of the Fc (SED ID 65-66) and it also has robust DNase enzymatic activity, but a little less than the DNase-Ig in the upper panel of FIG. 11a. The top panel of FIG. 11b shows the DNase enzymatic activity of another bi-specific nuclease, this Fc fusion protein has the DNase on the C-terminus of the Fc connected to the Fc via a specially engineered NLG linker (SEQ ID 67-68). As is apparent by the data this enzyme also has robust DNase enzymatic activity and appears to be more active than the other bi-specific nucleases examined here. The bottom panel of FIG. 11b shows the DNase enzymatic activity of another bi-specific nuclease molecule that is lacking the (G4S)4 linker (SEQ ID NO: 108) connecting the RNase module with the Fc (SEQ ID 69-70). This bi-specific nuclease also has good DNase activity but it appears to be somewhat less than the other two bi-specific nuclease Fc fusion proteins shown in this experiment. This data suggests that all of the bi-specific nucleases have good DNase activity, which is an unexpected given the past efforts of others in this regard (Dwyer et al. JBC; Vol 271, No. 14; pp 9738-9743). Furthermore the position of the DNase in the construct as well as the linker length and composition connecting the DNase to the Fc are critical in creating a highly active DNase enzyme in the context of a bi-specific nuclease Fc fusion protein.

Example 13: Analysis of Enzyme Kinetics

Figure 12:
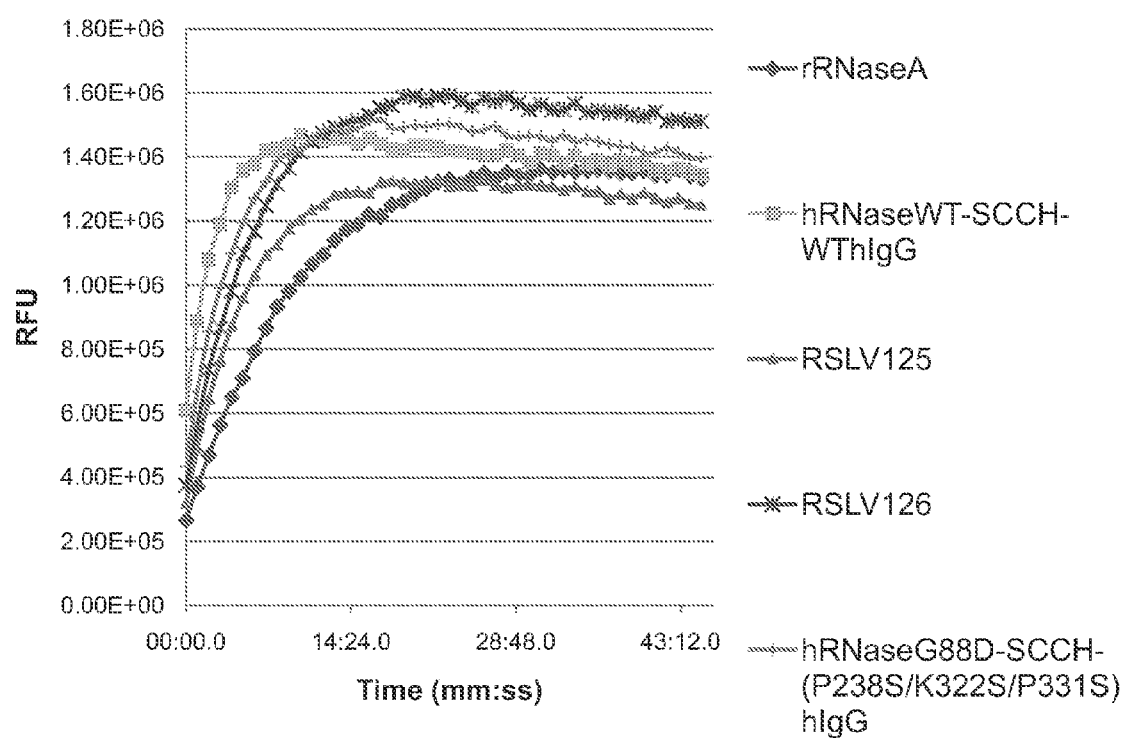
FIG. 12 shows the RFU (relative fluorescence units) as a function of time for each protein.

FIGS. 12-13 show results from a kinetic fluorescence enzyme activity assay comparing the RNase enzyme activity of recombinant RNase A (Ambion), RSLV 125, RSLV 126, hRNase WT-SCCH-WThIgG1, and hRNaseG88D-SCCH—(P238S/K322S/P331S)hIgG1. To further define the functional characteristics of the bivalent mRNase-Ig fusion protein, we studied the enzyme kinetics of different nuclease fusion proteins using the RNase Alert Substrate (Ambion/IDT) and fluorescence was quantified with a Biotek Synergy2 microplate reader. Data was analyzed using Gen5 software (Biotek Instruments, Inc., Winooski, Vt.). Relative fluorescence units as a function of time were assayed very minute over the course of a 45 minute experiment incubated at 37 C according to manufacturer's instructions, using decreasing enzyme concentrations starting from 10 pg/ul and serially diluting to 0.1 pg/ul by 0.67x increments. Each sample included a fixed concentration of RNase Alert substrate (200 nM) in 1xRNase Alert Reaction Buffer.

FIG. 12 shows the RFU (relative fluorescence units) versus time for each protein at equimolar concentrations, with the test proteins at 4.5 pg/ul or 4.5 ng/ml, and the recombinant RNaseA control at 1.3 pg/ul in the presence of 200 nM RNase Alert substrate.

FIG. 13 shows a Lineweaver Burk plot of the different molecules. In order to estimate the Vmax and Km, RNase Alert kinetic fluorescence assays were set up using 105 pM enzyme, and the substrate concentration was decreased from 200 nM to 50 pM in four fold increments. Thus, the enzyme concentration was fixed and substrate concentration titrated in this series of experiments. The data show the Lineweaver Burk plots generated for the different fusion proteins under these conditions. Taken together the data in FIGS. 12 and 13 demonstrate that the RNase moieties are highly active in the three RNase Fc fusion proteins constructed and tested here.

Example 14: Assessment of In Vitro Cytotoxicity Against Human THP-1 Cell Line

Figure 15:
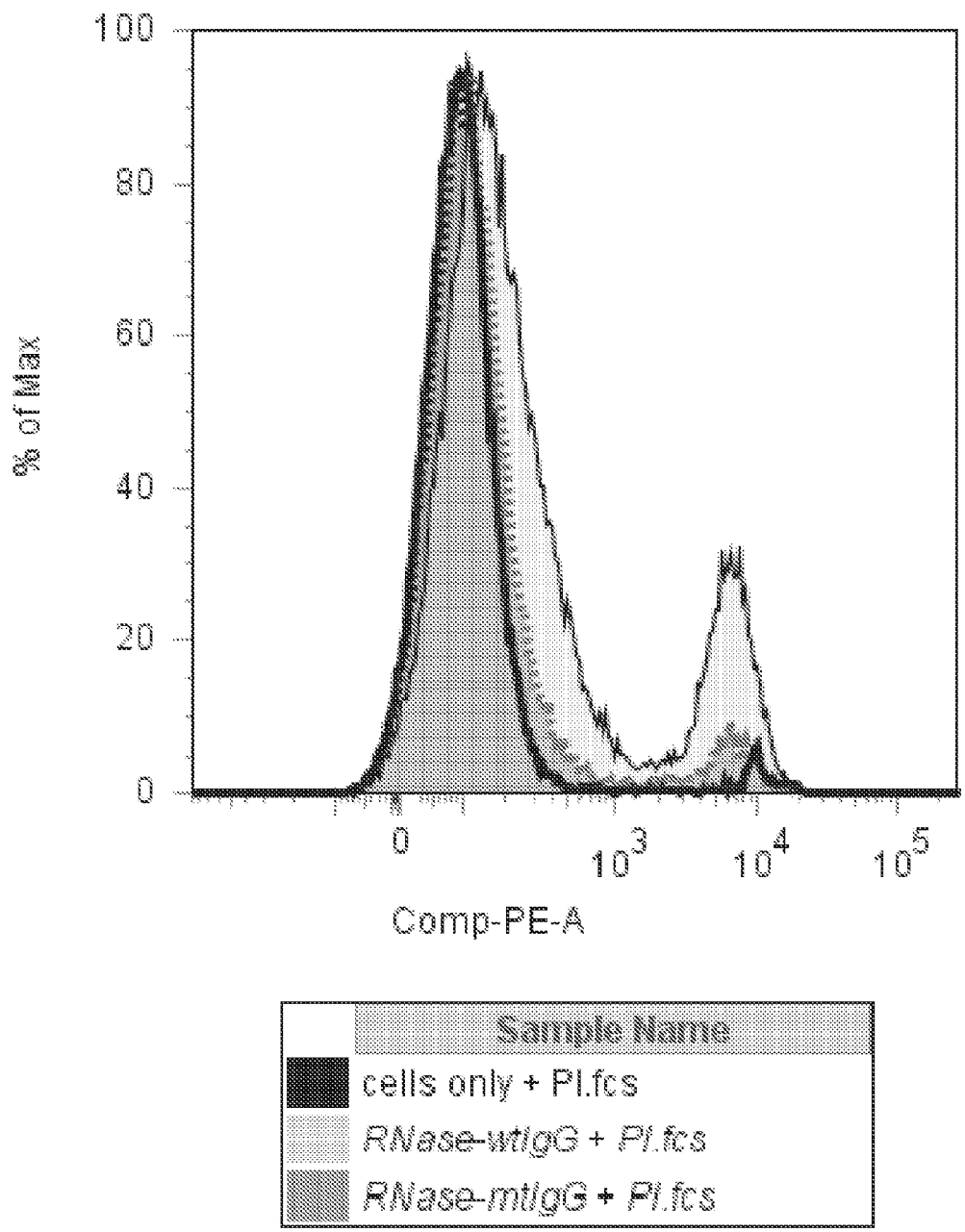
FIG. 15 shows histogram overlays of THP-1 stained cells after 72 hours.

FIGS. 14-15 show results of in vitro studies analyzing the effects of RNaseIg fusion proteins with wild type or mutant (including SCC, P238S, P331S)-IgG Fc domains on the survival of a human monocytic cell line, THP 1. The THP 1 cells were maintained in logarithmic growth in RPMI/10% FBS prior to harvest for the assays. Cells were greater than 98% viable prior to use in cytotoxicity assays. THP1 cells were plated in 96 well plates at a cell density of 1×10e6 c/ml, or 100,000 cells per well. Hybrid nuclease proteins were added to successive wells using a two-fold serial dilution series starting at 5 micrograms/ml and ending with 0.01 microgram/ml fusion protein per reaction. In this experiment an RNase-Fc fusion protein with a wild type IgG1 Fc (wtRNasewtIgG) was compared with an RNase-Fc with a mutant Fc (P238S, P331S) that had significantly reduced Fc receptor binding and internalization (mtRNasemgIgG), with respect to their ability to induce cytotoxicity in the cultured THP1 cells. Reactions were incubated in 96 well plates for three days at 37° C., 5% CO2 prior to cell harvest and analysis. After three days, cells were harvested by centrifugation at 1000 rpm, washed in PBS/2% FBS, and incubated with FITC Annexin V apoptosis detection kit reagents (#556547, Becton Dickinson/Pharmingen), according to manufacturer's instructions. Cells were washed with 100 microliters cold binding buffer supplied with the kit, and annexin V-FITC/Propidium Iodide (PI) added at 1:100 in 100 ul binding buffer. Samples were incubated on ice for 20 minutes, after which 400 μl additional binding buffer was added to each sample. Stained samples were analyzed by flow cytometry using a FACS Canto (Becton Dickinson) and data analyzed using Flowjo software (Treestar, Ashland, Oreg.).

FIG. 14 shows the effect of RNase Fc fusion proteins with a wild type or mutant Fc domain on cell death as measured by two methods, Annexin V binding (top panel) and propidium iodide binding (bottom panel), both are sensitive measure of cell death. This experiment demonstrates that binding of the RNase fusion protein with mutant Fc (P238S, P331S) has reduced binding to Fc recptors on the surface of the THP1 cells, and subsequent internalization of the protein. The results show a significant decrease in cell death by the RNase-Fc mutant compared to RNase-wild type Fc fusion proteins (e.g., an approximately 3-fold decrease at 1.25 μg/ml of protein). FIG. 15 presents the results of fluorescence-activated cell sorting (FACS) experiments to examine the cytotoxicity of RNase Fc fusions constructs with a wild type or mutant Fc domain (RNase-wtIgG or RNase-mtIgG respectively). The data demonstrate a significant decrease in the number of dead cells when the THP1 cells are incubated with the RNase Fc construct with a mutant Fc (smaller peak size to the right of the graph for the RNase Fc mutant compared to RNase-wtIgG). These data show an approximately 3- to 5-fold decrease in cell death by the RNase Fc mutant compared to wild type. These and other experiments examining Fc receptor binding clearly show that in the presence of cells bearing Fc receptors the RNase Fc construct with a mutated Fc region has reduced binding to Fc receptors and less internalization by cells, resulting in less cell death due to the RNase activity of the construct. Such constructs are particularly useful in treating autoimmune diseases as it may be undesirable to use a protein therapeutic which is cytotoxic to Fc receptor bearing cells.

Figure 16:
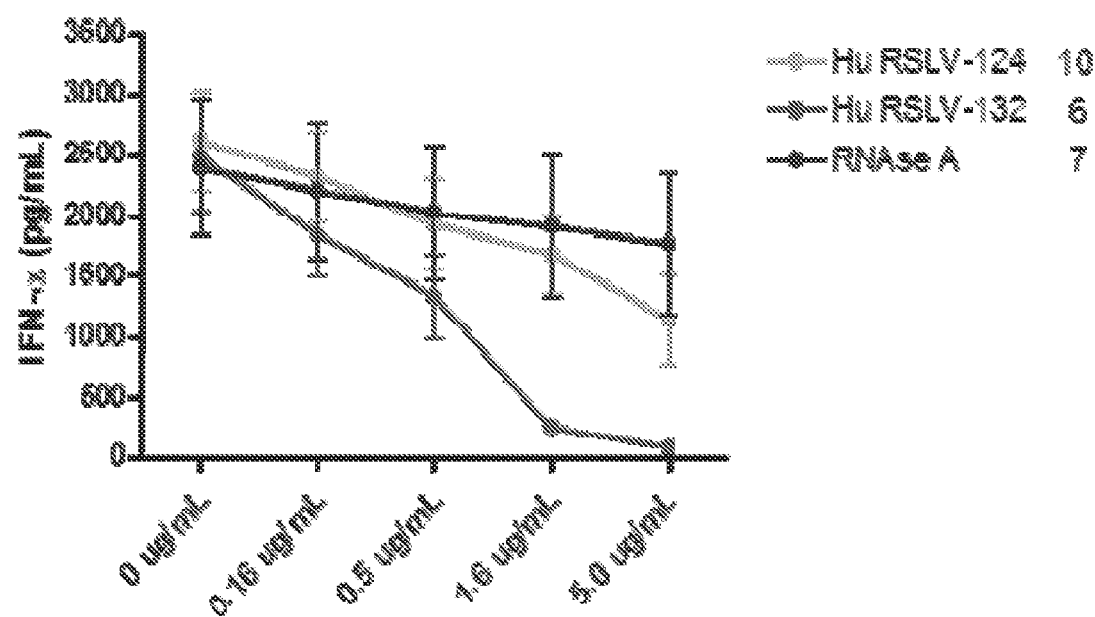
FIG. 16 shows the ability of RSLV-132 to inhibit interferon-α production induced by SLE patient immune complexes.

Example 15: IFN-Alpha Production by Human PBMCs is Inhibited by RSLV-132 Addition to Cultures In Vitro RSLV 132 addition abolished the induction of interferon-α from human peripheral blood mononuclear cells stimulated using immune complexes formed with serum from three SLE patients plus necrotic cell extract (NCE) (FIG. 16). To measure the ability of RSLV-132 to bind to and degrade RNA contained in the immune complexes of lupus patients, and in vitro bioassay was developed. The experiment involves the formation of immune complexes in vitro using the autoantibodies from lupus patients and NCE from cultured human cells (U937). Combining the lupus patient serum with the NCE results in the formation of immune complexes (IC) which are very potenti inducers of interferon, normal human serum does not stimulate the production of interferon. The IC are incubated with normal human peripheral blood mononuclear cells (PBMC's) as reporter cells. The production of interferon by the reporter cell sis measured using an interferon-α ELISA. Reporter cells were obtained from normal volunteers by Ficoll density gradient centrifugation. Lupus patient or healthy normal volunteer serum was obtained under University of Washington Institutional Rreview Board #HSD No. 3971, the serum was diluted 1/1000 and added to 10% (v/v) of necrotic cell extract (NCE) derived from cultured U937 cells as above. Diluted lupus patient or normal volunteer serum was incubated with the NCE for 15 minutes at room temperature, the resulting IC's were incubated with or without various doses of RSLV-132, RSLV-124, or wild type RNase for 15 minutes then incubated with normal PBMC's for 20 hours in the presence of 500 U/mL Universal IFN followed by measurement of the amount of IFN secreted from the PBMC culture. Serum was obtained from three (3) different lupus patients with various degrees of disease activity ranging from mild to active. The NCE was incubated with either lupus patient serum or healthy normal volunteer serum at room temperature for 15 minutes followed by 20 hour incubation with PBMC's. IFN-α was quantitated by ELISA where IFN-α is captured using a mouse MAb against human IFN alpha (MMHA-11) [PBL Biomedical Laboratories, product #2112-1] and was detected using a rabbit polyclonal antibody against IFN alpha [PBL Biomedical Laboratories, product #31101-1], followed by development using anti-rabbit HRP [Jackson Immuno Research, product #711-035-152] and TMB substrate. In some cases prior to addition of the NCE to the PBMC's, the test article (RSLV-124 or RSLV-132) was added at concentrations of 0.16, 0.5, 1.6 and 5.0 ug/mL or RNAse was added at concentrations of 0.05, 0.16, 0.5 and 1.6 ug/mL (equimolar) to the NCE. The ability of the lupus patient serum to stimulate production of IFN from the PBMC's was reduced by approximately 50% with the addition of 5.0 ug/mL RSLV-124. This inhibition mirrored that of an equimolar quantity of RNAse. Addition of the same concentration of huRSLV-132 was as or more effective at inhibiting IFN than RSLV-124, with almost completely abolished IFN production with the addition of 5.0 ug/mL of huRSLV-132. When combined with NCE, lupus patient anti-RNA/DNA antibodies are potent induces of IFN from freshly isolated PBMC's. Serum from normal volunteers does not have this same ability to stimulate IFN production from the reporter cells. This data indicates that the auto-antibodies circulating in lupus patient serum are able to form immune complexes which presumably trigger TLR7 and the subsequent production of IFN. The exact type and subtypes of IFN were not analyzed. This data indicates that RSLV-132 binds to its molecular target, the RNA associated with the lupus patient IC's and potently degrades it, thereby preventing the stimulation of IFN from the PBMC's (FIG. 16). RSLV-132 appears to be more active than RSLV-124 in this assay.

Figure 17:
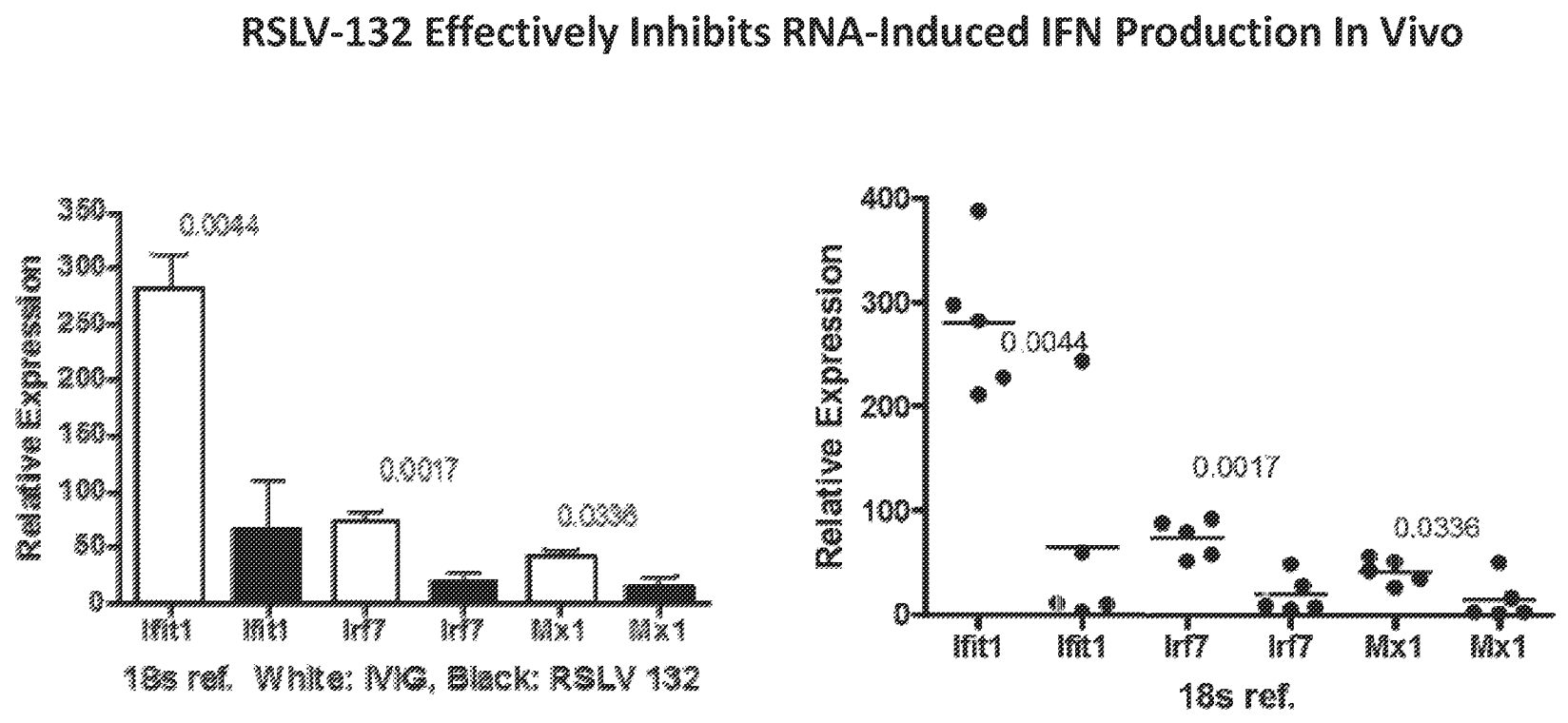

Example 16: RSLV-132 is a Potent In Vivo Inhibitor of RNA-Induced Interferon Activation To assess the ability of RSLV-132 to bind to and degrade RNA in the circulation of the mouse, a pharmacodynamic model was developed using an RNA mimetic polyinosinic:polycytidilic acid (poly I:C) which is a robust activator of the interferon pathway. Poly(I:C) is a mismatched double-stranded RNA with one strand being a polymer of inosinic acid, the other a polymer of cytidylic acid. It is know to interact with toll-like receptor 3 (TLR3) which is expressed in the membrane of B cells, macrophages and dendritic cells. Poly(I:C) is available from Invitrogen. The effects of poly I:C can be quantitated by measuring the expression levels of interferon stimulated genes in the spleen of the mouse following administration. On day zero 10 B6 mice, three months of age, were treated with either RSLV-132 (250 ug per mouse) or intravenous immunoglobulin (IVIG) (Privigen, Behring) (250 ug per mouse) as a control, both via intraperitoneal injection. Twenty hours after injection of RSLV-132 or IVIG, poly(I:C) was injected into the mice at 200 ug per mouse intraperitoneally. Two hours later, the animals were sacrificed by CO2 exposure, the spleens were collected into RNAlater (Qiagen) and stored at −80 C for later study of the expression of Interferon stimulated genes (ISGs). Spleen samples were subjected to study of the expression of ISGs, including Ifit1 (Interferon-induced protein with tetratricopeptide repeats 1 (UniProt Q64282)), Irf7 (Interferon regulatory factor 7 (UniProt P70434)) and Mx1 gene by qPCR. The results from these experiments demonstrate that intraperitoneal injection of RSLV-132 results in serum concentrations of RSLV-132 which are able to bind to circulating poly (I:C) and effectively degrade the RNA mimetic, thereby effectively preventing stimulation of the Interferon pathway and the three ISG's monitored (FIG. 17).

Example 17. Analysis of Enzyme Kinetics for RSLV-132 and RSLV-133

Figure 18:
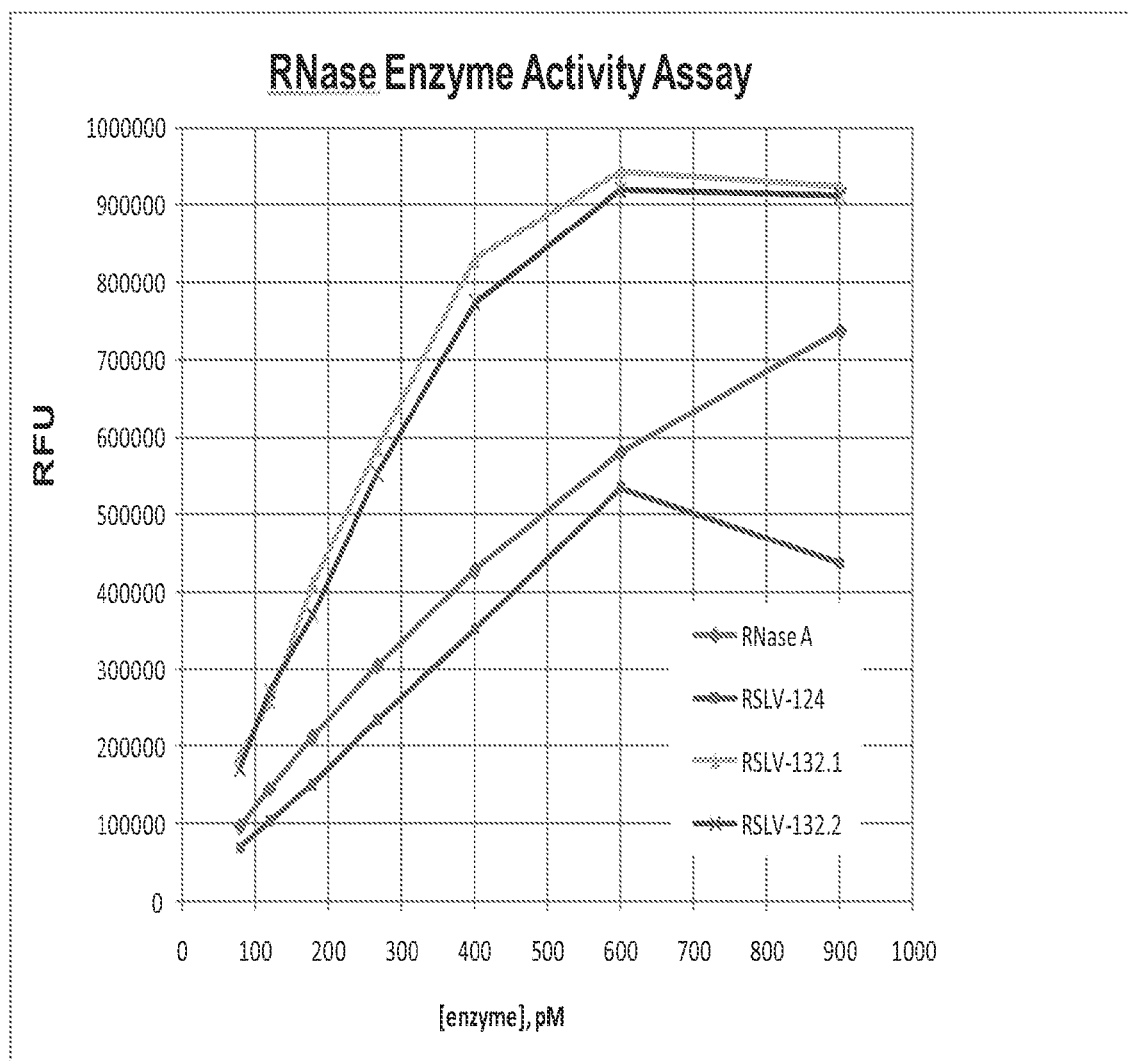
FIG. 18 shows an RNase enzymatic activity assay of two production lots of RSLV-132 having been stored for up to 8 weeks at 4 C, compared to wild type RNase and RSLV-124.

RSLV-132 and RSLV-133 were transiently expressed in CHO cells and purified using protein-A. The RNase activity of these RNase Fc fusion proteins was quantitated using the RNaseAlert QC kit from Ambion (Cat #AM1966). Various amounts of the RNase Fc fusion protein were used and the results shown in FIG. 18 in relative fluorescence units (RFU's) over time. The results demonstrate that RSLV-132 is a highly active RNase enzyme, and has increased RNase activity relative to other RNase Fc fusion constructs such as RSLV-124 and wild type RNase For example using equal amounts (400 pM) of RSLV132 and RSLV-124 yields more than twice the RFU's (80,000 vs. 35,000) for RSLV-132 vs. RSLV-124. In addition, two production lots were tested for their stability at 4 C. RSLV-132.1 was stored at 4 C for 8 weeks prior to this experiment and RSLV-132.2 was stored at −80 C and thawed just prior to testing, demonstrating that the protein is stable at 4 C for up to 2 months. The stability of the drug and increased catalytic activity may provide increased efficacy in a therapeutic setting.

Figure 19:
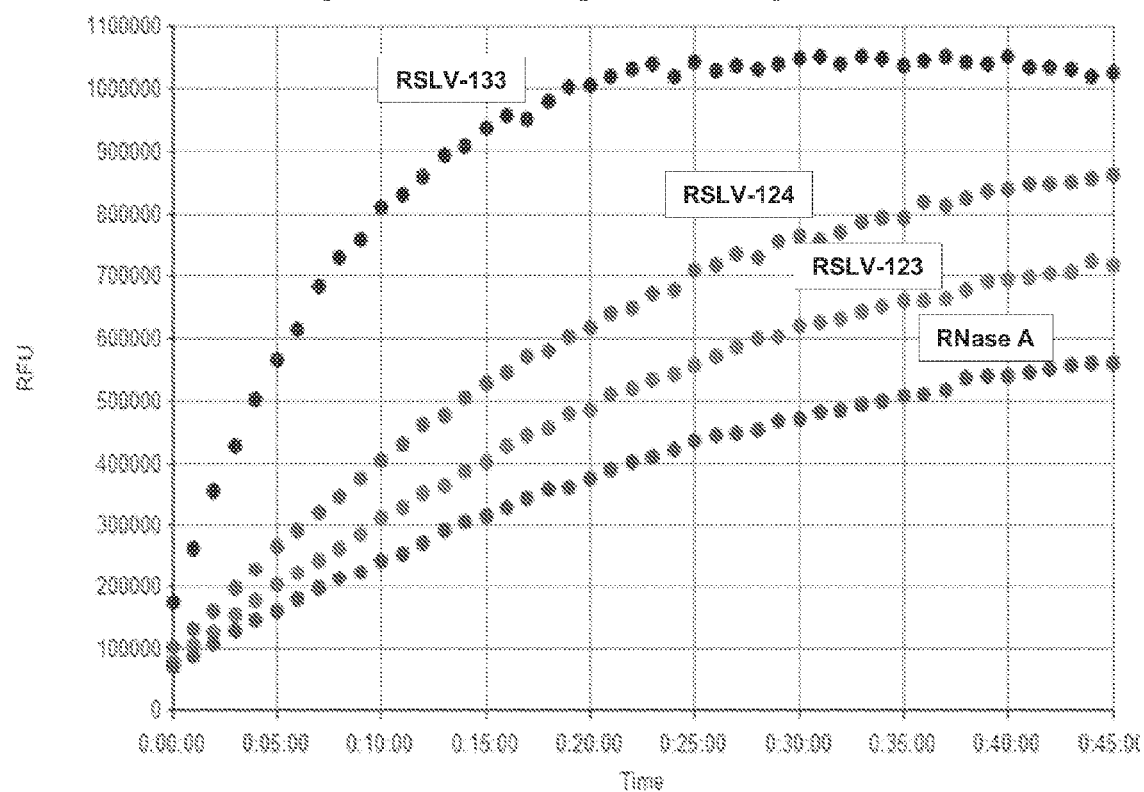
FIG. 19 shows an RNase enzymatic activity assay of RSLV-133, RSLV-123 and RSLV-124 relative to RNase A as measured in RFUs over time.
Figure 20:
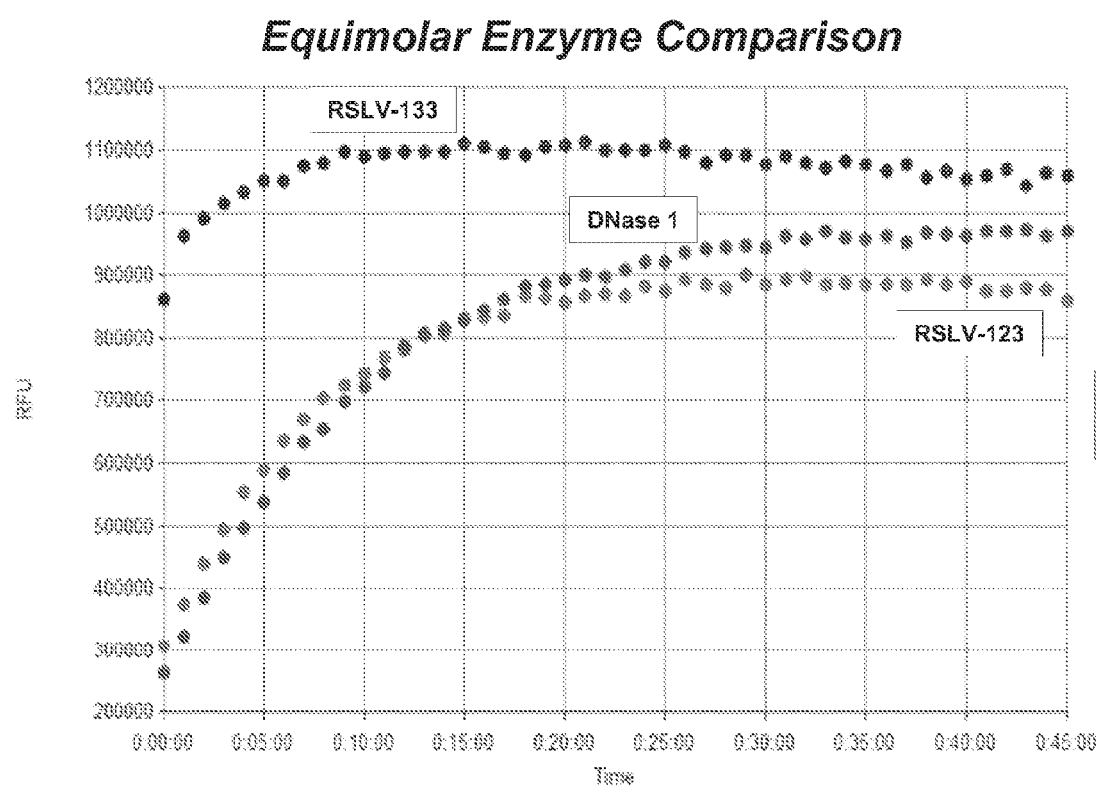
FIG. 20 shows a DNase enzymatic activity assay of RSLV-133 and RSLV-123 relative to DNase 1 as measured in RFUs over time.
Figure 21:
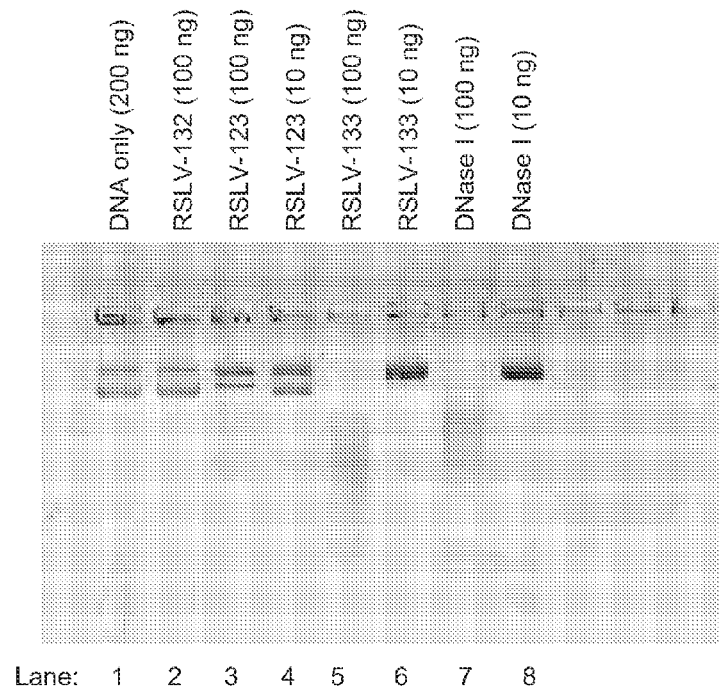
FIG. 21 shows the results of an in-gel digestion experiment comparing the ability of RSLV-133 to digest DNA relative to RSLV-123 and wild type DNase 1.

FIG. 19 shows the RNase enzymatic activity in RFUs over time, comparing the amount of RNase activity of the bi-specific RSLV-133 molecule with the monospecific RSLV-132, and wild type RNase. As demonstrated in FIG. 19 the RSLV-133 molecule has significantly increased RNase activity relative to the monospecific RSLV-124 molecule or, an earlier bispecific nuclease Fc, RSLV-123, or wild type RNase, yielding greater than 2-fold more RFU's with an equal amount of protein. FIG. 20 show the results of a DNase enzymatic activity assay of the RLSV-133 molecule in comparison to RSLV-123, a previous bi-specific nuclease construct, and wild type DNase. In this experiment DNase enzymatic activity was quantitated using the DNase-Alert Kit from Integrated DNA Technologies, Cleavage of the DNA substrate yielded a fluorescent emission which was quantitated using a Synergy2 Multi-Mode Microplate Reader (BioTek Instruments, Inc., Winooski, Vt.). FIG. 20 shows the RFU's of DNase enzymatic activity over time for RSLV-133, RSLV-123, or wild type DNase. The results of the experiment demonstrate that RSLV-133 has increased DNase activity relative to wild type DNase and RSLV-123, the earlier bi-specific nuclease molecule, yielding more than 3-fold more DNase activity in the linear range of the experiment. FIG. 21 demonstrates the ability of the RSLV-133 molecule to digest DNA in an in-gel digestion experiment. The results show that RSLV-133 is able to digest DNA in this assay as effectively as wild type DNase (compare lanes 5&7). Given the relative molecular weights of RSLV-133 and wild type DNase it appears that RSLV-133 is more effective in digesting DNA in this assay as well.

Example 18: RSLV-132 Demonstrates Decreased Fc Receptor Binding

Figure 22:
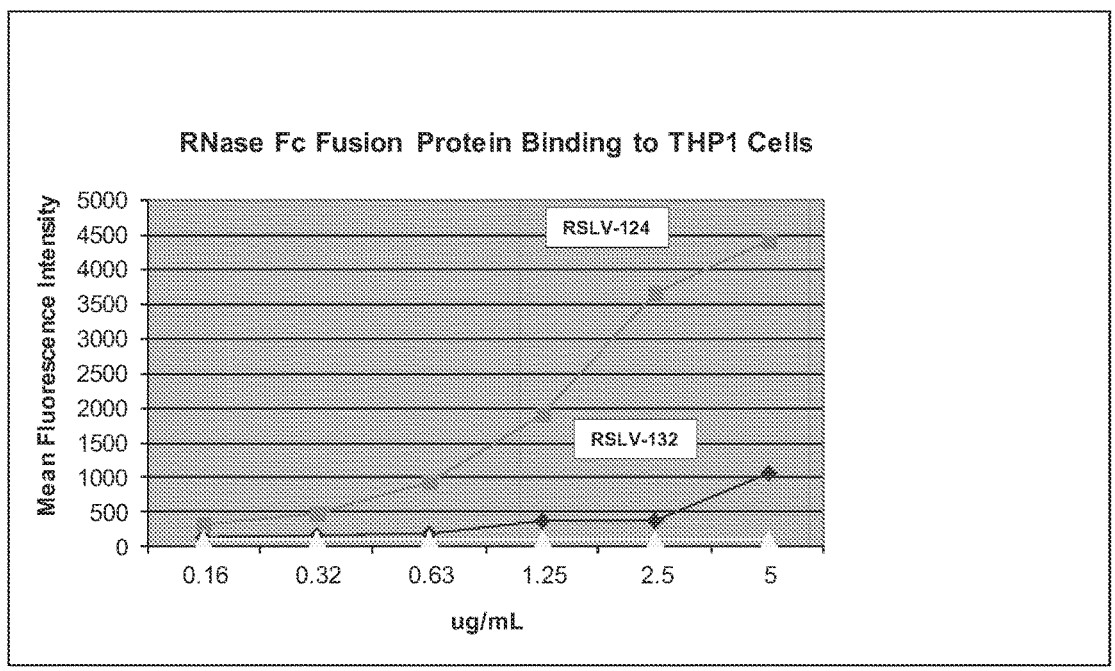
FIG. 22 shows binding of RSLV-124 and RSLV-132 to Fc-receptor bearing THP1 cells by FACS analysis measuring mean fluorescence intensity.

To examine the ability of RNase Fc fusion proteins to bind Fc receptors in vitro, RSLV124 (wild type Fc domain) and RSLV-132 (mutant Fc domain; P238S/P331S) were incubated with an Fc bearing human myeloid cell line, THP1 and the specific binding to the cells was quantitated by fluorescence-activated cell sorting (FACS) analysis. RLSV-124 and RSLV-132 were fluorescently labeled using alexa fluor dye AF-647 from Invitrogen (Cat # A20006). After dialyzing the RNase Fc fusion proteins to remove the unbound dye, varying amounts of the labeled proteins were incubated with THP1 cells for one hour, the cells were washed stringently to remove unbound RNase Fc fusion protein, and the specifically bound protein was quantitated by FACS measuring mean fluorescence intensity. The results in FIG. 22 demonstrate that the RSLV-132 protein which has a mutant Fc domain has significantly less Fc receptor binding than RSLV-124 which has a wild type Fc domain, exhibiting greater than 4-fold reduction in Fc receptor binding This finding is consistent with our previous findings that RNase Fc fusion proteins with a mutant Fc domain (P238S/P331S) have significantly decreased cytotoxicity.

Example 19: In Vitro Assessment of Hybrid Nuclease Molecule Biological Activity

One or more hybrid nuclease molecules are purified, e.g., by affinity or ion exchange chromatography as previously described in the examples above. In some instances the hybrid nuclease molecule is a polypeptide. In some instances, the hybrid nuclease molecule includes one or more sequences from Table 1. In some instances, the hybrid nuclease molecule includes a nuclease domain linked to a mutant Fc domain. In some instances, the hybrid nuclease molecule includes a mutant Fc domain. In some instances, the mutant Fc domain comprises mutations in the hinge, CH2, and/or CH3 domains. In some instances, the mutant Fc domain comprises P238S and/or P331S, and may include mutations in one or more of the three hinge cysteines. In some instances, the mutant Fc domain comprises P238S and/or P331S, and/or mutations in the three hinge cysteines. In some instances, the mutant Fc domain comprises P238S and/or P331S, and/or mutations in the three hinge cysteines to SSS. In some instances, the mutant Fc domain comprises P238S and P331S and mutations in the three hinge cysteines. In some instances, the mutant Fc domain comprises P238S and P331S and SSS. In some instances the mutant Fc domain is shown in SEQ ID NOs 59, 60, 61. In some instances, the hybrid nuclease molecule is shown in SEQ ID NOs. Various linker domains (e.g., those described herein) can be used to link the Fc domains to nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. Molecules are assayed for the specific nuclease activity in vitro using qualitative assays to verify that they possess the desired nuclease function. Specific activities are generally then determined by fluorescence based kinetic assays utilizing substrates such as the RNase or DNase Alert Kit reagents, and a fluorescence plate reader set to take readings as a function of time. In addition, protein solutions are generally checked for endotoxin contamination using a commercially available kits, such as the Pyrotell Limulus Amebocyte Lysate (LAL) kit, 0.06 EU/ml detection limit from Cape Cod, Inc. (E. Palmouth, Mass.). Molecules are then assayed using a variety of in vitro assays for biological activity.

One series of in vitro assays will measure the effect of the molecules on cytokine production by human PBMC in response to various stimuli, in the presence or absence of the molecules in the cultures. Normal or patient human PBMC (approximately 1×10e6 cells) are cultured for 24, 48, or 96 hours depending on the assay. PBMC are cultured in the presence of stimuli such as TLR ligands, costimulatory antibodies, immune complexes, and normal or autoimmune sera. The effects of the molecules on cytokine production is measured using commercially available reagents, such as the antibody pair kits from Biolegend (San Diego, Calif.) for IL-6, IL-8, IL-10, IL-4, IFN-gamma, TNF-alpha. Culture supernatants from in vitro cultures are harvested at 24, 48 hours or later time points to determine the effects of the molcules on cytokine production. IFN-alpha production is measured using, e.g., anti-human IFN-alpha antibodies and standard curve reagents available from PBL interferon source (Piscataway, N.J.). A similar set of assays is performed using human lymphocyte subpopulations (isolated monocytes, B cells, pDCs, T cells, etc.); purified using, e.g., commercially available magnetic bead based isolation kits available from Miltenyi Biotech (Auburn, Calif.).

In addition, the effect of the molecules on expression of lymphocyte activation receptors such as CD5, CD23, CD69, CD80, CD86, and CD25 is assessed at various time points after stimulation. PBMC or isolated cell subpopulations are subjected to multi-color flow cytometry to determine how these molecules affect the expression of different receptors associated with immune cell activation.

Another set of assays will measure the effects of these molecules on the proliferation of different lymphocyte subpopulations in vitro. These assays will utilize, e.g., CFDA-SE staining (Invitrogen, Carlsbad, Calif.) of human PBMCs prior to stimulation. CFSE at 5 mM is diluted 1:3000 in PBS/0.5% BSA with 10e7-10e8 PBMCS or purified cell subsets and labeling reactions incubated for 3-4 minutes at 37 C prior to washing several times in RPMI/10% FBS to remove remaining CFSE. CFSE labeled cells are then incubated in co-culture reactions with various stimuli (TLR ligands, costimulatory antibodies, etc.) and the molecules for 4 days prior to analysis of cell proliferation by flow cytometry using dye-conjugated cell subpopulation specific antibodies.

Another assay will measure the cytotoxicity of one or more molecules. This assay will measure toxicity using Annexin 5 staining (e.g., Annexin 5-FITC). Cells of interest (e.g., monocytes or a monocyte cell line) are contacted with a hybrid nuclease molecule of interest (e.g., a hybrid nuclease molecule having a mutant Fc domain) or one or more controls. At various time points following contact, cells are separated from culture and stained with Annexin 5. The number of apoptotic or dead cells are then counted, e.g., using flow cytometry or a fluorescence microscope. Cells contacted with a hybrid nuclease molecule of interest show lower numbers of cells staining positive for Annexin 5 compared to positive controls.

The effect of these molecules on in vitro maturation of monocytes into DCs and macrophages is also assessed using both normal and patient PBMC samples.

The effectiveness of a hybrid nuclease molecule is demonstrated by comparing the results of an assay from cells treated with a hybrid nuclease molecule disclosed herein to the results of the assay from cells treated with control formulations. After treatment, the levels of the various markers (e.g., cytokines, cell-surface receptors, proliferation) described above are generally improved in an effective molecule-treated group relative to the marker levels existing prior to the treatment, or relative to the levels measured in a control group.

Example 20: Administration of a Hybrid Nuclease Molecule to a Mammal in Need Thereof Mammals (e.g., mice, rats, rodents, humans, guinea pigs) are used in the study. Mammals are administered (e.g., intravenously) one or more hybrid nuclease molecules comprising one or more sequences from Table 1 or a control. In some instances the hybrid nuclease molecule is a polypeptide. In some instances, the hybrid nuclease molecule includes one or more sequences from Table 1. In some instances, the hybrid nuclease molecule includes a nuclease domain linked to a mutant Fc domain. In some instances, the hybrid nuclease molecule includes a mutant Fc domain. In some instances, the mutant Fc domain comprises mutations in the hinge, CH2, and/or CH3 domains. In some instances, the mutant Fc domain comprises P238S and/or P331S, and may include mutations in one or more of the three hinge cysteines. In some instances, the mutant Fc domain comprises P238S and/or P331S, and/or mutations in the three hinge cysteines. In some instances, the mutant Fc domain comprises P238S and/or P331S, and/or mutations in the three hinge cysteines to SSS. In some instances, the mutant Fc domain comprises P238S and P331S and mutations in the three hinge cysteines. In some instances, the mutant Fc domain comprises P238S and P331S and SSS. In some instances the mutant Fc domain is shown in SEQ ID NOs 59, 60, 61. In some instances, the hybrid nuclease molecule is shown in SEQ ID NOs. Various linker domains (e.g., those described herein) can be used to link the Fc domains to nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. In some instances the hybrid nuclease molecule is formulated a pharmaceutically acceptable carrier. In some instances the molecule is formulated as described in the pharmaceutical compositions section above. The hybrid nuclease molecule targets RNase and/or DNase.

Multiple rounds of doses are used where deemed useful. Effects on IFN-alpha levels, IFN-alpha response gene levels, autoantibody titers, kidney function and pathology, and/or circulating immune complex levels are monitored in the mammals. Similar studies are performed with different treatment protocols and administration routes (e.g., intramuscular administration, etc.). The effectiveness of a hybrid nuclease molecule is demonstrated by comparing the IFN-alpha levels, IFN-alpha response gene levels, autoantibody titers, kidney function and pathology, and/or circulating immune complex levels in mammals treated with a hybrid nuclease molecule disclosed herein to mammals treated with control formulations.

In an example, a human subject in need of treatment is selected or identified. The subject can be in need of, e.g., reducing a cause or symptom of SLE. The identification of the subject can occur in a clinical setting, or elsewhere, e.g., in the subject's home through the subject's own use of a self-testing kit.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

In another example, a rodent subject in need of treatment is selected or identified. The identification of the subject can occur in a laboratory setting or elsewhere.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLES

TABLE 1

| SEQ ID NO: | DESCRIPTION | SEQUENCE (NUCLEOTIDE SEQUENCES ARE 5'-3') |
|---|---|---|
| 30 | g4s4lnk | agatctctccggaggaggtggctcaggtggtggaggatctggaggaggtgggag tggtggaggtggttctaccggtctcgag |

TABLE 1-continued

| SEQ ID NO: | DESCRIPTION | SEQUENCE (NUCLEOTIDE SEQUENCES ARE 5'-3') |
|---|---|---|
| 31 | G4S5-1 | agatctctccggaggaggtggctcaggtggtggaggatctggaggaggtggctc aggtggtggaggatctggaggaggtgggagtaccggtctcgag |
| 32 | G4S5-2 | agatctctccggaggaggtggctcaggtggtggaggatctggaggaggtggctc aggtggtggaggatctggaggaggtgggagtctcgag |
| 33 | 3'hRNaseG88D | gtcgacggagctagcagccccgtgaacgtgagcagccccagcgtgcaggatatc ccttccctgggcaaggaatcccgggccaagaaattccagcggcagcatatggac tcagacagttcccccagcagcagctccacctactgtaaccaaatgatgaggcgc cggaatatgacacaggggcggtgcaaaccagtgaacacctttgtgcacgagccc ctggtagatgtccagaatgtctgtttccaggaaaaggtcacctgcaagaacggg cagggcaactgctacaagagcaactccagcatgcacatcacagactgccgcctg acaaacgactccaggtaccccaactgtgcataccggaccagcccgaaggagaga cacatcattgtggcctgtgaagggagcccatatgtgccagtccactttgatgct tctgtggaggactctacctaataatctaga |
| 34 | hDNase1-3'-G105R; A114F | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcaggaac gacaccttcaaccgagagccattcattgtcaggttcttctcccggttcacagag gtcagggagtttgccattgttcccctgcatgcggccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagcccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactgcccaagccatcagt gaccactatccagtggaggtgatgctgaagtgataatctaga |
| 35 | hDNase1-3'-WT | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccagccattgtcaggttcttctcccggttcacagag gtcagggagtttgccattgttcccctgcatgcggccccggggacgcagtagcc gagatcgacgctctccatgacgtctacctggacgtccaagagaaatggggcttg gaggacgtcatgttgatgggcgacttcaatgcgggctgcagctatgtgagaccc tcccagtggtcatccatccgcctgtggacaagcccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactgcccaagccatcagt gaccactatccagtggaggtgatgctgaaatgataatctaga |
| 36 | hDNase1-3'A114F | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccattcattgtcaggttcttctcccggttcacagag gtcagggagtttgccattgttcccctgcatgcggccccggggacgcagtagcc gagatcgacgctctctatgacgtctacctggatgtccaagagaaatgggggctta gaggacgtcatgttgatgggcgacttcaatgcgggctgcagctatgtgagaccc tcccagtggtcatccatccgcctgtggacaagcccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactgcccaagccatcagt gaccactatccagtggaggtgatgctgaagtgataatctaga |
| 37 | hDNase1-5'-G105R; A114F | accggtctgaagatcgcagccttcaacatccagacatttggggagaccaagatg tccaatgccaccctcgtcagctacattgtgcagatcctgagccgctatgacatc gccctggtccaggaggtcagagacaaccacctgactgccgtgggaaactgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcaggaac gacaccttcaaccgagagccattcattgtcaggttcttctcccggttcacagag gtcaggggagtttgccattgttcccctgcatgcggccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagcccaccttccagtggctgatc cccgacagcgctgacaccacagctacacccacgcactgtgcctatgacaggatc |

TABLE 1-continued

| SEQ ID NO: DESCRIPTION | SEQUENCE (NUCLEOTIDE SEQUENCES ARE 5'-3') |
|---|---|
| | gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 38 hDNase1-5'-<br>WT | accggtctgaagatcgcagccttcaacatccagacatttggggagaccaagatg<br>tccaatgccaccctcgtcagctacattgtgcagatcctgagccgctatgacatc<br>gccctggtccaggaggtcagagacagccaccctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccagccattgtcaggttcttctcccggttcacagag<br>gtcaggagtttgccattgttcccctgcatgcggcccgggggacgcagtagcc<br>gagatcgacgctctctatgacgtctacctggatgtccaagagaaatggggcttg<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 39 hDNase1-5'-<br>A114F | accggtctgaagatcgcagccttcaacatccagacatttggggagaccaagatg<br>tccaatgccaccctcgtcagctacattgtgcagatcctgagccgctatgacatc<br>gccctggtccaggaggtcagagacagccaccctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccattcattgtcaggttcttctcccggttcacagag<br>gtcaggagtttgccattgttcccctgcatgcggcccgggggacgcagtagcc<br>gagatcgacgctctctatgacgtctacctggatgtccaagagaaatggggctta<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 40 hIgG1WT | agatctcgagcccaaatcttctgacaaaactcacacatgtccaccgtgcccagc<br>acctgaactcctggggggaccgtcagtcttcctcttccccccaaaacccaagga<br>caccctcatgatctcccggacccctgaggtcacatgcgtggtggtggacgtgag<br>ccacgaagaccctgaggtcaagttcaactggtacgtggacggcgtggaggtgca<br>taatgccaagacaaagccgcgggaggagcagtacaacagcacgtaccgtgtggt<br>cagcgtcctcaccgtcctgcaccaggactggctgaatggcaaggagtacaagtg<br>caaggtctccaacaaagcccctcccagcccccatcgagaaaaccatctccaaagc<br>caaagggcagccccgagaaccacaggtgtacaccctgcccccatcccgggatga<br>gctgaccaagaaccaggtcagcctgacctgcctggtcaaaggcttctatcccag<br>cgacatcgccgtggagtgggagagcaatgggcagccggagaacaactacaagac<br>cacgcctcccgtgctggactccgacggctccttcttcctctacagcaagctcac<br>cgtggacaagagcaggtggcagcaggggaacgtcttctcatgctccgtgatgca<br>tgaggctctgcacaaccactacacgcagaagagcctctctctgtctccgggtaa<br>atgataatctaga |
| 41 hDNase1 +<br>VK3 LP | gttaagcttgccaccatggaaacccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccaccctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcgggaacgacaccttcaaccgagagccagccattgtcaggttcttc<br>tcccggttcacagaggtcaggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaagtga |
| 42 hDNase1L3 | atgtcacgggagctggccccactgctgcttctcctcctctccatccacagcgcc<br>ctggccatgaggatctgctccttcaacgtcaggtcctttggggaaagcaagcag<br>gaagacaagaatgccatgatgtcattgtgaaggtcatcaaacgctgtgacatc<br>atactcgtgatggaaatcaaggacagcaacaacaggatctgccccatactgatg<br>gagaagctgaacagaaattcaaggagaggcataacatacaactatgtgattagc<br>tctcggcttggaagaaacacatataaagaacaatatgccttctctctacaaggaa<br>aagctggtgtctgtgaagaggagttatcactaccatgactatcaggatggagac<br>gcagatgtgttttccagggagccctttgtggtctggttccaatctccccacact |

TABLE 1-continued

| SEQ ID NO: | DESCRIPTION | SEQUENCE (NUCLEOTIDE SEQUENCES ARE 5'-3') |
|---|---|---|
| | | gctgtcaaagacttcgtgattatcccctgcacaccaccccagagacatccgtt aaggagatcgatgagttggttgaggtctacacggacgtgaaacaccgctggaag gcggagaatttcattttcatgggtgacttcaatgccggctgcagctacgtcccc aagaaggcctggaagaacatccgcttgaggactgaccccaggtttgtttggctg atcggggaccaagaggacaccacggtgaagaagagcaccaactgtgcatatgac aggattgtgcttagaggacaagaaatcgtcagttctgttgttcccaagtcaaac agtgtttttgacttccagaaagcttacaagctgactgaagaggaggccctggat gtcagcgaccactttccagttgaatttaaactacagtcttcaagggccttcacc aacagcaaaaaatctgtcactctaaggaagaaaacaaagagcaaacgctcctag |
| 43 | human pancreatic ribonuclease | atgggtctggagaagtctcttgtccggctccttctgcttgtcctgatactgctg gtgctgggctgggtccagccttccctgggcaaggaatcccgggccaagaaattc cagcggcagcatatggactcagacagttcccccagcagcagctccacctactgt aaccaaatgatgaggcgccggaatatgacacaggggcggtgcaaaccagtgaac accttttgtgcacgagcccctggtagatgtccagaatgtctgtttccaggaaaag gtcacctgcaagaacgggcagggcaactgctacaagagcaactccagcatgcac atcacagactgccgcctgacaaacggctccaggtaccccaactgtgcataccgg accagcccgaaggagagacacatcattgtggcctgtgaagggagcccatatgtg ccagtccactttgatgctactgtgtag |
| 44 | NLG linker | gtcgacggcgcggccgccagccccgtgaacgtgagcagccccagcgtgcaggat atc |
| 45 | g4s4lnk | ggggsggggsggggsggggs |
| 46 | G4S5-1 | ggggsggggsggggsggggsggggs |
| 47 | G4S5-2 | ggggsggggsggggsggggsggggs |
| 48 | hDNase1-3'- G105R; A114F | lkiaafniqtfgetkmsnatlvsyivqilsrydialvqevrdshltavgkll dnlnqdapdtyhyvvseplgrnsykerylfvyrpdqvsavdsyyyddgcepcrn dtfnrepfivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk* |
| 49 | hDNase1-3'- WT | lkiaafniqtfgetkmsnatlvsyivqilsrydialvqevrdshltavgkll dnlnqdapdtyhyvvseplgrnsykerylfvyrpdqvsavdsyyyddgcepcgn dtfnrepaivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk* |
| 50 | hDNase1- 3'A114F | lkiaafniqtfgetkmsnatlvsyivqilsrydialvqevrdshltavgkll dnlnqdapdtyhyvvseplgrnsykerylfvyrpdqvsavdsyyyddgcepcgn dtfnrepfivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk* |
| 51 | hDNase1-5'- G105R | lkiaafniqtfgetkmsnatlvsyivqilsrydialvqevrdshltavgkll dnlnqdapdtyhyvvseplgrnsykerylfvyrpdqvsavdsyyyddgcepcrn dtfnrepfivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk |
| 52 | hDNase1-5'- WT | lkiaafniqtfgetkmsnatlvsyivqilsrydialvqevrdshltavgkll dnlnqdapdtyhyvvseplgrnsykerylfvyrpdqvsavdsyyyddgcepcgn dtfnrepaivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk |
| 53 | hDNase1-5'- A114F | lkiaafniqtfgetkmsnativsyivqilsrydialvqevrdshltavgkll dnlnqdapdtyhyvvseplgrnsykerylfvyrpdqvsavdsyyyddgcepcgn dtfnrepfivrffsrftevrefaivplhaapgdavaeidalydvyldvqekwgl edvmlmgdfnagcsyvrpsqwssirlwtsptfqwlipdsadttatpthcaydri vvagmllrgavvpdsalpnfqaayglsdqlaqaisdhypvevmlk |
| 54 | hIgG1 (SCC) | lepkssdkthtcppcpapellggpsvflfppkpkdtlmisrtpevtcvvvdvs hedpevkfnwyvdgvevhnaktkpreeqynstyrvvsvltvlhqdwlngkeykc kvsnkalpapiektiskakgqprepqvytlppsrdeltknqvsltclvkgfyps diavewesngqpennykttppvldsdgsfflyskltvdksrwqqgnvfscsvmh ealhnhytqkslslspgk |
| 55 | hRNase- G88D-3' | kesrakkfqrqhmdsdsspsssstycnqmmrrrnmtqgrckpv ntfvheplvdvqnvcfqekvtckngqgncyksnssmhitdcrl tndsrypncayrtspkerhiivacegspyvphfdasvedst* |

TABLE 1-continued

| SEQ ID NO: | DESCRIPTION | SEQUENCE (NUCLEOTIDE SEQUENCES ARE 5'-3') |
|---|---|---|
| 56 | human DNase1 + VK3L P | metpaqllflllllwlpdttglkiaafniqtfgetkmsnatlvsyivqilsrydi alvqevrdshltavgklldnlnqdapdtyhyvvseplgrnsykerylfvyrpdq vsavdsyyyddgcepcgndtfnrepaivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlk* |
| 57 | DNase1L3 | msrelaplllllllsihsalamricsfnvrsfgeskqedknamdvivkvikrcdi ilvmeikdsnnricpilmeklnrnsrrgitynyvissrlgrntykeqyaflyke klvsvkrsyhyhdyqdgdadvfsrepfvvwfqsphtavkdfviiplhttpetsv keidelvevytdvkhrwkaenfifmgdfnagcsyvpkkawknirlrtdprfvwl igdqedttvkkstncaydrivlrgqeivssvvpksnsvfdfqkayklteeeald vsdhfpvefklqssraftnskksvtlrkktkskrs* |
| 58 | human pancreatic ribonuclease (Uniprot P07998) | Malekslvrllllvlillvlgwvqpslgkesrakkfqrqhmdsdsspsssstyc nqmmrrrnmtqgrckpvntfvheplvdvqnvcfqekvtckngqgncyksnssmh itdcrltngsrypncayrtspkerhiivacegspyvpvhfdasvedst |
| 59 | Fc domain with SSS | cccaaatcttctgacaaaactcacacatctccaccgtctccagcacctgaactc ctgggggaccgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccttccagcccccatcgagaaaaccatctctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaa |
| 60 | Fc domain with SSS | lepkssdkthtsppspapellggpsvflfppkpkdtlmisrtpevtcvvvdvsh edpevkfnwyvdgvevhnaktkpreeqynstyrvvsvltvlhqdwlngkeykck vsnkalpapiektiskakgqprepqvytlppsrdeltknqvsltclvkgfypsd iavewesngqpennykttppvldsdgsfflysklvdksrwqqgnvfscsvmhe alhnhytqkslslspgk |
| 61 | RSLV125: huVK3LP- wthRNase- SSS-mthIgG1 P238S P331S | atggaaacccctgcccagctgctgttcctgctgctgctgtggctgcccgacacc accggtaaggaatcccgggccaagaaattccagcggcagcatatggactcagac agttcccccagcagcagctccacctactgtaaccaaatgatgaggcgccggaat atgacacagggcggtgcaaaccagtgaacacctttgtgcacgagcccctggta gatgtccagaatgtctgttccaggaaaaggtcacctgcaagaacggcagggc aactgctacaagagcaactccagcatgcacatcacagactgccgcctgacaaac ggctccaggtaccccaactgtgcataccggaccagcccgaaggagagacacatc attgtggcctgtgaagggagcccatatgtgccagtccactttgatgcttctgtg gaggactctaccctcgagcccaaatcttctgacaaaactcacacatctccaccg agcccagcacctgaactcctgggaggatcgtcagtcttcctcttccccccaaaa cccaaggacacccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagcccttccagcccccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggaaaatga |
| 62 | RSLV125: huVK3LP- wthRNase- SSS-mthIgG1 P238S P331S | metpaqllflllllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstlepkssdkthtspp spapellggsvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn ykttppvldsdgsfflysklvdksrwqqgnvfscsvmhealhnhytqkslsls pqk |
| 63 | RSLV126: huVK3LP- WThRNase- | atggaaacccctgcccagctgctgttcctgctgctactctggctcccagatacc accggtaaggaatcccgggccaagaaattccagcggcagcatatggactcagac agttcccccagcagcagctccacctactgtaaccaaatgatgaggcgccggaat |

TABLE 1-continued

| SEQ ID NO: | DESCRIPTION | SEQUENCE (NUCLEOTIDE SEQUENCES ARE 5'-3') |
|---|---|---|
| | (g4s)4-SSS-mthIgG1-P238S-P331S | atgacacaggggcggtgcaaaccagtgaacacctttgtgcacgagcccctggta gatgtccagaatgtctgtttccaggaaaaggtcacctgcaagaacgggcagggc aactgctacaagagcaactccagcatgcacatcacagactgccgcctgacaaac ggctccaggtaccccaactgtgcataccggaccagcccgaaggagagacacatc attgtggcctgtgaagggagcccatatgtgccagtccactttgatgcttctgtg gaggactctacagatctctccggaggaggtggctcaggtggtggaggatctgga ggaggtgggagtggtggaggtggttctaccggtctcgagcccaaatcttctgac aaaactcacacatctccaccgagcccagcacctgaactcctgggaggatcgtca gtcttcctcttccccccaaaacccaaggacaccctcatgatctcccggacccct gaggtcacatgcgtggtggtggacgtgagccacgaagaccctgaggtcaagttc aactggtacgtggacggcgtggaggtgcataatgccaagacaaagccgcgggag gagcagtacaacagcacgtaccgtgtggtcagcgtcctcaccgtcctgcaccag gactggctgaatggcaaggagtacaagtgcaaggtctccaacaaagcccttcca gcctccatcgagaaaaccatctccaaagccaaagggcagccccgagaaccacag gtgtacaccctgccccatcccgggatgagctgaccaagaaccaggtcagcctg acctgcctggtcaaaggcttctatcccagcgacatcgccgtggagtgggagagc aatgggcagccggagaacaactacaagaccacgcctcccgtgctggactccgac ggctccttcttcctctacagcaagctcaccgtggacaagagcaggtggcagcag gggaacgtcttctcatgctccgtgatgcatgaggctctgcacaaccactacacg cagaagagcctctctctctctccgggaaaatga |
| 64 | RSLV126: huVK3LP-WThRNase-(g4s)4-SSS-mthIgG1-P238S-P331S | metpaqllflllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstgggggsggggsg gggsggggslepkssdkthtsppspapellggssvflfppkpkdtltlmisrtp evtcvvvdvshedpevkfnwyvdgvevhnaktkpreeqynstyrvvsvltvlhq dwlngkeykckvsnkalpasiektiskakgqprepqvytlppsrdeltknqvsl tclvkgfypsdiavewesngqpennykttppvldsdgsfflyskltvdksrwqq gnvfscsvmhealhnhytqkslslspgk |
| 65 | RSLV127: huVK3LP-hDNase1 105/114-(g4s)4-SSS-mthIgG1-P238S-P331S-NLG-RNase | atggaaacccagcgcagcttctcttcctcctgctactctggctcccagatacc accggtctgaagatcgcagccttcaacatccagacatttggggagaccaagatg tccaatgccaccctcgtcagctacattgtgcagatcctgagccgctatgacatc gccctggtccaggaggtcagagacagctccacctgactgccgtggggaagctgctg gacaacctcaatcaggatgcaccagacacctatcactacgtggtcagtgagcca ctgggacgaacagctataaggagcgctacctgttcgtgtacaggcctgaccag gtgtctgcggtggacagctactactacgatgatggctgcgagcctgcaggaac gacacccttcaaccgagagccattcattgtcaggttcttctcccggttcacagag gtcagggagtttgccattgttcccctgcatgcggccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagcccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaaagatctctccggaggaggtggctca ggtggtggaggatctggaggaggtgggagtggtggaggttctaccggtctcgag cccaaatcttctgacaaaactcacacatctccaccgagcccagcacctgaactc ctgggaggatcgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgccctc accgtcctgcaccaggactggctgaatggcaaggagtacaagtgcaaggtctcc aacaaagccctcccagcctccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctctctccgggaaaagtcgacgga gctagcagcccgtgaacgtgagcagccccagaatgcaggatatcccttccctg ggcaaggaatcccgggccaagaaattccagcggcagcatatggactcagacagt tcccccagcagcagctccacctactgtaaccaaatgatgaggcgccggaatatg acacagggcggtgcaaaccagtgaacacctttgtgcacgagcccctggtagat gtccagaatgtctgtttccaggaaaaggtcacctgcaagaacgggcagggcaag tggtacaagagcaactccagcatgcacatcacagactgccgcctgacaaacggc tccaggtaccccaactgtgcataccgaaccagcccgaaggagagacacatcatt gtggcctgtgaagggagcccatatgtgccagtccactttgatgcttgctgtggag gactctacctaa |
| 66 | RSLV127: huVK3LP-hDNase1 105/114-(g4s)4-SSS-mthIgG1- | metpaqllflllwlpdttglkiaafniqtfgetkmsnatlvsyivqilsrydi alvqevrdshltavgklldnlnqdapdtyhvvveseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkggggsggggsggggsggggslepkssdkthtsppspapel |

TABLE 1-continued

| SEQ ID NO: | DESCRIPTION | SEQUENCE (NUCLEOTIDE SEQUENCES ARE 5'-3') |
|---|---|---|
| | P238S-<br>P331S-NLG-<br>RNase | lggssvflfppkpkdtlmisrtpevtcvvvdvshedpevkfnwyvdgvevhnak<br>tkpreeqynstyrvvsvltvlhqdwlngkeykckvsnkalpasiektiskakgq<br>prepqvytlppsrdeltknqvsltclvkgfypsdiavewesngqpennykttpp<br>vldsdgsfflyskltvdksrwqqgnvfscsvmhealhnhytqkslslspgkvdg<br>asspvnvsspsvqdikesrakkfqrqhmdsdsspsssstycnqmmrrrnm<br>tqgrckpvntfvheplvdvqnvcfqekvtckngqgkwncyksnssmhitdcrlt<br>ngsrypncayrtspkerhiivacegspyvpvhfdasvedst |
| 67 | RSLV128:<br>huVK3LP-<br>hRNase WT-<br>(g4s)4-SSS-<br>mthIgG1-<br>P238S-<br>P331S-NLG-<br>hDNase<br>105/114 | atggaaaccccagcgcagcttctcttcctcctgctactctggctcccagatacc<br>accggtaaggaatcccgggccaagaaattccagcggcagcatatggactcagac<br>agttcccccagcagcagctccacctactgtaaccaaatgatgaggcgccggaat<br>atgacacaggggcggtgcaaaccagtgaacacctttgtgcacgagcccctggta<br>gatgtccagaatgtctgtttccaggaaaaggtcacctgcaagaacgggcagggc<br>aactgctacaagagcaactccagcatgcacatcacagactgccgcctgacaaac<br>ggctccaggtaccccaactgtgcataccggaccagcccgaaggagagacacatc<br>attgtggcctgtgaagggagcccatatgtgccagtccactttgatgcttctgtg<br>gaggactctacagatctctccggaggaggtggctcaggtggtggaggatctgga<br>ggaggtgggagtggtggaggtggttctaccggtctcgagcccaaatcttctgac<br>aaaactcacacatctccaccgagcccagcacctgaactcctgggaggatcgtca<br>gtcttcctcttccccccaaaacccaaggacaccctcatgatctcccggacccct<br>gaggtcacatgcgtggtggtggacgtgagccacgaagaccctgaggtcaagttc<br>aactggtacgtggacggcgtggaggtgcataatgccaagacaaagccgcgggag<br>gagcagtacaacagcacgtaccgtgtggtcagcgtcctcaccgtcctgcaccag<br>gactggctgaatggcaaggagtacaagtgcaaggtctccaacaaagccctccca<br>gcctccatcgagaaaaccatctccaaagccaaagggcagccccgagaaccacag<br>gtgtacaccctgcccccatcccgggatgagctgaccaagaaccaggtcagcctg<br>acctgcctggtcaaaggcttctatcccagcgacatcgccgtggagtgggagagc<br>aatgggcagccggagaacaactacaagaccacgcctcccgtgctggactccgac<br>ggctccttcttcctctacagcaagctcaccgtggacaagagcaggtggcagcag<br>gggaacgtcttctcatgctccgtgatgcatgaggctctgcacaaccactacacg<br>cagaagagcctctctctctctccgggaaaagtcgacggagctagcagccccgtg<br>aacgtgagcagccccagaatgcaggatatcctgaagatcgcagccttcaacatc<br>cagacatttggggagaccaagatgtccaatgccaccctcgtcagctacattgtg<br>cagatcctgagccgctatgacatcgccctggtccaggaggtcagagacagccac<br>ctgactgccgtggggaagctgctggacaacctcaatcaggatgcaccagacacc<br>tatcactacgtggtcagtgagccactgggacggaacagctataaggagcgctac<br>ctgttcgtgtacaggcctgaccaggtgtctgcggtggacagctactactacgat<br>gatggctgcgagccctgcaggaacgacaccttcaaccgagagccattcattgtc<br>aggttcttctcccggttcacagaggtcagggagtttgccattgttcccctgcat<br>gcggccccgggggacgcagtagccgagatcgacgctctctatgacgtctacctg<br>gatgtccaagagaaatggggcttggaggacgtcatgttgatgggcgacttcaat<br>gcgggctgcagctatgtgagaccctcccagtggtcatccatccgcctgtggaca<br>agccccaccttccagtggctgatccccgacagcgctgacaccacagctacaccc<br>acgcactgtgcctatgacaggatcgtggttgcagggatgctgctccgaggcgcc<br>gttgttcccgactcggctcttccctttaacttccaggctgcctatggcctgagt<br>gaccaactggcccaagccatcagtgaccactatccagtggaggtgatgctgaaa<br>tga |
| 68 | RSLV128:<br>huVK3LP-<br>hRNase WT-<br>(g4s)4-SSS-<br>mthIgG1-<br>P238S-<br>P331S-NLG-<br>hDNase<br>105/114 | metpaqllflllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstggggsggggsg<br>gggsggggslepkssdkthtsppspapellggssvflfppkpkdtlmisrtp<br>evtcvvvdvshedpevkfnwyvdgvevhnaktkpreeqynstyrvvsvltvlhq<br>dwlngkeykckvsnkalpasiektiskakgqprepqvytlppsrdeltknqvsl<br>tclvkgfypsdiavewesngqpennykttppvldsdgsfflyskltvdksrwqq<br>gnvfscsvmhealhnhytqkslslspgkvdgasspvnvsspsvqdilkiaafni<br>qtfgetkmsnativsyivqilsrydialvqevrdshltavgklldnlnqdapdt<br>yhyvvseplgrnsykerylfvyrpdqvsavdsyyyddgcepcrndtfnrepfiv<br>rffsrftevrefaivplhaapgdavaeidalydvyldvqekwgledvmlmgdfn<br>agcsyvrpsqwssirlwtsptfqwlipdsadttatpthcaydrivvagmllrga<br>vvpdsalpfnfqaayglsdqlaqaisdhypvevmlk |
| 69 | RSLV129:<br>huVK3LP-<br>hRNAseWT-<br>SSS-<br>mthIgG1-<br>P238S-<br>P331S-NLG-<br>hDNAse<br>105/114 | atggaaacccctgcccagctgctgttcctgctgctgctgtggctgcccgacacc<br>accggtaaggaatcccgggccaagaaattccagcggcagcatatggactcagac<br>agttcccccagcagcagctccacctactgtaaccaaatgatgaggcgccggaat<br>atgacacaggggcggtgcaaaccagtgaacacctttgtgcacgagcccctggta<br>gatgtccagaatgtctgtttccaggaaaaggtcacctgcaagaacgggcagggc<br>aactgctacaagagcaactccagcatgcacatcacagactgccgcctgacaaac<br>ggctccaggtaccccaactgtgcataccggaccagcccgaaggagagacacatc<br>attgtggcctgtgaagggagcccatatgtgccagtccactttgatgcttctgtg<br>gaggactctaccctcgagcccaaatcttctgacaaaactcacacatctccaccg<br>agcccagcacctgaactcctgggaggatcgtcagtcttcctcttccccccaaaa<br>cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag |

TABLE 1-continued

| SEQ ID NO: | DESCRIPTION | SEQUENCE (NUCLEOTIDE SEQUENCES ARE 5'-3') |
|---|---|---|
| | | tacaagtgcaaggtctccaacaaagccctcccagcctccatcgagaaaaccatc tccaaagccaaagggcagccccgagaaccacaggtgtacaccctgccccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctctct ccgggaaaagtcgacggagctagcagccccgtgaacgtgagcagccccagaatg caggatatcctgaagatcgcagccttcaacatccagacatttggggagaccaag atgtccaatgccaccctcgtcagctacattgtgcagatcctgagccgctatgac atcgccctggtccaggaggtcagagacagccacctgactgccgtggggaagctg ctggacaacctcaatcaggatgcaccagacacctatcactacgtggtcagtgag ccactgggacggaacagctataaggagcgctacctgttcgtgtacaggcctgac caggtgtctgcggtggacagctactactacgatgatggctgcgagccctgcagg aacgacaccttcaaccgagagccattcattgtcaggttcttctcccggttcaca gaggtcagggagtttgccattgttcccctgcatgcggccccgggggacgcagta gccgagatcgacgctctctatgacgtctacctggatgtcaagagaaatggggc ttggaggacgtcatgttgatgggcgacttcaatgcgggctgcagctatgtgaga ccctcccagtggtcatccatccgcctgtggacaagcccaccttccagtggctg atccccgacagcgctgacaccacagctacacccacgcactgtgcctatgacagg atcgtggttgcagggatgctgctccgaggcgccgttgttcccgactcggctctt cccttaacttccaggctgcctatggcctgagtgaccaactggcccaagccatc agtgaccactatccagtggaggtgatgctgaaatga |
| 70 | RSLV129: huVK3LP-hRNAseWT-SSS-mthIgG1-P238S-P331S-NLG-hDNAse 105/114 | metpaqllflllllwlpdttgkesrakkfqrqhmdadsspssssstycnqmmrrrn mtqgrckpvntfvheplvdvqnvcfqekvtckngqgncyksnssmhitdcrltn gsrypncayrtspkerhiivacegspyvpvhfdasvedstlepkssdkthtspp spapellggssvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn ykttppvldsdgsfflysklтvdksrwqqgnvfscsvmhealhnhytqkslsls pgkvdgasspvnvsspsvqdilkiaafniqtfgetkmsnatlvsyivqilsryd ialvqevrdshltavgklldnlnqdapdtyhyvvseplgrnsykerylfvyrpd qvsavdsyyyddgcepcrndtfnrepfivrffsrftevrefaivplhaapgdav aeidalydvyldvqekwgledvmlmgdfnagcsyvrpsqwssirlwtsptfqwl ipdsadttatpthcaydrivvagmllrgavvpdsalpfnfqaayglsdqlaqai sdhypvevmlk |
| 71 | Fc domain with P238S-2 (SCC hinge) | cccaaatcttctgacaaaactcacacatgtccaccgtgcccagcacctgaactc ctgggaggatcgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccttcccagccccatcgagaaaaccatctccaaagccaaagggcag ccccgagaaccacaggtgtacaccctgccccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagccctctctctctccgggaaaa |
| 72 | Fc domain with P238S-2 (SCC hinge) | lepkssdkthtcppcpapellggssvflfppkpkdtlmisrtpevtcvvvdvsh edpevkfnwyvdgvevhnaktkpreeqynstyrvvsvltvlhqdwlngkeykck vsnkalpapiektiskakgqprepqvytlppsrdeltknqvsltclvkgfypsd iavewesngqpennykttppvldsdgsfflysklтvdksrwqqgnvfscsvmhe alhnhytqkslslspgk |
| 73 | Fc domain with P331S-2 | cccaaatcttctgacaaaactcacacatgtccaccgtgcccagcacctgaactc ctgggaggaccgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccctccagcctccatcgagaaaaccatctccaaagccaaagggcag ccccgagaaccacaggtgtacaccctgccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctctctccgggaaaa |

TABLE 1-continued

| SEQ ID NO: | DESCRIPTION | SEQUENCE (NUCLEOTIDE SEQUENCES ARE 5'-3') |
|---|---|---|
| 74 | Fc domain with P331S-2 | lepkssdkthtcppcpapellggpsvflfppkpkdtlmisrtpevtcvvvdvsh edpevkfnwyvdgvevhnaktkpreeqynstyrvvsvltvlhqdwlngkeykck vsnkalpasiektiskakgqprepqvytlppsrdeltknqvsltclvkgfypsd iavewesngqpennykttppvldsdgsfflysklvdksrwqqgnvfscsvmhe alhnhytqkslslspgk |
| 75 | Fc domain with SSS, P238S, and P331S-2 | cccaaatcttctgacaaaactcacacatctccaccgagcccagcacctgaactc ctgggaggatcgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccccagcctccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctctctccgggaaaa |
| 76 | Fc domain with SSS, P238S, and P331S-2 | lepkssdkthtsppspapellggssvflfppkpkdtlmisrtpevtcvvvdvsh edpevkfnwyvdgvevhnaktkpreeqynstyrvvsvltvlhqdwlngkeykck vsnkalpasiektiskakgqprepqvytlppsrdeltknqvsltclvkgfypsd iavewesngqpennykttppvldsdgsfflysklvdksrwqqgnvfscsvmhe alhnhytqkslslspgk |
| 77 | RSLV125-2: huVK3LP-wthRNase-SCC-mthIgG1 P238S P331S | atggaaacccctgcccagctgctgttcctgctgctgctgtggctgcccgacacc accggtaaggaatcccgggccaagaaattccagcggcagcatatggactcagac agttcccccagcagcagctccacctactgtaaccaaatgatgaggcgccggaat atgacacaggggcggtgcaaaccagtgaacacctttgtgcacgagcccctggta gatgtccagaatgtctgtttccaggaaaaggtcacctgcaagaacgggcagggc aactgctacaagagcaactccagcatgcacatcacagactgccgcctgacaaac ggctccaggtaccccaactgtgcataccggaccagcccgaaggagagacacatc attgtggcctgtgaagggagcccatatgtgccagtccactttgatgcttctgtg gaggactctaccctcgagcccaaatcttctgacaaaactcacacatgtccaccg tgcccagcacctgaactcctgggaggatcgtcagtcttcctcttccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagcccccagcctccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctctct ccgggaaaatga |
| 78 | RSLV125-2: huVK3LP-wthRNase-SCC-mthIgG1 P238S P331S | metpaqllflllllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstlepkssdkthtcpp cpapellggssvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn ykttppvldsdgsfflysklvdksrwqqgnvfscsvmhealhnhytqkslsls pgk |
| 79 | RSLV126-2: huVK3LP-WThRNase-(g4s)4-SCC-mthIgG1-P238S-P331S | atggaaacccctgcgcagcttctcttcctcctgctactctggctcccagatacc accggtaaggaatcccgggccaagaaattccagcggcagcatatggactcagac agttcccccagcagcagctccacctactgtaaccaaatgatgaggcgccggaat atgacacaggggcggtgcaaaccagtgaacacctttgtgcacgagcccctggta gatgtccagaatgtctgtttccaggaaaaggtcacctgcaagaacgggcagggc aactgctacaagagcaactccagcatgcacatcacagactgccgcctgacaaac ggctccaggtaccccaactgtgcataccggaccagcccgaaggagagacacatc attgtggcctgtgaagggagcccatatgtgccagtccactttgatgcttctgtg gaggactctacagatctctcggaggaggtggctcaggtggtggaggatctgga ggaggtgggagtggtggaggtggttctaccggtctcgagcccaaatcttctgac aaaactcacacatgtccaccgtgcccagcacctgaactcctgggaggatcgtca gtcttcctcttccccccaaaacccaaggacaccctcatgatctcccggacccct gaggtcacatgcgtggtggtggacgtgagccacgaagaccctgaggtcaagttc aactggtacgtggacggcgtggaggtgcataatgccaagacaaagccgcgggag gagcagtacaacagcacgtaccgtgtggtcagcgtcctcaccgtcctgcaccag gactggctgaatggcaaggagtacaagtgcaaggtctccaacaaagcccctccc gcctccatcgagaaaaccatctccaaagccaaagggcagccccgagaaccacag |

TABLE 1-continued

| SEQ ID NO: | DESCRIPTION | SEQUENCE (NUCLEOTIDE SEQUENCES ARE 5'-3') |
|---|---|---|
| | | gtgtacaccctgcccccatcccgggatgagctgaccaagaaccaggtcagcctg<br>acctgcctggtcaaaggcttctatcccagcgacatcgccgtggagtgggagagc<br>aatgggcagccggagaacaactacaagaccacgcctcccgtgctggactccgac<br>ggctccttcttcctctacagcaagctcaccgtggacaagagcaggtggcagcag<br>gggaacgtcttctcatgctccgtgatgcatgaggctctgcacaaccactacacg<br>cagaagagcctctctctctccgggaaaatga |
| 80 | RSLV126-2: huVK3LP-WThRNase-(g4s)4-SCC-mthIgG1-P238S-P331S | metpaqllflllllwlpdttgkesrakkfqrqhmdsdsspssssstycnqmmrrrn<br>mtqgrckpvntfvheplvdvqnvcfqekvtckngqgncyksnssmhitdcrltn<br>gsrypncayrtspkerhiivacegspyvpvhfdasvedstgggggsggggsg<br>gggsggggslepkssdkthtcppcpapellggssvflfppkpkdtlmisrtp<br>evtcvvvdvshedpevkfnwyvdgvevhnaktkpreeqynstyrvvsvltvlhq<br>dwlngkeykckvsnkalpasiektiakakgqprepqvytlppsrdeltknqvsl<br>tclvkgfypsdiavewesngqpennykttppvldsdgsfflyskltvdksrwqq<br>gnvfscsvmhealhnhytqkslslspgk |
| 81 | RSLV127-2: huVK3LP-hDNase1 105/114-(g4s)4-SCC-mthIgG1-P238S-P331S-NLG-RNase | atggaaacccagcgcagcttctcttcctcctgctactctggctcccagatacc<br>accggtctgaagatcgcagccttcaacatccagacatttggggagaccaagatg<br>tccaatgccacccgtcagctacattgtgcagatcctgagccgctatgacatc<br>gccctggtccaggaggtcagagacagccacctgactgccgtggggaagctgctg<br>gacaacctcaatcaggatgccaccagacactcactacgtgctggtgagcca<br>ctgggacgaaacagctataaggagcgctacctgttcgtgtacaggcctgaccag<br>gtgtctgcggtggacagctactactacgatgatggctgcgagcctgcaggaac<br>gacaccttcaaccgagagccattcattgtcaggctcttctcccggttcacagag<br>gtcagggagtttgccattgttccctgcatgcggccccggggacgcagtagcc<br>gagatcgacgctctctatgacgtctacctggatgtccaagagaaatggggcttg<br>gaggacgtcatgttgatgggcgacttcaatgcgggctgcagctatgtgagaccc<br>tccagtggtcatccatccgcctgtggacaagcccccaccttccagtggctgatc<br>ccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctctccggaggaggtggctca<br>ggtggtggaggatctggaggaggtgggagtggtggaggttctaccggtctcgag<br>cccaaatcttctgacaaaactcacacatgtcaccgtgcccagcacctgaactc<br>ctgggaggatcgtcagtcttcctcttccccccaaaacccaaggacacactcatg<br>atctcccggaccctgaggtcacatgcgtggtggtggacgtgagccacgaagac<br>cctgaggtcaagttcaactggtacgtggacggcgtggaggtgcataatgccaag<br>acaaagccgcgggaggagcagtcaacagcacgtaccgtgtggtcagcgtcctc<br>accgtcctgcaccaggactggctgaatggcaaggagtacaagtgcaaggtctcc<br>aacaaagcccctcccagcctccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctctcccgggaaaatgacgacgga<br>gctagcagccccgtgaacgtgagcagccccagaatgcaggatatcccttccctg<br>ggcaaggaatcccgggccaagaaattccagcggcagcatatggactcagacagt<br>tcccccagcagcagctccacctactgtaaccaaatgatgaggcgccggaatatg<br>acacagggcggtgcaaaccagtgaacacctttgtgcacgagcccctggtagat<br>gtccagaatgtctgtttccaggaaaaggtcacctgcaagaacgggcagggcaag<br>tggtacaagagcaactccagcatgcacatcacagactgccgcctgacaaacggc<br>tccaggtaccccaactgtgcataccgaaccagcccgaaggagacacatcatt<br>gtggcctgtgaaggagcccatatgtgccagtccactttgatgcttgctgtggag<br>gactctacctaa |
| 82 | RSLV127-2: huVK3LP-hDNase1 105/114-(g4s)4-SCC-mthIgG1-P238S-P331S-NLG-RNase | metpaqllflllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkggggsggggsggggsggggslepkssdkthtcppcpapel<br>lggssvflfppkpkdtlmisrtpevtcvvvdvshedpevkfnwyvdgvevhnak<br>tkpreeqynstyrvvsvltvlhqdwlngkeykckvsnkalpasiektiskakgq<br>prepqvytlppsrdeltknqvsltclvkgfypsdiavewesngqpennykttpp<br>vldsdgsfflyskltvdksrwqqgnvfscsvmhealhnhytqkslslspgkvdg<br>asspvnvsspsvqdikesrakkfqrqhmdsdsspssssstycnqmmrrrnm<br>tqgrckpvntfvheplvdvqnvcfqekvtckngqgncyksnssmhitdcrltng<br>srypncayrtspkerhiivacegspyvpvhfdasvedst |
| 83 | RSLV128-2: huVK3LP-hRNase WT-(g4s)4-SCC-mthIgG1-P238S- | atggaaacccagcgcagcttctcttcctcctgctactctggctcccagatacc<br>accggtaaggaatcccgggccaagaaattccagcggcagcatatggactcagac<br>agttcccccagcagcagctccacctactgtaaccaaatgatgaggcgccggaat<br>atgacacagggcggtgcaaaccagtgaacacctttgtgcacgagcccctggta<br>gatgtccagaatgtctgtttccaggaaaaggtcacctgcaagaacgggcagggc<br>aactgctacaagagcaactccagcatgcacatcacagactgccgcctgacaaac |

TABLE 1-continued

| SEQ ID NO: | DESCRIPTION | SEQUENCE (NUCLEOTIDE SEQUENCES ARE 5'-3') |
|---|---|---|
|  | P331S-NLG-hDNase 105/114 | ggctccaggtaccccaactgtgcataccggaccagcccgaaggagagacacatc attgtggcctgtgaagggagcccatatgtgccagtccactttgatgcttctgtg gaggactctacagatctctccggaggaggtggctcaggtggtggaggatctgga ggaggtgggagtggtggaggtggttctaccggtctcgagcccaaatcttctgac aaaactcacacatgtccaccgtgcccagcacctgaactcctgggaggatcgtca gtcttcctcttccccccaaaacccaaggacaccctcatgatctcccggacccct gaggtcacatgcgtggtggtggacgtgagccacgaagaccctgaggtcaagttc aactggtacgtggacggcgtggaggtgcataatgccaagacaaagccgcgggag gagcagtacaacagcacgtaccgtgtggtcagcgtcctcaccgtcctgcaccag gactggctgaatggcaaggagtacaagtgcaaggtctccaacaaagccctccca gcctccatcgagaaaaccatctccaaagccaaagggcagccccgagaaccacag gtgtacaccctgcccccatcccgggatgagctgaccaagaaccaggtcagcctg acctgcctggtcaaaggcttctatcccagcgacatcgccgtggagtgggagagc aatgggcagccggagaacaactacaagaccacgcctcccgtgctggactccgac ggctccttcttcctctacagcaagctcaccgtggacaagagcaggtggcagcag gggaacgtcttctcatgctccgtgatgcatgaggctctgcacaaccactacacg cagaagagcctctctctctccggaaaagtcgacggagctagcagccccgtg aacgtgagcagccccagaatgcaggatatcctgaagatcgcagccttcaacatc cagacatttggggagaccaagatgtccaatgccacccttgtcagctacattgtg cagatcctgagccgctatgacatcgcccggtccaggaggtcagagacagccac ctgactgccgtggggaagctgctggacaacctcaatcaggatgcaccagacacc tatcactacgtggtcagtgagccactgggacggaacagctataaggagcgctac ctgttcgtgtacaggcctgaccaggtgtctgcggtggacagctactactacgat gatggctgcgagccctgcaggaacgacaccttcaaccgagagccattcattgtc aggttcttctcccccggttcacagaggtcagggagtttgccattgttcccctgcat gcggcccccggggacgcagtagccgagatcgacgctctctatgacgtctacctg gatgtccaagagaaatggggcttggaggacgtcatgttgatgggcgacttcaat gcgggctgcagctatgtgagaccctcccagtggtcatccatccgcctgtggaca agccccaccttccagtggctgatcccgacagcgctgacaccacagctacaccc acgcactgtgcctatgacaggatcgtggttgcagggatgctgctccggaggcgcc gttgttcccgactcggctcttcccttttaacttccaggctgcctatggcctgagt gaccaactggcccaagccatcagtgaccactatccagtggaggtgatgctgaaa tga |
| 84 | RSLV128-2: huVK3LP-hRNase WT-(g4s)4-SCC-mthIgG1-P238S-P331S-NLG-hDNase 105/114 | metpaqllflllllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstggggsggggsg gggsggggslepkssdkthtcppcpapellggssvflfppkpkdtlmisrtp evtcvvvdvshedpevkfnwyvdgvevhnaktkpreeqynstyrvvsvltvlhq dwlngkeykckvsnkalpasiektiskakgqprepqvytlppsrdeltknqvsl tclvkgfypsdiavewesngqpennykttppvldsdgsfflysklvdksrwqq gnvfscsvmhealhnhytqkslslspgkvdgasspvnvsspsvqdilkiaafni qtfgetkmsnatlvsyivqilsrydialvqevrdshltavgklldnlnqdapdt yhyvvseplgrnsykerylfvyrpdqvsavdsyyyddgcepcrndtfnrepfiv rffsrftevrefaivplhaapgdavaeidalydvyldvqekwgledvmlmgdfn agcsyvrpsqwssirlwtsptfqwlipdsadttatpthcaydrivvagmllrga vvpdsalpfnfqaayglsdqlaqaisdhypvevmlk |
| 85 | RSLV129-2: huVK3LP-hRNAseWT-SCC-mthIgG1-P238S-P331S-NLG-hDNAse 105/114 | atggaaacccctgcccagctgctgttcctgctgctgctgtggctgcccgacacc accggtaaggaatcccgggccaagaaattccagcggcagcatatggactcagac agttcccccagcagcagctccacctactgtaaccaaatgatgaggcgccgaat atgacacaggggcggtgcaaaccagtgaacacctttgtgcacgagcccctggta gatgtccagaatgtctgtttccaggaaaaggtcacctgcaagaacgggcagggc aactgctacaagagcaactccagcatgcacatcacagactgccgcctgacaaac ggctccaggtaccccaactgtgcataccggaccagcccgaaggagagacacatc attgtggcctgtgaagggagcccatatgtgccagtccactttgatgcttctgtg gaggactctaccctcgagcccaaatcttctgacaaaactcacacatgtccaccg tgcccagcacctgaactcctgggaggatcgtcagtcttcctcttccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagccctcccagcctccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctctct ccggaaaagtcgacggagctagcagccccgtgaacgtgagcagccccagaatg caggatatcctgaagatcgcagccttcaacatccagacatttggggagaccaag atgtccaatgccacccttgtcagctacattgtgcagatcctgagccgctatgac atcgccctggtccaggaggtcagagacagccacctgactgccgtggggaagctg ctggacaacctcaatcaggatgcaccagacacctatcactacgtggtcagtgag ccactgggacggaacagctataaggagcgctacctgttcgtgtacaggcctgac caggtgtctgcggtggacagctactactacgatgatggctgcgagccctgcagg |

TABLE 1-continued

| SEQ ID NO: | DESCRIPTION | SEQUENCE (NUCLEOTIDE SEQUENCES ARE 5'-3') |
|---|---|---|
| | | aacgacaccttcaaccgagagccattcattgtcaggttcttctcccggttcaca gaggtcagggagtttgccattgttcccctgcatgcggccccggggacgcagta gccgagatcgacgctctctatgacgtctacctggatgtccaagagaaatgggc ttggaggacgtcatgttgatgggcgacttcaatgcgggctgcagctatgtgaga ccctcccagtggtcatccatccgcctgtggacaagccccaccttccagtggctg atccccgacagcgctgacaccacagctacacccacgcactgtgcctatgacagg atcgtggttgcagggatgctgctcccgaggcgccgttgttcccgactcggctctt cccttttaacttccaggctgcctatggcctgagtgaccaactggcccaagccatc agtgaccactatccagtggaggtgatgctgaaatga |
| 86 | RSLV129-2: huVK3LP- hRNAseWT- SCC- mthIgG1- P238S- P331S-NLG- hDNAse 105/114 | metpaqllflllllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstlepkssdkthtcpp cpapellggssvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn yktttppvldsdgsfflysklvtdksrwqqgnvfscsvmhealhnhytqkslsls pgkvdgassspvnvsspsvqdilkiaafniqtfgetkmsnativsyivqilsryd ialvqevrdshltavgklldnlnqdapdtyhyvvseplgrnsykerylfvyrpd qvsavdsyyyddgcepcrndtfnrepfivrffsrftevrefaivplhaapgdav aeidalydvyldvqekwgledvmlmgdfnagcsyvrpsqwssirlwtsptfqwl ipdsadttatpthcaydrivvagmllrgavvpdsalpfnfqaayglsdqlaqai sdhypvevmlk |
| 87 | Fc domain with SCC | cccaaatcttctgacaaaactcacacatgtccaccgtgtccagcacctgaactc ctgggggaccgtcagtcttcctcttccccccaaaacccaaggacacccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccctcccagccccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaa |
| 88 | Fc domain with SCC | lepkssdkthtcppcpapellggpsvflfppkpkdtlmisrtpevtcvvvdvsh edpevkfnwyvdgvevhnaktkpreeqynstyrvvsvltvlhqdwlngkeykck vsnkalpapiektiskakgqprepqvytlppsrdeltknqvsltclvkgfypsd iavewesngqpennyktttppvldsdgsfflysklvtdksrwqqgnvfscsvmhe alhnhytqkslslspgk |
| 89 | Fc domain with SCC, P238S, and P331S-2 | cccaaatcttctgacaaaactcacacatgtccaccgtgcccagcacctgaactc ctgggaggatcgtcagtcttcctcttccccccaaaacccaaggacacccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccctcccagccccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggaaaa |
| 90 | Fc domain with SCC, P238S, and P331S-2 | lepkssdkthtcppcpapellggssvflfppkpkdtlmisrtpevtcvvvdvsh edpevkfnwyvdgvevhnaktkpreeqynstyrvvsvltvlhqdwlngkeykck vsnkalpasiektiskakgqprepqvytlppsrdeltknqvsltclvkgfypsd iavewesngqpennyktttppvldsdgsfflysklvtdksrwqqgnvfscsvmhe alhnhytqkslslspgk |
| 91 | RSLV132: huVK3LP- wthRNase- SCC-mthIgG1 P238S P331S | atgaaacccctgcccagctgctgttcctgctgctgctgtggctgcctgacacc accggcaaagagtcccgggccaagaagttccagcggcagcacatggactccgac tccagccctctccagctcctccacctactgcaaccagatgatgcggcggaaac atgacccagggccggtgcaagcccgtgaacacctttgtgcacgagcccctggtg gacgtgcagaacgtgtgttttcaagagaaagtgacctgcaagaacggccagggc aactgctacaagtccaactcctccatgcacatcaccgactgccggctgaccaac ggctccagataccccaactgcgcctaccggacctccccccaagaaacggcacatc atcgtggcctgcgagggctctccttacgtgccgtgcacttcgacgcctccgtg gaagattccacccctggaacccaagtcctccgacaagacccacacctgtcccct tgtcctgcccctgaactgctgggcggctcctccgtgttcctgttccccccaaag cccaaggacaccctgatgatctcccggacccccgaagtgacatgcgtggtggtg gatgtgtccccacgaggaccctgaagtgaagttcaattggtacgtggacggggtg |

TABLE 1-continued

| SEQ ID NO: DESCRIPTION | SEQUENCE (NUCLEOTIDE SEQUENCES ARE 5'-3') |
|---|---|
| | gaagtgcacaacgccaagaccaagcccagagaggaacagtacaacagcacctac cgggtggtgtccgtgctgaccgtgctgcaccaggattggctgaacggaaaagag tacaagtgcaaggtgtccaacaaggccctgcccgcctccatcgaaaagaccatc tccaaggccaagggccagccccgggaaccccaggtgtacacactgcccccdagc agggacgagctgaccaagaaccaggtgtccctgacctgcctcgtgaagggcttc taccccdccgatatcgccgtggaatgggagtccaacggccagcctgagaacaac tacaagaccacccccctgtgctggacagcgacggctcattcttcctgtactcc aagctgacagtggacaagtcccggtggcagcagggcaacgtgttctcctgctcc gtgatgcacgaggctctgcacaaccactacacccagaagtccctgtccctgagc cccggcaaatga |
| 92 RSLV132: huVK3LP- wthRNase- SCC-mthIgG1 P238S P331S | metpaqllflllllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstlepkssdkthtcpp cpapellggssvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn ykttppvldsdgsfflysklkvdksrwqqgnvfscsvmhealhnhytqkslsls pgk |
| 93 RSLV133: huVK3LP- hRNAseWT- SCC- mthIgG1- P238S- P331S-NLG- hDNAse 105/114 | atggaaaccctgcccagctgctgttcctgctgctgctgtggctgcccgacacc accggcaaagagagccgggccaagaagttccagcggcagcacatggacagcgac agcagccccagcagctccagcaccactgcaaccagatgatgcggcggagaaac atgacccaggggccggtgcaagcccgtgaacacccttcgtgcacgagcccctggtg gacgtgcagaacgtgtgttttcaagaaaaagtgacctgcaagaacggccagggc aactgctacaagagcaacagcagcatgcacatcaccgactgccggctgaccaac ggcagcagataccccaactgcgcctaccggaccagccccaagaacggcacatc atcgtggcctgcgagggcagcccttacgtgcccgtgcactttgacgccagcgtg gaagatagcacccctggaaccaagagcagcgacaagacccacacctgtccccc tgccctgccctgagctgctgggcggaagcagcgtgttcctgttccccccaaag cccaaggacaccctgatgatcagccggacccccgaagtgacctgcgtggtggtg gatgtgtcccacgaggaccccgaagtgaagttcaattggtacgtggacggcgtg gaagtgcacaacgccaagaccaagcccagagaggaacagtacaacagcacctac cggtggtgtccgtgctgaccgtgctgcaccaggactggctgaacggcaaagag tacaagtgcaaggtctccaacaaggccctgcccgccagcatcgagaaaaccatc agcaaggccaagggccagcctcgcgagccccaggtgtacacactgcccccagc cgggacgagctgaccaagaaccaggtgtccctgacctgcctggtgaaaggcttc taccccagcgatatcgccgtggaatgggagagcaacggccagcccgagaacaac tacaagaccacccccctgtgctggactccgacggctcattcttcctgtacagc aagctgaccgtggacaagagccggtggcagcagggcaacgtgttcagctgcagc gtgatgcacgaggccctgcacaaccactacacccagaagtccctgagcctgagc cccggcaaggtggacggcgccagctcccctgtgaacgtgtccagccccagcgtg caggacatcctgaagatcgccgccttcaacatccagaccttcggcgagacaaag atgagcaacgccacccctggtgtcctacatcgtgcagatcctgagcagatacgat atcgccctggtgcaagaagtgcgggacagccacctgaccgccgtgggcaagctg ctggacaacctgaaccaggacgcccccgacacctaccactacggtgtgtccgag cctctgggccggaacagctacaaagaaagatacctgttcgtgtaccggcccgat caggtgtccgccgtggacagctactactacgacgacggctgcgagcctgccgg aacgacaccttcaaccgcgagcccttcatcgtgcggttcttcagccggttcacc gaagtgcgcgagttcgccatcgtgccctgcatgctgcccctggcgacgccgtg gccgagatcgatgccctgtacgacgtgtacctggatgtgcaagaaaagtggggc ctggaagatgtgatgctgatgggcgacttcaacgccggctgcagctacgtgcgg cccagccagtggtccagcatcagactgtggacctccccaccttccagtggctg atccccgacagcgccgataccaccgcacccccacccactgtgcctacgacaga atcgtggtggccggcatgctgctgagaggcgccgtggtgcctgacagcgccctg ccattcaattttcaagccgcctacggcctgagcgatcagctggcccaggccatc agcgaccactaccccgtggaagtgatgctgaagtga |
| 94 RSLV133: huVK3LP- hRNAseWT- SCC- mthIgG1- P238S- P331S-NLG- hDNAse 105/114 | metpaqllflllllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstlepksadkthtcpp cpapellggssvflfppkpkdtlmisrtpevtcvvvdvshedpevkfnwyvdgv evhnaktkpreeqynstyrvvsvltvlhqdwlngkeykckvsnkalpasiekti skakgqprepqvytlppsrdeltknqvsltclvkgfypsdiavewesngqpenn ykttppvldsdgsfflysklkvdksrwqqgnvfscsvmhealhnhytqkslsls pgkvdgasspvnvsspsvqdilkiaafniqtfgetkmsnatlvsyivqilsryd ialvqevrdshltavgklldnlnqdapdtyhyvvseplgrnsykerylfvyrpd qvsavdsyyyddgcepcrndtfnrepfivrffsrftevrefaivplhaapgdav aeidalydvyldvqekwgledvmlmgdfnagcsyvrpsqwssirlwtsptfqwl ipdsadttatpthcaydrivvagmllrgavvpdsalpfnfqaayglsdqlaqai sdhypvevmlk |

TABLE 1-continued

| SEQ ID NO: DESCRIPTION | SEQUENCE (NUCLEOTIDE SEQUENCES ARE 5'-3') |
|---|---|
| 95 RSLV132: wthRNase-SCC-mthIgG1 P238S P331S | aaagagtcccgggccaagaagttccagcggcagcacatggactccgactccagc ccttccagctcctccacctactgcaaccagatgatgcggcggagaaacatgacc cagggccggtgcaagcccgtgaacacctttgtgcacgagcccctggtggacgtg cagaacgtgtgttttcaagagaaagtgacctgcaagaacggccagggcaactgc tacaagtccaactcctccatgcacatcaccgactgccggctgaccaacggctcc agataccccaactgcgcctaccggacctcccccaaagaacggcacatcatcgtg gcctgcgagggctctccttacgtgcccgtgcacttcgacgcctccgtggaagat tccaccctggaacccaagtcctccgacaagacccacacctgtcccccttgtcct gcccctgaactgctgggcggctcctccgtgttcctgttcccccccaaagcccaag gacaccctgatgatctcccggaccccccgaagtgacatgcgtggtggtggatgtg tcccacgaggacccctgaagtgaagttcaattggtacgtggacggggtggaagtg cacaacgccaagaccaagcccagagaggaacagtacaacagcacctaccgggtg gtgtccgtgctgaccgtgctgcaccaggattggctgaacggaaaagagtacaag tgcaaggtgtccaacaaggccctgcccgcctccatcgaaaagaccatctccaag gccaagggccagccccgggaaccccaggtgtacacactgcccccctagcagggac gagctgaccaagaaccaggtgtccctgacctgcctcgtgaaggcttctaccccc tccgatatcgccgtggaatgggagtccaacggccagcctgagaacaactacaag accaccccccctgtgctggacagcgacggctcattcttcctgtactccaagctg acagtggacaagtcccggtggcagcagggcaacgtgttctcctgctccgtgatg cacgaggctctgcacaaccactacacccagaagtccctgtccctgagccccggc aaatga |
| 96 RSLV132: wthRNase-SCC-mthIgG1 P238S P331S | kesrakkfqrqhmdsdsspssssstycnqmmrrrnmtqgrckpvntfvheplvdv qnvcfqekvtckngqgncyksnssmhitdcrltngsrypncayrtspkerhiiv acegspyvpvhfdasvedstlepkssdkthtcppcpapellggssvflfppkpk dtlmisrtpevtcvvvdvshedpevkfnwyvdgvevhnaktkpreeqynstyrv vsvltvlhqdwlngkeykckvsnkalpasiektiskakgqprepqvytlppsrd eltknqvsltclvkgfypsdiavewesngqpennykttppvldsdgsffflyskl tvdksrwqqgnvfscsvmhealhnhytqkslslspgk |
| 97 RSLV133: hRNAseWT-SCC-mthIgG1-P238S-P331S-NLG-hDNAse 105/114 | aaagagagccgggccaagaagttccagcggcagcacatggacagcgacagcagc cccagcagctccagcacctactgcaaccagatgatgcggcggagaaacatgacc cagggccggtgcaagcccgtgaacaccttcgtgcacgagcccctggtggacgtg cagaacgtgtgttttcaagaaaaagtgacctgcaagaacggccagggcaactgc tacaagagcaacagcagcatgcacatcaccgactgccggctgaccaacggcagc agataccccaactgcgcctaccggaccagccccaaagaacggcacatcatcgtg gcctgcgagggcagccccttacgtgcccgtgcactttgacgccagcgtggaagat agcaccctggaacccaagagcagcgacaagacccacacctgtcccccctgccct gcccctgagctgctgggcggaagcagcgtgttcctgttcccccccaaagcccaag gacaccctgatgatcagccggaccccccgaagtgacctgcgtggtggtggatgtg tcccacgaggacccccgaagtgaagttcaattggtacgtggacggcgtggaagtg cacaacgccaagaccaagcccagagaggaacagtacaacagcacctaccgggtg gtgtccgtgctgaccgtgctgcaccaggactggctgaacggcaaagagtacaag tgcaaggtctccaacaaggccctgcccgccagcatcgagaaaaccatcagcaag gccaagggccagcctcgcgagccccaggtgtacacactgccccccagccgggac gagctgaccaagaaccaggtgtccctgacctgcctggtgaaaggcttctacccc agcgatatcgccgtggaatgggagagcaacggccagcccgagaacaactacaag accaccccccctgtgctggactccgacggctcattcttcctgtacagcaagctg accgtggacaagagccggtggcagcagggcaacgtgttcagctgcagcgtgatg cacgaggccctgcacaaccactacacccagaagtccctgagcctgagccccggc aaggtggacggcgccagctcccctgtgaacgtgtccagccccagcgtgcaggac atcctgaagatcgccgccttcaacatccagaccttcggcgagacaaagatgagc aacgccaccctggtgtcctacatcgtgcagatcctgagcagatacgatatcgcc ctggtgcaagaagtgcgggacagccacctgaccgccgtgggcaagctgctggac aacctgaaccaggacgcccccgacacctaccactacgtggtgtccgagcctctg ggccggaacagctacaaagaaagatacctgttcgtgtaccggcccgatcaggtg tccgccgtggacagctactactacgacgacggctgcgagccctgccgggaacgac acctttcaaccgcgagcccttcatcgtgcggttcttcagccggttcaccgaagtg cgcgagttcgccatcgtgcccctgcatgctgcccctggcgacgccgtggccgag atcgatgccctgtacgacgtgtacctggatgtgcaagaaaagtggggcctggaa gatgtgatgctgatgggcgacttcaacgccggctgcagctacgtgcggcccagc cagtggtccagcatcagactgtggaccctcccccaccttccagtggctgatcccc gacagcgccgataccaccgccacccccaccactgtgcctacgacagaatcgtg gtgccggcatgctgctgagaggcgccgtggtgcctgacagcgccctgccattc aattttcaagccgcctacggcctgagcgatcagctggcccaggccatcagcgac cactaccccgtggaagtgatgctgaagtga |
| 98 RSLV133: hRNAseWT-SCC-mthIgG1-P238S-P331S-NLG- | kesrakkfqrqhmdsdsspssssstycnqmmrrrnmtqgrckpvntfvheplvdv qnvcfqekvtckngqgncyksnssmhitdcrltngsrypncayrtspkerhiiv acegspyvpvhfdasvedstlepkssdkthtcppcpapellggssvflfppkpk dtlmisrtpevtcvvvdvshedpevkfnwyvdgvevhnaktkpreeqynstyrv vsvltvlhqdwlngkeykckvsnkalpasiektiskakgqprepqvytlppsrd eltknqvsltclvkgfypsdiavewesngqpennykttppvldsdgsffflyskl |

TABLE 1-continued

| SEQ ID NO: DESCRIPTION | SEQUENCE (NUCLEOTIDE SEQUENCES ARE 5'-3') |
|---|---|
| hDNAse 105/114 | tvdksrwqqgnvfscsvmhealhnhytqkslslspgkvdgasspvnvsspsvqd ilkiaafniqtfgetkmsnatlvsyivqilsrydialvqevrdshltavgkllld nlnqdapdtyhyvvseplgrnsykerylfvyrpdqvsavdsyyyddgcepcrnd tfnrepfivrffsrftevrefaivplhaapgdavaeidalydvyldvqekwgle dvmlmgdfnagcsyvrpsqwssirlwtsptfqwlipdsadttatpthcaydriv vagmllrgavvpdsalpfnfqaayglsdqlaqaisdhypvevmlk |
| 99 NLGlnk2 | vdgasspvnvsspsvqdi |
| 100 VK3LP leader | metpaqllflllwlpdttg |
| 101 hRNaseWT (mature) UniProt P07998) | kesrakkfqrqhmdsdsspssssstycnqmmrrrnmtqgrckpvntfvheplvdv qnvcfqekvtckngqgncyksnssmhitdcrltngsrypncayrtspkerhiiv acegspyvpvhfdasvedst |
| 102 hDNase 1 (mature) UniProt P24855 | lkiaafniqtfgetkmsnatlvsyivqilsrydialvqevrdshltavgkllln lnqdapdtyhyvvseplgrnsykerylfvyrpdqvsavdsyyyddgcepcgndt fnrepaivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlaqaisdhypvevmlk |
| 103 hDNase 1L3 (mature) UniProt Q13609 | mricsfnvrsfgeskqedknamdvivkvikrcdiilvmeikdsnnricpilmek lnrnsrrgitynyvissrlgrntykeqyaflykeklvsvkrsyhyhdyqdgdad vfsrepfvvwfqsphtavkdfviiplhttpetsvkeidelvevytdvkhrwkae nfifmgdfnagcsyvpkkawknirlrtdprfvwligdqedttvkkstncaydri vlrgqeivssvvpksnsvfdfqkayklteeealdvsdhfpveflqssraftns kksvtlrkktkskrs |
| 104 hTREX1 | mgpgarrqgrivqgrpemcfcpppptplpplriltlgthtptpcsspgsaagtyp tmgsqalppgpmqtliffdmeatglpfsqpkvtelcllavhrcalespptsqgp pptvppppprvvdkslslcvapgkacspaaseitglstavlaahgrqcfddnlanl llaflrrqpqpwclvahngdrydfpllqaelamlgltsaldgafcvdsitalka lerassphpehgprksyslgsiytrlygqsppdshtaegdvlallsicqwrpqal lrwvdaharpfgtirpmygvtasartkprpsavtttahlattrntspslgesrg tkdlppvkdpgalsregllaplgllailtlavatlyglslatpge |
| 105 hTREX1 (C-terminal 72 aa truncated) | mgpgarrqgrivqgrpemcfcpppptplpplriltlgthtptpcsspgsaagtyp tmgsqalppgpmqtliffdmeatglpfsqpkvtelcllavhrcalespptsqgp pptvppppprvvdkslslcvapgkacspaaseitglstavlaahgrqcfddnlanl llaflrrqpqpwclvahngdrydfpllqaelamlgltsaldgafcvdsitalka lerassphpehgprksyslgsiytrlygqsppdshtaegdvlallsicqwrpqal lrwvdaharpfgtirpmygvtasartk |
| 106 RSLV-124 hVK3LP-hRNase(WT)-hIgG1 WT | metpaqllflllwlpdttgkesrakkfqrqhmdsdsspssssstycnqmmrrrnm tqgrckpvntfvheplvdvqnvcfqekvtckngqgncyksnssmhitdcrltngs rypncayrtspkerhiivacegspyvpvhfdasvedstlepkssdkthtcppcp apellggpsvflfppkpkdtlmisrtpevtcvvvdvshedpevkfnwyvdgvevh naktkpreeqynstyrvvsvltvlhqdwlngkeykckvsnkalpapiektiskak gqprepqvytlppsrdeltknqvsltclvkgfypsdiavewesngqpennykttp pvldsdgsfflyskltvdksrwqqgnvfscsvmhealhnhytqkslslspgk |
| 107 NLGlnk | vdgasspvnvsspsvgdi |

The invention claimed is:

1. A method of treating systemic lupus erythematosus (SLE) in a subject comprising administering to the subject a composition comprising: a polypeptide consisting of human RNase 1 operatively coupled with or without a linker to a mutant human IgG1 Fc domain, wherein the Fc domain comprises a P238S mutation and a P331S mutation, numbering according to the EU index, and wherein the Fc domain does not contain a variable region that binds antigen; and a pharmaceutically acceptable carrier.

2. The method of claim 1, wherein the Fc domain has decreased binding to Fcγ receptors on human cells.

3. The method of claim 1, wherein the polypeptide has at least 1, 2, 3, 4, or 5-fold less cytotoxicity relative to a polypeptide having wild type Fc domain.

4. The method of claim 1, wherein the polypeptide has an increased serum half-life relative to a polypeptide comprising human RNase 1 without an Fc domain.

5. The method of claim 1, wherein the polypeptide degrades circulating RNA and RNA in immune complexes, or inhibits interferon-γ production, or both.

6. The method of claim 1, wherein the Fc domain comprises a hinge domain, a CH2 domain and a CH3 domain.

7. The method of claim 1, wherein the Fc domain further comprises a substitution of one or more of three hinge region cysteine residues with serine.

8. The method of claim 1, wherein the Fc domain further comprises an additional mutation selected from the group consisting of SCC, SSS (residues 220, 226, and 229), G236R, L328R, L234A, and L235A, numbering according to the EU index.

9. The method of claim 1, wherein the Fc domain further comprises an SCC mutation (residues 220, 226, and 229), numbering according to the EU index.

10. The method of claim 1, wherein the human RNase 1 is linked to the N-terminus of the Fc domain.

11. The method of claim 1, wherein the human RNase 1 is linked to the C-terminus of the Fc domain.

12. The method of claim 1, wherein the human RNase 1 is operatively coupled to the Fc domain without a linker domain.

13. The method of claim 1, wherein the human RNase 1 is operatively coupled to the Fc domain via a linker domain.

14. The method of claim 13, wherein the linker domain is a polypeptide linker.

15. The method of claim 14, wherein the polypeptide linker is a gly-ser linker.

16. The method of claim 1, wherein the human RNase 1 comprises the amino acid sequence set forth in SEQ ID NO: 101.

17. The method of claim 1, wherein the Fc domain comprises the amino acid sequence set forth in SEQ ID NO: 90.

18. A method of treating SLE in a subject comprising administering to the subject a composition comprising: a polypeptide consisting of human RNase 1 operatively coupled without a linker to the N-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen; and a pharmaceutically acceptable carrier.

19. The method of claim 18, wherein the Fc domain comprises a hinge domain, a CH2 domain and a CH3 domain.

20. The method of claim 18, wherein the human RNase 1 comprises the amino acid sequence set forth in SEQ ID NO: 101.

21. The method of claim 18, wherein the Fc domain comprises the amino acid sequence set forth in SEQ ID NO: 90.

22. A method of treating SLE in a subject comprising administering to the subject a composition comprising: a polypeptide consisting of human RNase 1 operatively coupled without a linker to the C-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen and a pharmaceutically acceptable carrier.

23. The method of claim 22, wherein the Fc domain comprises a hinge domain, a CH2 domain and a CH3 domain.

24. The method of claim 22, wherein the human RNase 1 comprises the amino acid sequence set forth in SEQ ID NO: 101.

25. The method of claim 22, wherein the Fc domain comprises the amino acid sequence set forth in SEQ ID NO: 90.

26. A method of degrading RNA containing immune complexes in a subject comprising administering to the subject a composition comprising: a polypeptide consisting of human RNase 1 operatively coupled with or without a linker to a mutant human IgG1 Fc domain, wherein the Fc domain comprises a P238S mutation and a P331S mutation, numbering according to the EU index, and wherein the Fc domain does not contain a variable region that binds antigen; and a pharmaceutically acceptable carrier.

27. A method of treating SLE in a subject, comprising administering to the subject a composition comprising a polypeptide consisting of the amino acid sequence set forth in SEQ ID NO: 96; and a pharmaceutically acceptable carrier.

28. A method of treating Sjogren's syndrome in a subject, comprising administering to the subject a composition comprising a polypeptide consisting of the amino acid sequence set forth in SEQ ID NO: 96; and a pharmaceutically acceptable carrier.

29. The method of claim 1, wherein the composition is formulated for intravenous administration.

30. The method of claim 27, wherein the composition is formulated for intravenous administration.

31. The method of claim 28, wherein the composition is formulated for intravenous administration.

32. A method of treating Sjogren's syndrome in a subject comprising administering to the subject a composition comprising: a polypeptide consisting of human RNase 1 operatively coupled with or without a linker to a mutant human IgG1 Fc domain, wherein the Fc domain comprises a P238S mutation and a P331S mutation, numbering according to the EU index, and wherein the Fc domain does not contain a variable region that binds antigen; and a pharmaceutically acceptable carrier.

33. The method of claim 32, wherein the Fc domain has decreased binding to Fcγ receptors on human cells.

34. The method of claim 32, wherein the polypeptide has at least 1, 2, 3, 4, or 5-fold less cytotoxicity relative to a polypeptide having wild type Fc domain.

35. The method of claim 32, wherein the polypeptide has an increased serum half-life relative to a polypeptide comprising human RNase 1 without an Fc domain.

36. The method of claim 32, wherein the polypeptide degrades circulating RNA and RNA in immune complexes, or inhibits interferon-γ production, or both.

37. The method of claim 32, wherein the Fc domain comprises a hinge domain, a CH2 domain and a CH3 domain.

38. The method of claim 32, wherein the Fc domain further comprises a substitution of one or more of three hinge region cysteine residues with serine.

39. The method of claim 32, wherein the Fc domain further comprises an additional mutation selected from the group consisting of SCC, SSS (residues 220, 226, and 229), G236R, L328R, L234A, and L235A, numbering according to the EU index.

40. The method of claim 32, wherein the Fc domain further comprises an SCC mutation (residues 220, 226, and 229), numbering according to the EU index.

41. The method of claim 32, wherein the human RNase 1 is linked to the N-terminus of the Fc domain.

42. The method of claim 32, wherein the human RNase 1 is linked to the C-terminus of the Fc domain.

43. The method of claim 32, wherein the human RNase 1 is operatively coupled to the Fc domain without a linker domain.

44. The method of claim 32, wherein the human RNase 1 is operatively coupled to the Fc domain via a linker domain.

45. The method of claim 44, wherein the linker domain is a polypeptide linker.

46. The method of claim 45, wherein the polypeptide linker is a gly-ser linker.

47. The method of claim 32, wherein the human RNase 1 comprises the amino acid sequence set forth in SEQ ID NO: 101.

48. The method of claim 32, wherein the Fc domain comprises the amino acid sequence set forth in SEQ ID NO: 90.

49. A method of treating Sjogren's syndrome in a subject comprising administering to the subject a composition comprising: a polypeptide consisting of human RNase 1 operatively coupled without a linker to the N-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen; and a pharmaceutically acceptable carrier.

50. The method of claim 49, wherein the Fc domain comprises a hinge domain, a CH2 domain and a CH3 domain.

51. The method of claim 49, wherein the human RNase 1 comprises the amino acid sequence set forth in SEQ ID NO: 101.

52. The method of claim 49, wherein the Fc domain comprises the amino acid sequence set forth in SEQ ID NO: 90.

53. A method of treating Sjogren's syndrome in a subject comprising administering to the subject a composition comprising: a polypeptide consisting of human RNase 1 operatively coupled without a linker to the C-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen; and a pharmaceutically acceptable carrier.

54. The method of claim 53, wherein the Fc domain comprises a hinge domain, a CH2 domain and a CH3 domain.

55. The method of claim 53, wherein the human RNase 1 comprises the amino acid sequence set forth in SEQ ID NO: 101.

56. The method of claim 53, wherein the Fc domain comprises the amino acid sequence set forth in SEQ ID NO: 90.

57. The method of claim 32, wherein the composition is formulated for intravenous administration.

58. The method of claim 26, wherein the Fc domain has decreased binding to Fcγ receptors on human cells.

59. The method of claim 26, wherein the polypeptide has at least 1, 2, 3, 4, or 5-fold less cytotoxicity relative to a polypeptide having wild type Fc domain.

60. The method of claim 26, wherein the polypeptide has an increased serum half-life relative to a polypeptide comprising human RNase 1 without an Fc domain.

61. The method of claim 26, wherein the polypeptide degrades circulating RNA and RNA in immune complexes, or inhibits interferon-γ production, or both.

62. The method of claim 26, wherein the Fc domain comprises a hinge domain, a CH2 domain and a CH3 domain.

63. The method of claim 26, wherein the Fc domain further comprises a substitution of one or more of three hinge region cysteine residues with serine.

64. The method of claim 26, wherein the Fc domain further comprises an additional mutation selected from the group consisting of SCC, SSS (residues 220, 226, and 229), G236R, L328R, L234A, and L235A, numbering according to the EU index.

65. The method of claim 26, wherein the Fc domain further comprises an SCC mutation (residues 220, 226, and 229), numbering according to the EU index.

66. The method of claim 26, wherein the human RNase 1 is linked to the N-terminus of the Fc domain.

67. The method of claim 26, wherein the human RNase 1 is linked to the C-terminus of the Fc domain.

68. The method of claim 26, wherein the human RNase 1 is operatively coupled to the Fc domain without a linker domain.

69. The method of claim 26, wherein the human RNase 1 is operatively coupled to the Fc domain via a linker domain.

70. The method of claim 69, wherein the linker domain is a polypeptide linker.

71. The method of claim 70, wherein the polypeptide linker is a gly-ser linker.

72. The method of claim 26, wherein the human RNase 1 comprises the amino acid sequence set forth in SEQ ID NO: 101.

73. The method of claim 26, wherein the Fc domain comprises the amino acid sequence set forth in SEQ ID NO: 90.

74. A method of degrading RNA containing immune complexes in a subject comprising administering to the subject a composition comprising: a polypeptide consisting of human RNase 1 operatively coupled without a linker to the N-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen; and a pharmaceutically acceptable carrier.

75. The method of claim 74, wherein the Fc domain comprises a hinge domain, a CH2 domain and a CH3 domain.

76. The method of claim 74, wherein the human RNase 1 comprises the amino acid sequence set forth in SEQ ID NO: 101.

77. The method of claim 74, wherein the Fc domain comprises the amino acid sequence set forth in SEQ ID NO: 90.

78. A method of degrading RNA containing immune complexes in a subject, comprising administering to the subject a composition comprising a polypeptide consisting of the amino acid sequence set forth in SEQ ID NO: 96; and a pharmaceutically acceptable carrier.

79. A method of degrading RNA containing immune complexes in a subject comprising administering to the subject a composition comprising: a polypeptide consisting of human RNase 1 operatively coupled without a linker to the C-terminus of a mutant human IgG1 Fc domain, wherein the Fc domain comprises an SCC mutation (residues 220, 226, and 229), a P238S mutation, and a P331S mutation, numbering according to the EU index, and wherein the Fc domain does not contain a variable region that binds antigen; and a pharmaceutically acceptable carrier.

80. The method of claim 79, wherein the Fc domain comprises a hinge domain, a CH2 domain and a CH3 domain.

81. The method of claim 79, wherein the human RNase 1 comprises the amino acid sequence set forth in SEQ ID NO: 101.

82. The method of claim 79, wherein the Fc domain comprises the amino acid sequence set forth in SEQ ID NO: 90.

83. The method of claim 26, wherein the composition is formulated for intravenous administration.

84. The method of claim 78, wherein the composition is formulated for intravenous administration.

* * * * *

SEQUENCE LISTING

<160> NUMBER OF SEQ ID NOS: 126

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gttaagcttg ccaccatggg tctggagaag tccctcattc tg           42

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gataccaccg gtagggaatc tgcagcacag aagtttcag                                   39

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ggctcgagca cagtagcatc aaagtggact ggtacgtagg                                  40

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aaatctagac ctcaaccagg tagggaatct gcagcacaga agtttcag                         48

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tctagactat cacacagtag catcaaagtg gactggtacg tag                              43

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgtccaccgt gtccagcacc tgaactcctg ggtggatcgt cagtcttcc                        49

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
agatctcgag cccaaatctt ctgacaaaac tcacacatgt ccaccgtgt                        49

-continued

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctagattat catttacccg gagacagaga gaggctcttc tgcgtgtagt g          51

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctccatgca aatgcccagc acctaacctc ttgggtggat catccgtctt catcttcc    58

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaagatctcg agcccagagg tcccacaatc aagccctctc ctcca                 45

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtttctagat tatcatttac ccggagtccg agagaagctc ttagtcgt              48

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agatctcgag cccaaatctt ctgacaaaac tcacacatgt ccaccgtgt             49

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttttctcga tggaggctgg gagggctttg ttggagacc                        39

<210> SEQ ID NO 14

<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aaggtctcca acaaagccct cccagcctcc atcgagaaaa caatctcc        48

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tctagattat catttacccg gagacagaga gaggctcttc tgcgtgtagt g        51

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gttaccggtc tgaagatcgc agccttcaac atccag        36

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gttctcgaga tctttcagca tcacctccac tggatagtg        39

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gttgatatcc tgaagatcgc agccttcaac atccag        36

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtttctagat tatcacttca gcatcacctc cactggatag tg        42

<210> SEQ ID NO 20
<211> LENGTH: 58

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctccaccga gcccagcacc tgaactcctg ggaggatcgt cagtcttcct cttccccc        58

<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agatctcgag cccaaatctt ctgacaaaac tcacacatct ccaccgagcc cagcacct        58

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtctccaaca aagccctccc agcctccatc gagaaaacca tctcca                    46

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tggagatggt tttctcgatg ggggctggga gggctttgtt ggagacc                   47

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tctagattat cattttcccg gagagagaga gaggctcttc tgcgtgtagt g               51

<210> SEQ ID NO 25
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctccaccga gcccagcacc tgaactcctg ggaggatcgt cagtcttcct cttccccc        58

<210> SEQ ID NO 26
<211> LENGTH: 58
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 26
agatctcgag cccaaatctt ctgacaaaac tcacacatct ccaccgagcc cagcacct        58

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggagatggt tttctcgatg ggggctggga gggctttgtt ggagacc                    47

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctagattat cattttcccg gagagagaga gaggctcttc tgcgtgtagt g               51

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatatcctgc acgctagggc tgctcacatt                                       30

<210> SEQ ID NO 30
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agatctctcc ggaggaggtg gctcaggtgg tggaggatct ggaggaggtg ggagtggtgg      60
aggtggttct accggtctcg ag                                               82

<210> SEQ ID NO 31
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agatctctcc ggaggaggtg gctcaggtgg tggaggatct ggaggaggtg gctcaggtgg      60
tggaggatct ggaggaggtg ggagtaccgg tctcgag                               97
```

<210> SEQ ID NO 32
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
agatctctcc ggaggaggtg gctcaggtgg tggaggatct ggaggaggtg gctcaggtgg      60
tggaggatct ggaggaggtg ggagtctcga g                                    91

<210> SEQ ID NO 33
<211> LENGTH: 462
<212> TYPE: DNA
<213> ORGANISM: Homo sapiens

<400> SEQUENCE: 33
gtcgacggag ctagcagccc cgtgaacgtg agcagcccca gcgtgcagga tatcccttcc      60
ctgggcaagg aatcccgggc caagaaattc cagcggcagc atatggactc agacagttcc     120
cccagcagca gctccaccta ctgtaaccaa atgatgaggc gccggaatat gacacagggg     180
cggtgcaaac cagtgaacac cttttgtgcac gagcccctgg tagatgtcca gaatgtctgt     240
ttccaggaaa aggtcacctg caagaacggg cagggcaact gctacaagag caactccagc     300
atgcacatca cagactgccg cctgacaaac gactccaggt accccaactg tgcataccgg     360
accagcccga aggagagaca catcattgtg gcctgtgaag ggagcccata tgtgccagtc     420
cactttgatg cttctgtgga ggactctacc taataatcta ga                        462

<210> SEQ ID NO 34
<211> LENGTH: 798
<212> TYPE: DNA
<213> ORGANISM: Homo sapiens

<400> SEQUENCE: 34
gatatcctga agatcgcagc cttcaacatc cagacatttg gggagaccaa gatgtccaat      60 gccacccctcg tcagctacat tgtgcagatc ctgagccgct atgacatcgc cctggtccag     120
gaggtcagag acagccacct gactgccgtg ggaagctgc tggacaacct caatcaggat      180
gcaccagaca cctatcacta cgtggtcagt gagccactgg acggaacag ctataaggag       240 cgctacctgt tcgtgtacag gcctgaccag gtgtctgcgg tggacagcta ctactacgat     300
gatggctgcg agccctgcag gaacgacacc ttcaaccgag agccattcat tgtcaggttc     360
ttctcccggt tcacagaggt cagggagttt gccattgttc ccctgcatgc ggccccgggg     420
gacgcagtag ccgagatcga cgctctctat gacgtctacc tggatgtcca agagaaatgg     480
ggcttggagg acgtcatgtt gatgggcgac ttcaatgcgg gctgcagcta tgtgagaccc     540
tcccagtggt catccatccg cctgtggaca agccccacct tccagtggct gatccccgac     600
agcgctgaca ccacagctac acccacgcac tgtgcctatg acaggatcgt ggttgcaggg     660
atgctgctcc gaggcgccgt tgttcccgac tcggctcttc cctttaactt ccaggctgcc     720
tatggcctga gtgaccaact ggcccaagcc atcagtgacc actatccagt ggaggtgatg     780
ctgaagtgat aatctaga                                                   798

<210> SEQ ID NO 35
<211> LENGTH: 798
<212> TYPE: DNA
<213> ORGANISM: Homo sapiens

<400> SEQUENCE: 35

```
gatatcctga agatcgcagc cttcaacatc cagacatttg gggagaccaa gatgtccaat    60
gccaccctcg tcagctacat tgtgcagatc ctgagccgct atgacatcgc cctggtccag   120
gaggtcagag acagccacct gactgccgtg gggaagctgc tggacaacct caatcaggat   180
gcaccagaca cctatcacta cgtggtcagt gagccactgg gacggaacag ctataaggag   240
cgctacctgt tcgtgtacag gcctgaccag gtgtctgcgg tggacagcta ctactacgat   300
gatggctgcg agccctgcgg gaacgacacc ttcaaccgag agccagccat tgtcaggttc   360
ttctcccggt tcacagaggt cagggagttt gccattgttc ccctgcatgc ggccccgggg   420
gacgcagtag ccgagatcga cgctctctat gacgtctacc tggatgtcca agagaaatgg   480
ggcttggagg acgtcatgtt gatgggcgac ttcaatgcgg gctgcagcta tgtgagaccc   540
tcccagtggt catccatccg cctgtggaca agccccacct tccagtggct gatccccgac   600
agcgctgaca ccacagctac acccacgcac tgtgcctatg acaggatcgt ggttgcaggg   660
atgctgctcc gaggcgccgt tgttcccgac tcggctcttc cctttaactt ccaggctgcc   720
tatggcctga gtgaccaact ggcccaagcc atcagtgacc actatccagt ggaggtgatg   780
ctgaaatgat aatctaga                                                  798
```

<210> SEQ ID NO 36
<211> LENGTH: 798
<212> TYPE: DNA
<213> ORGANISM: Homo sapiens

<400> SEQUENCE: 36

```
gatatcctga agatcgcagc cttcaacatc cagacatttg gggagaccaa gatgtccaat    60
gccaccctcg tcagctacat tgtgcagatc ctgagccgct atgacatcgc cctggtccag   120
gaggtcagag acagccacct gactgccgtg gggaagctgc tggacaacct caatcaggat   180
gcaccagaca cctatcacta cgtggtcagt gagccactgg gacggaacag ctataaggag   240
cgctacctgt tcgtgtacag gcctgaccag gtgtctgcgg tggacagcta ctactacgat   300
gatggctgcg agccctgcgg gaacgacacc ttcaaccgag agccattcat tgtcaggttc   360
ttctcccggt tcacagaggt cagggagttt gccattgttc ccctgcatgc ggccccgggg   420
gacgcagtag ccgagatcga cgctctctat gacgtctacc tggatgtcca agagaaatgg   480
ggcttagagg acgtcatgtt gatgggcgac ttcaatgcgg gctgcagcta tgtgagaccc   540
tcccagtggt catccatccg cctgtggaca agccccacct tccagtggct gatccccgac   600
agcgctgaca ccacagctac acccacgcac tgtgcctatg acaggatcgt ggttgcaggg   660
atgctgctcc gaggcgccgt tgttcccgac tcggctcttc cctttaactt ccaggctgcc   720
tatggcctga gtgaccaact ggcccaagcc atcagtgacc actatccagt ggaggtgatg   780
ctgaagtgat aatctaga                                                  798
```

<210> SEQ ID NO 37
<211> LENGTH: 795
<212> TYPE: DNA
<213> ORGANISM: Homo sapiens

<400> SEQUENCE: 37

```
accggtctga agatcgcagc cttcaacatc cagacatttg gggagaccaa gatgtccaat    60
gccaccctcg tcagctacat tgtgcagatc ctgagccgct atgacatcgc cctggtccag   120
```

| | |
|---|---|
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcag gaacgacacc ttcaaccgag agccattcat tgtcaggttc | 360 |
| ttctcccggt tcacagaggt cagggagttt gccattgttc cctgcatgc ggccccgggg | 420 |
| gacgcagtag ccgagatcga cgctctctat gacgtctacc tggatgtcca agagaaatgg | 480 |
| ggcttggagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaaagatc tcgag | 795 |

<210> SEQ ID NO 38
<211> LENGTH: 795
<212> TYPE: DNA
<213> ORGANISM: Homo sapiens

<400> SEQUENCE: 38

| | |
|---|---|
| accggtctga agatcgcagc cttcaacatc cagacatttg gggagaccaa gatgtccaat | 60 |
| gccaccctcg tcagctacat tgtgcagatc ctgagccgct atgacatcgc cctggtccag | 120 |
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcgg gaacgacacc ttcaaccgag agccagccat tgtcaggttc | 360 |
| ttctcccggt tcacagaggt cagggagttt gccattgttc cctgcatgc ggccccgggg | 420 |
| gacgcagtag ccgagatcga cgctctctat gacgtctacc tggatgtcca agagaaatgg | 480 |
| ggcttggagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaaagatc tcgag | 795 |

<210> SEQ ID NO 39
<211> LENGTH: 795
<212> TYPE: DNA
<213> ORGANISM: Homo sapiens

<400> SEQUENCE: 39

| | |
|---|---|
| accggtctga agatcgcagc cttcaacatc cagacatttg gggagaccaa gatgtccaat | 60 |
| gccaccctcg tcagctacat tgtgcagatc ctgagccgct atgacatcgc cctggtccag | 120 |
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcgg gaacgacacc ttcaaccgag agccattcat tgtcaggttc | 360 |

```
ttctcccggt tcacagaggt cagggagttt gccattgttc ccctgcatgc ggccccgggg    420
gacgcagtag ccgagatcga cgctctctat gacgtctacc tggatgtcca agagaaatgg    480
ggcttagagg acgtcatgtt gatgggcgac ttcaatgcgg gctgcagcta tgtgagaccc    540
tcccagtggt catccatccg cctgtggaca agccccacct tccagtggct gatccccgac    600
agcgctgaca ccacagctac acccacgcac tgtgcctatg acaggatcgt ggttgcaggg    660
atgctgctcc gaggcgccgt tgttcccgac tcggctcttc cctttaactt ccaggctgcc    720
tatggcctga gtgaccaact ggcccaagcc atcagtgacc actatccagt ggaggtgatg    780
ctgaaagatc tcgag                                                     795
```

<210> SEQ ID NO 40
<211> LENGTH: 715
<212> TYPE: DNA
<213> ORGANISM: Homo sapiens

<400> SEQUENCE: 40

```
agatctcgag cccaaatctt ctgacaaaac tcacacatgt ccaccgtgcc cagcacctga     60
actcctgggg ggaccgtcag tcttcctctt ccccccaaaa cccaaggaca ccctcatgat    120
ctcccggacc cctgaggtca catgcgtggt ggtggacgtg agccacgaag accctgaggt    180
caagttcaac tggtacgtgg acggcgtgga ggtgcataat gccaagacaa agccgcggga    240
ggagcagtac aacagcacgt accgtgtggt cagcgtcctc accgtcctgc accaggactg    300
gctgaatggc aaggagtaca gtgcaaggt ctccaacaaa gccctcccag cccccatcga    360
gaaaaccatc tccaaagcca aagggcagcc ccgagaacca caggtgtaca ccctgccccc    420
atcccgggat gagctgacca agaaccaggt cagcctgacc tgcctggtca aaggcttcta    480
tcccagcgac atcgccgtgg agtgggagag caatgggcag ccggagaaca actacaagac    540
cacgcctccc gtgctggact ccgacggctc cttcttcctc tacagcaagc tcaccgtgga    600
caagagcagg tggcagcagg ggaacgtctt ctcatgctcc gtgatgcatg aggctctgca    660
caaccactac acgcagaaga gcctctctct gtctccgggt aaatgataat ctaga         715
```

<210> SEQ ID NO 41
<211> LENGTH: 858
<212> TYPE: DNA
<213> ORGANISM: Homo sapiens

<400> SEQUENCE: 41

```
gttaagcttg ccaccatgga aaccccagcg cagcttctct cctcctgct actctggctc     60 ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
ctggtccagg aggtcagaga cagccaccta actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcggg aacgacacct tcaaccgaga gccagccatt    420
gtcaggttct ctctcccggt tcacagaggt cagggagttt gccattgttcc cctgcatgcg    480 gccccggggg acgcagtagc cgagatcgac gctctctatg acgtctacct ggatgtccaa    540
gagaaatggg gcttgaggga cgtcatgttg atgggcgact tcaatgcggg ctgcagctat    600
gtgagaccct cccagtggtc atccatccgc ctgtggacaa gccccacctt ccagtggctg    660
```

```
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaagtga                                                  858

<210> SEQ ID NO 42
<211> LENGTH: 918
<212> TYPE: DNA
<213> ORGANISM: Homo sapiens

<400> SEQUENCE: 42
atgtcacggg agctggcccc actgctgctt ctcctcctct ccatccacag cgccctggcc     60
atgaggatct gctccttcaa cgtcaggtcc tttggggaaa gcaagcagga agacaagaat    120
gccatggatg tcattgtgaa ggtcatcaaa cgctgtgaca tcatactcgt gatggaaatc    180
aaggacagca caacaggat ctgccccata ctgatggaga agctgaacag aaattcaagg    240
agaggcataa catacaacta tgtgattagc tctcggcttg aagaaacac atataaagaa    300 caatatgcct ttctctacaa ggaaaagctg gtgtctgtga agaggagtta tcactaccat    360
gactatcagg atggagacgc agatgtgttt tccaggagc cctttgtggt ctggttccaa    420 tctcccccaca ctgctgtcaa agacttcgtg attatccccc tgcacaccac cccagagaca    480
tccgttaagg agatcgatga gttggttgag gtctacacgg acgtgaaaca ccgctggaag    540
gcggagaatt tcattttcat gggtgacttc aatgccggct gcagctacgt ccccaagaag    600
gcctggaaga acatccgctt gaggactgac cccaggtttg tttggctgat cggggaccaa    660
gaggacacca cggtgaagaa gagcaccaac tgtgcatatg acaggattgt gcttagagga    720
caagaaatcg tcagttctgt tgttcccaag tcaaacagtg tttttgactt ccagaaagct    780
tacaagctga ctgaagagga ggccctggat gtcagcgacc actttccagt tgaatttaaa    840
ctacagtctt caagggcctt caccaacagc aaaaaatctg tcactctaag gaagaaaaca    900
aagagcaaac gctcctag                                                  918

<210> SEQ ID NO 43
<211> LENGTH: 459
<212> TYPE: DNA
<213> ORGANISM: Homo sapiens

<400> SEQUENCE: 43
atgggtctgg agaagtctct tgtccggctc cttctgcttg tcctgatact gctggtgctg     60
ggctgggtcc agccttccct gggcaaggaa tcccgggcca agaaattcca gcggcagcat    120
atggactcag acagttcccc cagcagcagc tccacctact gtaaccaaat gatgaggcgc    180
cggaatatga cacaggggcg gtgcaaacca gtgaacacct ttgtgcacga gcccctggta    240
gatgtccaga atgtctgttt ccaggaaaag gtcacctgca agaacgggca gggcaactgc    300
tacaagagca actccagcat gcacatcaca gactgccgcc tgacaaacgg ctccaggtac    360
cccaactgtg cataccggac cagcccgaag gagagacaca tcattgtggc ctgtgaaggg    420
agcccatatg tgccagtcca ctttgatgct actgtgtag                            459

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 44
gtcgacggcg cggccgccag ccccgtgaac gtgagcagcc ccagcgtgca ggatatc    57

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser Gly Gly Gly Ser Gly Gly Gly Gly Ser Gly
1               5                   10                  15

Gly Gly Gly Ser
            20

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 48
<211> LENGTH: 260
<212> TYPE: PRT
<213> ORGANISM: Homo sapiens

<400> SEQUENCE: 48

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

```
Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
                100                 105                 110

Pro Phe Ile Val Arg Phe Phe Ser Arg Phe Thr Glu Val Arg Glu Phe
            115                 120                 125

Ala Ile Val Pro Leu His Ala Ala Pro Gly Asp Ala Val Ala Glu Ile
            130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
            195                 200                 205

Cys Ala Tyr Asp Arg Ile Val Val Ala Gly Met Leu Leu Arg Gly Ala
210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 49
<211> LENGTH: 260
<212> TYPE: PRT
<213> ORGANISM: Homo sapiens

<400> SEQUENCE: 49

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
        50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
                100                 105                 110

Pro Ala Ile Val Arg Phe Phe Ser Arg Phe Thr Glu Val Arg Glu Phe
            115                 120                 125

Ala Ile Val Pro Leu His Ala Ala Pro Gly Asp Ala Val Ala Glu Ile
            130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
```

```
                    180                 185                 190
Gln Trp Leu Ile Pro Asp Ser Ala Asp Thr Thr Ala Thr Pro Thr His
            195                 200                 205

Cys Ala Tyr Asp Arg Ile Val Val Ala Gly Met Leu Leu Arg Gly Ala
        210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
            245                 250                 255

Val Met Leu Lys
        260

<210> SEQ ID NO 50
<211> LENGTH: 260
<212> TYPE: PRT
<213> ORGANISM: Homo sapiens

<400> SEQUENCE: 50

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 51
<211> LENGTH: 260
```

```
<212> TYPE: PRT
<213> ORGANISM: Homo sapiens

<400> SEQUENCE: 51

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
        50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 52
<211> LENGTH: 260
<212> TYPE: PRT
<213> ORGANISM: Homo sapiens

<400> SEQUENCE: 52

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
        50                  55                  60

Tyr Val Val Ser Glu Pro Leu Gly Arg Asn Ser Tyr Lys Glu Arg Tyr
65                  70                  75                  80
```

```
Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 53
<211> LENGTH: 260
<212> TYPE: PRT
<213> ORGANISM: Homo sapiens

<400> SEQUENCE: 53

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190
```

```
Gln Trp Leu Ile Pro Asp Ser Ala Asp Thr Thr Ala Thr Pro Thr His
            195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
            245                 250                 255

Val Met Leu Lys
            260

<210> SEQ ID NO 54
<211> LENGTH: 233
<212> TYPE: PRT
<213> ORGANISM: Homo sapiens

<400> SEQUENCE: 54

Leu Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 55
<211> LENGTH: 128
<212> TYPE: PRT
<213> ORGANISM: Homo sapiens

<400> SEQUENCE: 55

Lys Glu Ser Arg Ala Lys Lys Phe Gln Arg Gln His Met Asp Ser Asp
1               5                   10                  15
```

```
Ser Ser Pro Ser Ser Ser Thr Tyr Cys Asn Gln Met Met Arg Arg
        20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
 50                  55                  60

Cys Lys Asn Gly Gln Gly Asn Cys Tyr Lys Ser Asn Ser Ser Met His
 65                  70                  75                  80

Ile Thr Asp Cys Arg Leu Thr Asn Asp Ser Arg Tyr Pro Asn Cys Ala
                85                  90                  95

Tyr Arg Thr Ser Pro Lys Glu Arg His Ile Ile Val Ala Cys Glu Gly
                100                 105                 110

Ser Pro Tyr Val Pro Val His Phe Asp Ala Ser Val Glu Asp Ser Thr
            115                 120                 125
```

<210> SEQ ID NO 56
<211> LENGTH: 280
<212> TYPE: PRT
<213> ORGANISM: Homo sapiens

<400> SEQUENCE: 56

```
Met Glu Thr Pro Ala Gln Leu Leu Phe Leu Leu Leu Trp Leu Pro
 1               5                  10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
 50                  55                  60

Leu Thr Ala Val Gly Lys Leu Leu Asp Asn Leu Asn Gln Asp Ala Pro
 65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
                100                 105                 110

Asp Ser Tyr Tyr Tyr Asp Asp Gly Cys Glu Pro Cys Gly Asn Asp Thr
            115                 120                 125

Phe Asn Arg Glu Pro Ala Ile Val Arg Phe Phe Ser Arg Phe Thr Glu
        130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
                180                 185                 190

Cys Ser Tyr Val Arg Pro Ser Gln Trp Ser Ser Ile Arg Leu Trp Thr
            195                 200                 205

Ser Pro Thr Phe Gln Trp Leu Ile Pro Asp Ser Ala Asp Thr Thr Ala
        210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
```

```
                 260                 265                 270

Tyr Pro Val Glu Val Met Leu Lys
        275                 280

<210> SEQ ID NO 57
<211> LENGTH: 305
<212> TYPE: PRT
<213> ORGANISM: Homo sapiens

<400> SEQUENCE: 57

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 58
<211> LENGTH: 156
<212> TYPE: PRT
<213> ORGANISM: Homo sapiens
```

<400> SEQUENCE: 58

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155

<210> SEQ ID NO 59
<211> LENGTH: 693
<212> TYPE: DNA
<213> ORGANISM: Homo sapiens

<400> SEQUENCE: 59
cccaaatctt ctgacaaaac tcacacatct ccaccgtctc cagcacctga actcctgggg      60
ggaccgtcag tcttcctctt cccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cccccatcga gaaaaccatc     360
tccaaagcca agggcagccc cgagaaccca caggtgtaca ccctgccccc atcccgggat     420
gagctgacca agaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tacagcaagc tcaccgtgga caagagcagg     600
tggcagcagg ggaacgtctt ctcatgctcc gtgatgcatg aggctctgca caaccactac     660
acgcagaaga gcctctctct gtctccgggt aaa                                 693

<210> SEQ ID NO 60
<211> LENGTH: 233
<212> TYPE: PRT
<213> ORGANISM: Homo sapiens

<400> SEQUENCE: 60

Leu Glu Pro Lys Ser Ser Asp Lys Thr His Thr Ser Pro Pro Ser Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val

|  |  |  |  |  | 35 |  |  |  |  | 40 |  |  |  |  | 45 |  |
|---|---|---|---|---|---|---|---|---|---|---|---|---|---|---|---|---|

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 61
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atggaaaccc ctgcccagct gctgttcctg ctgctgctgt ggctgcccga caccaccggt        60
aaggaatccc gggccaagaa attccagcgg cagcatatgg actcagacag ttcccccagc       120
agcagctcca cctactgtaa ccaaatgatg aggcgccgga atatgacaca ggggcggtgc       180
aaaccagtga cacctttgt gcacgagccc ctggtagatg tccagaatgt ctgtttccag        240
gaaaaggtca cctgcaagaa cgggcagggc aactgctaca gagcaactc cagcatgcac        300 atcacagact gccgcctgac aaacggctcc aggtacccca actgtgcata ccggaccagc       360
ccgaaggaga gacacatcat tgtggcctgt gaagggagcc catatgtgcc agtccacttt       420
gatgcttctg tggaggactc taccctcgag cccaaatctt ctgacaaaac tcacacatct       480
ccaccgagcc cagcacctga actcctggga ggatcgtcag tcttcctctt ccccccaaaa       540
cccaaggaca ccctcatgat ctcccggacc cctgaggtca catgcgtggt ggtggacgtg       600
agccacgaag accctgaggt caagttcaac tggtacgtgg acggcgtgga ggtgcataat       660
gccaagacaa agccgcggga ggagcagtac aacagcacgt accgtgtggt cagcgtcctc       720
accgtcctgc accaggactg gctgaatggc aaggagtaca agtgcaaggt ctccaacaaa       780
gccctcccag cctccatcga gaaaaccatc tccaaagcca agggcagccc cgagaaccca       840
caggtgtaca ccctgccccc atcccgggat gagctgacca agaaccaggt cagcctgacc       900

-continued

```
tgcctggtca aaggcttcta tcccagcgac atcgccgtgg agtgggagag caatgggcag    960
ccggagaaca actacaagac cacgcctccc gtgctggact ccgacggctc cttcttcctc   1020
tacagcaagc tcaccgtgga caagagcagg tggcagcagg ggaacgtctt ctcatgctcc   1080
gtgatgcatg aggctctgca caaccactac acgcagaaga gcctctctct ctctccggga   1140
aaatga                                                              1146
```

<210> SEQ ID NO 62
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Ser
145                 150                 155                 160

Pro Pro Ser Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
```

```
                305                 310                 315                 320
Pro Glu Asn Asn Tyr Lys Thr Thr Pro Pro Val Leu Asp Ser Asp Gly
                    325                 330                 335

Ser Phe Phe Leu Tyr Ser Lys Leu Thr Val Asp Lys Ser Arg Trp Gln
                340                 345                 350

Gln Gly Asn Val Phe Ser Cys Ser Val Met His Glu Ala Leu His Asn
                355                 360                 365

His Tyr Thr Gln Lys Ser Leu Ser Leu Ser Pro Gly Lys
            370                 375                 380

<210> SEQ ID NO 63
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atggaaaccc cagcgcagct tctcttcctc ctgctactct ggctcccaga taccaccggt    60
aaggaatccc gggccaagaa attccagcgg cagcatatgg actcagacag ttcccccagc   120
agcagctcca cctactgtaa ccaaatgatg aggcgccgga atatgacaca ggggcggtgc   180
aaaccagtga acacctttgt gcacgagccc tggtagatg tccagaatgt ctgtttccag    240
gaaaaggtca cctgcaagaa cgggcagggc aactgctaca gagcaactc cagcatgca    300 atcacagact gccgcctgac aaacggctcc aggtacccca ctgtgcata ccggaccagc   360 ccgaaggaga gacacatcat tgtggcctgt gaagggagcc atatgtgcc agtccacttt    420 gatgcttctg tggaggactc tacagatctc tccggaggag gtggctcagg tggtggagga    480
tctggaggag gtgggagtgg tggaggtggt tctaccggtc tcgagcccaa atcttctgac    540
aaaactcaca catctccacc gagcccagca cctgaactcc tgggaggatc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagcctcc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct tcctctacag caagctcacc gtggacaaga gcaggtggca gcaggggaac   1140
gtcttctcat gctccgtgat gcatgaggct ctgcacaacc actacacgca gaagagcctc   1200
tctctctctc cgggaaaatg a                                             1221

<210> SEQ ID NO 64
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Glu Thr Pro Ala Gln Leu Leu Phe Leu Leu Leu Leu Trp Leu Pro
```

```
  1               5                  10                 15
Asp Thr Thr Gly Lys Glu Ser Arg Ala Lys Phe Gln Arg Gln His
               20                 25                 30
Met Asp Ser Asp Ser Ser Pro Ser Ser Ser Thr Tyr Cys Asn Gln
               35                 40                 45
Met Met Arg Arg Asn Met Thr Gln Gly Arg Cys Lys Pro Val Asn
 50                 55                 60
Thr Phe Val His Glu Pro Leu Val Asp Val Gln Asn Val Cys Phe Gln
 65                 70                 75                 80
Glu Lys Val Thr Cys Lys Asn Gly Gln Gly Asn Cys Tyr Lys Ser Asn
                    85                 90                 95
Ser Ser Met His Ile Thr Asp Cys Arg Leu Thr Asn Gly Ser Arg Tyr
                   100                105                110
Pro Asn Cys Ala Tyr Arg Thr Ser Pro Lys Glu Arg His Ile Ile Val
                   115                120                125
Ala Cys Glu Gly Ser Pro Tyr Val Pro Val His Phe Asp Ala Ser Val
                   130                135                140
Glu Asp Ser Thr Gly Gly Gly Ser Gly Gly Gly Ser Gly Gly
145                150                155                160
Gly Gly Ser Gly Gly Gly Ser Leu Glu Pro Lys Ser Ser Asp Lys
                   165                170                175
Thr His Thr Ser Pro Pro Ser Pro Ala Pro Glu Leu Leu Gly Gly Ser
                   180                185                190
Ser Val Phe Leu Phe Pro Pro Lys Pro Lys Asp Thr Leu Met Ile Ser
                   195                200                205
Arg Thr Pro Glu Val Thr Cys Val Val Val Asp Val Ser His Glu Asp
                   210                215                220
Pro Glu Val Lys Phe Asn Trp Tyr Val Asp Gly Val Glu Val His Asn
225                230                235                240
Ala Lys Thr Lys Pro Arg Glu Glu Gln Tyr Asn Ser Thr Tyr Arg Val
                   245                250                255
Val Ser Val Leu Thr Val Leu His Gln Asp Trp Leu Asn Gly Lys Glu
                   260                265                270
Tyr Lys Cys Lys Val Ser Asn Lys Ala Leu Pro Ala Ser Ile Glu Lys
                   275                280                285
Thr Ile Ser Lys Ala Lys Gly Gln Pro Arg Glu Pro Gln Val Tyr Thr
                   290                295                300
Leu Pro Pro Ser Arg Asp Glu Leu Thr Lys Asn Gln Val Ser Leu Thr
305                310                315                320
Cys Leu Val Lys Gly Phe Tyr Pro Ser Asp Ile Ala Val Glu Trp Glu
                   325                330                335
Ser Asn Gly Gln Pro Glu Asn Asn Tyr Lys Thr Thr Pro Pro Val Leu
                   340                345                350
Asp Ser Asp Gly Ser Phe Phe Leu Tyr Ser Lys Leu Thr Val Asp Lys
                   355                360                365
Ser Arg Trp Gln Gln Gly Asn Val Phe Ser Cys Ser Val Met His Glu
                   370                375                380
Ala Leu His Asn His Tyr Thr Gln Lys Ser Leu Ser Leu Ser Pro Gly
385                390                395                400
Lys

<210> SEQ ID NO 65
<211> LENGTH: 2064
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atggaaaccc cagcgcagct tctcttcctc ctgctactct ggctcccaga taccaccggt      60
ctgaagatcg cagccttcaa catccagaca tttggggaga ccaagatgtc caatgccacc     120
ctcgtcagct acattgtgca gatcctgagc cgctatgaca tcgccctggt ccaggaggtc     180
agagacagcc acctgactgc cgtggggaag ctgctggaca acctcaatca ggatgcacca     240
gacacctatc actacgtggt cagtgagcca ctggacggaa cagctataa ggagcgctac      300
ctgttcgtgt acaggcctga ccaggtgtct gcggtggaca gctactacta cgatgatggc     360
tgcgagccct gcaggaacga caccttcaac cgagagccat tcattgtcag gttcttctcc     420
cggttcacag aggtcaggga gtttgccatt gttcccctgc atgcggcccc ggggacgca      480
gtagccgaga tcgacgctct ctatgacgtc tacctggatg ccaagagaa atggggcttg     540
gaggacgtca tgttgatggg cgacttcaat gcgggctgca gctatgtgag accctcccag    600
tggtcatcca tccgcctgtg acaagcccc accttccagt ggctgatccc cgacagcgct     660
gacaccacag ctacacccac gcactgtgcc tatgacagga tcgtggttgc agggatgctg    720
ctccgaggcg ccgttgttcc cgactcggct cttcccttta acttccaggc tgcctatggc    780
ctgagtgacc aactggccca agccatcagt gaccactatc cagtggaggt gatgctgaaa    840
gatctctccg gaggagtgg ctcaggtggt ggaggatctg gaggaggtgg gagtggtgga    900
ggttctaccg gtctcgagcc caaatcttct gacaaaactc acacatctcc accgagccca    960
gcacctgaac tcctgggagg atcgtcagtc ttcctcttcc ccccaaaacc caaggacacc   1020
ctcatgatct cccggacccc tgaggtcaca tgcgtggtgg tggacgtgag ccacgaagac   1080
cctgaggtca agttcaactg gtacgtggac ggcgtggagg tgcataatgc caagacaaag   1140
ccgcgggagg agcagtacaa cagcacgtac cgtgtggtca gcgtcctcac cgtcctgcac   1200
caggactggc tgaatggcaa ggagtacaag tgcaaggtct ccaacaaagc cctcccagcc   1260
tccatcgaga aaaccatctc caaagccaaa gggcagcccc gagaaccaca ggtgtacacc   1320
ctgcccccat cccgggatga gctgaccaag aaccaggtca gcctgacctg cctggtcaaa   1380
ggcttctatc ccagcgacat cgccgtggag tgggagagca atgggcagcc ggagaacaac   1440
tacaagacca cgcctcccgt gctggactcc gacggctcct tcttcctcta cagcaagctc   1500
accgtggaca agagcaggtg gcagcagggg aacgtcttct catgctccgt gatgcatgag   1560
gctctgcaca accactacac gcagaagagc ctctctctct ctccgggaaa agtcgacgga   1620
gctagcagcc ccgtgaacgt gagcagcccc agaatgcagg atatcccttc cctgggcaag   1680
gaatcccggg ccaagaaatt ccagcggcag catatggact cagacagttc ccccagcagc   1740
agctccacct actgtaacca aatgatgagg cgccggaata tgacacaggg gcggtgcaaa   1800
ccagtgaaca cctttgtgca cgagcccctg gtagatgtcc agaatgtctg tttccaggaa   1860
aaggtcacct gcaagaacgg gcagggcaag tggtacaaga gcaactccag catgcacatc   1920
acagactgcc gcctgacaaa cggctccagg taccccaact gtgcataccg aaccagcccg   1980
aaggagagac acatcattgt ggcctgtgaa ggagcccata tgtgccagtc cactttgatg   2040
cttgctgtgg aggactctac ctaa                                           2064
```

```
<210> SEQ ID NO 66
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Leu Glu Pro Lys
    290                 295                 300

Ser Ser Asp Lys Thr His Thr Ser Pro Pro Ser Pro Ala Pro Glu Leu
305                 310                 315                 320

Leu Gly Gly Ser Ser Val Phe Leu Phe Pro Pro Lys Pro Lys Asp Thr
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365
```

Glu Val His Asn Ala Lys Thr Lys Pro Arg Glu Glu Gln Tyr Asn Ser
370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Ser Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys Val Asp Gly Ala Ser Ser Pro Val Asn Val Ser
530                 535                 540

Ser Pro Ser Val Gln Asp Ile Lys Glu Ser Arg Ala Lys Lys Phe Gln
545                 550                 555                 560

Arg Gln His Met Asp Ser Asp Ser Ser Pro Ser Ser Ser Ser Thr Tyr
                565                 570                 575

Cys Asn Gln Met Met Arg Arg Arg Asn Met Thr Gln Gly Arg Cys Lys
            580                 585                 590

Pro Val Asn Thr Phe Val His Glu Pro Leu Val Asp Val Gln Asn Val
        595                 600                 605

Cys Phe Gln Glu Lys Val Thr Cys Lys Asn Gly Gln Gly Asn Cys Tyr
610                 615                 620

Lys Ser Asn Ser Ser Met His Ile Thr Asp Cys Arg Leu Thr Asn Gly
625                 630                 635                 640

Ser Arg Tyr Pro Asn Cys Ala Tyr Arg Thr Ser Pro Lys Glu Arg His
                645                 650                 655

Ile Ile Val Ala Cys Glu Gly Ser Pro Tyr Val Pro Val His Phe Asp
            660                 665                 670

Ala Ser Val Glu Asp Ser Thr
        675

<210> SEQ ID NO 67
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggaaaccc cagcgcagct tctcttcctc ctgctactct ggctcccaga taccaccggt      60
aaggaatccc gggccaagaa attccagcgg cagcatatgg actcagacag ttccccagc     120 agcagctcca cctactgtaa ccaaatgatg aggcgccgga atatgacaca ggggcggtgc     180
aaaccagtga acacctttgt gcacgagccc ctggtagatg tccagaatgt ctgtttccag     240

```
gaaaaggtca cctgcaagaa cgggcagggc aactgctaca agagcaactc cagcatgcac    300
atcacagact gccgcctgac aaacggctcc aggtacccca actgtgcata ccggaccagc    360
ccgaaggaga gacacatcat tgtggcctgt gaagggagcc atatgtgcc  agtccacttt    420 gatgcttctg tggaggactc tacagatctc tccggaggag gtggctcagg tggtggagga    480
tctggaggag gtgggagtgg tggaggtggt tctaccggtc tcgagcccaa atcttctgac    540
aaaactcaca catctccacc gagcccagca cctgaactcc tgggaggatc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagcctcc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct tcctctacag caagctcacc gtggacaaga gcaggtggca gcaggggaac   1140
gtcttctcat gctccgtgat gcatgaggct ctgcacaacc actacacgca gaagagcctc   1200
tctctctctc cgggaaaagt cgacggagct agcagccccg tgaacgtgag cagccccaga   1260
atgcaggata tcctgaagat cgcagccttc aacatccaga catttgggga gaccaagatg   1320
tccaatgcca cccctcgtcag ctacattgtg cagatcctga ccgctatga catcgccctg   1380 gtccaggagg tcagagacag ccacctgact gccgtgggga agctgctgga caacctcaat   1440
caggatgcac cagacaccta tcactacgtg gtcagtgagc cactgggacg gaacagctat   1500
aaggagcgct acctgttcgt gtacaggcct gaccaggtgt ctgcggtgga cagctactac   1560
tacgatgatg gctgcgagcc ctgcaggaac gacaccttca ccgagagcc  attcattgtc   1620 aggttcttct cccggttcac agaggtcagg gagtttgcca ttgttcccct gcatgcggcc   1680
ccgggggacg cagtagccga gatcgacgct ctctatgacg tctacctgga tgtccaagag   1740
aaatggggct tggaggacgt catgttgatg ggcgacttca atgcgggctg cagctatgtg   1800
agaccctccc agtggtcatc catccgcctg tggacaagcc ccaccttcca gtggctgatc   1860
cccgacagcg ctgacaccac agctacaccc acgcactgtg cctatgacag gatcgtggtt   1920
gcagggatgc tgctccgagg cgccgttgtt cccgactcgg ctcttccctt taacttccag   1980
gctgcctatg gcctgagtga ccaactggcc caagccatca gtgaccacta tccagtggag   2040
gtgatgctga aatga                                                    2055
```

<210> SEQ ID NO 68
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

```
Met Asp Ser Asp Ser Ser Pro Ser Ser Ser Thr Tyr Cys Asn Gln
             35                  40                  45

Met Met Arg Arg Arg Asn Met Thr Gln Gly Arg Cys Lys Pro Val Asn
 50                  55                  60

Thr Phe Val His Glu Pro Leu Val Asp Val Gln Asn Val Cys Phe Gln
 65                  70                  75                  80

Glu Lys Val Thr Cys Lys Asn Gly Gln Gly Asn Cys Tyr Lys Ser Asn
                 85                  90                  95

Ser Ser Met His Ile Thr Asp Cys Arg Leu Thr Asn Gly Ser Arg Tyr
             100                 105                 110

Pro Asn Cys Ala Tyr Arg Thr Ser Pro Lys Glu Arg His Ile Ile Val
         115                 120                 125

Ala Cys Glu Gly Ser Pro Tyr Val Pro Val His Phe Asp Ala Ser Val
130                 135                 140

Glu Asp Ser Thr Gly Gly Gly Ser Gly Gly Gly Ser Gly Gly
145                 150                 155                 160

Gly Gly Ser Gly Gly Gly Ser Leu Glu Pro Lys Ser Ser Asp Lys
             165                 170                 175

Thr His Thr Ser Pro Pro Ser Pro Ala Pro Glu Leu Leu Gly Gly Ser
             180                 185                 190

Ser Val Phe Leu Phe Pro Pro Lys Pro Lys Asp Thr Leu Met Ile Ser
         195                 200                 205

Arg Thr Pro Glu Val Thr Cys Val Val Val Asp Val Ser His Glu Asp
         210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
             260                 265                 270

Tyr Lys Cys Lys Val Ser Asn Lys Ala Leu Pro Ala Ser Ile Glu Lys
         275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
             340                 345                 350

Asp Ser Asp Gly Ser Phe Phe Leu Tyr Ser Lys Leu Thr Val Asp Lys
         355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

Lys Val Asp Gly Ala Ser Ser Pro Val Asn Val Ser Ser Pro Ser Val
                405                 410                 415

Gln Asp Ile Leu Lys Ile Ala Ala Phe Asn Ile Gln Thr Phe Gly Glu
             420                 425                 430

Thr Lys Met Ser Asn Ala Thr Leu Val Ser Tyr Ile Val Gln Ile Leu
         435                 440                 445

Ser Arg Tyr Asp Ile Ala Leu Val Gln Glu Val Arg Asp Ser His Leu
```

```
                 450                 455                 460
Thr Ala Val Gly Lys Leu Leu Asp Asn Leu Asn Gln Asp Ala Pro Asp
465                 470                 475                 480

Thr Tyr His Tyr Val Val Ser Glu Pro Leu Gly Arg Asn Ser Tyr Lys
                485                 490                 495

Glu Arg Tyr Leu Phe Val Tyr Arg Pro Asp Gln Val Ser Ala Val Asp
            500                 505                 510

Ser Tyr Tyr Tyr Asp Asp Gly Cys Glu Pro Cys Arg Asn Asp Thr Phe
        515                 520                 525

Asn Arg Glu Pro Phe Ile Val Arg Phe Phe Ser Arg Phe Thr Glu Val
    530                 535                 540

Arg Glu Phe Ala Ile Val Pro Leu His Ala Ala Pro Gly Asp Ala Val
545                 550                 555                 560

Ala Glu Ile Asp Ala Leu Tyr Asp Val Tyr Leu Asp Val Gln Glu Lys
                565                 570                 575

Trp Gly Leu Glu Asp Val Met Leu Met Gly Asp Phe Asn Ala Gly Cys
            580                 585                 590

Ser Tyr Val Arg Pro Ser Gln Trp Ser Ser Ile Arg Leu Trp Thr Ser
        595                 600                 605

Pro Thr Phe Gln Trp Leu Ile Pro Asp Ser Ala Asp Thr Thr Ala Thr
    610                 615                 620

Pro Thr His Cys Ala Tyr Asp Arg Ile Val Val Ala Gly Met Leu Leu
625                 630                 635                 640

Arg Gly Ala Val Val Pro Asp Ser Ala Leu Pro Phe Asn Phe Gln Ala
                645                 650                 655

Ala Tyr Gly Leu Ser Asp Gln Leu Ala Gln Ala Ile Ser Asp His Tyr
            660                 665                 670

Pro Val Glu Val Met Leu Lys
        675

<210> SEQ ID NO 69
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atggaaaccc ctgcccagct gctgttcctg ctgctgctgt ggctgcccga caccaccggt      60
aaggaatccc gggccaagaa attccagcgg cagcatatgg actcagacag ttccccccagc    120 agcagctcca cctactgtaa ccaaatgatg aggcgccgga atatgacaca ggggcggtgc    180
aaaccagtga caccctttgt gcacgagccc tggtagatg tccagaatgt ctgtttccag     240
gaaaaggtca cctgcaagaa cgggcagggc aactgctaca gagcaactc cagcatgcac    300 atcacagact gccgcctgac aaacggctcc aggtacccca ctgtgcata ccggaccagc    360 ccgaaggaga gacacatcat tgtggcctgt gaagggagcc catatgtgcc agtccacttt    420
gatgcttctg tggaggactc taccctcgag cccaaatctt ctgacaaaac tcacacatct    480
ccaccgagcc cagcacctga actcctggga ggatcgtcag tcttcctctt cccccccaaa    540
cccaaggaca ccctcatgat ctcccggacc cctgaggtca catgcgtggt ggtggacgtg    600
agccacgaag accctgaggt caagttcaac tggtacgtgg acggcgtgga ggtgcataat    660
gccaagacaa agccgcggga ggagcagtac aacagcacgt accgtgtggt cagcgtcctc    720
```

```
accgtcctgc accaggactg gctgaatggc aaggagtaca agtgcaaggt ctccaacaaa    780
gccctcccag cctccatcga gaaaaccatc tccaaagcca aagggcagcc ccgagaacca    840
caggtgtaca ccctgccccc atcccgggat gagctgacca agaaccaggt cagcctgacc    900
tgcctggtca aaggcttcta tcccagcgac atcgccgtgg agtgggagag caatgggcag    960
ccggagaaca actacaagac cacgcctccc gtgctggact ccgacggctc cttcttcctc   1020
tacagcaagc tcaccgtgga caagagcagg tggcagcagg ggaacgtctt ctcatgctcc   1080
gtgatgcatg aggctctgca caaccactac acgcagaaga gcctctctct ctctccggga   1140
aaagtcgacg gagctagcag ccccgtgaac gtgagcagcc ccagaatgca ggatatcctg   1200
aagatcgcag ccttcaacat ccagacattt ggggagacca agatgtccaa tgccacccte   1260
gtcagctaca ttgtgcagat cctgagccgc tatgacatcg ccctggtcca ggaggtcaga   1320
gacagccacc tgactgccgt ggggaagctg ctggacaacc tcaatcagga tgcaccagac   1380
acctatcact acgtggtcag tgagccactg gacggaaaca gctataagga gcgctacctg   1440
ttcgtgtaca ggcctgacca ggtgtctgcg gtggacagct actactacga tgatggctgc   1500
gagccctgca ggaacgacac cttcaaccga gagccattca ttgtcaggtt cttctcccgg   1560
ttcacagagg tcagggagtt tgccattgtt cccctgcatg cggccccggg ggacgcagta   1620
gccgagatcg acgctctcta tgacgtctac ctggatgtcc aagagaaatg gggcttggag   1680
gacgtcatgt tgatgggcga cttcaatgcg ggctgcagct atgtgagacc ctcccagtgg   1740
tcatccatcc gcctgtggac aagccccacc ttccagtggc tgatccccga cagcgctgac   1800
accacagcta cacccacgca ctgtgcctat gacaggatcg tggttgcagg gatgctgctc   1860
cgaggcgccg ttgttcccga ctcggctctt ccctttaact tccaggctgc ctatggcctg   1920
agtgaccaac tggcccaagc catcagtgac cactatccag tggaggtgat gctgaaatga   1980
```

<210> SEQ ID NO 70
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140
```

-continued

```
Glu Asp Ser Thr Leu Glu Pro Lys Ser Asp Lys Thr His Thr Ser
145                 150                 155                 160

Pro Pro Ser Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys Val Asp Gly
    370                 375                 380

Ala Ser Ser Pro Val Asn Val Ser Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
        435                 440                 445

Lys Leu Leu Asp Asn Leu Asn Gln Asp Ala Pro Asp Thr Tyr His Tyr
    450                 455                 460

Val Val Ser Glu Pro Leu Gly Arg Asn Ser Tyr Lys Glu Arg Tyr Leu
465                 470                 475                 480

Phe Val Tyr Arg Pro Asp Gln Val Ser Ala Val Asp Ser Tyr Tyr Tyr
                485                 490                 495

Asp Asp Gly Cys Glu Pro Cys Arg Asn Asp Thr Phe Asn Arg Glu Pro
            500                 505                 510

Phe Ile Val Arg Phe Phe Ser Arg Phe Thr Glu Val Arg Glu Phe Ala
        515                 520                 525

Ile Val Pro Leu His Ala Ala Pro Gly Asp Ala Val Ala Glu Ile Asp
    530                 535                 540

Ala Leu Tyr Asp Val Tyr Leu Asp Val Gln Glu Lys Trp Gly Leu Glu
545                 550                 555                 560
```

```
Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
        595                 600                 605

Ala Tyr Asp Arg Ile Val Val Ala Gly Met Leu Leu Arg Gly Ala Val
    610                 615                 620

Val Pro Asp Ser Ala Leu Pro Phe Asn Phe Gln Ala Ala Tyr Gly Leu
625                 630                 635                 640

Ser Asp Gln Leu Ala Gln Ala Ile Ser Asp His Tyr Pro Val Glu Val
                645                 650                 655

Met Leu Lys

<210> SEQ ID NO 71
<211> LENGTH: 693
<212> TYPE: DNA
<213> ORGANISM: Homo sapiens

<400> SEQUENCE: 71
cccaaatctt ctgacaaaac tcacacatgt ccaccgtgcc cagcacctga actcctggga      60
ggatcgtcag tcttcctctt ccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cccctatcga gaaaaccatc     360
tccaaagcca agggcagccc cgagaaccca ggtgtacac cctgccccc atcccgggat      420 gagctgacca agaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tacagcaagc tcaccgtgga caagagcagg     600
tggcagcagg ggaacgtctt ctcatgctcc gtgatgcatg aggctctgca caaccactac     660
acgcagaaga gcctctctct ctctccggga aaa                                  693

<210> SEQ ID NO 72
<211> LENGTH: 233
<212> TYPE: PRT
<213> ORGANISM: Homo sapiens

<400> SEQUENCE: 72

Leu Glu Pro Lys Ser Ser Asp Lys Thr His Thr Cys Pro Pro Cys Pro
1               5                   10                  15

Ala Pro Glu Leu Leu Gly Gly Ser Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
```

```
             100                 105                 110
Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 73
<211> LENGTH: 693
<212> TYPE: DNA
<213> ORGANISM: Homo sapiens

<400> SEQUENCE: 73

```
cccaaatctt ctgacaaaac tcacacatgt ccaccgtgcc cagcacctga actcctggga      60
ggaccgtcag tcttcctctt ccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cctccatcga gaaaaccatc     360
tccaaagcca agggcagccc cgagaaccag gtgtaca ccctgcccc atcccgggat       420
gagctgacca gaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tacagcaagc tcaccgtgga caagagcagg     600
tggcagcagg ggaacgtctt ctcatgctcc gtgatgcatg aggctctgca caaccactac     660
acgcagaaga gcctctctct ctctccggga aaa                                 693
```

<210> SEQ ID NO 74
<211> LENGTH: 233
<212> TYPE: PRT
<213> ORGANISM: Homo sapiens

<400> SEQUENCE: 74

```
Leu Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
```

```
                65                  70                  75                  80
Gln Tyr Asn Ser Thr Tyr Arg Val Val Ser Val Leu Thr Val Leu His
                    85                  90                  95
Gln Asp Trp Leu Asn Gly Lys Glu Tyr Lys Cys Lys Val Ser Asn Lys
                100                 105                 110
Ala Leu Pro Ala Ser Ile Glu Lys Thr Ile Ser Lys Ala Lys Gly Gln
                115                 120                 125
Pro Arg Glu Pro Gln Val Tyr Thr Leu Pro Pro Ser Arg Asp Glu Leu
            130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
                180                 185                 190
Tyr Ser Lys Leu Thr Val Asp Lys Ser Arg Trp Gln Gln Gly Asn Val
                195                 200                 205
Phe Ser Cys Ser Val Met His Glu Ala Leu His Asn His Tyr Thr Gln
                210                 215                 220
Lys Ser Leu Ser Leu Ser Pro Gly Lys
225                 230
```

<210> SEQ ID NO 75
<211> LENGTH: 693
<212> TYPE: DNA
<213> ORGANISM: Homo sapiens

<400> SEQUENCE: 75

```
cccaaatctt ctgacaaaac tcacacatct ccaccgagcc cagcacctga actcctggga    60
ggatcgtcag tcttcctctt ccccccaaaa cccaaggaca ccctcatgat ctcccggacc   120
cctgaggtca catgcgtggt ggtggacgtg agccacgaag accctgaggt caagttcaac   180
tggtacgtgg acggcgtgga ggtgcataat gccaagacaa agccgcggga ggagcagtac   240
aacagcacgt accgtgtggt cagcgtcctc accgtcctgc accaggactg gctgaatggc   300
aaggagtaca agtgcaaggt ctccaacaaa gccctcccag cctccatcga gaaaaccatc   360
tccaaagcca agggcagccc cgagaaccca caggtgtaca ccctgccccc atcccgggat   420
gagctgacca gaaccaggt cagcctgacc tgcctggtca aaggcttcta tcccagcgac   480
atcgccgtgg agtgggagag caatgggcag ccggagaaca actacaagac cacgcctccc   540
gtgctggact ccgacggctc cttcttcctc tacagcaagc tcaccgtgga caagagcagg   600
tggcagcagg ggaacgtctt ctcatgctcc gtgatgcatg aggctctgca caaccactac   660
acgcagaaga gcctctctct ctctccggga aaa                                693
```

<210> SEQ ID NO 76
<211> LENGTH: 233
<212> TYPE: PRT
<213> ORGANISM: Homo sapiens

<400> SEQUENCE: 76

```
Leu Glu Pro Lys Ser Ser Asp Lys Thr His Thr Ser Pro Pro Ser Pro
1               5                   10                  15
Ala Pro Glu Leu Leu Gly Gly Ser Ser Val Phe Leu Phe Pro Pro Lys
                20                  25                  30
Pro Lys Asp Thr Leu Met Ile Ser Arg Thr Pro Glu Val Thr Cys Val
```

```
                35                  40                  45
Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
             100                 105                 110

Ala Leu Pro Ala Ser Ile Glu Lys Thr Ile Ser Lys Ala Lys Gly Gln
         115                 120                 125

Pro Arg Glu Pro Gln Val Tyr Thr Leu Pro Pro Ser Arg Asp Glu Leu
     130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 77
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atggaaaccc ctgcccagct gctgttcctg ctgctgctgt ggctgcccga caccaccggt      60
aaggaatccc gggccaagaa attccagcgg cagcatatgg actcagacag ttcccccagc    120
agcagctcca cctactgtaa ccaaatgatg aggcgccgga atatgacaca ggggcggtgc    180
aaaccagtga cacctttgt gcacgagccc ctggtagatg tccagaatgt ctgtttccag     240
gaaaaggtca cctgcaagaa cgggcagggc aactgctaca gagcaactc cagcatgcac    300 atcacagact gccgcctgac aaacggctcc aggtacccca actgtgcata ccggaccagc    360
ccgaaggaga gacacatcat tgtggcctgt gaagggagcc catatgtgcc agtccacttt    420
gatgcttctg tggaggactc taccctcgag cccaaatctt ctgacaaaac tcacacatgt    480
ccaccgtgcc cagcacctga actcctggga ggatcgtcag tcttcctctt ccccccaaaa    540
cccaaggaca ccctcatgat ctcccggacc cctgaggtca catgcgtggt ggtggacgtg    600
agccacgaag accctgaggt caagttcaac tggtacgtgg acggcgtgga ggtgcataat    660
gccaagacaa agccgcggga ggagcagtac aacagcacgt accgtgtggt cagcgtcctc    720
accgtcctgc accaggactg gctgaatggc aaggagtaca agtgcaaggt ctccaacaaa    780 gcccteccag cctccatcga gaaaaccatc tccaaagcca aagggcagcc ccgagaacca    840
caggtgtaca cctgcccccc atcccgggat gagctgacca agaaccaggt cagcctgacc    900
```

```
tgcctggtca aaggcttcta tcccagcgac atcgccgtgg agtgggagag caatgggcag    960
ccggagaaca actacaagac cacgcctccc gtgctggact ccgacggctc cttcttcctc   1020
tacagcaagc tcaccgtgga caagagcagg tggcagcagg ggaacgtctt ctcatgctcc   1080
gtgatgcatg aggctctgca caaccactac acgcagaaga gcctctctct ctctccggga   1140
aaatga                                                              1146
```

<210> SEQ ID NO 78
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
```

```
                305                 310                 315                 320
Pro Glu Asn Asn Tyr Lys Thr Thr Pro Pro Val Leu Asp Ser Asp Gly
                    325                 330                 335

Ser Phe Phe Leu Tyr Ser Lys Leu Thr Val Asp Lys Ser Arg Trp Gln
                340                 345                 350

Gln Gly Asn Val Phe Ser Cys Ser Val Met His Glu Ala Leu His Asn
            355                 360                 365

His Tyr Thr Gln Lys Ser Leu Ser Leu Ser Pro Gly Lys
        370                 375                 380
```

<210> SEQ ID NO 79
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atggaaaccc cagcgcagct tctcttcctc ctgctactct ggctcccaga taccaccggt     60
aaggaatccc gggccaagaa attccagcgg cagcatatgg actcagacag ttcccccagc    120
agcagctcca cctactgtaa ccaaatgatg aggcgccgga atatgacaca ggggcggtgc    180
aaaccagtga acacctttgt gcacgagccc tggtagatg tccagaatgt ctgtttccag    240
gaaaaggtca cctgcaagaa cgggcagggc aactgctaca gagcaactc cagcatgca    300
atcacagact gccgcctgac aaacggctcc aggtacccca actgtgcata ccggaccagc    360
ccgaaggaga gacacatcat tgtggcctgt gaagggagcc catatgtgcc agtccacttt    420
gatgcttctg tggaggactc tacagatctc tccggaggag gtggctcagg tggtggagga    480
tctggaggag gtgggagtgg tggaggtggt tctaccggtc tcgagcccaa atcttctgac    540
aaaactcaca catgtccacc gtgcccagca cctgaactcc tgggaggatc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagcctcc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct tcctctacag caagctcacc gtggacaaga gcaggtggca gcaggggaac   1140
gtcttctcat gctccgtgat gcatgaggct ctgcacaacc actacacgca gaagagcctc   1200
tctctctctc cgggaaaatg a                                            1221
```

<210> SEQ ID NO 80
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Glu Thr Pro Ala Gln Leu Leu Phe Leu Leu Leu Leu Trp Leu Pro

```
1               5                   10                  15
Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
            35                  40                  45

Met Met Arg Arg Asn Met Thr Gln Gly Arg Cys Lys Pro Val Asn
50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
                100                 105                 110

Pro Asn Cys Ala Tyr Arg Thr Ser Pro Lys Glu Arg His Ile Ile Val
                115                 120                 125

Ala Cys Glu Gly Ser Pro Tyr Val Pro Val His Phe Asp Ala Ser Val
                130                 135                 140

Glu Asp Ser Thr Gly Gly Gly Ser Gly Gly Gly Ser Gly Gly
145                 150                 155                 160

Gly Gly Ser Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Ser
                180                 185                 190

Ser Val Phe Leu Phe Pro Pro Lys Pro Lys Asp Thr Leu Met Ile Ser
                195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
                260                 265                 270

Tyr Lys Cys Lys Val Ser Asn Lys Ala Leu Pro Ala Ser Ile Glu Lys
                275                 280                 285

Thr Ile Ser Lys Ala Lys Gly Gln Pro Arg Glu Pro Gln Val Tyr Thr
                290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
                340                 345                 350

Asp Ser Asp Gly Ser Phe Phe Leu Tyr Ser Lys Leu Thr Val Asp Lys
                355                 360                 365

Ser Arg Trp Gln Gln Gly Asn Val Phe Ser Cys Ser Val Met His Glu
                370                 375                 380

Ala Leu His Asn His Tyr Thr Gln Lys Ser Leu Ser Leu Ser Pro Gly
385                 390                 395                 400

Lys

<210> SEQ ID NO 81
<211> LENGTH: 2064
```

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 81

| | |
|---|---|
| atggaaaccc cagcgcagct tctcttcctc ctgctactct ggctcccaga taccaccggt | 60 |
| ctgaagatcg cagccttcaa catccagaca tttggggaga ccaagatgtc caatgccacc | 120 |
| ctcgtcagct acattgtgca gatcctgagc cgctatgaca tcgccctggt ccaggaggtc | 180 |
| agagacagcc acctgactgc cgtggggaag ctgctggaca acctcaatca ggatgcacca | 240 |
| gacacctatc actacgtggt cagtgagcca ctgggacgga cagctataa ggagcgctac | 300 |
| ctgttcgtgt acaggcctga ccaggtgtct gcggtggaca gctactacta cgatgatggc | 360 |
| tgcgagccct gcaggaacga caccttcaac cgagagccat tcattgtcag gttcttctcc | 420 |
| cggttcacag aggtcaggga gtttgccatt gttcccctgc atgcggcccc ggggacgca | 480 |
| gtagccgaga tcgacgctct ctatgacgtc tacctggatg ccaagagaa atggggcttg | 540 |
| gaggacgtca tgttgatggg cgacttcaat gcgggctgca gctatgtgag accctcccag | 600 |
| tggtcatcca tccgcctgtg acaagcccc accttccagt ggctgatccc cgacagcgct | 660 |
| gacaccacag ctacacccac gcactgtgcc tatgacagga tcgtggttgc agggatgctg | 720 |
| ctccgaggcg ccgttgttcc cgactcggct cttcccttta acttccaggc tgcctatggc | 780 |
| ctgagtgacc aactggccca agccatcagt gaccactatc cagtggaggt gatgctgaaa | 840 |
| gatctctccg gaggaggtgg ctcaggtggt ggaggatctg gaggaggtgg gagtggtgga | 900 |
| ggttctaccg gtctcgagcc caaatcttct gacaaaactc acacatgtcc accgtgccca | 960 |
| gcacctgaac tcctggggagg atcgtcagtc ttcctcttcc ccccaaaacc caaggacacc | 1020 |
| ctcatgatct cccggacccc tgaggtcaca tgcgtggtgg tggacgtgag ccacgaagac | 1080 |
| cctgaggtca agttcaactg gtacgtggac ggcgtggagg tgcataatgc caagacaaag | 1140 |
| ccgcgggagg agcagtacaa cagcacgtac cgtgtggtca gcgtcctcac cgtcctgcac | 1200 |
| caggactggc tgaatggcaa ggagtacaag tgcaaggtct ccaacaaagc cctcccagcc | 1260 |
| tccatcgaga aaaccatctc caaagccaaa gggcagcccc gagaaccaca ggtgtacacc | 1320 |
| ctgcccccat cccgggatga gctgaccaag aaccaggtca gcctgacctg cctggtcaaa | 1380 |
| ggcttctatc ccagcgacat cgccgtggag tgggagagca atgggcagcc ggagaacaac | 1440 |
| tacaagacca cgcctcccgt gctggactcc gacggctcct tcttcctcta cagcaagctc | 1500 |
| accgtggaca agagcaggtg gcagcagggg aacgtcttct catgctccgt gatgcatgag | 1560 |
| gctctgcaca accactacac gcagaagagc ctctctctct ctccgggaaa agtcgacgga | 1620 |
| gctagcagcc ccgtgaacgt gagcagcccc agaatgcagg atatcccttc cctgggcaag | 1680 |
| gaatcccggg ccaagaaatt ccagcggcag catatggact cagacagttc ccccagcagc | 1740 |
| agctccacct actgtaacca aatgatgagg cgccggaata tgacacaggg gcggtgcaaa | 1800 |
| ccagtgaaca cctttgtgca cgagcccctg gtagatgtcc agaatgtctg tttccaggaa | 1860 |
| aaggtcacct gcaagaacgg gcagggcaag tggtacaaga gcaactccag catgcacatc | 1920 |
| acagactgcc gcctgacaaa cggctccagg taccccaact gtgcataccg aaccagcccg | 1980 |
| aaggagagac acatcattgt ggcctgtgaa ggagcccata tgtgccagtc cactttgatg | 2040 |
| cttgctgtgg aggactctac ctaa | 2064 |

<210> SEQ ID NO 82
<211> LENGTH: 679
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Ser Gly Gly Gly
        275                 280                 285

Gly Ser Gly Gly Gly Ser Gly Gly Gly Ser Leu Glu Pro Lys
    290                 295                 300

Ser Ser Asp Lys Thr His Thr Cys Pro Pro Cys Pro Ala Pro Glu Leu
305                 310                 315                 320

Leu Gly Gly Ser Ser Val Phe Leu Phe Pro Pro Lys Pro Lys Asp Thr
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365
```

```
Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Ser Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys Val Asp Gly Ala Ser Ser Pro Val Asn Val Ser
530                 535                 540

Ser Pro Ser Val Gln Asp Ile Lys Glu Ser Arg Ala Lys Lys Phe Gln
545                 550                 555                 560

Arg Gln His Met Asp Ser Asp Ser Ser Pro Ser Ser Ser Ser Thr Tyr
                565                 570                 575

Cys Asn Gln Met Met Arg Arg Arg Asn Met Thr Gln Gly Arg Cys Lys
            580                 585                 590

Pro Val Asn Thr Phe Val His Glu Pro Leu Val Asp Val Gln Asn Val
        595                 600                 605

Cys Phe Gln Glu Lys Val Thr Cys Lys Asn Gly Gln Gly Asn Cys Tyr
610                 615                 620

Lys Ser Asn Ser Ser Met His Ile Thr Asp Cys Arg Leu Thr Asn Gly
625                 630                 635                 640

Ser Arg Tyr Pro Asn Cys Ala Tyr Arg Thr Ser Pro Lys Glu Arg His
                645                 650                 655

Ile Ile Val Ala Cys Glu Gly Ser Pro Tyr Val Pro Val His Phe Asp
            660                 665                 670

Ala Ser Val Glu Asp Ser Thr
        675

<210> SEQ ID NO 83
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atggaaaccc cagcgcagct tctcttcctc ctgctactct ggctcccaga taccaccggt      60
aaggaatccc gggccaagaa attccagcgg cagcatatgg actcagacag ttcccccagc     120
agcagctcca cctactgtaa ccaaatgatg aggcgccgga atatgacaca ggggcggtgc     180
aaaccagtga acacctttgt gcacgagccc ctggtagatg tccagaatgt ctgtttccag     240
```

```
gaaaaggtca cctgcaagaa cgggcagggc aactgctaca agagcaactc cagcatgcac    300
atcacagact gccgcctgac aaacggctcc aggtacccca actgtgcata ccggaccagc    360
ccgaaggaga gacacatcat tgtggcctgt gaagggagcc catatgtgcc agtccacttt    420
gatgcttctg tggaggactc tacagatctc tccggaggag gtggctcagg tggtggagga    480
tctggaggag gtgggagtgg tggaggtggt tctaccggtc tcgagcccaa atcttctgac    540
aaaactcaca catgtccacc gtgcccagca cctgaactcc tgggaggatc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagcctcc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct tcctctacag caagctcacc gtggacaaga gcaggtggca gcaggggaac   1140
gtcttctcat gctccgtgat gcatgaggct ctgcacaacc actacacgca gaagagcctc   1200
tctctctctc cgggaaaagt cgacggagct agcagcccg tgaacgtgag cagccccaga   1260
atgcaggata tcctgaagat cgcagccttc aacatccaga catttgggga gaccaagatg   1320
tccaatgcca ccctcgtcag ctacattgtg cagatcctga gccgctatga catcgccctg   1380
gtccaggagg tcagagacag ccacctgact gccgtgggga agctgctgga caacctcaat   1440
caggatgcac cagacaccta tcactacgtg gtcagtgagc cactgggacg gaacagctat   1500
aaggagcgct acctgttcgt gtacaggcct gaccaggtgt ctgcggtgga cagctactac   1560
tacgatgatg gctgcgagcc ctgcaggaac gacaccttca ccgagagcc attcattgtc   1620
aggttcttct cccggttcac agaggtcagg gagtttgcca ttgttcccct gcatgcggcc   1680
ccggggacg cagtagccga gatcgacgct ctctatgacg tctacctgga tgtccaagag   1740
aaatggggct tggaggacgt catgttgatg ggcgacttca atgcgggctg cagctatgtg   1800
agaccctccc agtggtcatc catccgcctg tggacaagcc ccaccttcca gtggctgatc   1860
cccgacagcg ctgacaccac agctacaccc acgcactgtg cctatgacag gatcgtggtt   1920
gcagggatgc tgctccgagg cgccgttgtt cccgactcgg ctcttccctt taacttccag   1980
gctgcctatg gcctgagtga ccaactggcc caagccatca gtgaccacta tccagtggag   2040
gtgatgctga aatga                                                   2055
```

<210> SEQ ID NO 84
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

-continued

```
Met Asp Ser Asp Ser Ser Pro Ser Ser Ser Thr Tyr Cys Asn Gln
             35                  40                  45
Met Met Arg Arg Arg Asn Met Thr Gln Gly Arg Cys Lys Pro Val Asn
 50                  55                  60
Thr Phe Val His Glu Pro Leu Val Asp Val Gln Asn Val Cys Phe Gln
 65                  70                  75                  80
Glu Lys Val Thr Cys Lys Asn Gly Gln Gly Asn Cys Tyr Lys Ser Asn
             85                  90                  95
Ser Ser Met His Ile Thr Asp Cys Arg Leu Thr Asn Gly Ser Arg Tyr
                 100                 105                 110
Pro Asn Cys Ala Tyr Arg Thr Ser Pro Lys Glu Arg His Ile Ile Val
            115                 120                 125
Ala Cys Glu Gly Ser Pro Tyr Val Pro Val His Phe Asp Ala Ser Val
130                 135                 140
Glu Asp Ser Thr Gly Gly Gly Ser Gly Gly Gly Ser Gly Gly
145                 150                 155                 160
Gly Gly Ser Gly Gly Gly Ser Leu Glu Pro Lys Ser Ser Asp Lys
            165                 170                 175
Thr His Thr Cys Pro Pro Cys Pro Ala Pro Glu Leu Leu Gly Gly Ser
            180                 185                 190
Ser Val Phe Leu Phe Pro Pro Lys Pro Lys Asp Thr Leu Met Ile Ser
            195                 200                 205
Arg Thr Pro Glu Val Thr Cys Val Val Val Asp Val Ser His Glu Asp
            210                 215                 220
Pro Glu Val Lys Phe Asn Trp Tyr Val Asp Gly Val Glu Val His Asn
225                 230                 235                 240
Ala Lys Thr Lys Pro Arg Glu Glu Gln Tyr Asn Ser Thr Tyr Arg Val
            245                 250                 255
Val Ser Val Leu Thr Val Leu His Gln Asp Trp Leu Asn Gly Lys Glu
            260                 265                 270
Tyr Lys Cys Lys Val Ser Asn Lys Ala Leu Pro Ala Ser Ile Glu Lys
            275                 280                 285
Thr Ile Ser Lys Ala Lys Gly Gln Pro Arg Glu Pro Gln Val Tyr Thr
            290                 295                 300
Leu Pro Pro Ser Arg Asp Glu Leu Thr Lys Asn Gln Val Ser Leu Thr
305                 310                 315                 320
Cys Leu Val Lys Gly Phe Tyr Pro Ser Asp Ile Ala Val Glu Trp Glu
            325                 330                 335
Ser Asn Gly Gln Pro Glu Asn Asn Tyr Lys Thr Thr Pro Pro Val Leu
            340                 345                 350
Asp Ser Asp Gly Ser Phe Phe Leu Tyr Ser Lys Leu Thr Val Asp Lys
            355                 360                 365
Ser Arg Trp Gln Gln Gly Asn Val Phe Ser Cys Ser Val Met His Glu
            370                 375                 380
Ala Leu His Asn His Tyr Thr Gln Lys Ser Leu Ser Leu Ser Pro Gly
385                 390                 395                 400
Lys Val Asp Gly Ala Ser Ser Pro Val Asn Val Ser Ser Pro Ser Val
            405                 410                 415
Gln Asp Ile Leu Lys Ile Ala Ala Phe Asn Ile Gln Thr Phe Gly Glu
            420                 425                 430
Thr Lys Met Ser Asn Ala Thr Leu Val Ser Tyr Ile Val Gln Ile Leu
            435                 440                 445
Ser Arg Tyr Asp Ile Ala Leu Val Gln Glu Val Arg Asp Ser His Leu
```

```
                450             455             460
Thr Ala Val Gly Lys Leu Leu Asp Asn Leu Asn Gln Asp Ala Pro Asp
465                 470                 475                 480

Thr Tyr His Tyr Val Val Ser Glu Pro Leu Gly Arg Asn Ser Tyr Lys
                485                 490                 495

Glu Arg Tyr Leu Phe Val Tyr Arg Pro Asp Gln Val Ser Ala Val Asp
            500                 505                 510

Ser Tyr Tyr Tyr Asp Asp Gly Cys Glu Pro Cys Arg Asn Asp Thr Phe
        515                 520                 525

Asn Arg Glu Pro Phe Ile Val Arg Phe Phe Ser Arg Phe Thr Glu Val
    530                 535                 540

Arg Glu Phe Ala Ile Val Pro Leu His Ala Ala Pro Gly Asp Ala Val
545                 550                 555                 560

Ala Glu Ile Asp Ala Leu Tyr Asp Val Tyr Leu Asp Val Gln Glu Lys
                565                 570                 575

Trp Gly Leu Glu Asp Val Met Leu Met Gly Asp Phe Asn Ala Gly Cys
            580                 585                 590

Ser Tyr Val Arg Pro Ser Gln Trp Ser Ser Ile Arg Leu Trp Thr Ser
        595                 600                 605

Pro Thr Phe Gln Trp Leu Ile Pro Asp Ser Ala Asp Thr Thr Ala Thr
    610                 615                 620

Pro Thr His Cys Ala Tyr Asp Arg Ile Val Val Ala Gly Met Leu Leu
625                 630                 635                 640

Arg Gly Ala Val Val Pro Asp Ser Ala Leu Pro Phe Asn Phe Gln Ala
                645                 650                 655

Ala Tyr Gly Leu Ser Asp Gln Leu Ala Gln Ala Ile Ser Asp His Tyr
            660                 665                 670

Pro Val Glu Val Met Leu Lys
        675

<210> SEQ ID NO 85
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atggaaaccc tgcccagct gctgttcctg ctgctgctgt ggctgcccga caccaccggt      60
aaggaatccc gggccaagaa attccagcgg cagcatatgg actcagacag ttccccagc    120 agcagctcca cctactgtaa ccaaatgatg aggcgccgga atatgacaca ggggcggtgc    180
aaaccagtga cacctttgt gcacgagccc tggtagatg tccagaatgt ctgtttccag      240
gaaaaggtca cctgcaagaa cgggcagggc aactgctaca agagcaactc cagcatgcac    300
atcacagact gccgcctgac aaacggctcc aggtacccca actgtgcata ccggaccagc    360
ccgaaggaga gacacatcat tgtggcctgt gaagggagcc atatgtgcc agtccacttt     420 gatgcttctg tggaggactc taccctcgag cccaaatctt ctgacaaaac tcacacatgt    480
ccaccgtgcc cagcacctga actcctggga ggatcgtcag tcttcctctt cccccccaaaa  540 cccaaggaca ccctcatgat ctcccggacc cctgaggtca catgcgtggt ggtggacgtg    600
agccacgaag accctgaggt caagttcaac tggtacgtgg acggcgtgga ggtgcataat    660
gccaagacaa agccgcggga ggagcagtac aacagcacgt accgtgtggt cagcgtcctc    720
```

```
accgtcctgc accaggactg gctgaatggc aaggagtaca agtgcaaggt ctccaacaaa    780
gccctcccag cctccatcga gaaaaccatc tccaaagcca aagggcagcc ccgagaacca    840
caggtgtaca ccctgccccc atcccgggat gagctgacca agaaccaggt cagcctgacc    900
tgcctggtca aaggcttcta tcccagcgac atcgccgtgg agtgggagag caatgggcag    960
ccggagaaca actacaagac cacgcctccc gtgctggact ccgacggctc cttcttcctc   1020
tacagcaagc tcaccgtgga caagagcagg tggcagcagg ggaacgtctt ctcatgctcc   1080
gtgatgcatg aggctctgca caaccactac acgcagaaga gcctctctct ctctccggga   1140
aaagtcgacg gagctagcag ccccgtgaac gtgagcagcc ccagaatgca ggatatcctg   1200
aagatcgcag ccttcaacat ccagacattt ggggagacca agatgtccaa tgccacccct   1260
gtcagctaca ttgtgcagat cctgagccgc tatgacatcg ccctggtcca ggaggtcaga   1320
gacagccacc tgactgccgt ggggaagctg ctggacaacc tcaatcagga tgcaccagac   1380
acctatcact acgtggtcag tgagccactg gacggaaca gctataagga gcgctacctg   1440
ttcgtgtaca ggcctgacca ggtgtctgcg gtggacagct actactacga tgatggctgc   1500
gagccctgca ggaacgacac cttcaaccga gagccattca ttgtcaggtt cttctcccgg   1560
ttcacagagg tcagggagtt tgccattgtt cccctgcatg cggccccggg ggacgcagta   1620
gccgagatcg acgctctcta tgacgtctac ctggatgtcc aagagaaatg gggcttggag   1680
gacgtcatgt tgatgggcga cttcaatgcg ggctgcagct atgtgagacc ctcccagtgg   1740
tcatccatcc gcctgtggac aagccccacc ttccagtggc tgatccccga cagcgctgac   1800
accacagcta cacccacgca ctgtgcctat gacaggatcg tggttgcagg gatgctgctc   1860
cgaggcgccg ttgttcccga ctcggctctt ccctttaact tccaggctgc ctatggcctg   1920
agtgaccaac tggcccaagc catcagtgac cactatccag tggaggtgat gctgaaatga   1980
```

<210> SEQ ID NO 86
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140
```

-continued

```
Glu Asp Ser Thr Leu Glu Pro Lys Ser Asp Lys Thr His Thr Cys
145                 150                 155                 160
Pro Pro Cys Pro Ala Pro Glu Leu Leu Gly Gly Ser Val Phe Leu
                165                 170                 175
Phe Pro Pro Lys Pro Lys Asp Thr Leu Met Ile Ser Arg Thr Pro Glu
            180                 185                 190
Val Thr Cys Val Val Val Asp Val Ser His Glu Asp Pro Glu Val Lys
            195                 200                 205
Phe Asn Trp Tyr Val Asp Gly Val Glu Val His Asn Ala Lys Thr Lys
    210                 215                 220
Pro Arg Glu Glu Gln Tyr Asn Ser Thr Tyr Arg Val Val Ser Val Leu
225                 230                 235                 240
Thr Val Leu His Gln Asp Trp Leu Asn Gly Lys Glu Tyr Lys Cys Lys
                245                 250                 255
Val Ser Asn Lys Ala Leu Pro Ala Ser Ile Glu Lys Thr Ile Ser Lys
                260                 265                 270
Ala Lys Gly Gln Pro Arg Glu Pro Gln Val Tyr Thr Leu Pro Pro Ser
            275                 280                 285
Arg Asp Glu Leu Thr Lys Asn Gln Val Ser Leu Thr Cys Leu Val Lys
    290                 295                 300
Gly Phe Tyr Pro Ser Asp Ile Ala Val Glu Trp Glu Ser Asn Gly Gln
305                 310                 315                 320
Pro Glu Asn Asn Tyr Lys Thr Thr Pro Pro Val Leu Asp Ser Asp Gly
                325                 330                 335
Ser Phe Phe Leu Tyr Ser Lys Leu Thr Val Asp Lys Ser Arg Trp Gln
                340                 345                 350
Gln Gly Asn Val Phe Ser Cys Ser Val Met His Glu Ala Leu His Asn
            355                 360                 365
His Tyr Thr Gln Lys Ser Leu Ser Leu Ser Pro Gly Lys Val Asp Gly
    370                 375                 380
Ala Ser Ser Pro Val Asn Val Ser Ser Pro Ser Val Gln Asp Ile Leu
385                 390                 395                 400
Lys Ile Ala Ala Phe Asn Ile Gln Thr Phe Gly Glu Thr Lys Met Ser
                405                 410                 415
Asn Ala Thr Leu Val Ser Tyr Ile Val Gln Ile Leu Ser Arg Tyr Asp
            420                 425                 430
Ile Ala Leu Val Gln Glu Val Arg Asp Ser His Leu Thr Ala Val Gly
    435                 440                 445
Lys Leu Leu Asp Asn Leu Asn Gln Asp Ala Pro Asp Thr Tyr His Tyr
    450                 455                 460
Val Val Ser Glu Pro Leu Gly Arg Asn Ser Tyr Lys Glu Arg Tyr Leu
465                 470                 475                 480
Phe Val Tyr Arg Pro Asp Gln Val Ser Ala Val Asp Ser Tyr Tyr Tyr
                485                 490                 495
Asp Asp Gly Cys Glu Pro Cys Arg Asn Asp Thr Phe Asn Arg Glu Pro
            500                 505                 510
Phe Ile Val Arg Phe Phe Ser Arg Phe Thr Glu Val Arg Glu Phe Ala
            515                 520                 525
Ile Val Pro Leu His Ala Ala Pro Gly Asp Ala Val Ala Glu Ile Asp
            530                 535                 540
Ala Leu Tyr Asp Val Tyr Leu Asp Val Gln Glu Lys Trp Gly Leu Glu
545                 550                 555                 560
```

Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
                595                 600                 605

Ala Tyr Asp Arg Ile Val Val Ala Gly Met Leu Leu Arg Gly Ala Val
        610                 615                 620

Val Pro Asp Ser Ala Leu Pro Phe Asn Phe Gln Ala Ala Tyr Gly Leu
625                 630                 635                 640

Ser Asp Gln Leu Ala Gln Ala Ile Ser Asp His Tyr Pro Val Glu Val
                645                 650                 655

Met Leu Lys

<210> SEQ ID NO 87
<211> LENGTH: 693
<212> TYPE: DNA
<213> ORGANISM: Homo sapiens

<400> SEQUENCE: 87

```
cccaaatctt ctgacaaaac tcacacatgt ccaccgtgtc cagcacctga actcctgggg    60
ggaccgtcag tcttcctctt cccccccaaaa cccaaggaca ccctcatgat ctcccggacc   120
cctgaggtca catgcgtggt ggtggacgtg agccacgaag accctgaggt caagttcaac   180
tggtacgtgg acggcgtgga ggtgcataat gccaagacaa agccgcggga ggagcagtac   240
aacagcacgt accgtgtggt cagcgtcctc accgtcctgc accaggactg gctgaatggc   300
aaggagtaca agtgcaaggt ctccaacaaa gccctcccag cccccatcga gaaaaccatc   360
tccaaagcca agggcagccc cgagaaccag gtgtacaccc tgcccccc atcccgggat   420
gagctgacca gaaccaggt cagcctgacc tgcctggtca aaggcttcta tcccagcgac   480
atcgccgtgg agtgggagag caatgggcag ccggagaaca actacaagac cacgcctccc   540
gtgctggact ccgacggctc cttcttcctc tacagcaagc tcaccgtgga caagagcagg   600
tggcagcagg ggaacgtctt ctcatgctcc gtgatgcatg aggctctgca caaccactac   660
acgcagaaga gcctctctct gtctccgggt aaa                                693
```

<210> SEQ ID NO 88
<211> LENGTH: 233
<212> TYPE: PRT
<213> ORGANISM: Homo sapiens

<400> SEQUENCE: 88

Leu Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys

```
            100                 105                 110
Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 89
<211> LENGTH: 693
<212> TYPE: DNA
<213> ORGANISM: Homo sapiens

<400> SEQUENCE: 89

```
cccaaatctt ctgacaaaac tcacacatgt ccaccgtgcc cagcacctga actcctggga      60
ggatcgtcag tcttcctctt cccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cctccatcga gaaaaccatc     360
tccaaagcca agggcagccc cgagaaccca ggtgtacca ccctgccccc atcccgggat     420
gagctgacca gaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tacagcaagc tcaccgtgga caagagcagg     600
tggcagcagg ggaacgtctt ctcatgctcc gtgatgcatg aggctctgca caaccactac     660
acgcagaaga gcctctctct ctctccggga aaa                                  693
```

<210> SEQ ID NO 90
<211> LENGTH: 233
<212> TYPE: PRT
<213> ORGANISM: Homo sapiens

<400> SEQUENCE: 90

```
Leu Glu Pro Lys Ser Ser Asp Lys Thr His Thr Cys Pro Pro Cys Pro
1               5                  10                  15

Ala Pro Glu Leu Leu Gly Gly Ser Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
```

```
                65                  70                  75                  80
Gln Tyr Asn Ser Thr Tyr Arg Val Val Ser Val Leu Thr Val Leu His
                    85                  90                  95
Gln Asp Trp Leu Asn Gly Lys Glu Tyr Lys Cys Lys Val Ser Asn Lys
                100                 105                 110
Ala Leu Pro Ala Ser Ile Glu Lys Thr Ile Ser Lys Ala Lys Gly Gln
                115                 120                 125
Pro Arg Glu Pro Gln Val Tyr Thr Leu Pro Pro Ser Arg Asp Glu Leu
            130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
                180                 185                 190
Tyr Ser Lys Leu Thr Val Asp Lys Ser Arg Trp Gln Gln Gly Asn Val
                195                 200                 205
Phe Ser Cys Ser Val Met His Glu Ala Leu His Asn His Tyr Thr Gln
                210                 215                 220
Lys Ser Leu Ser Leu Ser Pro Gly Lys
225                 230
```

<210> SEQ ID NO 91
<211> LENGTH: 1146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atggaaaccc ctgcccagct gctgttcctg ctgctgctgt ggctgcctga caccaccggc      60
aaagagtccc gggccaagaa gttccagcgg cagcacatgg actccgactc cagcccttcc     120
agctcctcca cctactgcaa ccagatgatg cggcggagaa acatgaccca gggccggtgc     180
aagcccgtga caccttttgt gcacgagccc tggtggacg tgcagaacgt gtgttttcaa      240
gagaaagtga cctgcaagaa cggccagggc aactgctaca gtccaactc ctccatgcac      300
atcaccgact gccggctgac caacggctcc agataccccca actgcgccta ccggacctcc   360
cccaagaac ggcacatcat cgtggcctgc gagggctctc cttacgtgcc cgtgcacttc      420
gacgcctccg tggaagattc caccctggaa cccaagtcct ccgacaagac ccacacctgt    480
cccccttgtc ctgcccctga actgctgggc ggctcctccg tgttcctgtt ccccccaaag    540
cccaaggaca ccctgatgat ctcccggacc cccgaagtga catgcgtggt ggtggatgtg    600
tcccacgagg accctgaagt gaagttcaat tggtacgtgg acggggtgga agtgcacaac    660
gccaagacca gcccagaga ggaacagtac aacagcacct accgggtggt gtccgtgctg    720
accgtgctgc accaggattg gctgaacgga aaagagtaca agtgcaaggt gtccaacaag    780
gccctgcccg cctccatcga aaagaccatc tccaaggcca agggccagcc ccgggaaccc    840
caggtgtaca cactgccccc tagcagggac gagctgacca gaaccaggt gtccctgacc     900
tgcctcgtga agggcttcta ccctccgat atcgccgtgg aatgggagtc caacggccag      960
cctgagaaca actacaagac caccccccct gtgctggaca cgacggctc attcttcctg    1020
tactccaagc tgacagtgga caagtccgg tggcagcagg gcaacgtgtt ctcctgctcc    1080
```

```
gtgatgcacg aggctctgca caaccactac acccagaagt ccctgtccct gagccccggc    1140
aaatga                                                               1146
```

<210> SEQ ID NO 92
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Met Glu Thr Pro Ala Gln Leu Leu Phe Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
```

```
                340                 345                 350
Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380

<210> SEQ ID NO 93
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atggaaaccc ctgcccagct gctgttcctg ctgctgctgt ggctgcccga caccaccggc      60
aaagagagcc gggccaagaa gttccagcgg cagcacatgg acagcgacag cagccccagc     120
agctccagca cctactgcaa ccagatgatg cggcggagaa acatgaccca gggccggtgc     180
aagcccgtga cacccttcgt gcacgagccc ctggtggacg tgcagaacgt gtgttttcaa     240
gaaaaagtga cctgcaagaa cggccagggc aactgctaca agagcaacag cagcatgcac     300
atcaccgact gccggctgac caacggcagc agatacccca ctgcgcctac cggaccagc      360 cccaaagaac ggcacatcat cgtggcctgc gagggcagcc cttacgtgcc cgtgcacttt     420
gacgccagcg tggaagatag caccctggaa cccaagagca gcgacaagac ccacacctgt     480
cccccctgcc ctgcccctga gctgctgggc ggaagcagcg tgttcctgtt ccccccaaag     540
cccaaggaca cccctgatga tcagccggac cccgaagtga cctgcgtggt ggtggatgtg     600
tcccacgagg accccgaagt gaagttcaat tggtacgtgg acggcgtgga agtgcacaac     660
gccaagacca agcccagaga ggaacagtac aacagcacct accgggtggt gtccgtgctg     720
accgtgctgc accaggactg gctgaacggc aaagagtaca agtgcaaggt ctccaacaag     780
gccctgcccg ccagcatcga aaaaccatc agcaaggcca agggccagcc tcgcgagccc     840
caggtgtaca cactgccccc cagccgggac gagctgacca gaaccaggt gtccctgacc     900 tgcctggtga aaggcttcta ccccagcgat atcgccgtgg aatgggagag caacggccag     960
cccgagaaca actacaagac cacccccct gtgctggact ccgacggctc attcttcctg    1020
tacagcaagc tgaccgtgga caagagccgg tggcagcagg gcaacgtgtt cagctgcagc    1080
gtgatgcacg aggccctgca caaccactac acccagaagt ccctgagcct gagccccggc    1140
aaggtggacg gcgccagctc ccctgtgaac gtgtccagcc ccagcgtgca ggacatcctg    1200
aagatcgccg ccttcaacat ccagaccttc ggcgagacaa agatgagcaa cgccaccctg    1260
gtgtcctaca tcgtgcagat cctgagcaga tacgatatcg ccctggtgca agaagtgcgg    1320
gacagccacc tgaccgccgt gggcaagctg ctggacaacc tgaaccagga cgcccccgac    1380
acctaccact acgtggtgtc cgagcctctg gccggaaaca gctacaaaga agatacctg     1440 ttcgtgtacc ggcccgatca ggtgtccgcc gtggacagct actactacga cgacggctgc    1500
gagccctgcc ggaacgacac cttcaaccgc gagcccttca tcgtgcggtt cttcagccgg    1560
ttcaccgaag tgcgcgagtt cgccatcgtg cccctgcatg ctgcccctgg cgacgccgtg    1620
gccgagatcg atgccctgta cgacgtgtac ctggatgtgc aagaaaagtg gggcctggaa    1680
gatgtgatgc tgatgggcga cttcaacgcc ggctgcagct acgtgcggcc cagccagtgg    1740
tccagcatca gactgtggac ctcccccacc ttccagtggc tgatccccga cagcgccgat    1800
```

```
accaccgcca cccccaccca ctgtgcctac gacagaatcg tggtggccgg catgctgctg    1860
agaggcgccg tggtgcctga cagcgccctg ccattcaatt ttcaagccgc ctacggcctg    1920
agcgatcagc tggcccaggc catcagcgac cactaccccg tggaagtgat gctgaagtga   1980
```

<210> SEQ ID NO 94
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
                20                  25                  30

Met Asp Ser Asp Ser Ser Pro Ser Ser Ser Ser Thr Tyr Cys Asn Gln
            35                  40                  45

Met Met Arg Arg Arg Asn Met Thr Gln Gly Arg Cys Lys Pro Val Asn
        50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335
```

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
            355                 360                 365

His Tyr Thr Gln Lys Ser Leu Ser Leu Ser Pro Gly Lys Val Asp Gly
            370                 375                 380

Ala Ser Ser Pro Val Asn Val Ser Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
            435                 440                 445

Lys Leu Leu Asp Asn Leu Asn Gln Asp Ala Pro Asp Thr Tyr His Tyr
    450                 455                 460

Val Val Ser Glu Pro Leu Gly Arg Asn Ser Tyr Lys Glu Arg Tyr Leu
465                 470                 475                 480

Phe Val Tyr Arg Pro Asp Gln Val Ser Ala Val Asp Ser Tyr Tyr Tyr
                485                 490                 495

Asp Asp Gly Cys Glu Pro Cys Arg Asn Asp Thr Phe Asn Arg Glu Pro
            500                 505                 510

Phe Ile Val Arg Phe Phe Ser Arg Phe Thr Glu Val Arg Glu Phe Ala
            515                 520                 525

Ile Val Pro Leu His Ala Ala Pro Gly Asp Ala Val Ala Glu Ile Asp
    530                 535                 540

Ala Leu Tyr Asp Val Tyr Leu Asp Val Gln Glu Lys Trp Gly Leu Glu
545                 550                 555                 560

Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
            595                 600                 605

Ala Tyr Asp Arg Ile Val Val Ala Gly Met Leu Leu Arg Gly Ala Val
    610                 615                 620

Val Pro Asp Ser Ala Leu Pro Phe Asn Phe Gln Ala Ala Tyr Gly Leu
625                 630                 635                 640

Ser Asp Gln Leu Ala Gln Ala Ile Ser Asp His Tyr Pro Val Glu Val
                645                 650                 655

Met Leu Lys

<210> SEQ ID NO 95
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
aaagagtccc gggccaagaa gttccagcgg cagcacatgg actccgactc cagcccttcc      60
agctcctcca cctactgcaa ccagatgatg cggcggagaa acatgaccca gggccggtgc     120
aagcccgtga acacctttgt gcacgagccc ctggtggacg tgcagaacgt gtgttttcaa     180

```
gagaaagtga cctgcaagaa cggccagggc aactgctaca agtccaactc ctccatgcac    240
atcaccgact gccggctgac caacggctcc agatacccca actgcgccta ccggacctcc    300
cccaaagaac ggcacatcat cgtggcctgc gagggctctc cttacgtgcc cgtgcacttc    360
gacgcctccg tggaagattc caccctggaa cccaagtcct ccgacaagac ccacacctgt    420
cccccttgtc ctgcccctga actgctgggc ggctcctccg tgttcctgtt cccccccaaag   480 cccaaggaca ccctgatgat ctcccggacc cccgaagtga catgcgtggt ggtggatgtg    540
tcccacgagg accctgaagt gaagttcaat tggtacgtgg acggggtgga agtgcacaac    600
gccaagacca gcccagaga ggaacagtac aacagcacct accgggtggt gtccgtgctg     660
accgtgctgc accaggattg gctgaacgga aaagagtaca agtgcaaggt gtccaacaag    720
gccctgcccg cctccatcga aaagaccatc tccaaggcca agggccagcc ccgggaaccc    780
caggtgtaca cactgccccc tagcagggac gagctgacca agaaccaggt gtccctgacc    840
tgcctcgtga agggcttcta ccctcccgat atcgccgtgg aatgggagtc caacggccag    900
cctgagaaca actacaagac cacccccct gtgctggaca cgacggctc attcttcctg      960 tactccaagc tgacagtgga caagtccgg tggcagcagg gcaacgtgtt ctcctgctcc     1020
gtgatgcacg aggctctgca caaccactac acccagaagt ccctgtccct gagccccggc    1080
aaatga                                                              1086

<210> SEQ ID NO 96
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
                20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
        50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

Leu Glu Pro Lys Ser Ser Asp Lys Thr His Thr Cys Pro Pro Cys Pro
    130                 135                 140

Ala Pro Glu Leu Leu Gly Gly Ser Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190
```

```
Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Ser Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

<210> SEQ ID NO 97
<211> LENGTH: 1920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
aaagagagcc gggccaagaa gttccagcgg cagcacatgg acagcgacag cagccccagc     60
agctccagca cctactgcaa ccagatgatg cggcggagaa acatgaccca gggccggtgc    120
aagcccgtga acaccttcgt gcacgagccc ctggtggacg tgcagaacgt gtgttttcaa    180
gaaaaagtga cctgcaagaa cggccagggc aactgctaca agagcaacag cagcatgcac    240
atcaccgact gccggctgac caacggcagc agataccccc actgcgccta ccggaccagc    300 cccaagaac ggcacatcat cgtggcctgc gagggcagcc cttacgtgcc cgtgcacttt    360
gacgccagcg tggaagatag caccctggaa cccaagagca cgacaagac ccacacctgt    420 ccccctgcc ctgcccctga gctgctgggc ggaagcagcg tgttcctgtt ccccccaaag    480
cccaaggaca cctgatgat cagccggacc cccgaagtga cctgcgtggt ggtggatgtg    540
tcccacgagg accccgaagt gaagttcaat tggtacgtgg acggcgtgga agtgcacaac    600
gccaagacca gcccagaga ggaacagtac aacagcacct accgggtggt gtccgtgctg    660
accgtgctgc accaggactg gctgaacggc aaagagtaca agtgcaaggt ctccaacaag    720
gccctgcccg ccagcatcga gaaaaccatc agcaaggcca agggccagcc tcgcgagccc    780
caggtgtaca cactgccccc cagccgggac gagctgacca gaaccaggt gtccctgacc    840 tgcctggtga aaggcttcta ccccagcgat atcgccgtgg aatgggagag caacggccag    900
cccgagaaca actacaagac cacccccct gtgctggact ccgacggctc attcttcctg    960
tacagcaagc tgaccgtgga caagagccgg tggcagcagg gcaacgtgtt cagctgcagc   1020
```

```
gtgatgcacg aggccctgca caaccactac acccagaagt ccctgagcct gagccccggc    1080
aaggtggacg gcgccagctc ccctgtgaac gtgtccagcc ccagcgtgca ggacatcctg    1140
aagatcgccg ccttcaacat ccagaccttc ggcgagacaa agatgagcaa cgccacactg    1200
gtgtcctaca tcgtgcagat cctgagcaga tacgatatcg ccctggtgca agaagtgcgg    1260
gacagccacc tgaccgccgt gggcaagctg ctggacaacc tgaaccagga cgccccgac    1320 acctaccact acgtggtgtc cgagcctctg ggccggaaca gctacaaaga agatacctg    1380 ttcgtgtacc ggcccgatca ggtgtccgcc gtggacagct actactacga cgacggctgc    1440
gagccctgcc ggaacgacac cttcaaccgc gagcccttca tcgtgcggtt cttcagccgg    1500
ttcaccgaag tgcgcgagtt cgccatcgtg ccctgcatg ctgcccctgg cgacgccgtg    1560
gccgagatcg atgccctgta cgacgtgtac ctggatgtgc aagaaaagtg gggcctggaa    1620
gatgtgatgc tgatgggcga cttcaacgcc ggctgcagct acgtgcggcc cagccagtgg    1680
tccagcatca gactgtggac ctcccccacc ttccagtggc tgatccccga cagcgccgat    1740
accaccgcca ccccaccca ctgtgcctac gacagaatcg tggtggccgg catgctgctg    1800
agaggcgccg tggtgcctga cagcgccctg ccattcaatt ttcaagccgc ctacggcctg    1860
agcgatcagc tggcccaggc catcagcgac cactaccccg tggaagtgat gctgaagtga    1920
```

<210> SEQ ID NO 98
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

Leu Glu Pro Lys Ser Ser Asp Lys Thr His Thr Cys Pro Pro Cys Pro
    130                 135                 140

Ala Pro Glu Leu Leu Gly Gly Ser Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205
```

```
Gln Tyr Asn Ser Thr Tyr Arg Val Val Ser Val Leu Thr Val Leu His
    210                 215                 220
Gln Asp Trp Leu Asn Gly Lys Glu Tyr Lys Cys Lys Val Ser Asn Lys
225                 230                 235                 240
Ala Leu Pro Ala Ser Ile Glu Lys Thr Ile Ser Lys Ala Lys Gly Gln
                245                 250                 255
Pro Arg Glu Pro Gln Val Tyr Thr Leu Pro Pro Ser Arg Asp Glu Leu
            260                 265                 270
Thr Lys Asn Gln Val Ser Leu Thr Cys Leu Val Lys Gly Phe Tyr Pro
        275                 280                 285
Ser Asp Ile Ala Val Glu Trp Glu Ser Asn Gly Gln Pro Glu Asn Asn
290                 295                 300
Tyr Lys Thr Thr Pro Pro Val Leu Asp Ser Asp Gly Ser Phe Phe Leu
305                 310                 315                 320
Tyr Ser Lys Leu Thr Val Asp Lys Ser Arg Trp Gln Gln Gly Asn Val
                325                 330                 335
Phe Ser Cys Ser Val Met His Glu Ala Leu His Asn His Tyr Thr Gln
            340                 345                 350
Lys Ser Leu Ser Leu Ser Pro Gly Lys Val Asp Gly Ala Ser Ser Pro
        355                 360                 365
Val Asn Val Ser Ser Pro Ser Val Gln Asp Ile Leu Lys Ile Ala Ala
370                 375                 380
Phe Asn Ile Gln Thr Phe Gly Glu Thr Lys Met Ser Asn Ala Thr Leu
385                 390                 395                 400
Val Ser Tyr Ile Val Gln Ile Leu Ser Arg Tyr Asp Ile Ala Leu Val
                405                 410                 415
Gln Glu Val Arg Asp Ser His Leu Thr Ala Val Gly Lys Leu Leu Asp
            420                 425                 430
Asn Leu Asn Gln Asp Ala Pro Asp Thr Tyr His Tyr Val Val Ser Glu
        435                 440                 445
Pro Leu Gly Arg Asn Ser Tyr Lys Glu Arg Tyr Leu Phe Val Tyr Arg
450                 455                 460
Pro Asp Gln Val Ser Ala Val Asp Ser Tyr Tyr Tyr Asp Asp Gly Cys
465                 470                 475                 480
Glu Pro Cys Arg Asn Asp Thr Phe Asn Arg Glu Pro Phe Ile Val Arg
                485                 490                 495
Phe Phe Ser Arg Phe Thr Glu Val Arg Glu Phe Ala Ile Val Pro Leu
            500                 505                 510
His Ala Ala Pro Gly Asp Ala Val Ala Glu Ile Asp Ala Leu Tyr Asp
        515                 520                 525
Val Tyr Leu Asp Val Gln Glu Lys Trp Gly Leu Glu Asp Val Met Leu
530                 535                 540
Met Gly Asp Phe Asn Ala Gly Cys Ser Tyr Val Arg Pro Ser Gln Trp
545                 550                 555                 560
Ser Ser Ile Arg Leu Trp Thr Ser Pro Thr Phe Gln Trp Leu Ile Pro
                565                 570                 575
Asp Ser Ala Asp Thr Thr Ala Thr Pro Thr His Cys Ala Tyr Asp Arg
            580                 585                 590
Ile Val Val Ala Gly Met Leu Leu Arg Gly Ala Val Val Pro Asp Ser
        595                 600                 605
Ala Leu Pro Phe Asn Phe Gln Ala Ala Tyr Gly Leu Ser Asp Gln Leu
610                 615                 620
```

```
Ala Gln Ala Ile Ser Asp His Tyr Pro Val Glu Val Met Leu Lys
625                 630                 635
```

```
<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Val Asp Gly Ala Ser Ser Pro Val Asn Val Ser Ser Pro Ser Val Gln
1               5                   10                  15

Asp Ile
```

```
<210> SEQ ID NO 100
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met Glu Thr Pro Ala Gln Leu Leu Phe Leu Leu Leu Leu Trp Leu Pro
1               5                   10                  15

Asp Thr Thr Gly
            20
```

```
<210> SEQ ID NO 101
<211> LENGTH: 128
<212> TYPE: PRT
<213> ORGANISM: Homo sapiens

<400> SEQUENCE: 101

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
                20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
                100                 105                 110

Ser Pro Tyr Val Pro Val His Phe Asp Ala Ser Val Glu Asp Ser Thr
            115                 120                 125
```

```
<210> SEQ ID NO 102
<211> LENGTH: 260
<212> TYPE: PRT
<213> ORGANISM: Homo sapiens

<400> SEQUENCE: 102

Leu Lys Ile Ala Ala Phe Asn Ile Gln Thr Phe Gly Glu Thr Lys Met
1               5                   10                  15
```

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 103
<211> LENGTH: 285
<212> TYPE: PRT
<213> ORGANISM: Homo sapiens

<400> SEQUENCE: 103

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
        35                  40                  45

Pro Ile Leu Met Glu Lys Leu Asn Arg Asn Ser Arg Arg Gly Ile Thr
    50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Ser Val Lys Arg Ser
                85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
        115                 120                 125

```
Phe Val Ile Ile Pro Leu His Thr Thr Pro Glu Thr Ser Val Lys Glu
                130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                    165                 170                 175

Val Pro Lys Lys Ala Trp Lys Asn Ile Arg Leu Arg Thr Asp Pro Arg
                180                 185                 190

Phe Val Trp Leu Ile Gly Asp Gln Glu Asp Thr Thr Val Lys Lys Ser
                195                 200                 205

Thr Asn Cys Ala Tyr Asp Arg Ile Val Leu Arg Gly Gln Glu Ile Val
210                 215                 220

Ser Ser Val Val Pro Lys Ser Asn Ser Val Phe Asp Phe Gln Lys Ala
225                 230                 235                 240

Tyr Lys Leu Thr Glu Glu Ala Leu Asp Val Ser Asp His Phe Pro
                    245                 250                 255

Val Glu Phe Lys Leu Gln Ser Ser Arg Ala Phe Thr Asn Ser Lys Lys
                260                 265                 270

Ser Val Thr Leu Arg Lys Lys Thr Lys Ser Lys Arg Ser
                275                 280                 285

<210> SEQ ID NO 104
<211> LENGTH: 369
<212> TYPE: PRT
<213> ORGANISM: Homo sapiens

<400> SEQUENCE: 104

Met Gly Pro Gly Ala Arg Arg Gln Gly Arg Ile Val Gln Gly Arg Pro
1               5                   10                  15

Glu Met Cys Phe Cys Pro Pro Thr Pro Leu Pro Pro Leu Arg Ile
                20                  25                  30

Leu Thr Leu Gly Thr His Thr Pro Thr Pro Cys Ser Ser Pro Gly Ser
                35                  40                  45

Ala Ala Gly Thr Tyr Pro Thr Met Gly Ser Gln Ala Leu Pro Pro Gly
                50                  55                  60

Pro Met Gln Thr Leu Ile Phe Phe Asp Met Glu Ala Thr Gly Leu Pro
65                  70                  75                  80

Phe Ser Gln Pro Lys Val Thr Glu Leu Cys Leu Leu Ala Val His Arg
                    85                  90                  95

Cys Ala Leu Glu Ser Pro Pro Thr Ser Gln Gly Pro Pro Pro Thr Val
                100                 105                 110

Pro Pro Pro Pro Arg Val Val Asp Lys Leu Ser Leu Cys Val Ala Pro
                115                 120                 125

Gly Lys Ala Cys Ser Pro Ala Ala Ser Glu Ile Thr Gly Leu Ser Thr
                130                 135                 140

Ala Val Leu Ala Ala His Gly Arg Gln Cys Phe Asp Asp Asn Leu Ala
145                 150                 155                 160

Asn Leu Leu Leu Ala Phe Leu Arg Arg Gln Pro Gln Pro Trp Cys Leu
                    165                 170                 175

Val Ala His Asn Gly Asp Arg Tyr Asp Phe Pro Leu Leu Gln Ala Glu
                180                 185                 190

Leu Ala Met Leu Gly Leu Thr Ser Ala Leu Asp Gly Ala Phe Cys Val
                195                 200                 205

Asp Ser Ile Thr Ala Leu Lys Ala Leu Glu Arg Ala Ser Ser Pro Ser
```

```
            210                 215                 220
Glu His Gly Pro Arg Lys Ser Tyr Ser Leu Gly Ser Ile Tyr Thr Arg
225                 230                 235                 240

Leu Tyr Gly Gln Ser Pro Pro Asp Ser His Thr Ala Glu Gly Asp Val
                245                 250                 255

Leu Ala Leu Leu Ser Ile Cys Gln Trp Arg Pro Gln Ala Leu Leu Arg
            260                 265                 270

Trp Val Asp Ala His Ala Arg Pro Phe Gly Thr Ile Arg Pro Met Tyr
        275                 280                 285

Gly Val Thr Ala Ser Ala Arg Thr Lys Pro Arg Pro Ser Ala Val Thr
    290                 295                 300

Thr Thr Ala His Leu Ala Thr Thr Arg Asn Thr Ser Pro Ser Leu Gly
305                 310                 315                 320

Glu Ser Arg Gly Thr Lys Asp Leu Pro Pro Val Lys Asp Pro Gly Ala
                325                 330                 335

Leu Ser Arg Glu Gly Leu Leu Ala Pro Leu Gly Leu Leu Ala Ile Leu
            340                 345                 350

Thr Leu Ala Val Ala Thr Leu Tyr Gly Leu Ser Leu Ala Thr Pro Gly
        355                 360                 365

Glu
```

<210> SEQ ID NO 105
<211> LENGTH: 297
<212> TYPE: PRT
<213> ORGANISM: Homo sapiens

<400> SEQUENCE: 105

```
Met Gly Pro Gly Ala Arg Arg Gln Gly Arg Ile Val Gln Gly Arg Pro
1               5                   10                  15

Glu Met Cys Phe Cys Pro Pro Thr Pro Leu Pro Pro Leu Arg Ile
            20                  25                  30

Leu Thr Leu Gly Thr His Thr Pro Thr Pro Cys Ser Ser Pro Gly Ser
            35                  40                  45

Ala Ala Gly Thr Tyr Pro Thr Met Gly Ser Gln Ala Leu Pro Pro Gly
    50                  55                  60

Pro Met Gln Thr Leu Ile Phe Phe Asp Met Glu Ala Thr Gly Leu Pro
65              70                  75                  80

Phe Ser Gln Pro Lys Val Thr Glu Leu Cys Leu Leu Ala Val His Arg
                85                  90                  95

Cys Ala Leu Glu Ser Pro Pro Thr Ser Gln Gly Pro Pro Pro Thr Val
            100                 105                 110

Pro Pro Pro Pro Arg Val Val Asp Lys Leu Ser Leu Cys Val Ala Pro
        115                 120                 125

Gly Lys Ala Cys Ser Pro Ala Ala Ser Glu Ile Thr Gly Leu Ser Thr
    130                 135                 140

Ala Val Leu Ala Ala His Gly Arg Gln Cys Phe Asp Asp Asn Leu Ala
145                 150                 155                 160

Asn Leu Leu Leu Ala Phe Leu Arg Arg Gln Pro Gln Pro Trp Cys Leu
                165                 170                 175

Val Ala His Asn Gly Asp Arg Tyr Asp Phe Pro Leu Leu Gln Ala Glu
            180                 185                 190

Leu Ala Met Leu Gly Leu Thr Ser Ala Leu Asp Gly Ala Phe Cys Val
        195                 200                 205

Asp Ser Ile Thr Ala Leu Lys Ala Leu Glu Arg Ala Ser Ser Pro Ser
```

-continued

```
                    210                 215                 220

Glu His Gly Pro Arg Lys Ser Tyr Ser Leu Gly Ser Ile Tyr Thr Arg
225                 230                 235                 240

Leu Tyr Gly Gln Ser Pro Asp Ser His Thr Ala Glu Gly Asp Val
                    245                 250                 255

Leu Ala Leu Leu Ser Ile Cys Gln Trp Arg Pro Gln Ala Leu Leu Arg
                260                 265                 270

Trp Val Asp Ala His Ala Arg Pro Phe Gly Thr Ile Arg Pro Met Tyr
                275                 280                 285

Gly Val Thr Ala Ser Ala Arg Thr Lys
                290                 295

<210> SEQ ID NO 106
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
                20                  25                  30

Met Asp Ser Asp Ser Ser Pro Ser Ser Ser Thr Tyr Cys Asn Gln
                35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
                100                 105                 110

Pro Asn Cys Ala Tyr Arg Thr Ser Pro Lys Glu Arg His Ile Ile Val
                115                 120                 125

Ala Cys Glu Gly Ser Pro Tyr Val Pro Val His Phe Asp Ala Ser Val
                130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Pro Ser Val Phe Leu
                165                 170                 175

Phe Pro Pro Lys Pro Lys Asp Thr Leu Met Ile Ser Arg Thr Pro Glu
                180                 185                 190

Val Thr Cys Val Val Val Asp Val Ser His Glu Asp Pro Glu Val Lys
                195                 200                 205

Phe Asn Trp Tyr Val Asp Gly Val Glu Val His Asn Ala Lys Thr Lys
                210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
                260                 265                 270
```

```
Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
        290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
                340                 345                 350

Gln Gly Asn Val Phe Ser Cys Ser Val Met His Glu Ala Leu His Asn
                355                 360                 365

His Tyr Thr Gln Lys Ser Leu Ser Leu Ser Pro Gly Lys
                370                 375                 380

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Asp Gly Ala Ser Ser Pro Val Asn Val Ser Ser Pro Ser Val Gln
1               5                   10                  15

Asp Ile

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Gly Ser Gly Gly Gly Gly Ser Gly Gly Gly Gly Ser Gly
1               5                   10                  15

Gly Gly Gly Ser
            20

<210> SEQ ID NO 109
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 0-5
      "Gly-Gly-Gly-Gly-Ser" repeating units

<400> SEQUENCE: 109

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 110
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 111
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1-10
      "Gly-Gly-Gly-Gly-Ser" repeating units

<400> SEQUENCE: 111

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gly Gly Gly Ser Gly Gly Gly Gly Ser Gly Gly Gly Gly Ser
1               5                   10                  15

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Gly Gly Gly Gly Ser
1               5

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 114

Ser Gly Gly Gly Gly Ser Gly Gly Gly Gly Ser
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Gly Gly Gly Gly Ser Gly Gly Gly Gly Ser Gly Gly Gly Gly Ser
1               5                   10                  15

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 117
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 118
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 119
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 119

Ser Gly Gly Gly Gly Ser Gly Gly Gly Ser Gly Gly Gly Ser
1               5                   10                  15

Gly Gly Gly Gly Ser Gly Gly Gly Ser Gly Gly Gly Ser Gly
                20                  25                  30

Gly Gly Gly Ser
        35

<210> SEQ ID NO 120
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ser Gly Gly Gly Gly Ser Gly Gly Gly Ser Gly Gly Gly Ser
1               5                   10                  15

Gly Gly Gly Gly Ser Gly Gly Gly Ser Gly Gly Gly Ser Gly
                20                  25                  30

Gly Gly Gly Ser Gly Gly Gly Gly Ser
        35                  40

<210> SEQ ID NO 121
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ser Gly Gly Gly Gly Ser Gly Gly Gly Ser Gly Gly Gly Ser
1               5                   10                  15

Gly Gly Gly Gly Ser Gly Gly Gly Ser Gly Gly Gly Ser Gly
                20                  25                  30

Gly Gly Gly Ser Gly Gly Gly Gly Ser Gly Gly Gly Gly Ser
        35                  40                  45

<210> SEQ ID NO 122
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ser Gly Gly Gly Gly Ser Gly Gly Gly Ser Gly Gly Gly Ser
1               5                   10                  15

Gly Gly Gly Gly Ser Gly Gly Gly Ser Gly Gly Gly Ser Gly
                20                  25                  30

Gly Gly Gly Ser Gly Gly Gly Ser Gly Gly Gly Ser Gly Gly
        35                  40                  45

Gly Gly Ser
    50

<210> SEQ ID NO 123
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 3-5
      "Gly-Gly-Gly-Gly-Ser" repeating units

<400> SEQUENCE: 123

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 124
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 1-5
      "Gly-Gly-Gly-Gly-Ser" repeating units

<400> SEQUENCE: 124

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Gly Gly Ser
1               5

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 126
tttttttttt tttttttt                                             18
```